US012662471B2

(12) United States Patent (10) Patent No.: US 12,662,471 B2
Giroux et al. (45) Date of Patent: Jun. 23, 2026

(54) 7- OR 8-HYDROXY-ISOQUINOLINE AND 7- OR 8-HYDROXY-QUINOLINE DERIVATIVES AS ALPHA-1-ANTITRYPSIN MODULATORS FOR TREATING ALPHA-1-ANTITRYPSIN DEFICIENCY (AATD)

(71) Applicant: Vertex Pharmaceuticals Incorporated, Boston, MA (US)

(72) Inventors: Simon Giroux, Cambridge, MA (US); Michael Philip Clark, Concord, MA (US); Michael Aaron Brodney, Newton, MA (US); Peter Jones, Sharon, MA (US); Michael Paul Deninno, Gales Ferry, CT (US); Wenxin Gu, Concord, MA (US); Qing Tang, Boxborough, MA (US); Steven David Stone, Quincy, MA (US); Timothy J. Senter, Arlington, MA (US); Zachary Gale-Day, Brookline, MA (US); Diane Marie Boucher, Beverly, MA (US); Lev T.D. Fanning, San Marcos, CA (US); Amy B. Hall, Wellesley Hills, MA (US); Dennis James Hurley, San Marcos, CA (US); Mac Arthur Johnson, Jr., Derry, NH (US); John Patrick Maxwell, Hingham, MA (US); Rebecca Jane Swett, Somerville, MA (US); Timothy Lewis Tapley, Cardiff, CA (US); Stephen A. Thomson, Durham, NC (US); Veronique Damagnez, Framingham, MA (US); Kevin Michael Cottrell, Cambridge, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 796 days.

(21) Appl. No.: 17/916,453

(22) PCT Filed: Apr. 2, 2021

(86) PCT No.: PCT/US2021/025623
§ 371 (c)(1),
(2) Date: Sep. 30, 2022

(87) PCT Pub. No.: WO2021/203028
PCT Pub. Date: Oct. 7, 2021

(65) Prior Publication Data
US 2023/0159504 A1 May 25, 2023

Related U.S. Application Data

(60) Provisional application No. 63/004,683, filed on Apr. 3, 2020.

(51) Int. Cl.
| | |
|---|---|
| *C07D 405/14* | (2006.01) |
| *C07D 215/20* | (2006.01) |
| *C07D 215/38* | (2006.01) |
| *C07D 217/24* | (2006.01) |
| *C07D 401/04* | (2006.01) |
| *C07D 401/12* | (2006.01) |
| *C07D 405/04* | (2006.01) |
| *C07D 409/04* | (2006.01) |
| *C07D 413/12* | (2006.01) |
| *C07D 413/14* | (2006.01) |
| *C07H 17/02* | (2006.01) |

(52) U.S. Cl.
CPC ......... *C07D 405/14* (2013.01); *C07D 215/20* (2013.01); *C07D 215/38* (2013.01); *C07D 217/24* (2013.01); *C07D 401/04* (2013.01); *C07D 401/12* (2013.01); *C07D 405/04* (2013.01); *C07D 409/04* (2013.01); *C07D 413/12* (2013.01); *C07D 413/14* (2013.01); *C07H 17/02* (2013.01); *C07B 2200/05* (2013.01)

(58) Field of Classification Search
CPC .. C07D 405/14; C07D 215/20; C07D 215/38; C07D 401/04; C07D 401/12; C07D 217/24; C07D 405/04; C07D 409/04; C07D 413/12; C07D 413/14; C07H 17/02
See application file for complete search history.

(56) References Cited

U.S. PATENT DOCUMENTS

| 2,538,341 A | 1/1951 | Ullyot |
|---|---|---|
| 2,612,503 A | 9/1952 | Ullyot |

(Continued)

FOREIGN PATENT DOCUMENTS

| CA | 3114672 A1 | 4/2020 |
|---|---|---|
| CN | 1704404 A | 7/2001 |

(Continued)

OTHER PUBLICATIONS

Stoller, J.K.; et al. "Alpha-1 antitrypsin deficiency: An under-recognized, treatable cause of COPD" 2016, Cleveland Clinic Journal of Medicine, vol. 83, pp. 507-514. (Year: 2016).*
Modi, A. R.; et al. "Isoquinolones: Part IV-Synthesis of 3-Methyl, 3-Formyl & Other 3-Substituted -N-Arylisoquinolones" 1979, Indian Journal of Chemistry, vol. 18B, pp. 304-306. (Year: 1979).*
STN database entry for CAS RN 73109-03-2 (entered STN on Nov. 16, 1984). (Year: 1984).*
STN database entry for CAS RN 2137577-83-2 (entered STN on Nov. 1, 2017). (Year: 2017).*

(Continued)

*Primary Examiner* — Andrea Olson
*Assistant Examiner* — Benjamin M Brandsen
(74) *Attorney, Agent, or Firm* — Finnegan, Henderson, Farabow, Garrett & Dunner, LLP

(57) ABSTRACT

7- or 8-hydroxy-isoquinoline and 7- or 8-hydroxy-quinoline derivatives as alpha-1-antitrypsin modulators for treating alpha-1-antitrypsin deficiency (AATD).

22 Claims, No Drawings

(56) References Cited

U.S. PATENT DOCUMENTS

| | | | |
|---|---|---|---|
| 4,198,415 A | 4/1980 | Kornfeld et al. | |
| 4,647,667 A | 3/1987 | Schaus et al. | |
| 4,778,894 A | 10/1988 | Schaus et al. | |
| 5,216,001 A | 6/1993 | Perregaard et al. | |
| 5,358,949 A * | 10/1994 | Tabusa | C07D 215/40 |
| | | | 544/321 |
| 6,201,129 B1 | 3/2001 | Miller et al. | |
| 11,623,924 B2 | 4/2023 | Bandarage et al. | |
| 11,884,672 B2 | 1/2024 | Bandarage et al. | |
| 12,331,057 B2 | 6/2025 | Bandarage et al. | |
| 2001/0051620 A1 | 12/2001 | Berger et al. | |
| 2003/0097000 A1 | 5/2003 | Bovy et al. | |
| 2003/0165712 A1 | 9/2003 | Lin et al. | |
| 2003/0212085 A1 | 11/2003 | McCall et al. | |
| 2004/0077865 A1 | 4/2004 | Zhao et al. | |
| 2005/0009754 A1 | 1/2005 | Pan et al. | |
| 2005/0043381 A1 | 2/2005 | Johnson et al. | |
| 2005/0153957 A1* | 7/2005 | Cuenoud | C07C 311/08 |
| | | | 514/367 |
| 2007/0027177 A1* | 2/2007 | Trotter | C07D 455/04 |
| | | | 546/141 |
| 2007/0232682 A1 | 10/2007 | Beard et al. | |
| 2007/0248947 A1* | 10/2007 | Cezar | G01N 33/5073 |
| | | | 702/19 |
| 2008/0021056 A1 | 1/2008 | Konradi et al. | |
| 2010/0016285 A1 | 1/2010 | Uchida et al. | |
| 2010/0076018 A1 | 3/2010 | Liu et al. | |
| 2011/0118221 A1 | 5/2011 | Nussbaum et al. | |
| 2013/0167932 A1 | 7/2013 | Maeda et al. | |
| 2013/0319530 A1 | 12/2013 | Maeda et al. | |
| 2014/0135359 A1 | 5/2014 | Martineau | |
| 2014/0341899 A1 | 11/2014 | Dinarello et al. | |
| 2016/0083363 A1 | 3/2016 | Hamm et al. | |
| 2016/0145271 A1 | 5/2016 | Vakalopoulos et al. | |
| 2018/0251460 A1 | 9/2018 | Aktoudianakis et al. | |
| 2020/0361939 A1 | 11/2020 | Bandarage et al. | |
| 2021/0260036 A1 | 8/2021 | Bozic et al. | |
| 2023/0157999 A1 | 5/2023 | Clark et al. | |
| 2023/0159502 A1 | 5/2023 | Giroux et al. | |
| 2023/0159504 A1 | 5/2023 | Giroux et al. | |
| 2023/0159521 A1 | 5/2023 | Giroux et al. | |
| 2023/0159580 A1 | 5/2023 | Giroux et al. | |
| 2023/0265080 A1 | 8/2023 | Bandarage et al. | |
| 2023/0279010 A1 | 9/2023 | Bligh et al. | |
| 2023/0339915 A1 | 10/2023 | Giroux et al. | |
| 2024/0002386 A1 | 1/2024 | Shi et al. | |
| 2024/0012010 A1 | 1/2024 | Penney et al. | |
| 2024/0158404 A1 | 5/2024 | Grey, Jr. et al. | |
| 2024/0336614 A1 | 10/2024 | Bandarage et al. | |

FOREIGN PATENT DOCUMENTS

| | | | | |
|---|---|---|---|---|
| CN | 1505613 A | 6/2004 | | |
| CN | 102850324 A | 1/2013 | | |
| CN | 103239451 | 8/2013 | | |
| CN | 107698505 A | 2/2018 | | |
| CN | 109111426 A * | 1/2019 | | C07D 413/06 |
| CN | 109414596 A | 3/2019 | | |
| CN | 110776459 A | 2/2020 | | |
| CN | 113164761 A | 7/2021 | | |
| CN | 115361946 A | 11/2022 | | |
| EP | 0 465 398 A2 | 1/1992 | | |
| EP | 1 396 488 A1 | 3/2004 | | |
| EP | 3571187 B1 | 11/2019 | | |
| EP | 3 699 179 A1 | 8/2020 | | |
| ES | 323287 A1 | 3/1967 | | |
| JP | 4856667 A | 8/1973 | | |
| JP | 2000072751 A * | 3/2000 | | |
| JP | 2000-281654 A | 10/2000 | | |
| JP | 5107589 B2 | 12/2012 | | |
| RU | 2337915 C1 | 11/2008 | | |
| RU | 2617405 C2 | 4/2017 | | |
| WO | WO 1996/037467 A1 | 11/1996 | | |
| WO | WO 00/35919 | 6/2000 | | |

| | | | |
|---|---|---|---|
| WO | WO 2000/075114 A1 | 12/2000 | |
| WO | WO 2001/044197 A2 | 6/2001 | |
| WO | WO 2002/008224 A1 | 1/2002 | |
| WO | WO 2002/094790 A1 | 11/2002 | |
| WO | WO 2003/099824 A1 | 12/2003 | |
| WO | WO 2004/065367 A1 | 8/2004 | |
| WO | WO 2004/108120 A1 | 12/2004 | |
| WO | WO 2006/019831 A1 | 2/2006 | |
| WO | WO 2006/093823 A1 | 9/2006 | |
| WO | WO 2007/022501 A2 | 2/2007 | |
| WO | WO 2007/115315 A2 | 10/2007 | |
| WO | WO 2009/060209 A1 | 5/2009 | |
| WO | WO 2009/127686 A1 | 10/2009 | |
| WO | WO 2009/158587 A1 | 12/2009 | |
| WO | WO 2011/056222 A1 | 5/2011 | |
| WO | WO 2011/110852 A1 | 9/2011 | |
| WO | WO 2012/016695 A2 | 2/2012 | |
| WO | WO 2012/038820 A2 | 3/2012 | |
| WO | WO 2016/154051 A1 | 9/2016 | |
| WO | WO 2017/035418 A1 | 3/2017 | |
| WO | WO 2017/117304 A1 | 7/2017 | |
| WO | WO 2017/197240 A1 | 11/2017 | |
| WO | WO 2017/207118 A1 | 12/2017 | |
| WO | WO 2018/218192 A1 | 11/2018 | |
| WO | WO 2019/076336 A1 | 4/2019 | |
| WO | WO 2019/089667 A1 | 5/2019 | |
| WO | WO 2019/116302 A1 | 6/2019 | |
| WO | WO 2019/149522 A1 | 8/2019 | |
| WO | WO 2019/243841 A1 | 12/2019 | |
| WO | WO 2020/002611 A1 | 1/2020 | |
| WO | WO 2020/033288 A1 | 2/2020 | |
| WO | WO 2020/048694 A1 | 3/2020 | |
| WO | WO 2020/081257 A1 | 4/2020 | |
| WO | WO 2020/247160 A1 | 12/2020 | |
| WO | WO 2021/067584 A1 | 4/2021 | |
| WO | WO 2021/155087 A1 | 8/2021 | |
| WO | WO 2021/203007 A1 | 10/2021 | |
| WO | WO 2021/203010 A1 | 10/2021 | |
| WO | WO 2021/203014 A1 | 10/2021 | |
| WO | WO 2021/203023 A1 | 10/2021 | |
| WO | WO 2021/203025 A1 | 10/2021 | |
| WO | WO 2021/203028 A1 | 10/2021 | |
| WO | WO 2022/026372 A2 | 2/2022 | |
| WO | WO 2022/104353 A1 | 5/2022 | |
| WO | WO 2022/109553 A2 | 5/2022 | |
| WO | WO 2024/054624 A1 | 3/2024 | |

OTHER PUBLICATIONS

Priya, N.; et al. "Characterization of 4-methyl-2-oxo-1,2-dihydroquinolin-6-yl acetate as an effective antiplatelet agent" 2010, Bioorganic and Medicinal Chemistry, vol. 18, pp. 4085-4094. (Year: 2010).*

STN database entry for CAS RN 56513-01-0 (entered STN on Nov. 16, 1984). (Year: 1984).*

STN database entry for CAS RN 1936181-19-9 (entered STN on Jun. 21, 2016). (Year: 2016).*

STN database entry for CAS RN 91348-44-6 (entered STN on Nov. 16, 1984). (Year: 1984).*

STN database entry for CAS RN 1893503-08-6 (entered STN on Apr. 20, 2016). (Year: 2016).*

STN database entry for CAS RN 73828-51-0 (entered STN on Nov. 16, 1984). (Year: 1984).*

STN database entry for CAS RN 1780592-67-7 (entered STN on Jun. 15, 2015). (Year: 2015).*

STN database entry for CAS RN 1785114-56-8 (entered STN on Jun. 21, 2015). (Year: 2015).*

English machine translation of JP 2000072751A (translated May 12, 2025). (Year: 2000).*

STN database entry for CAS RN 73828-43-0 (entered STN on Nov. 16, 1984). (Year: 1984).*

English language machine translation of CN109111426A; translated Sep. 30, 2025. (Year: 2019).*

American Thoracic Society & European Respiratory Society (2003) "American Thoracic Society/European Respiratory Society State-

(56)                 References Cited

OTHER PUBLICATIONS ment: Standards for the Diagnosis and Management of Individuals with Alpha-1 Antitrypsin Deficiency," *Am J Respir Crit Care Med.,* 168:818-900.

Balle, T. et al. (2003) "Synthesis and Structure-Affinity Relationship Investigations of 5-Aminomethyl and 5-Carbamoyl Analogues of the Antipsychotic Sertindole. A New Class of Selective $\alpha_1$ Adrenoceptor Antagonists," *Bioorg. Med. Chem.,* 11:1065-1078.

Bergin, D.A. et al. (2014) "The circulating proteinase inhibitor alpha-1 antitrypsin regulates neutrophil degranulation and autoimmunity," *Sci Transl Med.,* 6(217):217ra1 (70 pages).

Chemical Abstracts Service, CAS Registry No. 1516110-75-0. CA Index Name: Pyrrolo[2,3-f]benzimidazole-7-methanamine, 6-ethyl-3,5-dihydro-2-methyl-6-Ethyl-3,5-dihydro-2-methylpyrrolo[2,3-f]benzimidazole-7-methanamine Date: Jan. 10, 2014.

Chemical Abstracts Service, CAS Registry No. 2103889-64-9. CA Index Name: Pyrrolo[2,3-f]benzimidazole-7-carbonitrile, 3,5-dihydro-2,5,6-trimethyl Date: Jul. 27, 2017.

Donawade, D.S. et al. (Apr. 2007.) "Synthesis and antimicrobial activity of novel linearly fused 5-substituted-7-acetyl-2,6-dimethyloxazolo[4,5-f] indoles," *Indian Journal of Chemistry,* 46B:690-693.

Forbes, I.T. et al. (1996) "Synthesis, Biological Activity, and Molecular Modeling Studies of Selective $5\text{-HT}_{2C/2B}$ Receptor Antagonists," *J. Med. Chem.,* 39:4966-4977.

Fregonese, F. & J. Stolk (2008) "Hereditary alpha-1-antitrypsin deficiency and its clinical consequences," *Orphanet J. Rare Dis.,* 3:16 (9 pages).

Geraghty, P. et al. (Dec. 2014.), "$\alpha$1-Antitrypsin Activates Protein Phosphatase 2A to Counter Lung Inflammatory Responses," *Am J Respir Crit Care Med,* 190(11):1229-1242.

Grant & Hackh's Chemical Dictionary (5th ed. 1987), at p. 148.

Grinev, A.N. et al. (1975), "Synthesis of Aldehydes and Nitriles in the 5-Hydroxyindole Series," *Chem. Heterocycl. Compd.,* 11:1087-1090.

Gadaginamath, G.S. et al. (2000) "Chemoselective Reaction of 3,6-Diacetylindole Towards Hydroxylamine: Synthesis and Antimicrobial Activity of Novel Isoxazolo[4,5-f]indole Derivatives," *Rev. Roum. Chim.,* 45(10):929-933.

Ghorai, J. et al. (2016) "Cobalt(III)-Catalyzed Intramolecular Cross-Dehydrogenative C—H/X—H Coupling: Efficient Synthesis of Indoles and Benzofurans," *Chem. Eur. J.,* 22:16042-16046.

Ghorai, J. et al. (2018) "Divergent Functionalization of N-Alkyl-2-alkenylanilines: Efficient Synthesis of Substituted Indoles and Quinolines," *Chem. Asian J.,* 13(17):2499-2504.

Gosai, S. et al. (Nov. 2010.) "Automated High-Content Live Animal Drug Screening Using *C. elegans* Expressing the Aggregation Prone Serpin $\alpha$I-antitrypsin Z," *PLoS One,* 5(11):e15460 (16 pages).

He, L. et al. (2014) "Transition-metal-free synthesis of multisubstituted N-arylindoles via reaction of arynes and $\alpha$-amino ketones," *Tetrahedron,* 70:2400-2405.

International Search Report and Written Opinion from International Application No. PCT/US2021/025623, mailed Jun. 14, 2021 (18 pages).

Jafarpour, F. et al. (2019) "A Fast Track to Indoles and Annulated Indoles through ortho- vs ipso-Amination of Aryl Halides," *Org. Lett.,* 21:10143-10148.

Jiang, H. et al. (2016) "Multiple Roles of the Pyrimidyl Group in the Rhodium-Catalyzed Regioselective Synthesis and Functionalization of Indole-3-carboxylic Acid Esters," *Advanced Synthesis & Catalysis,* 358:188-194.

Kamat, A.G. et al. (Mar. 1994.), "Synthesis and Antimicrobial Activity of Furoindole Derivatives," *Indian J. Chem. Sect. B,* 33B(3):255-259.

Maity, S. et al. (Sep. 2012) "A Visible-Light-Mediated Oxidative C—N Bond Formation/Aromatization Cascade: A New Photocatalytic Preparation of N-Arylindoles," *Angew Chem Int Ed Engl.,* 51(38):9562-9566. NIH Public Access Author Manuscript; available in PMC Sep. 17, 2013 (11 pages).

Mali, R.S. et al. (1994) "Useful Syntheses of Pyrano- and Pyridoindoles," *Organic Preparations and Procedures International: The New Journal for Organic Synthesis,* 26(5):573-577.

Meti, P. et al. (2017) "Regioselective synthesis of dipyrrolopyrazine (DPP) derivatives via metal free and metal catalyzed amination and investigation of their optical and thermal properties," *RSC Adv.,* 7:18120-18131.

Notice of Allowance and Fee(s) Due for U.S. Appl. No. 16/593, 118, mailed Nov. 9, 2022.

Ogushi, F. et al. (1987) "Z-type $\alpha$1-antitrypsin is less competent than M1-type $\alpha$1-antitrypsin as an inhibitor of neutrophil elastase," *J Clin Invest.,* 80(5):1366-1374.

Piitulainen, E. & H.A. Tanash (2015), "The Clinical Profile of Subjects Included in the Swedish National Register on Individuals with Severe Alpha 1-Antitrypsin deficiency," *COPD,* 12(S1):36-41.

Saccarello, M.L. et al. (Sep. 1979) "A New Synthesis of 1-Alkyl-3-aminoindoles," *Synthesis,* 1979(9):727-729.

Song, X. et al. (2018) "Regioselective Synthesis of 2-Alkenylindoles and 2-Alkenylindole-3-carboxylates through the Cascade Reactions of N-Nitrosoanilines with Propargyl Alcohols," *J. Org. Chem.,* 83:8509-8521.

Tanash, H.A. et al. (2016) "Cause-specific mortality in individuals with severe alpha 1-antitrypsin deficiency in comparison with the general population in Sweden," *International Journal of COPD,* 2016(11):1663-1669.

Tidwell, R.R. et al. (1978) "Diarylamidine Derivatives with One or Both of the Aryl Moieties Consisting of an Indole or Indole-like Ring. Inhibitors of Arginine-Specific Esteroproteases," J Med Chem, vol. 21, No. 7:613-623.

Wen, W. et al. (2014) "Substituted indoles as selective protease activated receptor 4 (PAR-4) antagonists: Discovery and SAR of ML354," *Bioorg. Med. Chem. Lett.,* http://dx.doi.org/10.1016/j.bmcl.2014.08.021.

*Vertex Provides Update on its Clinical Programs Targeting Alpha-1 Antitrypsin Deficiency,* Vertex (Oct. 14, 2020), https://news.vrtx.com/press-release/vertex-provides-update-its-clinical-programs-targeting-alpha-1-antitrypsin-deficiency (4 pages).

*Vertex Announces Primary Endpoint Achieved in Phase 2 Study of VX-864 in Alpha-1 Antitrypsin Deficiency,* Vertex (Jun. 10, 2021), https://news.vrtx.com/press-release/vertex-announces-primary-endpoint-achieved-phase-2-study-vx-864-alpha-1-antitrypsin (5 pages).

Akhapkina, V.I. et al. (2012) "Fundamental bases of modulatory concept and classification of modulatory drugs", Russian Medical Journal, 19: 933-951.

Aldonyte, R. et al. (2004) "Analysis of systemic biomarkers in COPD patients", Journal of Chronic Obstructive PulmonaryDisease, 1(2):155-164.

Al-Shaar et al. The Synthesis of Heterocycles via Addition-Elimination Reactions of 4- and 5-aminoimidazoles. J. Chern. Soc. Perkin Trans. 1 (1992). (Year: 1992).

Belikov, V.G. (2007) "Pharmaceutical Chemistry", textbook, Moscow, MEDpress-inform, pp. 27-29.

Carta et al. "Reactions of alkylation of biologically interesting triazolo [4, 5-g] quinolines and triazolo [4, 5-g] quinoline-1-oxides with electrophilic reagents." Heterocycles 75.10 (2008): 2493-2505.

Chemical Abstracts Service, CAS Registry No. 2255-53-0. CA Index Name: Carbostyril, 3-ethyl-8-hydroxy-4-methoxy-(8Cl) Date: Nov. 16, 1984.

Chemical Abstracts Service, CAS Registry No. 73828-46-3. CA Index Name: 1(2H)-Isoquinolinone, 3-ethyl-7-hydroxy-2-methyl-Date: Nov. 16, 1984.

Chemical Abstracts Service, CAS Registry No. 73828-52-1. CA Index Name: 1(2H)-Isoquinolinone, 3-ethyl-7-hydroxy-2-(2-hydroxyethyl)- Date: Nov. 16, 1984.

Chemical Abstracts Service, CAS Registry No. 73828-55-4. CA Index Name: 1(2H)-Isoquinolinone, 3-ethyl-2,7-dihydroxy- Date: Nov. 16, 1984.

Chemical Abstracts Service, CAS Registry No. 872787-19-4. CA Index Name: 1(2H)-Isoquinolinone, 7-amino-3-ethyl- Date: Jan. 27, 2006.

Chemical Abstracts Service, CAS Registry No. 102559-86-4. CA Index Name: 8-Quinolinol, 4-chloro-2-[2-(diethylamino)ethyl]-3-ethyl- Date: Jun. 7, 1986.

(56) References Cited

OTHER PUBLICATIONS

Chemical Abstracts Service, CAS Registry No. 1045710-22-2. CA Index Name: 8-Quinolinol, 3-(1-methylethyl)-2-(2-methylpropyl)- Date: Sep. 2, 2008.

Chemical Abstracts Service, CAS Registry No. 105909-75-9. CA Index Name: 8-Quinolinol, 3-ethyl-2-methyl- Date: Dec. 25, 1986.

Chemical Abstracts Service, CAS Registry No. 1078095-05-2. CA Index Name: 8-Quinolinol, 3-ethyl-2-phenyl- Date: Dec. 1, 2008.

Chemical Abstracts Service, CAS Registry No. 1854272-23-3. CA Index Name: 4-Chloro-3-ethyl-2-methyl-8-(phenylmethoxy)quinoline Date: Jan. 28, 2016.

Chemical Abstracts Service, CAS Registry No. 1869801-41-1. CA Index Name: 3-Ethyl-N-methyl-7-(phenylmethoxy)-2-quinolinamine Date: Feb. 18, 2016.

Chemical Abstracts Service, CAS Registry No. 1873904-99-4. CA Index Name: 4-Chloro-3-ethyl-2-methyl-7-(phenylmethoxy)quinoline Date: Feb. 25, 2016.

Chemical Abstracts Service, CAS Registry No. 1875846-68-6. CA Index Name: N,3-Diethyl-7-(phenylmethoxy)-2-quinolinamine Date: Feb. 29, 2016.

Chemical Abstracts Service, CAS Registry No. 1877816-72-2. CA Index Name: N-Methyl-3-(1-methylethyl)-7-(phenylmethoxy)-2-quinolinamine Date: Mar. 2, 2016.

Chemical Abstracts Service, CAS Registry No. 1878025-01-4. CA Index Name: 4-Chloro-2-methyl-3-(1-methylethyl)-7-(phenylmethoxy)quinoline Date: Mar. 2, 2016.

Chemical Abstracts Service, CAS Registry No. 1880486-29-2. CA Index Name: 4-Chloro-2-methyl-3-(1-methylethyl)-8-(phenylmethoxy)quinoline Date: Mar. 6, 2016.

Chemical Abstracts Service, CAS Registry No. RN 2106364-27-4. Index Name: Pyrrolo[2,3-f]benzimidazole-7-carboxylic acid, 3,5-dihydro-2,5,6-trimethyl-, ethyl ester Date: Aug. 1, 2017.

Chou, T.-C. (2010) "Drug Combination Studies and Their Synergy Quantification Using the Chou-Talalay Method", Cancer Res; 70(2):440-446.

Dafforn, T. R. et al. (1999) "A kinetic mechanism for the polymerization of alpha1-antitrypsin", The Journal of Biological Chemistry, 274 (4): 9548-9555.

Eggenschwiler, R. et al. (2013) "Sustained Knockdown of a Disease-Causing Gene in Patient-Specific Induced Pluripotent Stem Cells Using Lentiviral Vector-Based Gene Therapy", Stem Cells Translational Medicine, 2 (9): 641-654.

Ferrarotti, I. et al. (2020) "Quantification of circulating alpha-1-antitrypsin polymers in dried blood spots", Molecular Pathology and Funct. Genomics, 56, p. 326.

Fujisawa, T. (1959) "Studies on the Utilisation of Safrole as Medicinal Raw Materials XII. Synthesis of Indole Derivatives" Journal of the Pharmaceutical Society of Japan, 79(6): 778-783.

Harkevich, D.A. (2010) Pharmacology/Textbook, 10th edition, pp. 72-82.

International Search Report and Written Opinion from International Application No. PCT/US2025/019485, mailed Jul. 2, 2025 (10 pages).

Jiang, B. et al. (2011) "A multi-component domino reaction for the direct access to polyfunctionalized indolesvia intermolecular allylic esterification and indolation," Chem. Commun., 2012,48,808-810.

Kapetanovic IM. (2008). Computer-aided drug discovery and development (CADDD): in silico-chemico-biological approach. Chem Biol Interact. 30;171(2):165-76.

Kathuria, A. et al. (2011). Substrate specificity of acetoxy derivatives of coumarins and quinolones towards Calreticulin mediated transacetylation: Investigations on antiplatelet function. Bioorganic & Medicinal Chemistry, vol. 20: 1624-1638.

Khusnutdinov, R. et al. (2015), "Quinoline Synthesis by the Reaction of Anilines with 1,2-diols Catalyzed by Iron Compounds," J. Heterocyclic Chem., vol. 53: 1022-1029.

Kummerer, K. (2010) "Pharmaceuticals in the environment", Annual Review of Environment and Resources, 35:57-75.

Kuznetsova, G.A. (2005) "Methodological instructions", Irkutsk State University, Department of General Physics, pp. 2-3.

Laffranchi, M. et al. (2018) "Heteropolymerization of [alpha]-1-antitrypsin mutants in cell models mimicking heterozygosity", Human Molecular Genetics, 27 (10): 1785-1793.

Liu, M. et al. (2016) "Synthesis and Antifungal Activities of Novel Strobilurin Derivatives Containing Quinolin-2(1H)-one Moiety," Chem. Res. Chin. Univ., 32(4): 600-606.

Lyubchanskaya, V. M. et al., Nenitzescu synthesis of derivatives of 5-hydroxybenzofuran and 5- and 6- hydroxyindoles,Khimiko-Farmatsevtichesik Zhurnal, 1992, 26(9-10), 108-112.

Mashkovsky (2001) M.D. Drugs, 14th edition, Moscow, 1:11.

Modi, A. R. et al., "Synthesis of 7-hydroxy-3-alkylisoquinolones and 7-hydroxy-3-alkylisocoumarins from 4-hydroxyhomophthalic acid", Indian Journal of Chemistry, 1979, vol. 17B, No. 4, pp. 360-363.

Stoller, J.K. "Alpha-1 antitrypsin deficiency: An underrecognized, treatable cause of COPD." Cleve Clin J Med 83, No. 7 (2016): 507-14.

U.S. Appl. No. 17/060,945, filed Oct. 1, 2020, by Bozic et al.

U.S. Appl. No. 18/630,559, filed Apr. 9, 2024, by Bozic et al.

Xu, M. et al, Facile Assembly of 11H-Indolo[3,2-c]quinoline by a Two-Step Protocol Involving a Regioselective 6-endo-Cyclization Promoted by the Hendrickson Reagent, Synthesis 2011, No. 4, pp. 0626-0634.

Zorgdrager, J. et al. (1989) "Synthesis of indoles using (N-arylaminomethyl)diphenylphosphine oxides," Recueil des Travaux Chimiques des Pays-Bas, 108 (12): 441-444.

* cited by examiner

7- OR 8-HYDROXY-ISOQUINOLINE AND 7- OR 8-HYDROXY-QUINOLINE DERIVATIVES AS ALPHA-1-ANTITRYPSIN MODULATORS FOR TREATING ALPHA-1-ANTITRYPSIN DEFICIENCY (AATD)

This application claims the benefit of priority of U.S. Provisional Application No. 63/004,683, filed Apr. 3, 2020, the contents of which are incorporated by reference herein in their entirety.

The disclosure provides compounds that are capable of modulating alpha-1 antitrypsin (AAT) activity and methods of treating alpha-1 antitrypsin deficiency (AATD) by administering one or more such compounds.

AATD is a genetic disorder characterized by low circulating levels of AAT. While treatments for AATD exist, there is currently no cure. AAT is produced primarily in liver cells and secreted into the blood, but it is also made by other cell types including lung epithelial cells and certain white blood cells. AAT inhibits several serine proteases secreted by inflammatory cells (most notably neutrophil elastase [NE], proteinase 3, and cathepsin G) and thus protects organs such as the lung from protease-induced damage, especially during periods of inflammation.

The mutation most commonly associated with AATD involves a substitution of lysine for glutamic acid (E342K) in the SERPINA1 gene that encodes the AAT protein. This mutation, known as the Z mutation or the Z allele, leads to misfolding of the translated protein, which is therefore not secreted into the bloodstream and can polymerize within the producing cell. Consequently, circulating AAT levels in individuals homozygous for the Z allele (PiZZ) are markedly reduced; only approximately 15% of mutant Z-AAT protein folds correctly and is secreted by the cell. An additional consequence of the Z mutation is that the secreted Z-AAT has reduced activity compared to wild-type protein, with 40% to 80% of normal antiprotease activity (American thoracic society/European respiratory society, Am J Respir Crit Care Med. 2003; 168(7):818-900; and Ogushi et al. J Clin Invest. 1987; 80(5):1366-74).

The accumulation of polymerized Z-AAT protein within hepatocytes results in a gain-of-function cytotoxicity that can result in cirrhosis or liver cancer later in life and neonatal liver disease in 12% of patients. This accumulation may spontaneously remit but can be fatal in a small number of children. The deficiency of circulating AAT results in unregulated protease activity that degrades lung tissue over time, resulting in emphysema, a form of chronic obstructive pulmonary disease (COPD). This effect is severe in PiZZ individuals and typically manifests in middle age, resulting in a decline in quality of life and shortened lifespan (mean 68 years of age) (Tanash et al. Int J Chron Obstruct Pulm Dis. 2016; 11:1663-9). The effect is more pronounced in PiZZ individuals who smoke, resulting in an even further shortened lifespan (58 years). (Piitulainen and Tanash, COPD 2015; 12(1):36-41). PiZZ individuals account for the majority of those with clinically relevant AATD lung disease. Accordingly, there is a need for additional and effective treatments for AATD.

A milder form of AATD is associated with the SZ genotype in which the Z-allele is combined with an S-allele. The S-allele is associated with somewhat reduced levels of circulating AAT but causes no cytotoxicity in liver cells. The result is clinically significant lung disease but not liver disease. (Fregonese and Stolk, Orphanet J Rare Dis. 2008; 33:16). As with the ZZ genotype, the deficiency of circulating AAT in subjects with the SZ genotype results in unregulated protease activity that degrades lung tissue over time and can result in emphysema, particularly in smokers.

The current standard of care for AAT deficient individuals who have or show signs of developing significant lung or liver disease is augmentation therapy or protein replacement therapy. Augmentation therapy involves administration of a human AAT protein concentrate purified from pooled donor plasma to augment the missing AAT. Although infusions of the plasma protein have been shown to improve survival or slow the rate of emphysema progression, augmentation therapy is often not sufficient under challenging conditions such as during an active lung infection. Similarly, although protein replacement therapy shows promise in delaying progression of disease, augmentation does not restore the normal physiological regulation of AAT in patients and efficacy has been difficult to demonstrate. In addition, augmentation therapy requires weekly visits for treatment and augmentation therapy cannot address liver disease, which is driven by the toxic gain-of-function of the Z-allele. Thus, there is a continuing need for new and more effective treatments for AATD.

One aspect of the disclosure provides compounds of Formulae I, Ia(i)-Ia(vi), Ib(i)-Ib(vi), Ic(i)-Ic(vi), and Id(i)-Id(vi), as well as tautomers of those compounds, deuterated derivatives of those tautomers and compounds, and pharmaceutically acceptable salts of those compounds, tautomers, or deuterated derivatives that can be employed in the treatment of AATD. For example, compounds of Formula I, tautomers thereof, deuterated derivatives of those compounds or tautomers, or pharmaceutically acceptable salts of any of the foregoing, can be depicted as:

Formula I wherein:
$R^1$ and $R^{1'}$ are selected from hydrogen, halogen, —OH, and —NH$_2$, wherein one of $R^1$ and
$R^{1'}$ is —OH or NH$_2$, and other is hydrogen or halogen;
W$_1$ and W$^2$ are each —CR$^x$; wherein R$^x$ is hydrogen or halogen;
X is selected from —C=O, —CR$^2$, N, and —NR$^3$;
Y is selected from —C=O, —CR$^2$, N, and —NR$^3$, wherein
  if X is —C=O, then Y is —NR$^3$,
  if X is —CR$^2$, then Y is N,
  if X is N, then Y is —CR$^2$, and
  if X is —NR$^3$, then Y is —C=O;
(z) is a double bond unless X or Y is C=O, and when X or Y is C=O, then (z) is a single bond;
R$^2$ is selected from —CN, —C(=O)OH, —C(=O)NH$_2$, —C(=O)NHR$_7$, —C(=O)NHCH$_2$R$^7$, —OCH$_2$R$^7$, —NHR$^7$, —NHCH$_2$R$^7$, C$_6$ or C$_{10}$ aryl, 5 to 10-membered heteroaryl, C$_1$-C$_8$ alkyl, C$_3$-C$_8$ cycloalkyl, C$_2$-C$_8$ alkenyl, C$_2$-C$_8$ heteroalkyl, and 3 to 10-membered heterocyclyl,
  wherein the alkyl, heteroalkyl, alkenyl, heterocyclyl, aryl, or heteroaryl of R$^2$ is optionally substituted with 1-3 groups independently selected from halogen, —C(═O)OH, and $C_1$-$C_6$ alkyl, $C_3$-$C_8$ cycloalkyl, $C_6$ or $C_{10}$ aryl, 3 to 10-membered heterocyclyl, and 5 to 10-membered heteroaryl (optionally further substituted with halogen, —OH, —OCH$_3$, —C(═O)OH) and/or $C_3$-$C_6$ cycloalkyl (optionally further substituted with halogen, —OH, —OCH$_3$, and/or —C(═O)OH), and wherein the heteroalkyl of $R^2$ contains 1-3 heteroatoms selected from N, O, and S;

$R^3$ is selected from hydrogen, $C_6$ or $C_{10}$ aryl, $C_1$-$C_8$ alkyl, and $C_3$-$C_8$ cycloalkyl;

wherein $R^3$ is optionally substituted with 1-3 groups independently selected from ═O, —OH, CH$_2$OH, —C(═O)OH, NH$_2$, $C_3$-$C_6$ cycloalkyl (optionally substituted with ═O, —CH$_2$OH, and/or —C(═O) OH), and 3 to 6-membered heterocyclyl (optionally substituted with ═O, —CH$_2$OH, and/or —C(═O) OH), and wherein the heterocyclyl of $R^3$ contains 1-3 nitrogen atoms; and wherein $R^3$ is optionally fused to a $C_3$-$C_6$ cycloalkyl;

$R^4$ is selected from halogen, —NR$^y$R$^y$, $C_1$-$C_6$ alkyl, $C_2$-$C_6$ alkenyl, $C_3$-$C_6$ cycloalkyl, $C_2$-$C_6$ heteroalkyl, 3 to 6-membered heterocyclyl, and 5 or 6-membered heteroaryl, wherein the heteroalkyl, heterocyclyl, or heteroaryl of $R^4$ contains 1-3 atoms selected from N, O, and S;

wherein the alkyl, alkenyl, cycloalkyl, heteroalkyl, heterocyclyl, aryl, and heteroaryl of $R^4$ is optionally substituted with 1-3 groups independently selected from halogen, ═O, —OH, —OCH$_3$, —CH$_3$ and —C(═O)OH; and wherein R$^y$ is independently selected from hydrogen and $C_1$-$C_3$ alkyl;

wherein the $C_1$-$C_3$ alkyl of R$^y$ is optionally substituted with halogen, ═O, —OH, —OCH$_3$, —CH$_3$ and —C(═O)OH;

$R^5$ is selected from halogen, hydrogen, $C_1$-$C_6$ alkyl, $C_6$ or $C_{10}$ aryl, —O(phenyl), 5 or 6-membered heteroaryl, $C_3$-$C_6$ carbocyclyl, and 3 to 6-membered heterocyclyl, wherein the heterocyclyl or heteroaryl contains 1-3 nitrogens and wherein $R^5$ is optionally substituted with (R$^6$)$_n$, wherein n is 1, 2, or 3;

provided that $R^5$ is not imidazolyl;

$R^6$ is each independently selected from from halogen, $C_1$-$C_3$ alkyl, $C_1$-$C_3$ haloalkyl, $C_1$-$C_3$ alkoxy, and $C_1$-$C_3$ haloalkoxy;

$R^7$ is selected from $C_1$-$C_8$ alkyl, $C_3$-$C_8$ cycloalkyl, $C_6$ or $C_{10}$ aryl, $C_2$-$C_8$ heteroalkyl, 3 to 8-membered heterocyclyl, and 5 to 8-membered heteroaryl, wherein $R^7$ is optionally substituted with 1-3 groups independently selected from halogen, ═O, —OH, —OCH$_3$, —CH$_3$, —C(═O)OH, —C(═O)NR$^8$, —CN, —NH$_2$, $C_1$-$C_6$ alkyl (optionally substituted with 1-3 groups selected from ═O, —OH, —CN, —C(═O)OH, and —NH$_2$), $C_3$-$C_6$ cycloalkyl (optionally substituted with 1-3 groups selected from ═O, —OH, —CN, —C(═O)OH, and —NH$_2$), $C_6$ or $C_{10}$ aryl (optionally substituted with 1-3 groups selected from ═O, —OH, —CN, —C(═O)OH, and —NH$_2$), $C_2$-$C_6$ heteroalkyl (optionally substituted with 1-3 groups selected from ═O, —OH, —CN, —C(═O)OH, and —NH$_2$), and 3 to 6-membered heterocyclyl (optionally substituted with 1-3 groups selected from halogen, ═O, OH, CN, COOH, and NH$_2$), 5 or 6-membered heteroaryl (optionally substituted with 1-3 groups selected from ═O, —OH, —CN, —COOH, and —NH$_2$), and wherein the heteroalkyl, heterocyclyl, or heteroaryl of $R^7$ contains 1-3 atoms selected from N, O, and S; and $R^8$ is selected from $C_1$-$C_6$ alkyl, $C_6$ or $C_{10}$ aryl, and wherein $R^8$ is optionally substituted with halogen and/or —OH.

The compounds of Formulae I, Ia(i)-Ia(vi), Ib(i)-Ib(vi), Ic(i)-Ic(vi), and Id(i)-Id(vi) are modulators of AAT activity. In some embodiments, the compounds of Formulae I, Ia(i)-Ia(vi), Ib(i)-Ib(vi), Ic(i)-Ic(vi), and Id(i)-Id(vi), as well as tautomers of those compounds, deuterated derivatives of those tautomers and compounds, and pharmaceutically acceptable salts of those compounds, tautomers, or deuterated derivatives have an $EC_{50}$ of 2.0 μM or less when tested in an AAT Function Assay. In some embodiments, the compounds of Formulae I, Ia(i)-Ia(vi), Ib(i)-Ib(vi), Ic(i)-Ic (vi), and Id(i)-Id(vi), as well as tautomers of those compounds, deuterated derivatives of those tautomers and compounds, and pharmaceutically acceptable salts of those compounds, tautomers, or deuterated derivatives have an $EC_{50}$ of less than 0.5 μM when tested in an AAT Function Assay.

In some embodiments, the compounds of Formulae I, Ia(i)-Ia(vi), Ib(i)-Ib(vi), Ic(i)-Ic(vi), and Id(i)-Id(vi), as well as tautomers of those compounds, deuterated derivatives of those tautomers and compounds, and pharmaceutically acceptable salts of those compounds, tautomers, or deuterated derivatives have an $IC_{50}$ of 5.0 μM or less when tested in a Z-AAT Elastase Activity Assay. In some embodiments, the compounds of Formulae I, Ia(i)-Ia(vi), Ib(i)-Ib(vi), Ic(i)-Ic(vi), and Id(i)-Id(vi), as well as tautomers of those compounds, deuterated derivatives of those tautomers and compounds, and pharmaceutically acceptable salts of those compounds, tautomers, or deuterated derivatives have an $IC_{50}$ of less than 2.0 μM when tested in a Z-AAT Elastase Activity Assay.

In some embodiments, the compounds of Formulae I, Ia(i)-Ia(vi), Ib(i)-Ib(vi), Ic(i)-Ic(vi), and Id(i)-Id(vi), as well as tautomers of those compounds, deuterated derivatives of those tautomers and compounds, and pharmaceutically acceptable salts of those compounds, tautomers, or deuterated derivatives have an $EC_{50}$ of 2.0 μM or less when tested in an AAT Function Assay and have an $IC_{50}$ of 5.0 μM or less when tested in a Z-AAT Elastase Activity Assay. In some embodiments, the compounds of Formulae I, Ia(i)-Ia(vi), Ib(i)-Ib(vi), Ic(i)-Ic(vi), and Id(i)-Id(vi), as well as tautomers of those compounds, deuterated derivatives of those tautomers and compounds, and pharmaceutically acceptable salts of those compounds, tautomers, or deuterated derivatives have an $EC_{50}$ of less than 0.5 μM when tested in an AAT Function Assay and have an $IC_{50}$ of 5.0 μM or less when tested in a Z-AAT Elastase Activity Assay. In some embodiments, the compounds of Formulae I, Ia(i)-Ia(vi), Ib(i)-Ib(vi), Ic(i)-Ic(vi), and Id(i)-Id(vi), as well as tautomers of those compounds, deuterated derivatives of those tautomers and compounds, and pharmaceutically acceptable salts of those compounds, tautomers, or deuterated derivatives have an $EC_{50}$ of 2.0 μM or less when tested in an AAT Function Assay and have an $IC_{50}$ of less than 2.0 μM when tested in a Z-AAT Elastase Activity Assay. In some embodiments, the compounds of Formulae I, Ia(i)-Ia(vi), Ib(i)-Ib (vi), Ic(i)-Ic(vi), and Id(i)-Id(vi), as well as tautomers of those compounds, deuterated derivatives of those tautomers and compounds, and pharmaceutically acceptable salts of those compounds, tautomers, or deuterated derivatives have an $EC_{50}$ of less than 0.5 μM when tested in an AAT Function Assay and have an $IC_{50}$ of less than 2.0 μM when tested in a Z-AAT Elastase Activity Assay.

In some embodiments, the compounds of Formulae I, Ia(i)-Ia(vi), Ib(i)-Ib(vi), Ic(i)-Ic(vi), and Id(i)-Id(vi), as well as tautomers of those compounds, deuterated derivatives of those tautomers and compounds, and pharmaceutically acceptable salts of those compounds, tautomers, or deuterated derivatives are provided for use in the treatment of AATD.

In one aspect of the disclosure, the compounds of Formula I are selected from Compounds 1-361, tautomers of those compounds, deuterated derivatives of those compounds or tautomers, and pharmaceutically acceptable salts of any of the foregoing for use in the treatment of AATD. In some embodiments of the disclosure, the compounds are selected from Compounds 1-361, tautomers of Compounds 1-361, deuterated derivatives of those compounds or tautomers, and pharmaceutically acceptable salts of any of the foregoing for use in the treatment of AATD.

In some embodiments, the disclosure provides pharmaceutical compositions comprising at least one compound selected from compounds of Formulae Ia(i), Ia(ii), Ia(iii), Ia(iv), Ia(v), and Ia(vi) ("Formulae Ia(i)-Ia(vi)"), tautomers of those compounds, deuterated derivatives of those compounds and tautomers, and pharmaceutically acceptable salts of any of the foregoing. In some embodiments, the disclosure provides pharmaceutical compositions comprising at least one compound selected from compounds of Formulae Ib(i), Ib(ii), Ib(iii), Ib(iv), Ib(v) and Ib(vi) ("Formulae Ib(i)-Ib(vi)"), tautomers of those compounds, deuterated derivatives of those compounds and tautomers, and pharmaceutically acceptable salts of any of the foregoing. In some embodiments, the disclosure provides pharmaceutical compositions comprising at least one compound selected from compounds of Formulae Ic(i), Ic(ii), Ic(iii), Ic(iv), Ic(v) and Ic(vi) ("Formulae Ic(i)-Ic(vi)"), tautomers of those compounds, deuterated derivatives of those compounds and tautomers, and pharmaceutically acceptable salts of any of the foregoing. In some embodiments, the disclosure provides pharmaceutical compositions comprising at least one compound selected from compounds of Formulae Id(i), Id(ii), Id(iii), Id(iv), Id(v) and Id(vi) ("Formulae Id(i)-Id(vi)"), tautomers of those compounds, deuterated derivatives of those compounds and tautomers, and pharmaceutically acceptable salts of any of the foregoing. In some embodiments, the pharmaceutical compositions may comprise a compound selected from Compounds 1-361, tautomers of those compounds, deuterated derivatives of those compounds and tautomers, and pharmaceutically acceptable salts of any of the foregoing. These compositions may further include at least one additional active pharmaceutical ingredient and/or at least one carrier.

Another aspect of the disclosure provides methods of treating AATD comprising administering to a subject in need thereof, at least one compound selected from compounds of Formulae I, Ia(i)-Ia(vi), Ib(i)-Ib(vi), Ic(i)-Ic(vi), Id(i)-Id(vi), tautomers of those compounds, deuterated derivatives of those compounds and tautomers, and pharmaceutically acceptable salts of any of the foregoing or a pharmaceutical composition comprising the at least one such compound, tautomer, deuterated derivative, or pharmaceutically acceptable salt. In some embodiments, the methods comprise administering a compound selected from Compounds 1-361, tautomers of those compounds, deuterated derivatives of those compounds and tautomers, and pharmaceutically acceptable salts of any of the foregoing.

In some embodiments, the methods of treatment include administration of at least one additional active agent to the subject in need thereof, either in the same pharmaceutical composition as the at least one compound selected from compounds of Formulae I, Ia(i)-Ia(vi), Ib(i)-Ib(vi), Ic(i)-Ic(vi), Id(i)-Id(vi), tautomers of those compounds, deuterated derivatives of those compounds and tautomers, and pharmaceutically acceptable salts of any of the foregoing, or as separate compositions. In some embodiments, the methods comprise administering a compound selected from Compounds 1-361, tautomers of those compounds, deuterated derivatives of those compounds and tautomers, and pharmaceutically acceptable salts of any of the foregoing with at least one additional active agent either in the same pharmaceutical composition or in a separate composition. In some embodiments, the subject in need of treatment carries the ZZ mutation. In some embodiments, the subject in need of treatment carries the SZ mutation.

In some embodiments, the methods of treatment include administration of at least one additional active agent to the subject in need thereof, either in the same pharmaceutical composition as the at least one compound selected from compounds of Formulae I, Ia(i)-Ia(vi), Ib(i)-Ib(vi), Ic(i)-Ic(vi), Id(i)-Id(vi), tautomers of those compounds, deuterated derivatives of those compounds and tautomers, and pharmaceutically acceptable salts of any of the foregoing, or as separate compositions, wherein the additional active agent is alpha-1 antitrypsin protein (AAT) from the blood plasma of healthy human donors. In some embodiments, the methods comprise administering a compound selected from Compounds 1-361, tautomers of those compounds, deuterated derivatives of those compounds and tautomers, and pharmaceutically acceptable salts of any of the foregoing with at least one additional active agent either in the same pharmaceutical composition or in a separate composition, wherein the additional active agent is alpha-1 antitrypsin protein (AAT) from the blood plasma of healthy human donors.

In some embodiments, the methods of treatment include administration of at least one additional active agent to the subject in need thereof, either in the same pharmaceutical composition as the at least one compound selected from compounds of Formulae I, Ia(i)-Ia(vi), Ib(i)-Ib(vi), Ic(i)-Ic(vi), Id(i)-Id(vi), tautomers of those compounds, deuterated derivatives of those compounds and tautomers, and pharmaceutically acceptable salts of any of the foregoing, or as separate compositions, wherein the additional active agent is recombinant AAT. In some embodiments, the methods comprise administering a compound selected from Compounds 1-361, tautomers of those compounds, deuterated derivatives of those compounds and tautomers, and pharmaceutically acceptable salts of any of the foregoing with at least one additional active agent either in the same pharmaceutical composition or in a separate composition, wherein the additional active agent is recombinant AAT.

Also provided are methods of modulating AAT, comprising administering to a subject in need thereof, at least one compound selected from compounds of Formulae I, Ia(i)-Ia(vi), Ib(i)-Ib(vi), Ic(i)-Ic(vi), Id(i)-Id(vi), tautomers of those compounds, deuterated derivatives of those compounds and tautomers, and pharmaceutically acceptable salts of any of the foregoing or a pharmaceutical composition comprising the at least one compound, tautomer, deuterated derivative, or pharmaceutically acceptable salt. In some embodiments, the methods of modulating AAT comprise administering at least one compound selected from Compounds 1-361, tautomers of those compounds, deuterated derivatives of those compounds and tautomers, and pharmaceutically acceptable salts of any of the foregoing or a pharmaceutical composition comprising the at least one such compound, tautomer, deuterated derivative or pharmaceutically acceptable salt.

Also provided is a compound of Formulae I, Ia(i)-Ia(vi), Ib(i)-Ib(vi), Ic(i)-Ic(vi), or Id(i)-Id(vi), and tautomers of those compounds, deuterated derivatives of those compounds and tautomers, and pharmaceutically acceptable salts of any of the foregoing, for use in therapy. In some embodiments, there is provided a compound selected from Compounds 1-361, tautomers of those compounds, deuterated derivatives of those compounds and tautomers, and pharmaceutically acceptable salts of any of the foregoing, for use in therapy.

Also provided is a pharmaceutical composition comprising a compound of Formulae I, Ia(i)-Ia(vi), Ib(i)-Ib(vi), Ic(i)-Ic(vi), or Id(i)-Id(vi), and tautomers of those compounds, deuterated derivatives of those compounds and tautomers, and pharmaceutically acceptable salts of any of the foregoing, for use in therapy. In some embodiments, there is provided a pharmaceutical composition comprising a compound selected from Compounds 1-361, tautomers of those compounds, deuterated derivatives of those compounds and tautomers, and pharmaceutically acceptable salts of any of the foregoing, for use in therapy.

I. Definitions

The term "AAT" as used herein means alpha-1 antitrypsin or a mutation thereof, including, but not limited to, the AAT gene mutations such as Z mutations. As used herein, "Z-AAT" means AAT mutants which have the Z mutation.

As used herein, "mutations" can refer to mutations in the SERPINA1 gene (the gene encoding AAT) or the effect of alterations in the gene sequence on the AAT protein. A "SERPINA1 gene mutation" refers to a mutation in the SERPINA1 gene, and an "AAT protein mutation" refers to a mutation that results in an alteration in the amino acid sequence of the AAT protein. A genetic defect or mutation, or a change in the nucleotides in a gene in general, results in a mutation in the AAT protein translated from that gene.

As used herein, a patient who is "homozygous" for a particular gene mutation has the same mutation on each allele.

As used herein, a patient who has the PiZZ genotype is a patient who is homozygous for the Z mutation in the AAT protein.

The term "AATD" as used herein means alpha-1 antitrypsin deficiency, which is a genetic disorder characterized by low circulating levels of AAT.

The term "compound," when referring to a compound of this disclosure, refers to a collection of molecules having an identical chemical structure unless otherwise indicated as a collection of stereoisomers (for example, a collection of racemates, a collection of cis/trans stereoisomers, or a collection of (E) and (Z) stereoisomers), except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this disclosure will depend upon a number of factors including the isotopic purity of reagents used to make the compound and the efficiency of incorporation of isotopes in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

Compounds of the disclosure may optionally be substituted with one or more substituents. It will be appreciated that the phrase "optionally substituted" is used interchangeably with the phrase "substituted or unsubstituted." In general, the term "substituted," whether preceded by the term "optionally" or not, refers to the replacement of hydrogen radicals in a given structure with the radical of a specified substituent. Unless otherwise indicated, an "optionally substituted" group may have a substituent at each substitutable position of the group, and when more than one position in any given structure may be substituted with more than one substituent chosen from a specified group, the substituent may be either the same or different at every position. Combinations of substituents envisioned by this disclosure are those that result in the formation of stable or chemically feasible compounds.

The term "isotopologue" refers to a species in which the chemical structure differs from a specific compound of this disclosure only in the isotopic composition thereof. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$ or $^{14}C$ are within the scope of this disclosure.

Unless otherwise indicated, structures depicted herein are also meant to include all isomeric forms of the structure, e.g., racemic mixtures, cis/trans isomers, geometric (or conformational) isomers, such as (Z) and (E) double bond isomers, and (Z) and (E) conformational isomers. Therefore, geometric and conformational mixtures of the present compounds are within the scope of the disclosure. Unless otherwise stated, all tautomeric forms of the compounds of the disclosure are within the scope of the disclosure.

The term "tautomer," as used herein, refers to one of two or more isomers of a compound that exist together in equilibrium, and are readily interchanged by migration of an atom or group within the molecule.

"Stereoisomer" refers to both enantiomers and diastereomers.

As used herein, "deuterated derivative" refers to a compound having the same chemical structure as a reference compound, but with one or more hydrogen atoms replaced by a deuterium atom ("D"). It will be recognized that some variation of natural isotopic abundance occurs in a synthesized compound depending on the origin of chemical materials used in the synthesis. The concentration of naturally abundant stable hydrogen isotopes, notwithstanding this variation is small and immaterial as compared to the degree of stable isotopic substitution of deuterated derivatives described herein. Thus, unless otherwise stated, when a reference is made to a "deuterated derivative" of a compound of the disclosure, at least one hydrogen is replaced with deuterium at well above its natural isotopic abundance (which is typically about 0.015%). In some embodiments, the deuterated derivatives of the disclosure have an isotopic enrichment factor for each deuterium atom, of at least 3500 (52.5% deuterium incorporation at each designated deuterium) at least 4500, (67.5% deuterium incorporation), at least 5000 (75% deuterium incorporation) at least 5500 (82.5% deuterium incorporation), at least 6000 (90% deuterium incorporation), at lease 6333.3 (95% deuterium incorporation, at least 6466.7 (97% deuterium incorporation, or at least 6600 (99% deuterium incorporation).

The term "isotopic enrichment factor" as used herein means the ratio between the isotopic abundance and the natural abundance of a specified isotope.

The term "alkyl" as used herein, means a straight-chain (i.e., linear or unbranched) or branched, substituted or unsubstituted hydrocarbon chain that is completely saturated or may contain one or more units of saturation, without being fully aromatic. Unless otherwise specified, alkyl groups contain 1-12 alkyl carbon atoms. In some embodiments, alkyl groups contain 1-10 aliphatic carbon atoms. In other embodiments, alkyl groups contain 1-8 aliphatic carbon atoms. In still other embodiments, alkyl groups contain 1-6 alkyl carbon atoms, in other embodiments alkyl groups contain 1-4 alkyl carbon atoms, and in yet other embodiments alkyl groups contain 1-3 alkyl carbon atoms and 1-2 alkyl carbon atoms.

The term "heteroalkyl" as used herein, refers to aliphatic groups wherein one or two carbon atoms are independently replaced by one or more of oxygen, sulfur, nitrogen, phosphorus, or silicon. Heteroalkyl groups may be substituted or unsubstituted, branched or unbranched.

The term "alkenyl" as used herein, means a straight-chain (i.e., linear or unbranched), branched, substituted or unsubstituted hydrocarbon chain that contains one or more carbon-to-carbon double bonds.

The terms "cycloalkyl," "cyclic alkyl," "carbocyclyl," and "carbocycle" refer to a fused, spirocyclic, or bridged monocyclic $C_{3-9}$ hydrocarbon or a fused, spirocyclic, or bridged bicyclic or tricyclic, $C_{8-14}$ hydrocarbon that is completely saturated or that contains one or more units of unsaturation, but which is not fully aromatic, wherein any individual ring in said bicyclic ring system has 3-9 members. Typically, a cycloalkyl is completely saturated, while a carbocyclyl may contain one or more units of unsaturation but is not aromatic. In some embodiments, the cycloalkyl or carbocycle group contains 3 to 12 carbon atoms. In some embodiments, the cycloalkyl or carbocycle group contains 3 to 8 carbon atoms. In some embodiments, the cycloalkyl or carbocycle group contains 3 to 6 carbon atoms.

The term "heterocycle," "heterocyclyl," or "heterocyclic" as used herein refers to fused, spirocyclic, or bridged non-aromatic, monocyclic, bicyclic, or tricyclic ring systems in which one or more ring members is a heteroatom. In some embodiments, "heterocycle," "heterocyclyl," or "heterocyclic" group has 3 to 14 ring members in which one or more ring members is a heteroatom independently selected from oxygen, sulfur, nitrogen, phosphorus, or silicon and each ring in the system contains 3 to 9 ring members. In some embodiments, the heterocyclyl contains 3 to 12 ring member atoms. In some embodiments, the heterocyclyl contains 3 to 8 ring member atoms. In some embodiments, the heterocyclyl contains 3 to 6 ring member atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "alkoxy" as used herein, refers to an alkyl group, as previously defined, wherein one carbon of the alkyl group is replaced by an oxygen ("alkoxy") atom, respectively, provided that the oxygen atom is linked between two carbon atoms. A "cyclic alkoxy" refers to a monocyclic, fused, spirocyclic, bicyclic, bridged bicyclic, tricyclic, or bridged tricyclic hydrocarbon that contains at least one alkoxy group, but is not aromatic. Non-limiting examples of cyclic alkoxy groups include tetrahydropyranyl, tetrahydrofuranyl, oxetanyl, 8-oxabicyclo[3.2.1]octanyl, and oxepanyl.

The terms "haloalkyl" and "haloalkoxy" means an alkyl or alkoxy, as the case may be, which is substituted with one or more halogen atoms. The term "halogen" or means F, Cl, Br, or I. In some embodiments, the halogen is selected from F, Cl, and Br. Examples of haloalkyls include —$CHF_2$, —$CH_2F$, —$CF_3$, —$CF_2$—, or perhaloalkyl, such as, —$CF_2CF_3$.

As used herein, "=O" refers to an oxo group.

As used herein, a "cyano" or "nitrile" groups refers to —C≡N.

As used herein, a "hydroxy" group refers to —OH.

As used herein, "aromatic groups" or "aromatic rings" refer to chemical groups that contain conjugated, planar ring systems with delocalized pi electron orbitals comprised of [4n+2] p orbital electrons, wherein n is an integer ranging from 0 to 6. Nonlimiting examples of aromatic groups include aryl and heteroaryl groups.

The term "aryl" refers to monocyclic, bicyclic, and tricyclic ring systems having a total of 5 to 14 ring members, wherein at least one ring in the system is aromatic and wherein each ring in the system contains 3 to 7 ring members. In some embodiments, an aryl contains 6 or 10 carbon atoms. A nonlimiting example of an aryl group is a phenyl ring.

The term "heteroaryl" refers to monocyclic, bicyclic, and tricyclic ring systems having a total of 5 to 10 ring members, wherein at least one ring in the system is aromatic, at least one ring in the system contains one or more heteroatoms, and wherein each ring in the system contains 3 to 7 ring members. In some embodiments, a heteroaryl contains 6 or 10 ring atoms.

Examples of useful protecting groups for nitrogen-containing groups, such as amine groups, include, for example, t-butyl carbamate (Boc), benzyl (Bn), tetrahydropyranyl (THP), 9-fluorenylmethyl carbamate (Fmoc) benzyl carbamate (Cbz), acetamide, trifluoroacetamide, triphenylmethylamine, benzylideneamine, and p-toluenesulfonamide. Methods of adding (a process generally referred to as "protecting") and removing (process generally referred to as "deprotecting") such amine protecting groups are well-known in the art and available, for example, in P. J. Kocienski, Protecting Groups, Thieme, 1994, which is hereby incorporated by reference in its entirety and in Greene and Wuts, *Protective Groups in Organic Synthesis, 3rd Edition* (John Wiley & Sons, New York, 1999).

Examples of suitable solvents that may be used in this disclosure include, but not limited to, water, methanol (MeOH), ethanol (EtOH), dichloromethane or "methylene chloride" ($CH_2Cl_2$), toluene, acetonitrile (MeCN), dimethylformamide (DMF), dimethyl sulfoxide (DMSO), methyl acetate (MeOAc), ethyl acetate (EtOAc), heptanes, isopropyl acetate (IPAc), tert-butyl acetate (t-BuOAc), isopropyl alcohol (IPA), tetrahydrofuran (THF), 2-methyl tetrahydrofuran (2-Me THF), methyl ethyl ketone (MEK), tert-butanol, diethyl ether ($Et_2O$), methyl-tert-butyl ether (MTBE), 1,4-dioxane, and N-methyl pyrrolidone (NMP).

Examples of suitable bases that may be used in this disclosure include, but not limited to, 1,8-diazabicyclo [5.4.0]undec-7-ene (DBU), potassium tert-butoxide (KOtBu), potassium carbonate ($K_2CO_3$), N-methylmorpholine (NMM), triethylamine (Et$_3$N; TEA), diisopropyl-ethyl amine (i-Pr$_2$EtN; DIPEA), pyridine, potassium hydroxide (KOH), sodium hydroxide (NaOH), lithium hydroxide (LiOH) and sodium methoxide (NaOMe; NaOCH$_3$).

The disclosure includes pharmaceutically acceptable salts of the compounds disclosed herein. A salt of a compound is formed between an acid and a basic group of the compound, such as an amino functional group, or a base and an acidic group of the compound, such as a carboxyl functional group.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this disclosure. Suitable pharmaceutically acceptable salts are, for example, those disclosed in S. M. Berge, et al. *J. Pharmaceutical Sciences,* 1977, 66, 1-19.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propane-sulfonate, naphthalene-1-sulfonate, naphthalene-2-sulfonate, mandelate and other salts. In some embodiments, pharmaceutically acceptable acid addition salts include those formed with mineral acids such as hydrochloric acid and hydrobromic acid, and those formed with organic acids such as maleic acid.

Pharmaceutically acceptable salts derived from appropriate bases include alkali metal, alkaline earth metal, ammonium, and N$^+$(C$_{1-4}$alkyl)$_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

The terms "patient" and "subject" are used interchangeably and refer to an animal including a human.

The terms "effective dose," "effective amount," "therapeutically effective dose," and "therapeutically effective amount" are used interchangeably herein and refer to that amount of a compound that produces the desired effect for which it is administered (e.g., improvement in AATD or a symptom of AATD, lessening the severity of AATD or a symptom of AATD, and/or reducing the rate of onset or incidence of AATD or a symptom of AATD). The exact amount of an effective dose will depend on the purpose of the treatment, and will be ascertainable by one skilled in the art using known techniques (see, e.g., Lloyd (1999) The Art, Science and Technology of Pharmaceutical Compounding).

As used herein, the term "treatment and its cognates" (e.g., "treat," "treating) refer to improving AATD or its symptoms in a subject, delaying the onset of AATD or its symptoms in a subject, or lessening the severity of AATD or its symptoms in a subject. "Treatment" and its cognates as used herein, include, but are not limited to the following: improved liver and/or spleen function, lessened jaundice, improved lung function, lessened lung diseases and/or pulmonary exacerbations (e.g., emphysema), lessened skin disease (e.g., necrotizing panniculitis), increased growth in children, improved appetite, and reduced fatigue. Improvements in or lessening the severity of any of these symptoms can be readily assessed according to methods and techniques known in the art or subsequently developed.

The terms "about" and "approximately", when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent. Typically, the term "about" refers to a variation of up to 10%, up to 5%, or up to 2% of a stated value.

Any one or more of the compounds of Formulae I, Ia(i)-Ia(vi), Ib(i)-Ib(vi), Ic(i)-Ic(vi), Id(i)-Id(vi) tautomers of those compounds, deuterated derivatives of those compounds or tautomers, and pharmaceutically acceptable salts of any of the foregoing may be administered once daily, twice daily, or three times daily for the treatment of AATD. In some embodiments, the any one or more compounds are selected from Compounds 1-361, tautomers of those compounds, deuterated derivatives of those compounds or tautomers, and pharmaceutically acceptable salts of any of the foregoing. In some embodiments, at least one compound chosen from compounds of Formulae I, Ia(i)-Ia(vi), Ib(i)-Ib (vi), Ic(i)-Ic(vi), Id(i)-Id(vi), tautomers of those compounds, deuterated derivatives of those compounds or tautomers, and pharmaceutically acceptable salts of any of the foregoing is administered once daily. In some embodiments, a compound selected from Compounds 1-361, tautomers of those compounds, deuterated derivatives of those compounds or tautomers, and pharmaceutically acceptable salts of any of the foregoing is administered once daily. In some embodiments, at least one compound selected from compounds of Formulae I, Ia(i)-Ia(vi), Ib(i)-Ib(vi), Ic(i)-Ic(vi), Id(i)-Id(vi), tautomers of those compounds, deuterated derivatives of those compounds or tautomers, and pharmaceutically acceptable salts of any of the foregoing are administered twice daily. In some embodiments, a compound selected from Compounds 1-361, tautomers of those compounds, deuterated derivatives of those compounds or tautomers, and pharmaceutically acceptable salts of any of the foregoing is administered twice daily. In some embodiments, at least one compound chosen from compounds of Formulae I, Ia(i)-Ia(vi), Ib(i)-Ib (vi), Ic(i)-Ic(vi), Id(i)-Id(vi), tautomers of those compounds, deuterated derivatives of those compounds or tautomers, and pharmaceutically acceptable salts of any of the foregoing are administered three times daily. In some embodiments, a compound selected from Compounds 1-361, tautomers of those compounds, deuterated derivatives of those compounds or tautomers, and pharmaceutically acceptable salts of any of the foregoing is administered three times daily.

Any one or more of the compounds of Formulae I, Ia(i)-Ia(vi), Ib(i)-Ib(vi), Ic(i)-Ic(vi), Id(i)-Id(vi), tautomers of those compounds, deuterated derivatives of those compounds or tautomers, and pharmaceutically acceptable salts of any of the foregoing may be administered in combination with AAT augmentation therapy or AAT replacement therapy for the treatment of AATD. In some embodiments, the any one or more compounds are selected from Compounds 1-361, tautomers of those compounds, deuterated derivatives of those compounds or tautomers, and pharmaceutically acceptable salts of any of the foregoing.

As used herein, "AAT augmentation therapy" refers to the use of alpha-1 antitrypsin protein (AAT) from the blood plasma of healthy human donors to augment (increase) the alpha-1 antitrypsin levels circulating in the blood. "AAT replacement therapy" refers to administration of recombinant AAT.

In some embodiments, 10 mg to 1,500 mg, 100 mg to 1,800 mg, 100 mg to 500 mg, 200 mg to 600 mg, 200 mg to 800 mg, 400 mg to 2,000 mg, 400 mg to 2,500 mg or 400 mg to 600 mg of a compound of Formulae I, Ia(i)-Ia(vi), Ib(i)-Ib(vi), Ic(i)-Ic(vi), Id(i)-Id(vi), tautomers of those compounds, deuterated derivatives of those compounds or tautomers, and pharmaceutically acceptable salts of any of the foregoing is administered once daily, twice daily, or three times daily. In some embodiments, 10 mg to 1,500 mg, 100 mg to 1,800 mg, 100 mg to 500 mg, 200 mg to 600 mg, 200 mg to 800 mg, 400 mg to 2,000 mg, or 400 mg to 600 mg of a compound selected from Compounds 1-361, is administered once daily, twice daily, or three times daily.

One of ordinary skill in the art would recognize that, when an amount of a compound is disclosed, the relevant amount of a pharmaceutically acceptable salt form of the compound is an amount equivalent to the concentration of the free base of the compound. It is noted that the disclosed amounts of the compounds, tautomers, deuterated derivatives, and pharmaceutically acceptable salts are based upon the free base form of the reference compound. For example, "10 mg of at least one compound chosen from compounds of Formula I and pharmaceutically acceptable salts thereof" includes 10 mg of a compound of Formula I and a concentration of a pharmaceutically acceptable salt of compounds of Formula I equivalent to 10 mg of compounds of Formula I.

As used herein, the term "ambient conditions" means room temperature, open air condition and uncontrolled humidity condition.

It should be understood that references herein to methods of treatment (e.g., methods of treating AATD) using one or more compounds (e.g., compounds of Formulae I, Ia(i)-Ia(vi), Ib(i)-Ib(vi), Ic(i)-Ic(vi), or Id(i)-Id(vi)), as well as tautomers of those compounds, deuterated derivatives of those compounds and tautomers, and pharmaceutically acceptable salts of those compounds) should also be interpreted as references to:

one or more compounds (e.g., compounds of Formulae I, Ia(i)-Ia(vi), Ib(i)-Ib(vi), Ic(i)-Ic(vi), or Id(i)-Id(vi)), as well as tautomers of those compounds, deuterated derivatives of those compounds and tautomers, and pharmaceutically acceptable salts of those compounds) for use in methods of treating, e.g., AATD; and/or the use of one or more compounds (e.g., compounds of Formulae I, Ia(i)-Ia(vi), Ib(i)-Ib(vi), Ic(i)-Ic(vi), and Id(i)-Id(vi)), as well as tautomers of those compounds, deuterated derivatives of those compounds and tautomers, and pharmaceutically acceptable salts of those compounds) in the manufacture of a medicament for treating, e.g., AATD.

Example Embodiments

Without limitation, some embodiments of the disclosure include:

1. A compound of Formula I:

a deuterated derivative of a compound of Formula I, and/or a pharmaceutically acceptable salt of any of the foregoing; wherein:

$R^1$ and $R^{1'}$ are selected from hydrogen, halogen, —OH, —O(benzyl), and —NH$_2$, wherein one of $R^1$ and $R^{1'}$ is —OH, —O(benzyl), or NH$_2$, and other is hydrogen or halogen;

$W^1$ and $W^2$ are each —CR$^x$; wherein $R^x$ is hydrogen or halogen;

X is selected from —C=O, —CR$^2$, N, and —NR$^3$;

Y is selected from —C=O, —CR$^2$, N, and —NR$^3$, wherein if X is —C=O, then Y is —NR$^3$, if X is —CR$^2$, then Y is N, if X is N, then Y is —CR$^2$, and if X is —NR$^3$, then Y is —C=O;

(z) is a double bond unless X or Y is C=O, and when X or Y is C=O, then (z) is a single bond;

$R^2$ is selected from —CN, —C(=O)OH, —C(=O)NH$_2$, —C(=O)NHR$_7$, —C(=O)NHCH$_2$R$^7$, —OCH$_2$R$^7$, —NHR$^7$, —NHCH$_2$R$^7$, C$_6$ or C$_{10}$ aryl, 5 to 10-membered heteroaryl, C$_1$-C$_8$ alkyl, C$_3$-C$_8$ cycloalkyl, C$_2$-C$_8$ alkenyl, C$_2$-C$_8$ heteroalkyl, and 3 to 10-membered heterocyclyl, wherein the alkyl, heteroalkyl, alkenyl, heterocyclyl, aryl, or heteroaryl of $R^2$ is optionally substituted with 1-3 groups independently selected from halogen, —C(=O)OH, and C$_1$-C$_6$ alkyl, C$_3$-C$_8$ cycloalkyl, C$_6$ or C$_{10}$ aryl, 3 to 10-membered heterocyclyl, and 5 to 10-membered heteroaryl (optionally further substituted with halogen, —OH, —OCH$_3$, —C(=O)OH) and/or C$_3$-C$_6$ cycloalkyl (optionally further substituted with halogen, —OH, —OCH$_3$, and/or —C(=O)OH), and wherein the heteroalkyl of $R^2$ contains 1-3 heteroatoms selected from N, O, and S;

$R^3$ is selected from hydrogen, C$_6$ or C$_{10}$ aryl, C$_1$-C$_8$ alkyl, and C$_3$-C$_8$ cycloalkyl;

wherein $R^3$ is optionally substituted with 1-3 groups independently selected from $=O$, $-OH$, $-CH_2OH$, $-C(=O)OH$, $NH_2$, $C_3$-$C_6$ cycloalkyl (optionally substituted with $=O$, $-CH_2OH$, and/or $-C(=O)OH$), and 3 to 6-membered heterocyclyl (optionally substituted with $=O$, $-CH_2OH$, and/or $-C(=O)OH$), and wherein the heterocyclyl of $R^3$ contains 1-3 nitrogen atoms; and wherein $R^3$ is optionally fused to a $C_3$-$C_6$ cycloalkyl;

$R^4$ is selected from halogen, $-NR^yR^y$, $C_1$-$C_6$ alkyl, $C_2$-$C_6$ alkenyl, $C_3$-$C_6$ cycloalkyl, $C_2$-$C_6$ heteroalkyl, 3 to 6-membered heterocyclyl, and 5 or 6-membered heteroaryl, wherein the heteroalkyl, heterocyclyl, or heteroaryl of $R^4$ contains 1-3 atoms selected from N, O, and S;

wherein the alkyl, alkenyl, cycloalkyl, heteroalkyl, heterocyclyl, aryl, and heteroaryl of $R^4$ is optionally substituted with 1-3 groups independently selected from halogen, $=O$, $-OH$, $-OCH_3$, $-CH_3$ and $-C(=O)OH$; and wherein $R^y$ is independently selected from hydrogen and $C_1$-$C_3$ alkyl;

wherein the $C_1$-$C_3$ alkyl of $R^y$ is optionally substituted with halogen, $=O$, $-OH$, $-OCH_3$, $-CH_3$ and $-C(=O)OH$;

$R^5$ is selected from halogen, hydrogen, $C_1$-$C_6$ alkyl, $C_6$ or $C_{10}$ aryl, $-O(phenyl)$, 5 or 6-membered heteroaryl, $C_3$-$C_6$ carbocyclyl, and 3 to 6-membered heterocyclyl, wherein the heterocyclyl or heteroaryl contains 1-3 nitrogens and wherein $R^5$ is optionally substituted with $(R^6)_n$, wherein n is 1, 2, or 3;

provided that $R^5$ is not imidazolyl;

$R^6$ is each independently selected from from halogen, $C_1$-$C_3$ alkyl, $C_1$-$C_3$ haloalkyl, $C_1$-$C_3$ alkoxy, and $C_1$-$C_3$ haloalkoxy;

$R^7$ is selected from $C_1$-$C_8$ alkyl, $C_3$-$C_8$ cycloalkyl, $C_6$ or $C_{10}$ aryl, $C_2$-$C_8$ heteroalkyl, 3 to 8-membered heterocyclyl, and 5 to 8-membered heteroaryl, wherein $R^7$ is optionally substituted with 1-3 groups independently selected from halogen, $=O$, $-OH$, $-OCH_3$, $-CH_3$, $-C(=O)OH$, $-C(=O)NR^8$, $-CN$, $-NH_2$, $C_1$-$C_6$ alkyl (optionally substituted with 1-3 groups selected from $=O$, $-OH$, $-CN$, $-C(=O)OH$, and $-NH_2$), $C_3$-$C_6$ cycloalkyl (optionally substituted with 1-3 groups selected from $=O$, $-OH$, $-CN$, $-C(=O)OH$, and $-NH_2$), $C_6$ or $C_{10}$ aryl (optionally substituted with 1-3 groups selected from $=O$, $-OH$, $-CN$, $-C(=O)OH$, and $-NH_2$), $C_2$-$C_6$ heteroalkyl (optionally substituted with 1-3 groups selected from $=O$, $-OH$, $-CN$, $-C(=O)OH$, and $-NH_2$), and 3 to 6-membered heterocyclyl (optionally substituted with 1-3 groups selected from halogen, $=O$, OH, CN, COOH, and $NH_2$), 5 or 6-membered heteroaryl (optionally substituted with 1-3 groups selected from $=O$, $-OH$, $-CN$, $-COOH$, and $-NH_2$), and wherein the heteroalkyl, heterocyclyl, or heteroaryl of $R^7$ contains 1-3 atoms selected from N, O, and S; and $R^8$ is selected from $C_1$-$C_6$ alkyl, $C_6$ or $C_{10}$ aryl, and wherein $R^8$ is optionally substituted with halogen and/or $-OH$.

2. The compound, deuterated derivative, or pharmaceutically acceptable salt of Formula I according to Embodiment 1, selected from compounds of Formulae Ia(i), Ia(ii), Ia(iii), Ia(iv), Ia(v), and Ia(vi):

Ia(i)

Ia(ii)

Ia(iii)

Ia(iv)

Ia(v)

17

-continued

Ia(vi)

and deuterated derivatives of Formulae Ia(i), Ia(ii), Ia(iii), Ia(iv), Ia(v), and Ia(vi), and pharmaceutically acceptable salts of any of the foregoing, wherein $R^{1'}$ is selected from hydrogen and halogen and $R^2$, $R^3$, $R^4$, $R^5$, $R^6$, and n are as defined in Embodiment 1.

3. The compound of Formula I according to Embodiment 1, selected from compounds of Formulae Ib(i), Ib(ii), Ib(iii), Ib(iv), Ib(v), and Ib(vi):

Ib(i)

Ib(ii)

Ib(iii)

Ib(iv)

18

-continued

Ib(v)

Ib(vi)

deuterated derivatives of Formulae Ib(i), Ib(ii), Ib(iii), Ib(iv), Ib(v), and Ib(vi), and pharmaceutically acceptable salts of any of the foregoing, wherein $R^{1'}$ is selected from hydrogen and halogen and $R^2$, $R^3$, $R^4$, $R^5$, $R^6$, and n are as defined in Embodiment 1.

4. The compound of Formula 1 according to Embodiment 1, selected from compounds of Formulae Ic(i), Ic(ii), Ic(iii), Ic(iv), Ic(v), and Ic(vi):

Ic(i)

Ic(ii)

19

-continued

Ic(iii)

Ic(iv)

Ic(v)

Ic(vi)

and deuterated derivatives of Formulae Ic(i), Ic(ii), Ic(iii), Ic(iv), Ic(v), and Ic(vi), and pharmaceutically acceptable salts of any of the foregoing, wherein $R^4$ is selected from hydrogen and halogen and $R^2$, $R^3$, $R^4$, $R^5$, $R^6$, and n are as defined in Embodiment 1.

5. The compound of Formula I according to Embodiment 1, selected from compounds of Formulae Id(i), Id(ii), Id(iii), Id(iv), Id(v), and Id(vi):

Id(i)

Id(ii)

Id(iii)

Id(iv)

Id(v)

Id(vi)

deuterated derivatives of Formulae Id(i), Id(ii), Id(iii), Id(iv), Id(v), and Id(vi), and pharmaceutically acceptable salts of any of the foregoing, wherein $R^1$ is selected from hydrogen and halogen and $R^2$, $R^3$, $R^4$, $R^5$, $R^6$, and n are as defined in Embodiment 1.

6. The compound, deuterated derivative, or pharmaceutically acceptable salt according to Embodiment 1, wherein $R^1$ is —OH.

7. The compound, deuterated derivative, or pharmaceutically acceptable salt according to Embodiment 1, wherein $R^{1'}$ is —OH.

8. The compound, deuterated derivative, or pharmaceutically acceptable salt according to Embodiment 1, wherein $R^1$ is —$NH_2$.

9. The compound, deuterated derivative, or pharmaceutically acceptable salt according to Embodiment 1, wherein $R^{1'}$ is —$NH_2$.

10. The compound, deuterated derivative, or pharmaceutically acceptable salt according to any one of Embodiments 1-9, wherein $R^3$ is selected from: phenyl and $C_3$-$C_8$ cycloalkyl wherein $R^3$ is optionally substituted with 1-2 groups independently selected from =O, —OH, —$CH_2$OH, —C(=O)OH, —$NH_2$, $C_3$-$C_6$ cycloalkyl (optionally further substituted with 1-2 groups independently selected from =O, —$CH_2$OH, and —C(=O)OH), and 3 to 6-membered heterocyclyl (optionally further substituted with 1-3 groups independently selected from =O, —$CH_2$OH, and —C(=O)OH);

wherein the 3 to 6-membered heterocyclyl contains 1-2 nitrogen atoms; and wherein $R^3$ is optionally fused to a $C_3$-$C_6$ cycloalkyl.

11. The compound, deuterated derivative, or pharmaceutically acceptable salt according to any one of Embodiments 1-9, wherein $R^3$ is selected from: $C_1$-$C_6$ alkyl optionally substituted with 1-2 groups independently selected from =O, —OH, —$CH_2$OH, —C(=O)OH, —$NH_2$, $C_3$-$C_6$ cycloalkyl (optionally further substituted with 1-2 groups independently selected from =O, —$CH_2$OH, and —C(=O) OH), and 3 to 6-membered heterocyclyl (optionally further substituted with 1-3 groups independently selected from =O, —$CH_2$OH, and —C(=O)OH), wherein the 3 to 6-membered heterocyclyl contains 1-2 nitrogen atoms; and wherein $R^3$ is optionally fused to a $C_3$-$C_6$ cycloalkyl.

12. The compound, deuterated derivative, or pharmaceutically acceptable salt according to any one of Embodiments 1-9, wherein $R^3$ is selected from $C_4$ cyclic and $C_8$ spirocyclic alkyls optionally substituted with 1-2 groups independently selected from =O, —OH, —$CH_2$OH, —C(=O)OH, and —$NH_2$.

13. The compound, deuterated derivative, or pharmaceutically acceptable salt according to any one of Embodiments 1-9, wherein $R^3$ is selected from:

-continued

14. The compound, deuterated derivative, or pharmaceutically acceptable salt according to any one of Embodiments 1-9, wherein $R^3$ is hydrogen.

15. The compound, deuterated derivative, or pharmaceutically acceptable salt according to any one of Embodiments 1-14, wherein $R^4$ is selected from halogen, —$NR^yR^y$, $C_1$-$C_6$ alkyl, $C_2$-$C_6$ alkenyl, $C_3$-$C_6$ cycloalkyl, $C_3$-$C_6$ heterocyclyl, and 5 or 6-membered heteroaryl, wherein the heterocyclyl or heteroaryl of $R^4$ contains 1-2 atoms selected from N, O, and S;

wherein $R^4$ is optionally substituted with 1-3 groups independently selected from halogen, —OH, —$OCH_3$, and —$CH_3$;

wherein $R^y$ is independently selected from hydrogen and $C_1$-$C_3$ alkyl; and wherein the $C_1$-$C_3$ alkyl of $R^y$ is optionally substituted with —$OCH_3$.

16. The compound, deuterated derivative, or pharmaceutically acceptable salt according to any one of Embodiments 1-15, wherein $R^4$ is selected from halogen, —$NR^yR^y$, $C_1$-$C_6$ alkyl (optionally substituted with 1-3 groups independently selected from halogen, —OH, —$OCH_3$, and —$CH_3$), 5 or 6-membered heterocyclyl (optionally substituted with 1-3 groups independently selected from halogen, —OH, —OCH$_3$, and —CH$_3$), and 5-membered heteroaryl, wherein the heterocyclyl contains 1-2 heteroatoms selected from N, O, and S; and wherein W is C$_1$-C$_2$ alkyl optionally substituted with —OCH$_3$.

17. The compound, deuterated derivative, or pharmaceutically acceptable salt according to any one of Embodiments 1-13, wherein R$^4$ is selected from:

18. The compound, deuterated derivative, or pharmaceutically acceptable salt according to any one of Embodiments 1-17, wherein R$^4$ is 19. The compound, deuterated derivative, or pharmaceutically acceptable salt according to any one of Embodiments 1-17, wherein R$^4$ is 20. The compound, deuterated derivative, or pharmaceutically acceptable salt according to Embodiments 1-19, wherein R$^5$ is selected from C$_6$ or C$_{10}$ aryl, —O(phenyl), 5 or 6-membered heteroaryl, C$_3$-C$_6$ carbocyclyl, and 3 to 6-membered heterocyclyl.

21. The compound, deuterated derivative, or pharmaceutically acceptable salt according to any one of Embodiments 1-20, wherein R$^5$ is selected from phenyl, 5 or 6-membered heteroaryl, C$_3$-C$_6$ carbocyclyl, and 3 to 6-membered heterocyclyl, wherein R$^5$ is optionally substituted with 1 or 2 groups independently selected from halogen and —CH$_3$.

22. The compound, deuterated derivative, or pharmaceutically acceptable salt according to any one of Embodiments 1-21, wherein R$^5$ is selected from: hydrogen, Br, —CH$_3$, 23. The compound, deuterated derivative, or pharmaceutically acceptable salt according to any one of Embodiments 1-22, wherein $R^5$ is selected from:

24. The compound, deuterated derivative, or pharmaceutically acceptable salt according to any one of Embodiments 1-23, wherein $R^2$ is selected from —$OR_7$.

25. The compound, deuterated derivative, or pharmaceutically acceptable salt according to any one of Embodiments 1-23, wherein $R^2$ is selected from —$NHR_7$.

26. The compound, deuterated derivative, or pharmaceutically acceptable salt according to any one of Embodiments 1-23, wherein $R^2$ is selected from —$C(=O)NHR^7$.

27. The compound, deuterated derivative, or pharmaceutically acceptable salt according to any one of Embodiments 1-23, wherein $R^2$ is selected from —$NHCH_2R^7$.

28. The compound, deuterated derivative, or pharmaceutically acceptable salt according to any one of Embodiments 1-23, wherein $R^2$ is selected from —CN, —$C(=O)OH$, —$C(=O)NH_2$, —$C(=O)NHCH_2R^7$, and —$OCH_2R^7$.

29. The compound, deuterated derivative, or pharmaceutically acceptable salt according to any one of Embodiments 24-28, wherein $R^7$ is selected from $C_1$-$C_8$ alkyl and $C_3$-$C_8$ cycloalkyl, each of which is optionally substituted with 1-3 groups independently selected from Br, Cl, F, —$CH_3$, —$C(=O)OH$, =O, —$OCH_3$, and —OH.

30. The compound, deuterated derivative, or pharmaceutically acceptable salt according to any one of Embodiments 24-28, wherein $R^7$ is selected from $C_2$-$C_8$ heteroalkyl and 3 to 8-membered heterocyclyl,
  wherein the heteroalkyl or heterocyclyl contains 1-3 heteroatoms selected from N, O, and S; and
  wherein the heteroalkyl or heterocyclyl is optionally substituted with 1-3 groups independently selected from Br, Cl, F, —$CH_3$, —$C(=O)OH$, =O, —$OCH_3$, and —OH.

31. The compound, deuterated derivative, or pharmaceutically acceptable salt according to any one of Embodiments 24-28, wherein $R^7$ is selected from aryl and 3 to 8-membered heteroaryl,
  wherein the heteroalkyl or heterocyclyl contain 1-3 heteroatoms selected from N, O, and S; and
  wherein the heteroalkyl or heterocyclyl is optionally substituted with 1-3 groups independently selected from Br, Cl, F, —$CH_3$, —$C(=O)OH$, =O, —$OCH_3$, and —OH.

32. The compound, deuterated derivative, or pharmaceutically acceptable salt according to any one of Embodiments 24-28, wherein $R^7$ is selected from $C_1$-$C_8$ alkyl, $C_3$-$C_8$ cycloalkyl, $C_2$-$C_8$ heteroalkyl, 3 to 8-membered heterocyclyl, phenyl, and 5 to 8-membered heteroaryl,
  wherein $R^7$ is optionally substituted with 1-3 groups independently selected from halogen, =O, —$C(=O)$ OH, phenyl, 5 to 8-membered heteroaryl, $C_1$-$C_6$ alkyl (optionally further substituted with 1-3 groups selected from =O, OH, CN, COOH, and $NH_2$), $C_3$-$C_6$ cycloalkyl (optionally further substituted with 1-3 groups selected from =O, —OH, —CN, —COOH, and —$NH_2$), $C_2$-$C_6$ heteroalkyl (optionally further substituted with 1-3 groups selected from halogen, =O, —OH, —CN, —COOH, and —$NH_2$), and 3 to 6-membered heterocyclyl (optionally further substituted with 1-3 groups selected from =O, —OH, —CN, —COOH, and —$NH_2$); and
  wherein the heteroalkyl, heterocyclyl, or heteroaryl of $R^7$ contains 1-3 atoms independently selected from N, O, and S.

33. The compound, deuterated derivative, or pharmaceutically acceptable salt according to any one of Embodiments 1-23, wherein $R^2$ is selected from

27

-continued

28

-continued

29

-continued

30

-continued

-continued

-continued

35. The compound, deuterated derivative, or pharmaceutically acceptable salt according to any one of Embodiments 1-23, wherein $R^2$ is selected from 34. The compound, deuterated derivative, or pharmaceutically acceptable salt according to any one of Embodiments 1-23, wherein $R^2$ is selected from 33
34
-continued
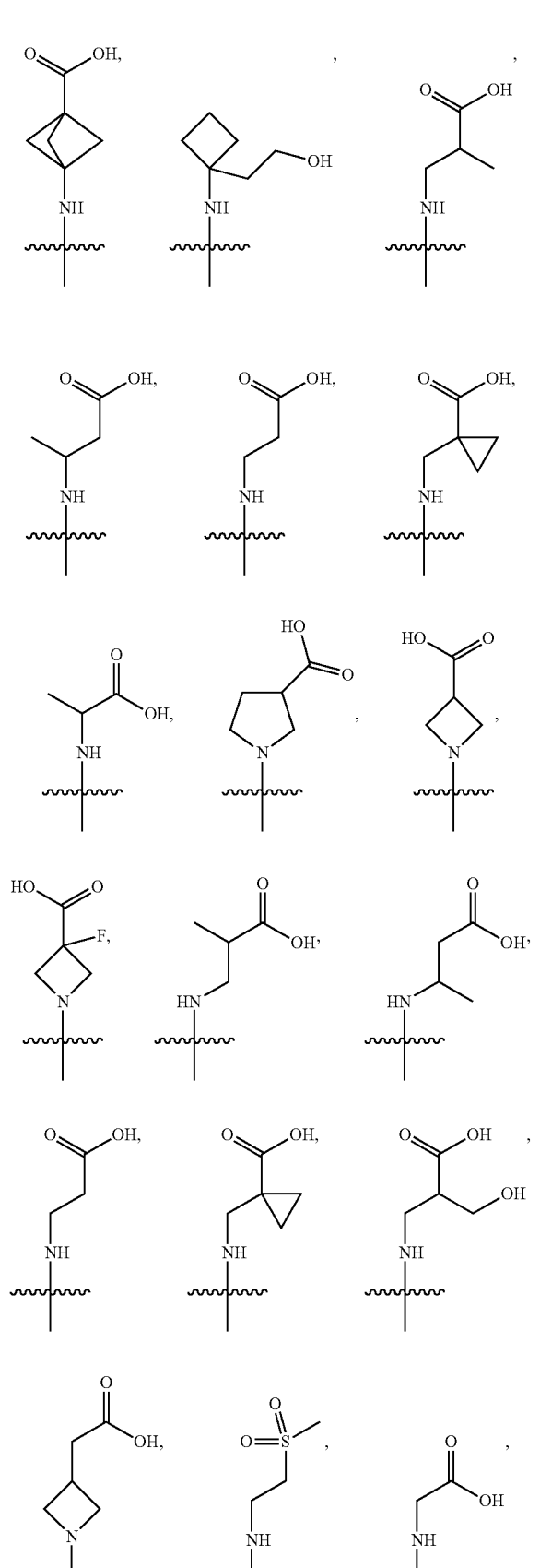
36. The compound, deuterated derivative, or pharmaceutically acceptable salt according to any one of Embodiments 1-23, wherein R² is selected from -continued 37. A compound selected from Compounds 1-361, deuterated derivatives thereof, and pharmaceutically acceptable salts of any of the foregoing.

38. A pharmaceutical composition comprising a compound according to any one of Embodiments 1-37, a deuterated derivative thereof, and/or a pharmaceutically acceptable salt of any of the foregoing, and a pharmaceutically acceptable carrier.

39. A method of treating alpha-1 antitrypsin deficiency comprising administering to a patient in need thereof at least one compound chosen from the compounds, deuterated derivatives, and pharmaceutically acceptable salts of any one of Embodiments 1-37 or a pharmaceutical composition according to Embodiment 38.

40. The method according to Embodiment 39, wherein the patient has a Z mutation in alpha-1 antitrypsin.

41. The method according to Embodiment 39, wherein the patient has an SZ mutation in alpha-1 antitrypsin.

42. The method according to Embodiment 40, wherein the patient is homozygous for Z-mutations in alpha-1 antitrypsin.

43. A method of modulating alpha-1 antitrypsin activity comprising contacting said alpha-1-antitrypsin with at least one compound chosen from the compounds, deuterated derivatives, and pharmaceutically acceptable salts according to any one of Embodiments 1-37 or a pharmaceutical composition according to Embodiment 38.

II. Compounds and Compositions

In some embodiments, a compound of the disclosure is a compound of Formula I:

I a deuterated derivative of a compound of Formula I, and/or a pharmaceutically acceptable salt of any of the foregoing, wherein:

$R^1$ and $R^{1'}$ are selected from hydrogen, halogen, —OH, and —$NH_2$, wherein one of $R^1$ and $R^{1'}$ is —OH or $NH_2$, and other is hydrogen or halogen;

$W^1$ and $W^2$ are each —$CR^x$, wherein $R^x$ is hydrogen or halogen;

X is selected from —C=O, —$CR^2$, N, and —$NR^3$;

Y is selected from —C=O, —$CR^2$, N, and —$NR^3$, wherein if X is —C=O, then Y is —$NR^3$, if X is —$CR^2$, then Y is N, if X is N, then Y is —$CR^2$, and if X is —$NR^3$, then Y is —C=O;

(z) is a double bond unless X or Y is C=O, and when X or Y is C=O, then (z) is a single bond;

$R^2$ is selected from —CN, —C(=O)OH, —C(=O)$NH_2$, —C(=O)$NHR^7$, —C(=O)$NHCH_2R^7$, —$OCH_2R^7$, —$NHR^7$, —$NHCH_2R^7$, $C_6$ or $C_{10}$ aryl, 5 to 10-membered heteroaryl, $C_1$-$C_8$ alkyl, $C_3$-$C_8$ cycloalkyl, $C_2$-$C_8$ alkenyl, $C_2$-$C_8$ heteroalkyl, and 3 to 10-membered heterocyclyl, wherein the alkyl, heteroalkyl, alkenyl, heterocyclyl, aryl, or heteroaryl of $R^2$ is optionally substituted with 1-3 groups independently selected from halogen, —C(=O)OH, and $C_1$-$C_6$ alkyl, $C_3$-$C_8$ cycloalkyl, $C_6$ or $C_{10}$ aryl, 3 to 10-membered heterocyclyl, and 5 to 10-membered heteroaryl (optionally further substituted with halogen, —OH, —$OCH_3$, —C(=O)OH) and/or $C_3$-$C_6$ cycloalkyl (optionally further substituted with halogen, —OH, —$OCH_3$, and/or —C(=O)OH), and wherein the heteroalkyl of $R^2$ contains 1-3 heteroatoms selected from N, O, and S;

$R^3$ is selected from hydrogen, $C_6$ or $C_{10}$ aryl, C1-$C_8$ alkyl, and $C_3$-$C_8$ cycloalkyl;

wherein $R^3$ is optionally substituted with 1-3 groups independently selected from =O, —OH, $CH_2OH$, —C(=O)OH, $NH_2$, $C_3$-$C_6$ cycloalkyl (optionally substituted with =O, —$CH_2OH$, and/or —C(=O)OH), and 3 to 6-membered heterocyclyl (optionally substituted with =O, —$CH_2OH$, and/or —C(=O)OH), and wherein the heterocyclyl of $R^3$ contains 1-3 nitrogen atoms; and wherein $R^3$ is optionally fused to a $C_3$-$C_6$ cycloalkyl;

$R^4$ is selected from halogen, —$NR^yR^y$, $C_1$-$C_6$ alkyl, $C_2$-$C_6$ alkenyl, $C_3$-$C_6$ cycloalkyl, $C_2$-$C_6$ heteroalkyl, 3 to 6-membered heterocyclyl, and 5 or 6-membered heteroaryl, wherein the heteroalkyl, heterocyclyl, or heteroaryl of $R^4$ contains 1-3 atoms selected from N, O, and S;

wherein the alkyl, alkenyl, cycloalkyl, heteroalkyl, heterocyclyl, aryl, and heteroaryl of $R^4$ is optionally substituted with 1-3 groups independently selected from halogen, =O, —OH, —$OCH_3$, —$CH_3$ and —C(=O)OH; and wherein $R^y$ is independently selected from hydrogen and $C_1$-$C_3$ alkyl;

wherein the $C_1$-$C_3$ alkyl of $R^y$ is optionally substituted with halogen, =O, —OH, —$OCH_3$, —$CH_3$ and —C(=O)OH;

$R^5$ is selected from halogen, hydrogen, $C_1$-$C_6$ alkyl, $C_6$ or $C_{10}$ aryl, —O(phenyl), 5 or 6-membered heteroaryl, $C_3$-$C_6$ carbocyclyl, and 3 to 6-membered heterocyclyl, wherein the heterocyclyl or heteroaryl contains 1-3 nitrogens and wherein $R^5$ is optionally substituted with $(R^6)_n$, wherein n is 1, 2, or 3;

provided that $R^5$ is not imidazolyl;

$R^6$ is each independently selected from from halogen, $C_1$-$C_3$ alkyl, $C_1$-$C_3$ haloalkyl, $C_1$-$C_3$ alkoxy, and $C_1$-$C_3$ haloalkoxy;

$R^7$ is selected from $C_1$-$C_8$ alkyl, $C_3$-$C_8$ cycloalkyl, $C_6$ or $C_{10}$ aryl, $C_2$-$C_8$ heteroalkyl, 3 to 8-membered heterocyclyl, and 5 to 8-membered heteroaryl, wherein $R^7$ is optionally substituted with 1-3 groups independently selected from halogen, =O, —OH, —OCH$_3$, —CH$_3$, —C(=O)OH, —C(=O)NR$^8$, —CN, —NH$_2$, $C_1$-$C_6$ alkyl (optionally substituted with 1-3 groups selected from =O, —OH, —CN, —C(=O)OH, and —NH$_2$), $C_3$-$C_6$ cycloalkyl (optionally substituted with 1-3 groups selected from =O, —OH, —CN, —C(=O)OH, and —NH$_2$), $C_6$ or $C_{10}$ aryl (optionally substituted with 1-3 groups selected from =O, —OH, —CN, —C(=O)OH, and —NH$_2$), $C_2$-$C_6$ heteroalkyl (optionally substituted with 1-3 groups selected from =O, —OH, —CN, —C(=O)OH, and —NH$_2$), and 3 to 6-membered heterocyclyl (optionally substituted with 1-3 groups selected from halogen, =O, OH, CN, COOH, and NH$_2$), 5 or 6-membered heteroaryl (optionally substituted with 1-3 groups selected from =O, —OH, —CN, —COOH, and —NH$_2$), and wherein the heteroalkyl, heterocyclyl, or heteroaryl of $R^7$ contains 1-3 atoms selected from N, O, and S; and $R^8$ is selected from $C_1$-$C_6$ alkyl, $C_6$ or $C_{10}$ aryl, and wherein $R^8$ is optionally substituted with halogen and/or —OH.

In some embodiments, the compound, tautomer, deuterated derivative, or pharmaceutically acceptable salt of the disclosure is represented by Formula Ia(i), Formula Ia(ii), Formula Ia(iii), Formula Ia(iv), Formula Ia(v), or Formula Ia(vi):

Ia(i)

Ia(ii)

-continued

Ia(iii)

Ia(iv)

Ia(v)

Ia(vi)

wherein $R^{1'}$ is selected from hydrogen and halogen and $R^2$, $R^3$, $R^4$, $R^5$, $R^6$, and n are as defined for Formula I.

In some embodiments, the compound, tautomer, deuterated derivative, or pharmaceutically acceptable salt of the disclosure is represented by Formula Ib(i), Formula Ib(ii), Formula Ib(iii), Formula Ib(iv), Formula Ib(v), or Formula Ib(vi):

-continued

Ib(i)

Ib(ii)

Ib(iii)

Ib(iv)

Ib(V)

(Ib(vi))

wherein $R^{1'}$ is selected from hydrogen and halogen and $R^2$, $R^3$, $R^4$, $R^5$, $R^6$, and n are as defined for Formula I.

In some embodiments, the compound, tautomer, deuterated derivative, or pharmaceutically acceptable salt of the disclosure is represented by Formula Ic(i), Formula Ic(ii), Formula Ic(iii), Formula Ic(iv), Formula Ic(v), or Formula Ic(vi):

Ic(i)

Ic(ii)

Ic(iii)

Ic(iv)

-continued

Ic(v)

Ic(vi)

wherein $R^1$ is selected from hydrogen and halogen and $R^2$, $R^3$, $R^4$, $R^5$, $R^6$, and n are as defined for Formula I.

In some embodiments, the compound, tautomer, deuterated derivative, or pharmaceutically acceptable salt of the disclosure is represented by Formula Id(i), Formula Id(ii), Formula Id(iii), Formula Id(iv), Formula Id(v), or Formula Id(vi):

Id(i)

Id(ii)

Id(iii)

-continued

Id(iv)

Id(v)

Id(vi)

wherein $R^1$ is selected from hydrogen and halogen and $R^2$, $R^3$, $R^4$, $R^5$, $R^6$, and n are as defined for Formula I.

In some embodiments, in the compound, tautomer, deuterated derivative, or pharmaceutically acceptable salt of the disclosure, $R^1$ is —OH; and all other variables are as defined for Formula I.

Alternatively, in some embodiments, in the compound, tautomer, deuterated derivative, or pharmaceutically acceptable salt of the disclosure, $R^1$ is —NH$_2$; and all other variables are as defined for Formula I.

In some embodiments, in the compound, tautomer, deuterated derivative, or pharmaceutically acceptable salt of the disclosure, $R^{1'}$ is —NH$_2$; and all other variables not specifically defined herein are as defined for Formula I.

In some embodiments, in the compound, tautomer, deuterated derivative, or pharmaceutically acceptable salt of the disclosure, $R^3$ is selected from: phenyl and $C_3$-$C_8$ cycloalkyl, wherein $R^3$ is optionally substituted with 1-2 groups independently selected from =O, —OH, —CH$_2$OH, —C(=O)OH, —NH$_2$, $C_3$-$C_6$ cycloalkyl (optionally further substituted with 1-2 groups independently selected from =O, —CH$_2$OH, and —C(=O)OH)), and 3 to 6-membered heterocyclyl (optionally further substituted with 1-3 groups independently selected from =O, —CH$_2$OH, and —C(=O)OH)), wherein the 3 to 6-membered heterocyclyl contains 1-2 nitrogen atoms; and wherein R$^3$ is optionally fused to a C$_3$-C$_6$ cycloalkyl;
and all other variables are as defined for any one of the preceding embodiments.

In some embodiments, in the compound, tautomer, deuterated derivative, or pharmaceutically acceptable salt of the disclosure, R$^3$ is selected from: C$_1$-C$_6$ alkyl optionally substituted with 1-2 groups independently selected from =O, OH, CH$_2$OH, —C(=O)OH, —NH$_2$, C$_3$-C$_6$ cycloalkyl (optionally further substituted with 1-2 groups independently selected from =O, —CH$_2$OH, and —C(=O)OH)), and 3 to 6-membered heterocyclyl (optionally further substituted with 1-3 groups independently selected from =O, —CH$_2$OH, and —C(=O)OH)), wherein the 3 to 6-membered heterocyclyl contains 1-2 nitrogen atoms; and wherein R$^3$ is optionally fused to a C$_3$-C$_6$ cycloalkyl;
and all other variables are as defined for any one of the preceding embodiments.

In some embodiments, in the compound, tautomer, deuterated derivative, or pharmaceutically acceptable salt of the disclosure, R$^3$ is selected from C$_8$ spiro-cycloalkyls optionally substituted with 1-2 groups independently selected from =O, —OH, —CH$_2$OH, —C(=O)OH, and —NH$_2$; and all other variables are as defined for any one of the preceding embodiments.

In some embodiments, in the compound, tautomer, deuterated derivative, or pharmaceutically acceptable salt of the disclosure, wherein R$^3$ is selected from:

and all other variables are as defined for any one of the preceding embodiments.

In some embodiments, in the compound, tautomer, deuterated derivative, or pharmaceutically acceptable salt of the disclosure, R$^3$ is hydrogen; and all other variables are as defined for any one of the preceding embodiments.

In some embodiments, in the compound, tautomer, deuterated derivative, or pharmaceutically acceptable salt of the disclosure, R$^4$ is selected from halogen, —NR$^y$R$^y$, C$_1$-C$_6$ alkyl, C$_2$-C$_6$ alkenyl, C$_3$-C$_6$ cycloalkyl, C$_3$-C$_6$ heterocyclyl, and 5 or 6-membered heteroaryl, wherein the heterocyclyl or heteroaryl of R$^4$ contains 1-2 atoms selected from N, O, and S;

wherein R$^4$ is optionally substituted with 1-3 groups independently selected from halogen, —OH, —OCH$_3$, and —CH$_3$;

wherein R$^y$ is independently selected from hydrogen and C$_1$-C$_3$ alkyl; and wherein the C$_1$-C$_3$ alkyl of R$^y$ is optionally substituted with —OCH$_3$;

and all other variables are as defined for any one of the preceding embodiments.

In some embodiments, in the compound, tautomer, deuterated derivative, or pharmaceutically acceptable salt of the disclosure, R$^4$ is selected from halogen, —NR$^y$R$^y$, C$_1$-C$_6$ alkyl (optionally substituted with 1-3 groups independently selected from halogen, —OH, —OCH$_3$, and —CH$_3$), 5 or 6-membered heterocyclyl (optionally substituted with 1-3 groups independently selected from halogen, —OH, —OCH$_3$, and —CH$_3$), and 5-membered heteroaryl;

wherein the heterocyclyl contains 1-2 heteroatoms selected from N, O, and S; and wherein W is C$_1$-C$_2$ alkyl optionally substituted with —OCH$_3$;
and all other variables are as defined for any one of the preceding embodiments.

In some embodiments, in the compound, tautomer, deuterated derivative, or pharmaceutically acceptable salt of the disclosure, R$^4$ is selected from:

and all other variables are as defined for any one of the preceding embodiments.

In some embodiments, in the compound, tautomer, deuterated derivative, or pharmaceutically acceptable salt of the disclosure, R$^4$ is and all other variables are as defined for any one of the preceding embodiments.

Alternatively, in some embodiments, in the compound, tautomer, deuterated derivative, or pharmaceutically acceptable salt of the disclosure, R$^4$ is and all other variables are as defined for any one of the preceding embodiments.

In some embodiments, in the compound, tautomer, deuterated derivative, or pharmaceutically acceptable salt of the disclosure, $R^5$ is selected from $C_6$ or $C_{10}$ aryl, —O(phenyl), 5 or 6-membered heteroaryl, $C_3$-$C_6$ carbocyclyl, and 3 to 6-membered heterocyclyl; and all other variables are as defined for any one of the preceding embodiments.

In some embodiments, in the compound, tautomer, deuterated derivative, or pharmaceutically acceptable salt of the disclosure, $R^5$ is selected from phenyl, 5 or 6-membered heteroaryl, $C_3$-$C_6$ carbocyclyl, and $C_3$-$C_6$ heterocyclyl; wherein $R^5$ is optionally substituted with 1 or 2 groups independently selected from halogen and —$CH_3$; and all other variables are as defined for any one of the preceding embodiments.

In some embodiments, in the compound, tautomer, deuterated derivative, or pharmaceutically acceptable salt of the disclosure, $R^5$ is selected from: hydrogen, Br, —$CH_3$, -continued and all other variables are as defined for any one of the preceding embodiments.

In some embodiments, in the compound, tautomer, deuterated derivative, or pharmaceutically acceptable salt of the disclosure, $R^5$ is selected from:

and all other variables are as defined for any one of the preceding embodiments.

In some embodiments, in the compound, tautomer, deuterated derivative, or pharmaceutically acceptable salt of the disclosure, $R^2$ is selected from —$OR^7$; and all other variables are as defined for any one of the preceding embodiments.

Alternatively, in some embodiments, in the compound, tautomer, deuterated derivative, or pharmaceutically acceptable salt of the disclosure, $R^2$ is selected from —$NHR^7$; and all other variables are as defined for any one of the preceding embodiments.

Alternatively, in some embodiments, in the compound, tautomer, deuterated derivative, or pharmaceutically acceptable salt of the disclosure, $R^2$ is selected from —$C(=O)$ $NHR^7$; and all other variables are as defined for any one of the preceding embodiments.

In some embodiments, in the compound, tautomer, deuterated derivative, or pharmaceutically acceptable salt of the disclosure, $R^2$ is selected from $NHCH_2R^7$; and all other variables are as defined for any one of the preceding embodiments.

In some embodiments, in the compound, tautomer, deuterated derivative, or pharmaceutically acceptable salt of the disclosure, $R^2$ is selected from —CN, —$C(=O)OH$, —$C(=O)NH_2$, —$C(=O)NHCH_2R^7$, and —$OCH_2R^7$; and all other variables are as defined for any one of the preceding embodiments.

In some embodiments, in the compound, tautomer, deuterated derivative, or pharmaceutically acceptable salt of the disclosure, $R^7$ is selected from $C_1$-$C_8$ alkyl and $C_3$-$C_8$ cycloalkyl, each of which is optionally substituted with 1-3 groups independently selected from Br, Cl, F, —$CH_3$, —$C(=O)OH$, =O, —$OCH_3$, and —OH; and all other variables are as defined for any one of the preceding embodiments.

Alternatively, in some embodiments, in the compound, tautomer, deuterated derivative, or pharmaceutically acceptable salt of the disclosure, $R^7$ is selected from aryl and 3 to 8-membered heteroaryl,

wherein the heteroalkyl or heterocyclyl contain 1-3 heteroatoms selected from N, O, and S, and wherein the heteroalkyl or heterocyclyl is optionally substituted with 1-3 groups independently selected from Br, Cl, F, —CH$_3$, —C(=O)OH, =O, —OCH$_3$, and —OH;

and all other variables are as defined for any one of the preceding embodiments.

Alternatively, in some embodiments, in the compound, tautomer, deuterated derivative, or pharmaceutically acceptable salt of the disclosure, R$^7$ is selected from C$_1$-C$_8$ alkyl, C$_3$-C$_8$ cycloalkyl, C$_2$-C$_8$ heteroalkyl, 3 to 8-membered heterocyclyl, phenyl, and 5 to 8-membered heteroaryl, wherein R$^7$ is optionally substituted with 1-3 groups independently selected from halogen, =O, —C(=O) OH, phenyl, 5 to 8-membered heteroaryl, C$_1$-C$_6$ alkyl (optionally further substituted with 1-3 groups selected from =O, OH, CN, COOH, and NH$_2$), C$_3$-C$_6$ cycloalkyl (optionally further substituted with 1-3 groups selected from =O, —OH, —CN, —COOH, and —NH$_2$), C$_2$-C$_6$ heteroalkyl (optionally further substituted with 1-3 groups selected from halogen, =O, —OH, —CN, —COOH, and —NH$_2$), and 3 to 6-membered heterocyclyl (optionally further substituted with 1-3 groups selected from =O, —OH, —CN, —COOH, and —NH$_2$), wherein the heteroalkyl, heterocyclyl, or heteroaryl of R$^7$ contains 1-3 atoms independently selected from N, O, and S, and all other variables are as defined for any one of the preceding embodiments.

In some embodiments, in the compound, tautomer, deuterated derivative, or pharmaceutically acceptable salt of the disclosure, R$^2$ is selected from:

49

50

51

52

-continued

-continued and all other variables are as defined for any one of the preceding embodiments.

In some embodiments, in the compound, tautomer, deuterated derivative, or pharmaceutically acceptable salt of the disclosure, wherein $R^2$ is selected from:

55

-continued

56

-continued and all other variables are as defined for any one of the preceding embodiments.

In some embodiments, in the compound, tautomer, deuterated derivative, or pharmaceutically acceptable salt of the disclosure, $R^2$ is selected from:

57

-continued

58

60 and all other variables are as defined for any one of the preceding embodiments.

In some embodiments, in the compound, tautomer, deuterated derivative, or pharmaceutically acceptable salt of the disclosure, $R^2$ is selected from:

59

60

61

-continued and all other variables are as defined for any one of the preceding embodiments.

In some embodiments, the compound, tautomer, deuterated derivative, or pharmaceutically acceptable salt of the disclosure is selected from Compounds 1-361 (as shown in Table A) tautomers of those compounds, deuterated derivatives of those compounds and tautomers, and pharmaceutically acceptable salts of any of the foregoing.

TABLE A

| Compounds 1-361 |
| --- |

1

2

62

TABLE A-continued

| Compounds 1-361 |
| --- |

3

4

5

6

63

TABLE A-continued

Compounds 1-361

64

TABLE A-continued

Compounds 1-361

7

11

8

12

9

13

10

14

65

Compounds 1-361

15

16

17

66

Compounds 1-361

18

19

20

67

68

TABLE A-continued

TABLE A-continued

Compounds 1-361

Compounds 1-361

21

24

22

25

23

26

TABLE A-continued

Compounds 1-361

TABLE A-continued

Compounds 1-361

27

28

29

30

31

32

33

34

71

TABLE A-continued

Compounds 1-361

35

36

37

38

72

TABLE A-continued

Compounds 1-361

39

40

41

42

73

TABLE A-continued

Compounds 1-361

74

TABLE A-continued

Compounds 1-361

43

44

45

46

47

48

49

75

76

Compounds 1-361

50

53

51

54

52

55

TABLE A-continued

Compounds 1-361

56

57

58

TABLE A-continued

Compounds 1-361

59

60

61

62

TABLE A-continued

Compounds 1-361

TABLE A-continued

Compounds 1-361

63

64

65

66

67

68

69

70

81

TABLE A-continued

Compounds 1-361

71

72

73

74

82

TABLE A-continued

Compounds 1-361

75

76

77

78

83

TABLE A-continued

Compounds 1-361

79

80

81

82

84

TABLE A-continued

Compounds 1-361

83

84

85

85

86

Compounds 1-361

86

87

88

89

90

91

92

93

TABLE A-continued

Compounds 1-361

94

95

96

97

TABLE A-continued

Compounds 1-361

98

99

100

101

89

Compounds 1-361

102

103

104

105

90

Compounds 1-361

106

107

108

109

91

TABLE A-continued

Compounds 1-361

110

111

112

113

92

TABLE A-continued

Compounds 1-361

114

115

116

117

TABLE A-continued

Compounds 1-361

118

TABLE A-continued

Compounds 1-361

121

119

122

120

123

95

Compounds 1-361

124

125

126

96

Compounds 1-361

127

128

129

TABLE A-continued

Compounds 1-361

130

131

132

TABLE A-continued

Compounds 1-361

133

134

135

TABLE A-continued

Compounds 1-361

136

137

138

139

TABLE A-continued

Compounds 1-361

140

141

142

143

101

TABLE A-continued

Compounds 1-361

144

145

146

102

TABLE A-continued

Compounds 1-361

147

148

149

103

TABLE A-continued

Compounds 1-361

150

151

152

104

TABLE A-continued

Compounds 1-361

153

154

155

105

Compounds 1-361

156

157

158

159

106

Compounds 1-361

160

161

162

163

107

108

TABLE A-continued

Compounds 1-361

TABLE A-continued

Compounds 1-361

164

165

166

167

168

169

170

171

109

110

172

173

174

175

176

177

178

111

Compounds 1-361

179

180

181

112

Compounds 1-361

182

183

184

113

TABLE A-continued

Compounds 1-361

185

186

187

188

114

TABLE A-continued

Compounds 1-361

189

190

191

192

115

116

Compounds 1-361

193

194

195

196

197

198

199

200

117

118

Compounds 1-361

201

202

203

204

205

206

207

208

119

TABLE A-continued

Compounds 1-361

120

TABLE A-continued

Compounds 1-361

209

210

211

212

213

214

215

216

121

Compounds 1-361

217

218

219

122

Compounds 1-361

220

221

222

123

TABLE A-continued

Compounds 1-361

223

224

225

226

124

TABLE A-continued

Compounds 1-361

227

228

229

230

125

Compounds 1-361

231

232

233

234

126

Compounds 1-361

235

236

237

238

127

128

TABLE A-continued

TABLE A-continued

Compounds 1-361

Compounds 1-361

239

243

240

244

241

245

242

246

129 130

Compounds 1-361

247

248

249

250

Compounds 1-361

251

252

253

254

131

132

Compounds 1-361

Compounds 1-361

255

256

257

258

259

260

261

262

133

Compounds 1-361

263

264

265

266

134

Compounds 1-361

267

268

269

270

135

Compounds 1-361

271

272

273

274

136

Compounds 1-361

275

276

277

278

137

Compounds 1-361

138

Compounds 1-361

279

280

281

282

283

284

285

286

139

Compounds 1-361

287

288

289

290

291

140

Compounds 1-361

292

293

294

295

296

141

TABLE A-continued

Compounds 1-361

297

298

299

300

142

TABLE A-continued

Compounds 1-361

301

302

303

304

143

TABLE A-continued

Compounds 1-361

144

TABLE A-continued

Compounds 1-361

305

306

307

308

309

310

311

312

313

145

146

TABLE A-continued

TABLE A-continued

Compounds 1-361

Compounds 1-361

314

318

315

319

316

320

317

321

147

TABLE A-continued

Compounds 1-361

322

323

324

325

148

TABLE A-continued

Compounds 1-361

326

327

328

329

330

| 149 | 150 |
|---|---|
| TABLE A-continued | TABLE A-continued |
| Compounds 1-361 | Compounds 1-361 |

331

332

333

334

335

336

337

151

Compounds 1-361

338

339

340

152

Compounds 1-361

341

342

343

153

Compounds 1-361

344

345

346

154

Compounds 1-361

347

348

349

TABLE A-continued

Compounds 1-361

350

351

352

TABLE A-continued

Compounds 1-361

353

354

355

356

TABLE A-continued

Compounds 1-361

357

358

359

360

TABLE A-continued

Compounds 1-361

361

Some embodiments of the disclosure include derivatives of Compounds 1-361 or compounds of Formulae I, Ia(i)-Ia (vi), Ib(i)-Ib(vi), Ic(i)-Ic(vi), Id(i)-Id(vi) or tautomers thereof. In some embodiments, the derivatives are silicon derivatives in which at least one carbon atom in a compound selected from Compounds 1-361 or compounds of Formulae I, Ia(i)-Ia(vi), Ib(i)-Ib(vi), Ic(i)-Ic(vi), Id(i)-Id(vi) has been replaced by silicon. In some embodiments, the derivatives are boron derivatives, in which at least one carbon atom in a compound selected from Compounds 1-361 or compounds of Formulae I, Ia(i)-Ia(vi), Ib(i)-Ib(vi), Ic(i)-Ic(vi), Id(i)-Id (vi) or tautomers thereof has been replaced by boron. In other embodiments, the derivatives are phosphate derivatives, in which at least one carbon atom in a compound selected from Compounds 1-361 or compounds of Formulae I, Ia(i)-Ia(vi), Ib(i)-Ib(vi), Ic(i)-Ic(vi), Id(i)-Id(vi) or tautomers thereof has been replaced by phosphorus. Because the general properties of silicon, boron, and phosphorus are similar to those of carbon, replacement of carbon by silicon, boron, or phosphorus can result in compounds with similar biological activity to a carbon containing original compound.

In some embodiments, the derivative is a silicon derivative in which one carbon atom in a compound selected from Compounds 1-361 or compounds of Formulae I, Ia(i)-Ia(vi), Ib(i)-Ib(vi), Ic(i)-Ic(vi), Id(i)-Id(vi) and tautomers thereof has been replaced by silicon. In other embodiments, two carbon atoms have been replaced by silicon. The carbon replaced by silicon may be a non-aromatic carbon. In some embodiments a quaternary carbon atom of a tert-butyl moiety, may be replaced by silicon. In some embodiments, the silicon derivatives of the disclosure may include one or more hydrogen atoms replaced by deuterium. For example, one or more hydrogens of a tert-butyl moiety in which the carbon has been replaced by silicon, may be replaced by deuterium. In other embodiments, a silicon derivative of a compound selected from Compounds 1-361 or compounds of Formulae I, Ia(i)-Ia(vi), Ib(i)-Ib(vi), Ic(i)-Ic(vi), Id(i)-Id (vi) and tautomers thereof may have silicon incorporated into a heterocycle ring.

Another aspect of the disclosure provides pharmaceutical compositions comprising a compound selected from compounds according to any of Formulae I, Ia(i)-Ia(vi), Ib(i)-Ib(vi), Ic(i)-Ic(vi), Id(i)-Id(vi), Compounds 1-361, tautomers of those compounds, deuterated derivatives of those compounds and tautomers, and pharmaceutically acceptable salts of any of the foregoing. In some embodiments, the pharmaceutical composition comprising at least one compound chosen from Formulae I, Ia(i)-Ia(vi), Ib(i)-Ib(vi), Ic(i)-Ic(vi), Id(i)-Id(vi) and Compounds 1-361, tautomers of those compounds, deuterated derivatives of those compounds and tautomers, and pharmaceutically acceptable salts of any of the foregoing is administered to a patient in need thereof.

A pharmaceutical composition may further comprise at least one pharmaceutically acceptable carrier. In some embodiments, the at least one pharmaceutically acceptable carrier is chosen from pharmaceutically acceptable vehicles and pharmaceutically acceptable adjuvants. In some embodiments, the at least one pharmaceutically acceptable is chosen from pharmaceutically acceptable fillers, disintegrants, surfactants, binders, lubricants.

It will also be appreciated that a pharmaceutical composition of this disclosure can be employed in combination therapies; that is, the pharmaceutical compositions described herein can further include at least one other active agent. Alternatively, a pharmaceutical composition comprising at least one compound of Formulae I, Ia(i)-Ia(vi), Ib(i)-Ib(vi), Ic(i)-Ic(vi), Id(i)-Id(vi), tautomers of those compounds, deuterated derivatives of those compounds and tautomers, and pharmaceutically acceptable salts of any of the foregoing can be administered as a separate composition concurrently with, prior to, or subsequent to, a composition comprising at least one additional active agent. In some embodiments, a pharmaceutical composition comprising at least one compound selected from Compounds 1-361 tautomers of those compounds, deuterated derivatives of those compounds and tautomers, and pharmaceutically acceptable salts of any of the foregoing can be administered as a separate composition concurrently with, prior to, or subsequent to, a composition comprising at least one additional active agent.

In some embodiments, a compound of Formula I, Ia(i)-Ia(vi), Ib(i)-Ib(vi), Ic(i)-Ic(vi), or Id(i)-Id(vi), tautomers of those compounds, deuterated derivatives of those compounds and tautomers, and pharmaceutically acceptable salts of any of the foregoing, is combined with at least one additional active agent for simultaneous, separate, or sequential use in the treatment of AATD. In some embodiments, when the use is simultaneous, the compound of Formula I, Ia(i)-Ia(vi), Ib(i)-Ib(vi), Ic(i)-Ic(vi), or Id(i)-Id(vi), tautomers of those compounds, deuterated derivatives of those compounds and tautomers, and pharmaceutically acceptable salts of any of the foregoing, and the at least one additional active agent are in separate pharmaceutical compositons. In some embodiments, when the use is simultaneous, the compound of Formula I, Ia(i)-Ia(vi), Ib(i)-Ib(vi), Ic(i)-Ic(vi), or Id(i)-Id(vi), tautomers of those compounds, deuterated derivatives of those compounds and tautomers, and pharmaceutically acceptable salts of any of the foregoing, and the at least one additional active agent are together in the same pharmaceutical composition. In some embodiments, the compound is a compound selected from Compounds 1-361, tautomers of those compounds, deuterated derivatives of those compounds and tautomers, and pharmaceutically acceptable salts of any of the foregoing.

In some embodiments, a compound of Formula I, Ia(i)-Ia(vi), Ib(i)-Ib(vi), Ic(i)-Ic(vi), or Id(i)-Id(vi), tautomers of those compounds, deuterated derivatives of those compounds and tautomers, and pharmaceutically acceptable salts of any of the foregoing, is provided for use in a method of treating AATD, wherein the method comprises co-administering the compound and an additional active agent. In some embodiments, the compound and the additional active agent are co-administered in the same pharmaceutical composition. In some embodiments, the compound and the additional active agent are co-administered in separate pharmaceutical compositions. In some embodiments, the compound and the additional active agent are co-administered simultaneously. In some embodiments, the compound and the additional active agent are co-administered sequentially. In some embodiments, the compound is selected from Compounds 1-361, tautomers of those compounds, deuterated derivatives of those compounds and tautomers, and pharmaceutically acceptable salts of any of the foregoing.

In some embodiments, a combination of a compound of Formula I, Ia(i)-Ia(vi), Ib(i)-Ib(vi), Ic(i)-Ic(vi), or Id(i)-Id(vi), tautomers of those compounds, deuterated derivatives of those compounds and tautomers, and pharmaceutically acceptable salts of any of the foregoing, and an additional active agent, is provided for use in a method of treating AATD. In some embodiments, the compound and the additional active agent are co-administered in the same pharmaceutical composition. In some embodiments, the compound and the additional active agent are co-administered in separate pharmaceutical compositions. In some embodiments, the compound and the additional active agent are co-administered simultaneously. In some embodiments, the compound and the additional active agent are co-administered sequentially. In some embodiments, the compound is selected from Compounds 1-361, tautomers of those compounds, deuterated derivatives of those compounds and tautomers, and pharmaceutically acceptable salts of any of the foregoing.

In some embodiments, an additional active agent is provided for use in a method of treating AATD, wherein the method comprises co-administrating the additional active agent and a compound of Formula I, Ia(i)-Ia(vi), Ib(i)-Ib(vi), Ic(i)-Ic(vi), or Id(i)-Id(vi), tautomers of those compounds, deuterated derivatives of those compounds and tautomers, and pharmaceutically acceptable salts of any of the foregoing. In some embodiments, the compound and the additional active agent are co-administered in the same pharmaceutical composition. In some embodiments, the compound and the additional active agent are co-administered in separate pharmaceutical compositions. In some embodiments, the compound and the additional active agent are co-administered simultaneously. In some embodiments, the compound and the additional active agent are co-administered sequentially. In some embodiments, the compound is selected from Compounds 1-361, tautomers of those compounds, deuterated derivatives of those compounds and tautomers, and pharmaceutically acceptable salts of any of the foregoing.

In some embodiments, a compound of Formula I, Ia(i)-Ia(vi), Ib(i)-Ib(vi), Ic(i)-Ic(vi), or Id(i)-Id(vi), tautomers of those compounds, deuterated derivatives of those compounds and tautomers, and pharmaceutically acceptable salts of any of the foregoing, is provided for use in a method of treating AATD, wherein the compound is prepared for administration in combination with an additional active agent. In some embodiments, the compound and the additional active agent are prepared for administration in the same pharmaceutical composition. In some embodiments, the compound and the additional active agent are prepared for administration in separate pharmaceutical compositions. In some embodiments, the compound and the additional active agent are prepared for simultaneous administration. In some embodiments, the compound and the additional active agent are prepared for sequential administration. In some embodiments, the compound is selected from Compounds 1-361, tautomers of those compounds, deuterated derivatives of those compounds and tautomers, and pharmaceutically acceptable salts of any of the foregoing.

In some embodiments, a combination of a compound of Formula I, Ia(i)-Ia(vi), Ib(i)-Ib(vi), Ic(i)-Ic(vi), or Id(i)-Id(vi), tautomers of those compounds, deuterated derivatives of those compounds and tautomers, and pharmaceutically acceptable salts of any of the foregoing, and an additional active agent, is provided for use in a method of treating AATD. In some embodiments, the compound and the additional active agent are prepared for administration in the same pharmaceutical composition. In some embodiments, the compound and the additional active agent are prepared for administration in separate pharmaceutical compositions. In some embodiments, the compound and the additional active agent are prepared for simultaneous administration. In some embodiments, the compound and the additional active agent are prepared for sequential administration. In some embodiments, the compound is selected from Compounds 1-361, tautomers of those compounds, deuterated derivatives of those compounds and tautomers, and pharmaceutically acceptable salts of any of the foregoing.

In some embodiments, an additional active agent is provided for use in a method of treating AATD, wherein the additional active agent is prepared for administration in combination with a compound of Formula I, Ia(i)-Ia(vi), Ib(i)-Ib(vi), Ic(i)-Ic(vi), or Id(i)-Id(vi), tautomers of those compounds, deuterated derivatives of those compounds and tautomers, and pharmaceutically acceptable salts of any of the foregoing. In some embodiments, the compound and the additional active agent are prepared for administration in the same pharmaceutical composition. In some embodiments, the compound and the additional active agent are prepared for administration in separate pharmaceutical compositions. In some embodiments, the compound and the additional active agent are prepared for simultaneous administration. In some embodiments, the compound and the additional active agent are prepared for sequential administration. In some embodiments, the compound is selected from Compounds 1-361, tautomers of those compounds, deuterated derivatives of those compounds and tautomers, and pharmaceutically acceptable salts of any of the foregoing.

In some embodiments, the additional active agent is selected the group consisting of alpha-1 antitrypsin protein (AAT) from the blood plasma of healthy human donors and recombinant AAT. In some embodiments, the additional active agent is alpha-1 antitrypsin protein (AAT) from the blood plasma of healthy human donors. In some embodiments, the additional active agent is alpha-1 antitrypsin protein (AAT) from the blood plasma of healthy human donors.

As described above, pharmaceutical compositions disclosed herein may optionally further comprise at least one pharmaceutically acceptable carrier. The at least one pharmaceutically acceptable carrier may be chosen from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. Remington: *The Science and Practice of Pharmacy,* 21st edition, 2005, ed. D. B. Troy, Lippincott Williams & Wilkins, Philadelphia, and *Encyclopedia of Pharmaceutical Technology,* eds. J. Swarbrick and J. C. Boylan, 1988-1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as human serum albumin), buffer substances (such as phosphates, glycine, sorbic acid, and potassium sorbate), partial glyceride mixtures of saturated vegetable fatty acids, water, salts, and electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as lactose, glucose and sucrose), starches (such as corn starch and potato starch), cellulose and its derivatives (such as sodium carboxymethyl cellulose, ethyl cellulose and cellulose acetate), powdered tragacanth, malt, gelatin, talc, excipients (such as cocoa butter and suppository waxes), oils (such as peanut oil, cottonseed oil, safflower oil, sesame oil, olive oil, corn oil and soybean oil), glycols (such as propylene glycol and polyethylene glycol), esters (such as ethyl oleate and ethyl laurate), agar, buffering agents (such as magnesium hydroxide and aluminum hydroxide), alginic acid, pyrogen-free water, isotonic saline, Ringer's solution, ethyl alcohol, phosphate buffer solutions, non-toxic compatible lubricants (such as sodium lauryl sulfate and magnesium stearate), coloring agents, releasing agents, coating agents, sweetening agents, flavoring agents, perfuming agents, preservatives, and antioxidants.

In another aspect of the disclosure, the compounds and the pharmaceutical compositions, described herein, are used to treat AATD. In some embodiments, the subject in need of treatment with the compounds and compositions of the disclosure carries the ZZ mutation. In some embodiments, the subject in need of treatment with the compounds and compositions of the disclosure carries the SZ mutation.

In some embodiments, the methods of the disclosure comprise administering to a patient in need thereof, a compound chosen from any of the compounds of Formulae I, Ia(i)-Ia(vi), Ib(i)-Ib(vi), Ic(i)-Ic(vi), Id(i)-Id(vi), tautomers of those compounds, deuterated derivatives of those compounds and tautomers, and pharmaceutically acceptable salts of any of the foregoing. In some embodiments, the compound of Formula (I) is selected from Compounds 1-361, tautomers of those compounds, deuterated derivatives of those compounds and tautomers, and pharmaceutically acceptable salts of any of the foregoing. In some embodiments, said patient in need thereof has a Z mutation in the alpha-1 antitrypsin gene. In some embodiments said patient in need thereof is homozygous for the Z-mutation in the alpha-1 antitrypsin gene.

Another aspect of the disclosure provides methods of modulating alpha-1 antitrypsin activity comprising the step of contacting said alpha-1-antitrypsin with at least one compound of Formulae I, Ia(i)-Ia(vi), Ib(i)-Ib(vi), Ic(i)-Ic (vi), or Id(i)-Id(vi), tautomers of those compounds, deuterated derivatives of those compounds and tautomers, and pharmaceutically acceptable salts of any of the foregoing. In some embodiments, the methods of modulating alpha-1 antitrypsin activity comprising the step of contacting said alpha-1-antitrypsin with at least one compound selected from Compounds 1-361, tautomers of those compounds, deuterated derivatives of those compounds and tautomers, and pharmaceutically acceptable salts of any of the foregoing.

In some embodiments, the methods of modulating alpha-1 antitrypsin activity take place in vivo. In some embodiments, the methods of modulating alpha-1 antitrypsin activity take place ex vivo and said alpha-1-antitrypsin is from a biological sample obtained from a human subject. In some embodiments, the methods of modulating AAT take place in vitro and said alpha-1-antitrypsin is from a biological sample obtained from a human subject. In some embodiments, the biological sample is a blood sample. In some embodiments, the biological sample is a sample taken from a liver biopsy.

III. Preparation of Compounds

All the generic, subgeneric, and specific compound formulae disclosed herein are considered part of the disclosure.
A. Compounds of Formula I
The compounds of the disclosure may be made according to standard chemical practices or as described herein. Throughout the following synthetic schemes and in the descriptions for preparing compounds of Formulae I, Ia(i)-

Ia(vi), Ib(i)-Ib(vi), Ic(i)-Ic(vi), Id(i)-Id(vi), Compounds 1-361, tautomers of those compounds, deuterated derivatives of those compounds and tautomers, and pharmaceutically acceptable salts of any of the foregoing, the following abbreviations are used:

Abbreviations

BrettPhos Pd G4=dicyclohexyl-[3,6-dimethoxy-2-[2,4,6-tri(propan-2-yl)phenyl]phenyl]phosphane;methane-sulfonic acid;N-methyl-2-phenylaniline;palladium DIPEA=N,N-Diisopropylethylamine or N-ethyl-N-iso-propyl-propan-2-amine DMA=dimethyl acetamide DMAP=dimethylamino pyridine DME=dimethoxyethane DMF=dimethylformamide DMSO=dimethyl sulfoxide EtOH=ethanol EtOAc=ethyl acetate HATU=[dimethylamino(triazolo[4,5-b]pyridin-3-yloxy)methylene]-dimethyl-ammonium (Phosphorus Hexafluoride Ion)

MeOH=methanol

MP-TMT scavenger resin=a macroporous polystyrene-bound trimercaptotriazine, a resin bound equivalent of 2,4,6-trimercaptotriazine (TMT).

MTBE=Methyl tert-butyl ether

NMM=N-methyl morpholine

NMP=N-methyl pyrrolidine

Pd(dppf)$_2$Cl$_2$=[1,1'-Bis(diphenylphosphino)ferrocene]di-chloropalladium(II)

PdCl$_2$=palladium(II) dichloride

PdCl$_2$(PPh$_3$)$_2$=Bis(triphenylphosphine)palladium(II) dichloride

SFC=super critical fluid chromatography

SPhos Pd G3=(2-Dicyclohexylphosphino-2',6'-dime-thoxybiphenyl) [2-(2'-amino-1,1'-biphenyl)]palladium (II) methanesulfonate TBAF=Tetrabutylammonium fluoride tBuXPhos Pd G1=Chloro[2-(di-tert-butylphosphino)-2', 4',6'-triisopropyl-1,1'-biphenyl][2-(2-aminoethyl)phe-nyl]palladium(II) or t-BuXPhos palladium(II) phen-ethylamine chloride tBuXPhos Pd G3=[(2-Di-tert-butylphosphino-2',4',6'-tri-isopropyl-1,1'-biphenyl)-2-(2'-amino-1,1'-biphenyl)] palladium(II) methanesulfonate tBuXPhos Pd G4=ditert-butyl-[2-(2,4,6-triisopropylphe-nyl)phenyl]phosphane;dichloromethane;methane-sulfonate;N-methyl-2-phenyl-aniline palladium (II)

TFA=trifluoroacetic acid

THF=tetrahydrofuran

XPhos Pd G1=(2-Dicyclohexylphosphino-2',4',6'-triiso-propyl-1,1'-biphenyl)[2-(2-aminoethyl)phenyl]palla-dium(II) chloride or (XPhos) palladium(II) phenethyl-amine chloride 9-BBN=9-borabicyclo[3.3.1]nonane In some embodiments, processes for preparing compounds of Formula (I), tautomers thereof, deuterated derivatives of those compounds and tautomers, or pharmaceutically acceptable salts of any of the foregoing, comprise reacting a compound of Formula (I), tautomer, deuterated derivative, or pharmaceutically acceptable salt with a depro-tection reagent as depicted in Schemes 1 through 15 below (wherein all variables are as defined for Formula (I)above):

Scheme 1

1-1

I

Scheme 1 shows processes for preparation of compounds of formula I from compounds of formula 1-1. W$^1$ is a group such as OPG where PG is any suitable alcohol protecting group. For example, PG may be benzyl, MOM, or methyl. In some embodiments, where W$^1$ is OBn, then compounds of formula I may be prepared from compounds of formula 1-1 by treatment with any suitable reagents for the removal of a benzyl group. In some examples, hydrogenolysis with a palladium on carbon catalyst may be used. The reaction may be carried out under an atmosphere of hydrogen gas, under increased pressure. In some examples, where PG is methyl or benzyl, the protecting group may be removed by treatment with a de-alkylation agent such as BBr$_3$. The reaction may be performed in a solvent such as dichlo-romethane. In some embodiments, where W$_1$ contains a MOM protecting group, a compound of formula I may be prepared by treatment of a compound of formula 1-1 with an acid reagent such as HCl. Any suitable reagent for the removal of an alcohol or amine protecting group may be used to prepare compounds of formula 1 form compounds of formula 1-1.

Scheme 2

2-1

I

A process for the preparation of compounds of formula I from compounds of formula 2-1 may be prepared as scheme shown in scheme 2. W$_2$ is a group such as OPG or NHPG where PG is any suitable group for the protecting of an alcohol or an amine. For example, in some embodiments, W$_2$ may be OBn or OMe.

Schemes 3 to 15 show processes for the preparation of compounds of formula 1-1. These processes may also be used in the preparation of compounds of formula 2-1.

Scheme 3

Scheme 3 shows methods for preparation of compounds 3-8 and 3-9 which may be used as intermediates in the preparation of compounds of formula I. $Q^1$ is a halogen such as Br, Cl, or I. $E^1$ is H or $SiMe_3$. Compounds of formula 3-3 may be prepared from compounds of formula 3-1 by Sonagashira coupling with an alkyne of formula 3-2. Any suitable conditions for performing an aryl-alkyne coupling may be used. In some embodiments, a catalyst such as $Pd(PPh_3)_2Cl_2$ may be used. The reaction may be performed on the presence of copper iodide. The reaction may be performed in the presence of a base such as triethylamine or diisopropylethylamine. A solvent such as dioxane may be used. The reaction may be performed in the presence of added heat (e.g. 90° C.). A compound of formula 3-4 may be prepared from 3-3 by reaction with a reagent such as hydroxylamine hydrochloride. The reaction may be performed in a solvent such as pyridine, acetonitrile and dichloroethane. The reaction may be performed at elevated temperature, for example, 50° C. A compound of formula 3-5 may be prepared from 3-4 by treatment with a reagent such as CuBr. A solvent such as N,N-dimethylacetate may be used. The reaction may be performed in the presence of added heat (e.g. 60° C.). A compound of formula 3-7 may be prepared by any suitable method for coupling an organometallic reagent (such as an alkyl zinc reagent, or boronic acid or ester) with an aryl halide. For example, in some embodiments Suzuki coupling conditions may be used. For example, where 3-6 is a boronic acid or ester, a catalyst such as $Pd(dppf)Cl_2$ may be used. The reaction may be performed in the presence of a base such as $Na_2CO_3$. The reaction may be performed in a solvent such as dioxane at 80° C. In some embodiments, where 3-6 is an alkyl zinc reagent, the reaction may be performed in the presence of $Pd(PPh_3)_4$ in THF at 80° C. An aryl chloride of formula 3-8 may be prepared from 3-7 by treatment with a suitable chlorinating reagent. For example, in some embodiments, a reagent such as $POCl_3$ may be used. A compound of formula 3-9 may be prepared from an N-oxide of formula 3-7 by treatment with DABCO reagent in the presence of a reagent such as trifluoroacetic anhydride. The reaction may be performed in a solvent such as dichloromethane at room temperature.

Scheme 4

4-1

4-2

4-3

4-5

4-6

4-7

3-8

Scheme 5

3-8

5-1

5-3

5-2

5-5

Deprotection

Deprotection

I

I

Scheme 4 shows an alternative process for the preparation of a compound of formula 3-8. Q3 is any halogen, such as Cl, Br or I. $R^{23}$ is a hydrogen or any alkyl suitable for the formation of a boronic ester. A compound of formula 4-3 may be prepared by coupling ethyl amine with any suitable reagent for the formation of an amide. For example, HATU or T3P may be used. A compound of formula 4-5 may be prepared from a compound of formula 4-2 using standard conditions suitable for a Suzuki coupling reaction. For example, Pd(dppf)Cl$_2$ may be used. The reaction may be performed in the presence of a base such as Na$_2$CO$_3$. A solvent such as 1,4-dioxane may be used. A compound of formula 4-7 may be prepared by reaction of a nitrile compound of formula 4-6 with 4-5. The reaction may be performed by treatment of compounds of formula 4-5 with a base such as LDA. The reaction may be performed at reduced temperatures (e.g. −20° C.) in a solvent such as THF. A process for the preparation of compound 3-8 from compounds of formula 4-7 is also shown in Scheme 4. Treatment of compound of formula 4-7 with a chlorinating reagent such as POCl$_3$ or SOCl$_2$ affords compounds of formula 3-8.

Scheme 5 shows processes for the preparation of compounds of formula I from aryl chlorides of formula 3-8. $R_{24}$ is hydrogen or any suitable alkyl group which forms a boronate ester. $X^2$ is a halogen such as I, Br or Cl. W1 is defines as above. All other variables are defined as above. A compound of formula 5-2 may be prepared by Suzuki coupling of a compound of formula 5-1 with an intermediate of formula 3-8. Any suitable conditions for performing Suzuki coupling reaction may be used. A compound of formula 5-5 may be prepared from a compound of formula 3-8 and an organozinc reagent of formula 5-3. In some embodiments, the reaction is performed in the presence of a palladium catalyst such as Pd(PPh$_3$)$_4$. The reaction may be performed in a solvent such as THF, at elevated temperature (e.g. 60° C.). Compounds of formula I may be prepared from compounds of formula 5-2 and 5-5 using standard methods for the deprotection of an alcohol protecting group. Reagents may vary depending on the exact protecting group used.

-continued

Scheme 6

3-7

6-2

6-3

Compounds of formula 6-3 may be prepared from N-oxides of formula 3-7 and amines of formula by 6-1 treatment with PyBrop in the presence of a base such a DIPEA. The reaction is performed in a solvent such a 1,2-dichloroethane in the presence of added heat (e.g. 80° C.).

Scheme 7

3-9

7-2

7-3

Scheme 7 shows a method for the preparation of compounds of formula 7-3. In some embodiments, a compound of formula 7-2 may be prepared by reaction of an alcohol of formula 7-1 and an intermediate of formula 3-9 in the presence of a base such as NaH. The reaction may be performed in a solvent such as DMF. Removal of the alcohol protecting group affords compounds of formula 6-3.

Scheme 8

4-7

8-2

8-3

Scheme 8 shows methods for the preparation of compounds of formula 8-3 from isoquinolinone compounds of formula 4-7. $LG^1$ is any suitable leaving group (e.g. tosylate, mesylate, or a halogen atom). Compounds of formula 8-2 may be prepared from compounds of formula 4-7 by alkylation with compounds of formula 8-1. In some embodiments, where $LG^1$ is a tosylate, the reaction is performed in the presence of CsF. The reaction may be performed in a solvent such as DMF at 50° C. In some example, where $LG^1$ is a halogen, a base such as $Cs_2CO_3$ may be used. Any other suitable condition for the alkylation of an isoquinolinone may be used.

Scheme 9 and a base such as $K_3PO_4$ may be used. A compound of formula 9-8 may be prepared from 9-6 and an amine of formula 9-7 using HATU reagent and DIPEA as a base, in a solvent such as DMF. Compounds of formula 9-9 may be prepared from 9-8 using standard deprotection methods appropriate to the protecting group used. For example, where a benzyl protecting group is used, hydrogenation may be used.

Scheme 10

Scheme 9 depicts processes for the preparation of compounds of formula 9-9. $Q_3$ is a halogen such as Cl, I, or Br. $E^1$ is H or $SiMe_3$. $R^{25}$ is hydrogen or any suitable alkyl group which affords a boronate ester. Compounds of formula 9-3 may be prepared from 9-1 using any suitable condition for performing a Sonagashira coupling reaction. A compound of formula 9-4 may be prepared from a compound of formula 9-3 by any suitable method for cyclization onto an alkyne. In some embodiments, treatment with iodine in dichloromethane solvent at room temperature afford a compound of formula 9-4. Suzuki coupling of a compound of formula 9-4 with a suitable boronate reagent of formula 9-5 affords compounds of formula 9-6. A catalyst such as RuPhos Pd G3

Scheme 10 shows methods for the preparation of compounds of formula 10-6 and 10-7. $R^{26}$ is hydrogen or any suitable alkyl group which forms a boronic ester. Compounds of formula 10-6 and 10-7 may be used as intermediates in the preparation of compounds of Formula I. Compounds of formula 10-4 may be prepared from 10-3 and a suitable boronic acid or ester. The reaction may be performed in the presence of a catalyst such as $Pd(TFA)_2$, in the presence of a ligand such as 5,5'-Dimethyl-2,2'-dipyridyl and an acid such as methane sulfonic acid. The reaction may be performed in a solvent such as 2-MeTHF at 80° C. Compounds of formula 10-5 may be prepared by HATU coupling of compounds with an 10-3 amine of formula 10-4. A compound of formula 10-6 may be prepared by treatment of 10-5 with a base such as NaOtBu in a solvent such at toluene at 110° C. A compound of formula 10-7 may be prepared from 10-6 using any suitable reagent for chlorination of a quinolinone. For example, a reagent such as $SOCl_2$ may be used. In alternative embodiments, as reagent such as $POCl_3$ may be used.

from 11-4 by oxidation with any oxidizing agent suitable for the preparation of an N-oxide from a pyridine. For example, in some embodiments, m-CPBA may be used. The reaction may be performed in a solvent such as dichloromethane at room temperature. A compound of formula 10-7 may be prepared from 11-5 using a chlorinating reagent such as $POCl_3$.

Scheme 11

11-1

11-3

11-4

11-5

10-7

Scheme 12

10-6

12-2 deprotection 12-3

Scheme 12 depicts processed for the preparation of compounds of formula 12-3 from 10-6 and alkylating agents such as 12-1. $LG^2$ is a halogen such as Br, Cl or I; or a tosylate or mesylate. A compound of formula 12-2 may be prepared from 10-6 by alkylation with 12-1 using a base such as $Cs_2CO_3$. Any other suitable method for alkylation may be used.

Scheme 13

10-7

An alternative process for the preparation of a compound of formula 10-7 is shown in scheme 11. $Q^6$ and $Q^7$ are halogen atoms such as Cl, Br or I. $R^{26}$ is hydrogen or any suitable alkyl group which forms a boronic ester. Sequential Suzuki coupling reactions between boronic acids or ester and intermediate of formula 11-1 affords compounds of formula 11-4. A compound of formula 11-5 may be prepared -continued 13-2 deprotection →

13-3

Scheme 13 shows processed for the preparation of compounds of formula 13-3 from 10-7. In some embodiments, a compound of formula 13-2 may be prepared from the reaction of 10-7 and 13-1 using a base such as $Cs_2CO_3$ in a solvent such as DMF. The reaction may be performed in the presence of added heat. Deprotection using standard methods appropriate to the protecting group affords compound of formula 13-3.

Scheme 14

11-5

10-7

$R_3$—$NH_2$
14-1

$R_3$—$NH_2$
14-1
Amination 14-2 deprotection ↓

14-3

Scheme 14 shows processes for the preparation of compound of formula 14-3. N-oxides of formula 11-5 may be treated with an amine of formula 14-1 in the presence on PyBrop reagent and a base such as DIPEA to afford compounds of formula 14-2. In an alternative process for the preparation of compound of formula 14-2, a compound of formula 11-5 may be treated with an amine of formula 14-1 and any suitable reagents for Buchwald amination. For example, the reaction may be performed in the presence of a catalysts such as $P(t-Bu)_3$ Pd G4 and a base such as $K_2CO_3$. The reaction may be performed in a solvent such as dioxane, in the presence of heat (e.g. 80° C.).

Scheme 15

10-7

$R_2$—$[MX^3]$
15-1
coupling →

15-2 deprotection →

15-3

Compounds of formula 15-3 may be prepared from compounds of formula 10-7 as depicted in Scheme 15. M is a metal such as Zn or B. $X^3$ is a halogen such as Br or I. Compounds of formula 15-1 are organometallic reagent such as alkyl zinc reagents or boronic acids or ester. Compound of formula 15-2 may be prepared using any suitable conditions for a Negeshi coupling reaction (where M=Zn), or conditions for Suzuki coupling reagents (where M=B). If appropriate as defined by $W_1$, deprotection using standard method for removal of an alcohol protecting group affords compounds of formula 15-3.

EXAMPLES

In order that the disclosure described herein may be more fully understood, the following examples are set forth. It should be understood that these examples are for illustrative purposes only and are not to be construed as limiting this disclosure in any manner.

Example 1

Synthesis of Compounds

All the specific and generic compounds, the methods for making those compounds, and the intermediates disclosed for making those compounds, are considered to be part of the disclosure.

A. Synthesis of Starting Materials

Preparations of S1-S36 describe synthetic routes to intermediates used in the synthesis of Compounds 1-361.

Preparation of S1

7-(benzyloxy)-4-(4-fluorophenyl)-3-(1-methoxy-2-methylpropan-2-yl)isoquinolin-1(2H)-one (S1)

Step 1. Synthesis of 5-benzyloxy-2-bromo-benzoic acid (C2)

To a solution of C1 (5 g, 15.57 mmol) in MeOH (20 mL) and THF (15 mL) was added aq. NaOH (15 mL of 2 M, 30.00 mmol) the resulting solution was stirred at RT for 2 hours. The solution was concentrated and neutralized with 6 M HCl (5 mL). The aqueous phase was extracted with EtOAc (30 mL×2) and the combined organic fractions were washed with brine (2×20 mL). The organic phase was dried over Na₂SO₄, filtered and concentrated in vacuo to provide C2 as a white solid (4.7 g, 97%). ¹H NMR (400 MHz, Chloroform-d) δ 7.64 (d, J=3.1 Hz, 1H), 7.61 (d, J=8.9 Hz, 1H), 7.49-7.35 (m, 6H), 7.04 (dd, J=8.8, 3.1 Hz, 1H), 5.12 (s, 2H). LCMS m/z 306.94 [M+H]⁺

Step 2. Synthesis of 5-benzyloxy-2-bromo-N,N-diethyl-benzamide (C3)

To a solution of C2 (4.7 g, 15.30 mmol) in EtOAc (50 mL) was added diethylamine (5 mL, 48.33 mmol) and a white precipitate crashed out. To this suspension was added EtOAc (25 mL) followed by dropwise addition of T3P (14.6 g of 50% w/w, 22.94 mmol) in EtOAc. The solution turned yellow in a few minutes and the solution was stirred for 2 hours. The reaction was quenched by addition of 1 M HCl (20 mL) and water (20 mL). The organic phase was separated, and the aqueous layer was extracted with EtOAc (2×30 mL). The combined organic phases were washed with water (2×20 mL), brine (1×20 mL), dried over MgSO4 and concentrated to dryness to provide C3 as a yellow oil. (5.6 g, quant.). ¹H NMR (400 MHz, Chloroform-d) δ 7.50-7.32 (m, 6H), 6.91-6.84 (m, 2H), 5.17-5.00 (m, 2H), 3.85 (dq, J=14.2, 7.1 Hz, 1H), 3.32 (dq, J=14.0, 7.1 Hz, 1H), 3.15 (qd, J=7.2, 3.9 Hz, 2H), 1.28 (t, J=7.1 Hz, 3H), 1.02 (t, J=7.1 Hz, 3H). LCMS m/z 362.09 [M+H]⁺

Step 3. Synthesis of 5-benzyloxy-N,N-diethyl-2-[(4-fluorophenyl)methyl]benzamide (C4)

A solution of C3 (6 g, 16.56 mmol), 2-[(4-fluorophenyl)methyl]-4,4,5,5-tetramethyl-1,3,2-dioxaborolane (5 g, 21.18 mmol) and Na₂CO₃ (28 mL of 2M, 56.00 mmol) in dioxane (90 mL) and water (30 mL) was degassed with a stream of N₂ for 5 min. Then, PdCl(dppf) (605 mg, 0.8268 mmol) was added and the solution was stirred at 100° C. for 15 hours. and kept overnight. The reaction mixture the was cooled down and EtOAc (50 mL) followed by water (20 mL) were added. The aqueous layer was separated and extracted with EtOAc (2×25 mL). The combined organic fractions were washed with brine (2×20 mL), dried over Na₂SO₄ and concentrated to dryness. Purification by silica gel chromatography (0-52% ethyl acetate in heptane) afforded C4 as a light-yellow oil. (5.3 g, 82%) ¹H NMR (400 MHz, Chloroform-d) δ 7.49-7.31 (m, 5H), 7.21-7.08 (m, 3H), 7.00-6.91 (m, 3H), 6.80 (d, J=2.7 Hz, 1H), 5.07 (d, J=9.2 Hz, 2H), 3.91 (d, J=21.7 Hz, 2H), 3.65 (s, 1H), 3.33 (s, 1H), 2.94 (s, 1H), 2.77 (s, 1H), 1.19 (t, J=7.1 Hz, 3H), 0.92 (d, J=7.1 Hz, 3H). LCMS m/z 392.25 [M+H]⁺

Step 4. Synthesis of 7-(benzyloxy)-4-(4-fluorophenyl)-3-(1-methoxy-2-methylpropan-2-yl)isoquinolin-1(2H)-one (S1)

To a solution of C4 (210 mg, 0.5364 mmol) and 3-methoxy-2,2-dimethyl-propanenitrile C5 (70 mg, 0.6186 mmol) in THF (2 mL) was added LDA (310 μL of 2 M, 0.62 mmol) in a dropwise fashion at 0° C. The solution was slowly warmed to RT over an hour and the reaction was quenched by the addition of water (2 mL). The mixture was concentrated in vacuo and EtOAc (50 mL) and water (10 ml) were added. The aqueous layer was separated and extracted with EtOAc (10 mL). Combined organic phases were washed with brine, dried over MgSO4, filtered and concentrated to give S1, which was used without further purification. (230 mg, 98%) ¹H NMR (400 MHz, Chloroform-d) δ 10.25 (s, 1H), 7.83 (d, J=2.8 Hz, 1H), 7.40-7.31 (m, 2H), 7.13-7.06 (m, 2H), 7.06-6.92 (m, 7H), 6.85-6.78 (m, 4H), 6.67 (d, J=2.7 Hz, 2H), 6.62 (d, J=9.1 Hz, 1H), 5.06 (s, 2H), 3.88-3.62 (m, 2H), 3.33 (s, 3H), 0.94 (s, 6H). LCMS m/z 432.27 [M+H]⁺

Preparation of S2

1-(4-aza-1-azoniabicyclo[2.2.2]octan-1-yl)-7-benzyloxy-8-fluoro-4-(4-fluorophenyl)-3-isopropyl-isoquinoline (S2)

C6

C7

C8

C9

C10

-continued

S2

Step 1. Synthesis of 3-benzyloxy-2-fluoro-6-(3-methylbut-1-ynyl)benzaldehyde (C7)

In a sealed tube, a suspension of C6 (3.0 g, 9.7047 mmol) in toluene (18.0 mL) and diisopropylamine (6.0 mL) was bubbled through with nitrogen for 10 min. Bis(triphenylphosphine)palladium(II) dichloride (143 mg, 0.2032 mmol) and CuI (81 mg, 0.4253 mmol) were added and bubbled through with N₂ for another 2 min. 3-methylbut-1-yne (999.00 mg, 1.5 mL, 14.666 mmol) was added and the tube was sealed, stirred and heated at 50° C. overnight. The reaction mixture was cooled to RT, diluted with EtOAc (100 mL). The organic layer was washed with 3M aq. HCl (2×30 mL), water (30 mL), brine, dried over anhydrous Na₂SO₄, filtered, loaded on silica gel and concentrated under reduced pressure. The residue was purified on silica gel chromatography, eluting from 0% to 20% ethyl acetate in heptanes to give, as orange oil, C7 (2.60 g, 89%). ¹H NMR (300 MHz, Chloroform-d) δ 1.22-1.32 (m, 6H), 2.67-2.90 (m, 1H), 5.18 (s, 2H), 7.04-7.24 (m, 2H), 7.30-7.47 (m, 5H), 10.50 (s, 1H). ¹⁹F NMR (282 MHz, Chloroform-d) δ −136.8 (d, J=9.2 Hz, 1F). LCMS m/z 297.2 [M+H]⁺

Step 2. Synthesis of 3-benzyloxy-2-fluoro-6-(3-methylbut-1-ynyl)benzaldehyde oxime (C8)

To a solution of hydroxylamine hydrochloride (6.17 g, 88.789 mmol) in pyridine (70.416 g, 72 mL, 890.22 mmol) was added acetonitrile (80 mL) at RT. Then, the solution was stirred and heated at 50° C. and a solution of C7 (8.74 g, 29.494 mmol) in 1,2-dichloroethane (55 mL) was added. The resulting mixture was heated at 50° C. for 1 hour. The solution was cooled to RT and diluted with EtOAc (100 mL) and water (100 mL) and decanted. The organic layer was washed with aqueous solution of 3 M HCl (4×50 mL), water (50 mL), brine, dried over anhydrous sodium sulfate, filtered and concentrated under reduced pressure to give, as light yellow solid, C8 (8.71 g, 85%) ¹H NMR (300 MHz, Chloroform-d) δ 1.28 (d, J=6.8 Hz, 6H), 2.70-2.88 (m, 1H), 5.16 (s, 2H), 6.92 (t, J=8.4 Hz, 1H), 7.14 (d, J=8.5 Hz, 1H), 7.29-7.50 (m, 5H), 8.54 (s, 1H), 8.73 (br. s., 1H). ¹⁹F NMR (282 MHz, Chloroform-d) δ −136.3 (d, J=9.2 Hz, 1F). LCMS m/z 312.2 [M+H]⁺

Step 3. Synthesis of 7-benzyloxy-4-bromo-8-fluoro-3-isopropyl-2-oxido-isoquinolin-2-ium (C9)

CuBr (15.7 g, 70.292 mmol) was added to a solution of C8 (8.71 g, 27.975 mmol) in N,N-dimethylacetamide (70 mL)

and the resulting mixture was heated at 60° C. for 1 hour. The reaction mixture was cooled to RT, then cooled to 0° C. and with vigorous stirring, an aqueous solution of ammonium hydroxide and water (2:1, 75 mL) was slowly added and stirred at 0° C. for 30 minutes. Then, the suspended solids were filtered and washed with water to give a tan solid. The solid was dissolved through filter paper with dichloromethane, decanted, dried over anhydrous $Na_2SO_4$, filtered and concentrated under reduced pressure and dried under vacuum. The residue was triturated in methyl tert-butylether (40 mL) for 1 hour, filtered and washed with heptanes to give C9 (8.716 g, 80%) as tan solid. $^1$H NMR (300 MHz, Chloroform-d) δ 1.56 (d, J=7.0 Hz, 6H), 4.11 (br. s., 1H), 5.33 (s, 2H), 7.32-7.50 (m, 6H), 7.84 (d, J=9.4 Hz, 1H), 8.87 (br. s., 1H). $^{19}$F NMR (282 MHz, Chloroform-d) δ −143.8 (d, J=6.1 Hz, 1F). LCMS m/z 390.1 [M+H]$^+$

Step 4. Synthesis of 7-benzyloxy-8-fluoro-4-(4-fluorophenyl)-3-isopropyl-2-oxido-isoquinolin-2-ium (C10)

A suspension of C9 (3.0 g, 7.6875 mmol), (4-fluorophenyl)boronic acid (1.62 g, 11.578 mmol) and an aqueous solution of $Na_2CO_3$ (8.0 mL of 2M, 16.0 mmol) in DMSO (27 mL) was heated to 100° C. and sparged with $N_2$ for 10 min. Pd(dppf)Cl$_2$·dichloromethane (327 mg, 0.4004 mmol) was added and the reaction was sparged for 2 minutes. The reaction was stirred at 100° C. for overnight. After about 20 minutes, an additional amount of DMSO (9 mL) and water (6 mL) were added due to the formation of a crust of solids on top of the mixture and difficult agitation. The reaction mixture was cooled to RT, water (60 mL) was added, stirred at room temperature for 15 minutes and the suspension was filtered and washed with water. The residue was then dissolved with dichloromethane (through filter paper). The filtrate was decanted, dried over anhydrous sodium sulfate, filtered, loaded on silica gel and concentrated under reduced pressure. The residue was purified on silica gel chromatography, eluting from 0% to 50% ethyl acetate in dichloromethane to give C10 (1.975 g, 63%) as light pink solid. $^1$H NMR (300 MHz, Chloroform-d) δ 1.40 (d, J=6.8 Hz, 6H), 3.21 (br. s., 1H), 5.28 (s, 2H), 6.81 (d, J=9.1 Hz, 1H), 7.14 (t, J=8.7 Hz, 1H), 7.22 (d, J=6.8 Hz, 4H), 7.31-7.48 (m, 5H), 8.96 (s, 1H). $^{19}$F NMR (282 MHz, Chloroform-d) δ −144.8 (d, J=6.1 Hz, 1F), −113.6-112.2 (m, 1F). LCMS m/z 406.2 [M+H]$^+$

Step 5. Synthesis of 1-(4-aza-1-azoniabicyclo[2.2.2] octan-1-yl)-7-benzyloxy-8-fluoro-4-(4-fluorophenyl)-3-isopropyl-isoquinoline (S2)

A solution of C10 (1.1 g, 2.710 mmol) and DABCO (1000 mg, 8.915 mmol) in dichloromethane (25 mL) was cooled to 0° C. and was added TFAA (1.5 mL, 10.79 mmol). The mixture was then allowed to warm to room temperature and was stirred for another 1 h and the reaction was concentrated to dryness. The residue was dissolved in a minimum of DMSO and was purified by reverse phase chromatography (C18, eluting from 10 to 100% acetonitrile in water with 0.1% TFA modifier) to give S2 bis trifluoroacetate salt as a white solid (1.85 g, 68%). $^1$H NMR (400 MHz, Methanol-d$_4$) δ 7.93 (t, J=8.9 Hz, 1H), 7.61-7.24 (m, 10H), 5.37 (s, 2H), 4.34 (t, J=7.3 Hz, 6H), 3.63 (t, J=7.3 Hz, 6H), 2.99 (p, J=6.8 Hz, 1H), 1.27 (d, J=6.8 Hz, 6H). LCMS m/z 500.38 [M+H]$^+$

Preparation of S3

4-(4-fluorophenyl)-3-isopropyl-7-methoxy-2H-iso-quinolin-1-one (S3)

Step 1. Synthesis of 2-bromo-N,N-diethyl-5-methoxy-benzamide (C12)

To a solution of C11 (5 g, 21.64 mmol) and N,N-diethylamine (7 mL, 67.67 mmol) in dichloromethane (75 mL) was added HATU (10 g, 26.30 mmol) at room temperature. After stirring for 24 hours, the reaction was quenched with by addition of water and the organic layer was washed in 1 M HCl (30 mL), water, and aqueous saturated $NaHCO_3$. The organic layer was then concentrated in vacuo to give a light brown liquid which was purified on silica gel chromatography, eluting from 0% to 50% ethyl acetate in heptane to give C12 as a colorless oil (5.63 g, 91%). $^1$H NMR (400 MHz, Chloroform-d) δ 7.47-7.35 (m, 1H), 6.76 (dd, J=6.3, 3.1 Hz, 2H), 3.76 (d, J=3.4 Hz, 4H), 3.38-3.22 (m, 1H), 3.14 (qt, J=7.4, 3.4 Hz, 2H), 1.25 (td, J=7.1, 3.0 Hz, 4H), 1.06 (td, J=7.2, 3.0 Hz, 3H). LCMS m/z 286.14 [M+H]$^+$

Step 2. Synthesis of N,N-diethyl-2-[(4-fluorophe-nyl)methyl]-5-methoxy-benzamide (C13)

A solution of C12 (2 g, 6.989 mmol), 2-[(4-fluorophenyl)methyl]-4,4,5,5-tetramethyl-1,3,2-dioxaborolane (2.5 g, 10.59 mmol) and Na$_2$CO$_3$ (12 mL of 2M, 24.00 mmol) in dioxane (36 mL) and water (12 mL) was degassed with N$_2$ for 5 minutes. Then, PdCl$_2$(dppf) (255 mg, 0.3485 mmol) was added and the solution was heated to 80° C. for 3 hours after which time the temperature was elevated to 100° C. and the solution was stirred for another 3 hours. LCMS showed the completion. The reaction mixture was cooled down to room temperature and EtOAc (50 mL) and water (20 mL) were added. The aqueous layer was separated and extracted with EtOAc (2×25 mL). The combined organic fractions were washed with brine (2×20 mL), dried over Na$_2$SO$_4$ and concentrated to dryness to give dark residue, which was purified on silica gel chromatography, eluting from 0% to 40% ethyl acetate in heptane to give C13 as a light yellow oil (2 g, 90%). $^1$H NMR (400 MHz, Chloroform-d) δ 7.20-7.06 (m, 3H), 6.94 (t, J=8.7 Hz, 2H), 6.85 (dd, J=8.5, 2.7 Hz, 1H), 6.73 (d, J=2.7 Hz, 1H), 3.80 (s, 2H), 3.74-3.23 (m, 2H), 3.08-2.65 (m, 2H), 1.19 (t, J=7.1 Hz, 3H), 0.99 (t, J=7.1 Hz, 3H). LCMS m/z 316.26 [M+H]$^+$

Step 3. Synthesis of 4-(4-fluorophenyl)-3-isopropyl-7-methoxy-2H-isoquinolin-1-one (S3)

To a solution of C13 (1 g, 3.171 mmol) in THF (15 mL) was added LDA (2.0 mL of 2 M, 4.0 mmol) at 0° C. The colorless solution turned purple and was stirred for another hour at 0° C. by which time isobutyronitrile (570 µL) was added dropwise and the reaction was allowed to warm up to room temperature and was stirred for a further 12 hours. The reaction solution was concentrated to dryness and NH$_4$Cl sat. (10 mL) and EtOAc (50 mL) were added. The organic layer was washed with brine, dried over Na$_2$SO$_4$, then concentrated to give a residue which was purified on silica gel chromatography, eluting from 0% to 50% ethyl acetate in dichloromethane to give S3 as light yellow oil (428 mg, 43%). $^1$H NMR (400 MHz, Chloroform-d) δ 9.79 (s, 1H), 7.87 (d, J=2.8 Hz, 1H), 7.26-7.10 (m, 5H), 6.97 (d, J=8.9 Hz, 1H), 3.95 (s, 3H), 2.86 (p, J=7.1 Hz, 1H), 1.27 (d, J=7.0 Hz, 6H). LCMS m/z 312.21 [M+H]$^+$

Preparation of S4

7-benzyloxy-4-bromo-3-isopropyl-2-oxido-isoquino-lin-2-ium (S4)

C14

C15

-continued

C16

S4

Step 1. Synthesis of 5-benzyloxy-2-(3-methylbut-1-ynyl)benzaldehyde (C15)

In a three-necked flask equipped with a reflux condenser, a solution of C14 (1.99 g, 6.8352 mmol) in dioxane (10.5 mL) and TEA (7.5 mL) was sparged with N$_2$ for 15 minutes. Bis(triphenylphosphine)palladium(II) dichloride (95 mg, 0.135 mmol) and CuI (56 mg, 0.294 mmol) were added under N$_2$ and the reaction was further bubbled for 2 m minutes in and 3-methylbut-1-yne (531.47 g, 0.84 mL, 7.4122 mmol) was added. The reaction turned from yellow to dark brown. The reaction was stirred at 60° C. overnight, cooled to room temperature, diluted with EtOAc (30 mL), washed with 1M aq. HCl (2×30 mL), water (20 ml) and brine (20 mL). The combined organic layers were dried over Na$_2$SO$_4$, filtered and concentrated under reduced pressure. The crude product was purified by chromatography on a silica plug eluted with Heptane/EtOAc (95:5) to yield C15 (1.88 g, 99%) as a dark brown oil. $^1$H NMR (300 MHz, Chloroform-d) δ 1.29 (d, J=6.8 Hz, 6H), 2.84 (dt, J=13.7, 6.8 Hz, 1H), 5.12 (s, 2H), 7.16 (dd, J=8.5, 2.6 Hz, 1H), 7.28-7.62 (m, 7H), 10.50 (s, 1H). LCMS m/z 279.2 [M+H]$^+$

Step 2. Synthesis of 5-benzyloxy-2-(3-methylbut-1-ynyl)benzaldehyde oxime (C16)

To a solution of hydroxylamine hydrochloride (834 mg, 12.002 mmol) in pyridine (9.2308 g, 9.4 mL, 116.70 mmol) was added acetonitrile (11 mL) at RT. The solution was stirred at 50° C. and a solution of C15 (1.155 g, 3.8798 mmol) in 1,2-dichloroethane (7 mL) was added. The resulting mixture was heated at 50° C. for 45 minutes. The suspension was cooled to RT and diluted with EtOAc (30 mL) and water (30 mL) and decanted. The organic layer was washed with aqueous solution of 3M HCl (2×20 mL), water (20 mL), brine (15 mL), dried over anhydrous Na$_2$SO$_4$, filtered and concentrated under reduced pressure. The resulting product still contained pyridine. The residue was dissolved in EtOAc (30 mL) and washed with 3 M HCl (30 mL) and brine (30 mL), dried over Na$_2$SO$_4$, filtered and concentrated under reduced pressure. The residue was triturated in heptane, filtered and dried under reduced pressure to yield C16 (844 mg, 74%) as a beige solid. $^1$H NMR (300 MHz, Chloroform-d) δ 1.28 (s, 3H), 1.30 (s, 3H), 2.82 (dquin, J=13.7, 6.8 Hz, 1H), 5.08 (s, 2H), 6.95 (dd, J=8.7, 2.8 Hz, 1H), 7.31-7.48 (m, 7H), 7.58 (br. s., 1H), 8.59 (s, 1H). LCMS m/z 294.2 [M+H]$^+$

Step 3. Synthesis of 7-benzyloxy-4-bromo-3-isopropyl-2-oxido-isoquinolin-2-ium (S4)

CuBr (10.599 g, 47.454 mmol) was added to a solution of C16 (5.6 g, 19.089 mmol) in N,N-dimethylacetamide (95 mL) and the resulting mixture was heated at 60° C. for 45 min. The reaction mixture was cooled to room temperature, then cooled to 0° C. and with vigorous stirring, an aqueous solution of ammonium hydroxide and water (2:1, 42 mL) was slowly added and stirred at 0° C. for 30 min. Then, the suspended solids were filtered and washed with water to give a tan solid. The solid was dissolved through filter paper with dichloromethane. The organic filtrate was washed with water (50 mL) and brine (50 mL), dried over anhydrous sodium sulfate, filtered and concentrated under reduced pressure and dried under vacuum. The residue was triturated in methyl tert-butylether (±20 mL), filtered and washed with heptanes and dried under reduced pressure to yield S4 (4.735 g, 67%) as an off-white powder. $^1$H NMR (300 MHz, Chloroform-d) δ 1.55 (s, 3H), 1.58 (s, 3H), 4.13 (br. s., 1H), 5.19 (s, 2H), 6.97 (d, J=2.3 Hz, 1H), 7.30-7.55 (m, 6H), 8.06 (d, J=9.4 Hz, 1H), 8.61 (br. s., 1H). LCMS m/z 372.1 $[M+H]^+$

Preparation of S5

7-benzyloxy-4-(4-fluorophenyl)-3-isopropyl-2H-isoquinolin-1-one (S5)

C17

C18 = C1

C19

C20

-continued

C4

S5

Step 1. Synthesis of methyl 5-benzyloxy-2-bromo-benzoate (C18)

To a solution of C17 (25.8 g, 111.67 mmol) in anhydrous DMF (180 mL) cooled at 0° C. was added $K_2CO_3$ (33.4 g, 241.67 mmol) followed by benzyl bromide (21.570 g, 15 mL, 126.12 mmol). The mixture was stirred for 15 minutes at 0° C. then for 5 hours at RT. MTBE (1.25 L) was added and the organic phase was washed with 5% aqueous $NaHCO_3$ (5×250 mL), water (5×250 mL) and brine (1×250 mL), dried over $Na_2SO_4$, filtered and the solvent was removed under reduced pressure. The residue was triturated in heptanes (1×125 mL), filtered and dried to afford C18 (34.2 g, 95%) as a white solid. $^1$H NMR (300 MHz, Chloroform-d) δ 7.53 (d, J=8.7 Hz, 1H), 7.45-7.29 (m, 6H), 6.95 (dd, J=8.7, 3.0 Hz, 1H), 5.06 (s, 2H), 3.93 (s, 3H). LCMS m/z 321.0 $[M+H]^+$

Step 2. Synthesis of methyl 5-benzyloxy-2-[(4-fluorophenyl)methyl]benzoate (C19)

A solution of C18 (10.0 g, 31.137 mmol), 2-[(4-fluorophenyl)methyl]-4,4,5,5-tetramethyl-1,3,2-dioxaborolane (10.0 g, 42.357 mmol), $Na_2CO_3$ (60.0 mL of 2M, 120.00 mmol) in a mixture of dioxane (180 mL) and water (60 mL) was heated at 100° C. and bubbled through with nitrogen for 20 min. Then, PdCl$_2$(dppf)•dichloromethane (1.28 g, 1.5674 mmol) was added and bubbled with nitrogen for 5 minutes. The reaction mixture was heated at 100° C. for 2.25 hours. The reaction mixture was cooled to room temperature, diluted with EtOAc (300 mL) and water (200 mL) and decanted. The organic layer was washed with brine, dried over anhydrous sodium sulfate, filtered, loaded on silica gel and concentrated under reduced pressure. The residue was purified by silica gel chromatography, eluting from 5% to 20% EtOAc in heptanes to give C19 (9.68 g, 82%) as white solid. $^1$H NMR (300 MHz, Chloroform-d) δ 3.82 (s, 3H), 4.27 (s, 2H), 5.08 (s, 2H), 6.88-7.01 (m, 2H), 7.02-7.17 (m, 4H), 7.30-7.49 (m, 5H), 7.54 (d, J=2.6 Hz, 1H). $^{19}$F NMR (282 MHz, Chloroform-d) δ −118.0-117.6 (m, 1F). LCMS m/z 351.1 [M+H]$^+$

Step 3. Synthesis of 5-benzyloxy-2-[(4-fluorophenyl)methyl]benzoic acid (C20)

Grounded NaOH (4.44 g, 111.01 mmol) was added to a mixture of C19 (9.68 g, 27.627 mmol) in a mixture of THF (35 mL), MeOH (35 mL) and water (35 mL). The reaction mixture was stirred vigorously and heated at 50° C. for 2.25 hours. The reaction mixture was concentrated under reduced pressure to remove most of the THF and MeOH, then water (50 mL) was added. 1 M HCl (100 mL) was added to acidified until pH±1-2 and extracted with EtOAc (350 mL+150 mL). The combined organic layers were washed with water (100 mL), brine (100 mL), dried over Na$_2$SO$_4$, filtered and concentrated under reduced pressure to give C20 (9.03 g, 89%) as a white solid. $^1$H NMR (300 MHz, Chloroform-d) δ 7.67 (d, J=2.1 Hz, 1H), 7.52-7.30 (m, 5H), 7.17-7.05 (m, 4H), 7.01-6.88 (m, 2H), 5.10 (s, 2H), 4.34 (s, 2H). $^{19}$F NMR (282 MHz, Chloroform-d) δ −117.5-117.9 (m, 1F). LCMS m/z 359.1 [M+H]$^+$

Step 4. Synthesis of 5-benzyloxy-N,N-diethyl-2-[(4-fluorophenyl)methyl]benzamide (C4)

To a suspension of C20 (9.0 g, 26.757 mmol) in dichloromethane (85 mL) was added triethylamine (10.890 g, 15 mL, 107.62 mmol) and N-ethylethanamine (2.9694 g, 4.2 mL, 40.601 mmol). The reaction mixture was placed in a cold water bath for the slow addition of T3P (50% wt in EtOAc) (19.0 mL, 32.1 mmol) over 5 min. The resulting mixture was stirred at RT overnight. The reaction mixture was diluted with EtOAc (200 mL) and saturated Na$_2$CO$_3$ (75 mL). The layers were decanted and the organic layer was washed with water:brine (1:1), brine, dried over anhydrous Na$_2$SO$_4$, filtered and concentrated under reduced pressure. The residue was purified by silica gel chromatography, eluting from 0% to 40% ethyl acetate in heptanes. The oil was co-evaporated with THF (3×20 mL) and dried under vacuum to give C4 (9.77 g, 88%) as a light yellow oil. $^1$H NMR (300 MHz, Chloroform-d) δ 7.48-7.29 (m, 5H), 7.20-7.04 (m, 3H), 7.00-6.87 (m, 3H), 6.78 (d, J=2.6 Hz, 1H), 5.17-4.94 (m, 2H), 4.04-3.80 (m, 2H), 3.71-3.51 (m, 1H), 3.43-3.18 (m, 1H), 3.04-2.59 (m, 2H), 1.17 (t, J=7.0 Hz, 3H), 0.89 (t, J=7.0 Hz, 3H). LCMS m/z 392.3 [M+H]$^+$

Step 5. Synthesis of 7-benzyloxy-4-(4-fluorophenyl)-3-isopropyl-2H-isoquinolin-1-one (S5)

To a solution of C4 (100 mg, 0.2401 mmol) in THF (1 mL), at −20° C., was added dropwise a THF/hexanes solution of LDA (0.19 mL of 1.5 M, 0.2850 mmol) and the resulting mixture was stirred at −20° C. for 2 hours. Then, 2-methylpropanenitrile (34.650 mg, 45 μL, 0.5014 mmol) was slowly added and the reaction mixture was stirred at RT overnight. Saturated aqueous solution of ammonium chloride (5 mL) and water (5 mL) were added and extracted with EtOAc (30 mL) and decanted. The organic layer was washed with brine and concentrated under reduced pressure to give a beige solid. The residue was triturated in acetonitrile (about 5 mL), filtered and dried under vacuum to give S5 (44 mg, 47%) as white solid. $^1$H NMR (300 MHz, DMSO-d$_6$) δ 11.14 (s, 1H), 7.75 (d, J=2.6 Hz, 1H), 7.52-7.44 (m, 2H), 7.44-7.25 (m, 8H), 6.83 (d, J=8.8 Hz, 1H), 5.22 (s, 2H), 2.69-2.56 (m, 1H), 1.16 (d, J=7.0 Hz, 6H). $^{19}$F NMR (282 MHz, DMSO-d$_6$) δ −114.75-115.06 (m, 1F). LCMS m/z 388.2 [M+H]$^+$

Preparation of S6

1-(4-aza-1-azoniabicyclo[2.2.2]octan-1-yl)-7-benzyloxy-4-(4-fluorophenyl)-3-isopropyl-isoquinoline (S6)

Step 1. Synthesis of 7-benzyloxy-4-(4-fluorophenyl)-3-isopropyl-2-oxido-isoquinolin-2-ium (C21)

A suspension of S4 (5 g, 13.432 mmol) and (4-fluorophenyl)boronic acid (2.82 g, 20.154 mmol), an aqueous solution of Na$_2$CO$_3$ (13.5 mL of 2M, 27.000 mmol) in DMSO (45 mL) was heated to 100° C. and sparged with N$_2$ for 15 minutes. PdCl$_2$(dppf)•dichloromethane (565 mg, 0.6919 mmol) was added and the reaction was sparged for 2 min. The reaction was stirred at 100° C. for overnight. The reaction mixture was cooled to RT, cooled to 0° C., water (90 mL) was added, stirred at 0° C. for 20 min and the suspension was filtered and washed with water. The residue was then dissolved with dichloromethane (through filter paper). The filtrate was decanted, dried over anhydrous $Na_2SO_4$, filtered, loaded on silica gel and concentrated under reduced pressure. The residue was purified on silica gel chromatography, eluting from 0% to 60% EtOAc in dichloromethane to give C21 (4.49 g, 86%) as tan solid. $^1$H NMR (300 MHz, Chloroform-d): δ 8.71 (s, 1H), 7.50-7.34 (m, 5H), 7.24 (d, J=6.8 Hz, 4H), 7.15-6.99 (m, 3H), 5.18 (s, 2H), 3.21 (br. s., 1H), 1.41 (d, J=7.0 Hz, 6H). $^{19}$F NMR (282 MHz, Chloroform-d) δ −113.06-113.52 (m, 1F) LCMS m/z 388.2 [M+H]$^+$

Step 2. Synthesis of 1-(4-aza-1-azoniabicyclo[2.2.2]octan-1-yl)-7-benzyloxy-4-(4-fluorophenyl)-3-isopropyl-isoquinoline (S6)

To a solution of C21 (2000 mg, 5.147 mmol) and DABCO (2500 mg, 22.29 mmol) in dichloromethane (40 mL) was added TFAA (2000 μL, 14.39 mmol) at 0° C. The mixture was allowed to warmed to RT and stirred for 1 h, concentrated in vacuo and the residue was purified by chromatography (C18, 10-100% MeCN:water, 0.1% TFA modifier) to give S6 bis trifluoroacetate salt (3.43 g, 83%) as an off-white solid. 1H NMR (300 MHz, DMSO-d$_6$) δ 7.78 (d, J=2.3 Hz, 1H), 7.68 (dd, J=9.4, 2.0 Hz, 1H), 7.58-7.50 (m, 2H), 7.50-7.31 (m, 8H), 5.51 (s, 2H), 4.15 (t, J=7.3 Hz, 6H), 3.36 (t, J=7.3 Hz, 6H), 2.97-2.82 (m, 2H), 1.20 (d, J=6.7 Hz, 6H). LCMS m/z 482.37 [M+H]$^+$

Preparation of S7

7-benzyloxy-1-chloro-4-(4-fluorophenyl)-3-isopropyl-isoquinoline (S7)

C21

S7

Step 1. Synthesis of 7-benzyloxy-1-chloro-4-(4-fluorophenyl)-3-isopropyl-isoquinoline (S7)

Oxalyl chloride (1 mL of 2M, 2.000 mmol) was added to a solution of C21 (410 mg, 1.058 mmol) and DIEA (400 μL, 2.296 mmol) in dry dichloromethane (5 mL) at −78° C. The reaction was allowed to warm to 0° C. over 2 h and then quenched by the addition of methanol (~0.5 mL). The mixture was concentrated in vacuo and the residue triturated with methanol, filtered (washing with cold methanol) and dried under vacuum to afford S7 (395 mg, 92%) as a colorless solid. $^1$H NMR (300 MHz, Chloroform-d) δ 7.69 (d, J=2.4 Hz, 1H), 7.58-7.48 (m, 2H), 7.48-7.36 (m, 3H), 7.32 (dd, J=9.2, 2.5 Hz, 1H), 7.27-7.15 (m, 5H), 5.25 (s, 2H), 2.93 (hept, J=6.7 Hz, 1H), 1.24 (d, J=6.7 Hz, 6H). LCMS m/z 0.99 [M+H]$^+$

Preparation of S8

7-benzyloxy-1,3-dichloro-4-(4-fluoro-3-methyl-phenyl)isoquinoline (S8)

C22

C23
(= S17)

C24

C25

-continued

S8

Step 1. Synthesis of 1,3-dichloro-4-iodo-7-methoxy-isoquinoline (C23)

To a solution of C22 (1 g, 4.385 mmol) in THF (50 mL) was added LDA (2.6 mL of 2 M, 5.2 mmol) at room temperature and the solution was stirred for 30 min by which time the initial cloudy solution became clear. 12 (2.3 g, 9.062 mmol) was then added portion-wise and the solution was stirred for 15 hours. Water (20 mL) was added and the aqueous layer was extracted with EtOAc (2×50 mL). The combined organic layer was washed with 1 M Na$_2$S$_2$O$_3$ solution and brine, dried over MgSO$_4$, then filtered and concentrated to give C23 as a yellow solid (1.38 g, 84%). $^1$H NMR (400 MHz, Chloroform-d) δ 8.05 (dd, J=9.2, 0.5 Hz, 1H), 7.49-7.41 (m, 2H), 4.00 (s, 3H). LCMS m/z 354.37 [M+H]$^+$

Step 2. Synthesis of 1,3-dichloro-4-(4-fluoro-3-methyl-phenyl)-7-methoxy-isoquinoline (C24)

To a solution of C23 (1.38 g, 3.675 mmol) in 1,4-dioxane (40 mL) was added (4-fluoro-3-methyl-phenyl)boronic acid (720 mg, 4.677 mmol) and Na$_2$CO$_3$ (6 mL of 2M, 12.00 mmol) in water (10 mL), then the solution was degassed by bubbling with N$_2$ for 10 min, the PdCl$_2$(dppf)•dichloromethane (318 mg, 0.3894 mmol) was added and bubbled with N$_2$ for another 5 minutes. The solution was heated to 60° C. for 15 h. EtOAc (100 mL) was added in one portion and the solution was washed with water, aq. NaHSO$_3$ and brine. After drying over MgSO$_4$ and filtration, the solution was concentrated to dryness and the residue was purified by MPLC: 40 g column, eluting with 0-30% EtOAc in Hexanes to give C24 desired product as white solid. (1.25 g, 97%) $^1$H NMR (400 MHz, Chloroform-d) δ 7.57 (d, J=2.5 Hz, 1H), 7.42 (dd, J=9.3, 0.5 Hz, 1H), 7.33 (dd, J=9.2, 2.6 Hz, 1H), 7.21-7.09 (m, 3H), 4.02 (s, 3H), 2.38 (d, J=1.9 Hz, 3H). LCMS m/z 336.1 [M+H]$^+$

Step 3. Synthesis of 1,3-dichloro-4-(4-fluoro-3-methyl-phenyl)isoquinolin-7-ol (C25)

To a solution of C24 (1.9 g, 5.531 mmol) in dichloromethane (30 mL) was added BBr$_3$ (11.5 mL of 1M, 11.50 mmol) at 0° C. in a dropwise fashion. The solution was then allowed to warm up to room temperature slowly and stirred for 1 hour. The solution was then cooled down to 0° C. in ice bath, ice was added to quench the reaction. The solution was concentrated and the residue was loaded onto column with MeOH/dichloromethane solution. MPLC: 12 g column, eluting with 0-5% MeOH in dichloromethane to give C25 (1.75 g, 96%) LCMS m/z 322.16 [M+H]$^+$

Step 4. Synthesis of 7-benzyloxy-1,3-dichloro-4-(4-fluoro-3-methyl-phenyl)isoquinoline (S8)

To a solution of C25 (1.75 g, 5.315 mmol) and K$_2$CO$_3$ (1.5 g, 10.85 mmol) in DMF (20 mL) was added BnBr (700 µL, 5.885 mmol) and the solution was stirred at room temperature for 15 hours. Then additional BnBr (700 µL, 5.885 mmol) and K$_2$CO$_3$ (1.5 g, 10.85 mmol) were added and the solution was stirred for 24 hours. Then a solution of sat. NH$_4$Cl was added and the aqueous phase was extracted with EtOAc. After evaporation of the organic phase, the residue was purified by MPLC: 12 g column, eluting with 0-20% EtOAc in Hexanes to give two products S8 as a white solid (1.02 g, 46%). $^1$H NMR (400 MHz, Chloroform-d) δ 7.56 (d, J=2.3 Hz, 1H), 7.40 (d, J=7.5 Hz, 2H), 7.37-7.23 (m, 5H), 7.14-6.98 (m, 3H), 5.15 (s, 2H), 2.26 (d, J=1.9 Hz, 3H) LCMS m/z 412.24 [M+H]$^+$

Preparation of S9

7-benzyloxy-4-(4-fluoro-3-methyl-phenyl)-3-isopropyl-2-oxido-isoquinolin-2-ium (S9)

S4

S9

Step 1. Synthesis of 7-benzyloxy-4-(4-fluoro-3-methyl-phenyl)-3-isopropyl-2-oxido-isoquinolin-2-ium (S9)

A suspension of S4 (14.635 g, 39.314 mmol), (4-fluoro-3-methyl-phenyl)boronic acid (8.960 g, 58.202 mmol) and an aqueous solution of Na$_2$CO$_3$ (40 mL of 2M, 80.000 mmol) in DMSO (130 mL) was heated to 100° C. and sparged with nitrogen for 15 min. PdCl$_2$(dppf)•dichloromethane (1.652 g, 2.0229 mmol) was added and the reaction was sparged with N$_2$ for 2 min. The reaction was stirred at 100° C. for 15 h. The reaction mixture was cooled to room temperature, cooled to 0° C., water (200 mL) was added, stirred at 0° C. for 20 minutes and the suspension was filtered and washed with water. The residue was then dissolved with dichloromethane (through filter paper). The filtrate was decanted, dried over anhydrous $Na_2SO_4$, filtered and concentrated under reduced pressure. The crude product was purified by flash chromatography on an ISCO Combi-Flash Companion loaded with dichloromethane (300 g $SiO_2$, dichloromethane/EtOAc 100:0 to 30:70). The mixed fractions were combined and purified by flash chromatography on a ISCO CombiFlash Companion loaded with dichloromethane (120 g $SiO_2$, dichloromethane/EtOAc 100:0 to 30:70). All fractions containing the clean product were combined and the solvents were removed by rotary evaporation. The product was dried under reduced pressure to yield S9 (14.2 g, 90%) as a tan powder. $^1$H NMR (300 MHz, Chloroform-d): δ 8.70 (s, 1H), 7.50-7.32 (m, 5H), 7.21-6.98 (m, 6H), 5.17 (s, 2H), 3.21 (br. s., 1H), 2.37 (d, J=1.8 Hz, 3H), 1.41 (d, J=5.9 Hz, 6H). $^{19}$F NMR (282 MHz, Chloroform-d): δ –117.7 (s, 1F). LCMS m/z 402.2 [M+H]$^+$

Preparation of S10

1-(4-aza-1-azoniabicyclo[2.2.2]octan-1-yl)-7-benzyloxy-4-(4-fluoro-3-methyl-phenyl)-3-isopropyl-isoquinoline (S10)

S9

TFAA, DABCO

S10

Step 1. Synthesis of 1-(4-aza-1-azoniabicyclo[2.2.2]octan-1-yl)-7-benzyloxy-4-(4-fluoro-3-methyl-phenyl)-3-isopropyl-isoquinoline (S10)

To a solution of S9 (2 g, 4.872 mmol) and DABCO (2.73 g, 24.34 mmol) in dichloromethane (45 mL) was added TFAA (2.0 mL, 14.39 mmol) at 0° C. The reaction was stirred for 1 hour and was concentrated to a crude residue, which was purified via reverse phase chromatography (ISCO, 50 g C18 column, 0-95% MeCN in $H_2O$ gradient with TFA modifier) to provide the desired product S10 (as a white solid (mono trifluoroacetate salt) (2.4 g, 80%). LCMS m/z 496.38 [M+H]$^+$

Preparation of S11

7-benzyloxy-4-bromo-2-oxido-3-tetrahydropyran-4-yl-isoquinolin-2-ium (S11)

C14

$PdCl_2(PPh_3)_4$
CuI, TEA
dioxane

C26

$HONH_2 \cdot HCl$
pyridine

C27

CuBr

S11

Step 1. Synthesis of 5-benzyloxy-2-(2-tetrahydropyran-4-ylethynyl)benzaldehyde (C26)

In a sealed tube, a solution of C14 (5.693 g, 19.554 mmol) in dioxane (20 mL) and triethylamine (20 mL) was degassed by bubbling $N_2$ for 15 min. 4-Ethynyltetrahydropyran (3.765 g, 74.9% w/w, 25.600 mmol) in dioxane (10 mL), $PdCl_2(PPh_3)_2$ (271 mg, 0.3850 mmol) and CuI (139 mg, 0.7299 mmol) were added under $N_2$ and the reaction were further inserted for 2 min. The reaction turned from yellow to dark brown. The vial was sealed and the reaction was stirred at 50° C. for 2 hours, cooled to RT, diluted with EtOAc (100 mL), washed with 1 M aq. HCl (2×50 mL), water (30 ml) and brine (30 mL). The combined organic layers were dried over $Na_2SO_4$, filtered and concentrated under reduced pressure. The residue was triturated in MeCN, filtered, washed with a minimal amount of ACN and dried under reduced pressure to yield C26 (4.598 g, 73%) as an off-white solid.

<sup></sup>$^1$H NMR (300 MHz, Chloroform-d) δ 1.71-1.86 (m, 2H), 1.88-2.01 (m, 2H), 2.92 (tt, J=8.6, 4.3 Hz, 1H), 3.58 (ddd, J=11.4, 8.5, 2.9 Hz, 2H), 3.90-4.02 (m, 2H), 5.12 (s, 2H), 7.17 (dd, J=8.7, 2.8 Hz, 1H), 7.31-7.51 (m, 7H), 10.50 (s, 1H). LCMS m/z 321.1 [M+H]$^+$

Step 2. Synthesis of 5-benzyloxy-2-(2-tetrahydropyran-4-ylethynyl)benzaldehyde oxime (C27)

To a solution of hydroxylamine hydrochloride (12.637 g, 181.85 mmol) was added acetonitrile (210 mL). The reaction was warmed to 50° C. and a solution of C26 (19.135 g, 59.726 mmol) in DCE (125 mL) was added. The reaction was stirred 2 hours at 50° C., cooled to RT and diluted with EtOAc (300 mL). The organic layer was washed with 1 M aq. HCl (5×150 mL), water (100 mL), brine (100 mL), dried over Na$_2$ SO$_4$, filtered and concentrated under reduced pressure. The residue was triturated in acetonitrile, filtered and dried under reduced pressure to yield C27 (18.463 g, 92%) as a pale orange solid. $^1$H NMR (300 MHz, Chloroform-d) δ 1.70-1.86 (m, 2H), 1.88-2.02 (m, 2H), 2.89 (tt, J=8.6, 4.2 Hz, 1H), 3.58 (ddd, J=11.6, 8.7, 2.9 Hz, 2H), 3.97 (ddd, J=11.7, 5.4, 3.8 Hz, 2H), 5.09 (s, 2H), 6.95 (dd, J=8.5, 2.6 Hz, 1H), 7.30-7.48 (m, 6H), 7.56 (s, 1H), 8.59 (s, 1H). LCMS m/z 336.2 [M+H]$^+$

Step 3. Synthesis of 7-benzyloxy-4-bromo-2-oxido-3-tetrahydropyran-4-yl-isoquinolin-2-ium (S11)

CuBr (20.78 g, 93.036 mmol) was added to a solution of C27 (12.45 g, 37.120 mmol) in N,N-dimethylacetamide (100 mL) and the resulting mixture was heated at 60° C. for 1 hour. The reaction mixture was cooled to room temperature, then cooled to 0° C. and with vigorous stirring, an aqueous solution of ammonium hydroxide and water (2:1, 75 mL) was slowly added and stirred at 0° C. for 45 minutes. Then, the suspended solids were filtered and washed with water to give a tan solid. The solid was dissolved through filter paper with dichloromethane, decanted, dried over anhydrous sodium sulfate, filtered and concentrated under reduced pressure. The residue was triturated in methyl tert-butylether, filtered and washed with heptanes, then triturated in acetonitrile (50 mL) to S11 (11.129 g, 72%) as beige solid. $^1$H NMR (300 MHz, Chloroform-d) δ 1.54 (d, J=12.3 Hz, 2H), 2.86-3.32 (m, 2H), 3.59 (t, J=11.7 Hz, 2H), 3.87-4.24 (m, 3H), 5.20 (s, 2H), 6.97 (d, J=2.3 Hz, 1H), 7.30-7.60 (m, 6H), 8.08 (d, J=9.4 Hz, 1H), 8.64 (br.s., 1H). LCMS m/z 414.1 [M+H]$^+$

Preparation of S12

1-(4-aza-1-azoniabicyclo[2.2.2]octan-1-yl)-7-benzyloxy-4-(4-fluoro-3-methyl-phenyl)-3-tetrahydropyran-4-yl-isoquinoline (S12)

-continued

C28

S12

Step 1. Synthesis of 7-benzyloxy-4-(4-fluoro-3-methyl-phenyl)-2-oxido-3-tetrahydropyran-4-yl-isoquinolin-2-ium (C28)

A solution of S11 (7.66 g, 18.489 mmol), (4-fluoro-3-methyl-phenyl)boronic acid (4.26 g, 27.672 mmol) and Na$_2$CO$_3$ (19 mL of 2 M in water, 38.000 mmol) in DMSO (80 mL) was heated to 100° C. and sparged with N$_2$ for 15 minutes. PdCl$_2$(dppf)•dichloromethane (789 mg, 0.9662 mmol) was added and the reaction was sparged for 2 minutes. The reaction was stirred at 100° C. for 4 hours, cooled to room temperature, diluted with EtOAc (300 mL), washed with a pH7 0.1M potassium phosphate buffer (2×150 mL). A solid precipitated and was filtered off, dissolved in dichloromethane, filtered over Celite®, washed with dichloromethane and concentrated under reduced pressure to yield C28 (2.314 g, 28%) as a tan solid. The organic layer was further washed with water (3×100 mL), brine (100 mL), dried over Na$_2$SO$_4$, filtered and concentrated under reduced pressure. The crude product was purified by flash chromatography on an ISCO CombiFlash Companion loaded with dichloromethane (220 g SiO$_2$, dichloromethane/MeOH 100:0 to 95:5). The fractions containing the product were combined and recrystallized in ACN (about 250 mL), filtered and dried under reduced pressure to yield C28 (3.7 g, 45%) as tan crystals. Both batches were combined to yield C28 (6.014 g, 71%) as a grey solid. 41 NMR (300 MHz, Chloroform-d) δ 1.41 (d, J=11.7 Hz, 2H), 2.38 (d, J=1.5 Hz, 3H), 2.51-2.96 (m, 2H), 3.28 (t, J=11.3 Hz, 3H), 3.97 (dd, J=11.0, 3.4 Hz, 2H), 5.18 (s, 2H), 6.93-7.22 (m, 6H), 7.31-7.52 (m, 5H), 8.73 (s, 1H). 19F NMR (282 MHz, Chloroform-d) δ −117.1 (s, 1F). LCMS m/z 444.2 [M+H]$^+$

Step 2. Synthesis of 1-(4-aza-1-azoniabicyclo[2.2.2]octan-1-yl)-7-benzyloxy-4-(4-fluoro-3-methyl-phenyl)-3-tetrahydropyran-4-yl-isoquinoline (S12)

To a solution of C28 (1.4 g, 3.068 mmol) and DABCO (1.72 g, 15.33 mmol) in dichloromethane (30.7 mL) was added TFAA (1.27 mL, 9.137 mmol) at 0° C. and the reaction was stirred for another hour before being allowed to warm to room temperature and stirred for another 3 hours. Then, the reaction mixture was concentrated in vacuo and the crude residue purified by ISCO reverse phase flash chromatography (5-95% MeCN in $H_2O$ with 0.1% TFA modifier, 150 gram C18 column) to provide S12 (mono trifluoroacetate salt) as a white powder(1.52 g, 71%) LCMS m/z 538.36 $[M+H]^+$

Preparation of S13

1-(4-aza-1-azoniabicyclo[2.2.2]octan-1-yl)-7-benzyloxy-4-(4-fluorophenyl)-3-tetrahydropyran-4-yl-isoquinoline (S13)

198

Step 1. Synthesis of 7-benzyloxy-4-(4-fluorophenyl)-2-oxido-3-tetrahydropyran-4-yl-isoquinolin-2-ium (C29)

A suspension of S11 (2 g, 4.8275 mmol), (4-fluorophenyl) boronic acid (1.02 g, 7.2899 mmol) and $Na_2CO_3$ (4.80 mL of 2 M in water, 9.6000 mmol) in DMSO (20 mL) was heated to 100° C. and sparged with $N_2$ for 15 minutes. $PdCl_2$(dppf)•dichloromethane (204 mg, 0.2498 mmol) was added and the reaction was sparged for 2 min. The reaction was stirred at 100° C. for 3 hours, cooled to room temperature, diluted with EtOAc (150 mL), washed with a pH7 0.1M potassium phosphate buffer (2×75 mL), water (3×75 mL), brine (75 mL), dried over $Na_2SO_4$, filtered and concentrated under reduced pressure. The residue was dissolved in dichloromethane and filtered on a pad of Celite. The filtrate was concentrated under reduced pressure and the residue was triturated in acetonitrile (±30 mL) to give C29 (1.196 g, 56%) as a grey solid. $^1H$ NMR (300 MHz, Chloroform-d) δ 1.41 (d, J=11.7 Hz, 2H), 2.36-2.92 (m, 2H), 3.16-3.38 (m, 3H), 3.96 (dd, J=11.3, 3.7 Hz, 2H), 5.18 (s, 2H), 6.98-7.09 (m, 2H), 7.09-7.17 (m, 1H), 7.19-7.30 (m, 5H), 7.31-7.57 (m, 4H), 8.75 (s, 1H). $^{19}F$ NMR (282 MHz, Chloroform-d) δ −112.8-112.4 (m, 1F). LCMS m/z 430.2 $[M+H]^+$

Step 2. Synthesis of 1-(4-aza-1-azoniabicyclo[2.2.2]octan-1-yl)-7-benzyloxy-4-(4-fluorophenyl)-3-tetrahydropyran-4-yl-isoquinoline (S13)

To a solution of C29 (2.955 g, 6.550 mmol) and DABCO (3.67 g, 32.72 mmol) in dichloromethane (70 mL) was added TFAA (4.13 g, 19.66 mmol) at 0° C. The reaction was then stirred at 0° C. for 1 hour and then allowed to warm to room temperature and stirring was continued for an additional 3 hours. The reaction mixture was concentrated in vacuo to provide the desired S13 (tris-Trifluoroacetate salt) (10.5 g, 93%) LCMS m/z 525.11 $[M+H]^+$

Preparation of S14

1-(4-aza-1-azoniabicyclo[2.2.2]octan-1-yl)-7-benzyloxy-4-(4-chlorophenyl)-3-isopropyl-isoquinoline (S14)

199

-continued

C30

Step 1. Synthesis of 7-benzyloxy-4-(4-chlorophe-
nyl)-3-isopropyl-2-oxido-isoquinolin-2-ium (C30)

A suspension of S4 (27 g, 72.53 mmol), (4-chlorophenyl)
boronic acid (14 g, 100.1 mmol) and Na$_2$CO$_3$ (25 g, 235.9
mmol in 70 mL of water) in DMSO (400 mL) was heated to
100° C. and sparged with N$_2$ for 5 min. PdCl$_2$(dppf)•dichlo-
romethane (2.5 g, 3.061 mmol) was added and the reaction
was sparged for 5 minutes. The resulting reaction mixture
was warmed to 100° C., stirred at this temperature for 2
hours at which time TLC revealed consumption of the
starting material. The reaction mixture was cooled to room
temperature, partitioned between EtOAc (~1 L) and ice/
water (~300 mL), the organic phase was separated, washed
with water (~60 mL), brine (~100 mL), dried over MgSO$_4$,
filtered through a Florisil® bed and concentrated under
reduced pressure. The residue was triturated with MTBE (~1
L) to afford C30 (21.6 g, 74%) $^1$H NMR (400 MHz,
DMSO-d$_6$) δ 8.87 (s, 1H), 7.69-7.61 (m, 2H), 7.54-7.47 (m,
2H), 7.46-7.29 (m, 6H), 7.18 (dd, J=9.2, 2.6 Hz, 1H), 6.93
(d, J=9.2 Hz, 1H), 5.21 (s, 2H), 3.05 (d, J=18.8 Hz, 1H), 1.30
(d, J=7.0 Hz, 6H). LCMS m/z 404.41 [M+H]$^+$ Step 2. Synthesis of 1-(4-aza-1-azoniabicyclo[2.2.2]
octan-1-yl)-7-benzyloxy-4-(4-chlorophenyl)-3-iso-
propyl-isoquinoline (S14)

To a solution of C30 (5 g, 12.38 mmol) and DABCO (4
g, 35.66 mmol) in dichloromethane (120 mL) was added
TFAA (4 mL, 28.78 mmol) at −10° C. The reaction was then
stirred from −4° C. to 0° C. over 3 hours. The reaction
mixture was concentrated in vacuo and triturated with Et$_2$O
(200 mL) to provide the desired S14 (9 g, 95%) (trifluoro-
acetate salt) as a tan solid. LCMS m/z 498.62 [M+H]$^+$

200

Preparation of S15

N,N-diethyl-2-[(4-fluorophenyl)methyl]-5-methoxy-
benzamide (S15)

Intermediate S15 was prepared as described for the prepa-
ration of C13 in the synthetic route to intermediate S3 above.

Preparation of S16

1-(4-aza-1-azoniabicyclo[2.2.2]octan-1-yl)-7-benzy-
loxy-4-(3,4-difluorophenyl)-3-tetrahydropyran-4-yl-
isoquinoline (S16)

-continued

S16

Step 1. Synthesis of 7-benzyloxy-4-(3,4-difluoro-phenyl)-2-oxido-3-tetrahydropyran-4-yl-isoquinolin-2-ium (C31)

A suspension of S11 (320 mg, 0.7692 mmol), (3,4-difluorophenyl)boronic acid (180 mg, 1.140 mmol) and aqueous solution of $Na_2CO_3$ (1.0 mL of 2 M, 2.0 mmol) in DMSO (5 mL) was sparged with $N_2$ for 5 minutes. Pd(dppf) $Cl_2$·dichloromethane (50 mg, 0.0612 mmol) was added and the reaction was sparged with $N_2$ for another 5 minutes. The resulting mixture was heated to 100° C. and stirred for 4 h. The reaction mixture was cooled to room temperature, water (50 mL) was added, stirred at room temperature for 30 minutes, and the suspension was filtered and washed with water. The residue was then dissolved with dichloromethane. The filtrate was decanted, dried over anhydrous $Na_2SO_4$, filtered, and concentrated under reduced pressure to give C31 (379 mg, 82%). LCMS m/z 448.51 $[M+H]^+$

Step 2. Synthesis of 1-(4-aza-1-azoniabicyclo[2.2.2] octan-1-yl)-7-benzyloxy-4-(3,4-difluorophenyl)-3-tetrahydropyran-4-yl-isoquinoline (S16)

A solution of C31 (379 mg, 0.6298 mmol) and DABCO (300 mg, 2.674 mmol) in dichloromethane (20 mL) was cooled to 0° C., and to this was added TFAA (300 μL, 2.158 mmol). The resulting mixture was allowed to warm to room temperature and stirred for another 1 hours and then concentrated to dryness. The residue was dissolved in minimum of DMSO and purified by reverse phase chromatography (C18, eluting with 10% to 100% $CH_3CN$ in water with 0.1% TFA modifier) to give S16 bis trifluoroacetate salt (440 mg, 90%). LCMS m/z 542.32 $[M+H]^+$

Preparation of S17

1,3-dichloro-4-iodo-7-methoxy-isoquinoline (S17)

Compound S17 (equivalent to C23) was prepared as described for the C23 in the preparation of S8.

Preparation of S18

4-chloro-3-isopropenyl-7-methoxy-quinoline (S18)

Synthesis of 4-chloro-3-isopropenyl-7-methoxy-quinoline (S18)

A suspension of C32 (2.97 g, 10.90 mmol), 2-isopropenyl-4,4,5,5-tetramethyl-1,3,2-dioxaborolane (2.0 mL, 10.64 mmol), $K_2CO_3$ (6.34 g, 45.87 mmol) in 1,4-dioxane (35 mL) and water (3 mL) was sparged with $N_2$ for 2 minutes. Pd(dppf)$Cl_2$·dichloromethane (431 mg, 0.5278 mmol) was added and the reaction was heated at 70° C. and stirred for 12 hours. The reaction mixture was cooled to room temperature, diluted with water and extracted with dichloromethane. The organic layer was dried over MgSO4, filtered, and concentrated under reduced pressure. The residue was purified by silica gel chromatography eluting with 0% to 40% EtOAc in heptane to give S18 (1.78 g, 63%) as a colorless oil. $^1H$ NMR (300 MHz, Chloroform-d) δ 8.56 (s, 1H), 8.09 (dd, J=9.3, 0.4 Hz, 1H), 7.34 (d, J=2.6 Hz, 1H), 7.22 (dd, J=9.2, 2.6 Hz, 1H), 5.35 (p, J=1.6 Hz, 1H), 5.08-4.98 (m, 1H), 2.13 (dd, J=1.6, 0.9 Hz, 3H). LCMS m/z 233.72 $[M+H]^+$

Preparation of S19

1,3-dichloro-7-(methoxymethoxy)isoquinoline (S19)

-continued

S19

Step 1. Synthesis of 1,3-dichloroisoquinolin-7-ol (C33)

A solution of BBr$_3$ (150 mL of 1 M in dichloromethane, 150.0 mmol) was added dropwise to a solution of C22 (10 g, 43.85 mmol) at 0° C. The resulting mixture was allowed to warm up to room temperature and stirred for 18 hours. After completion of reaction, the mixture was cooled down to 0° C., quenched with ice, and concentrated to remove dichloromethane. Water was added and the mixture was extracted with EtOAc (3×500 mL). The combined organic layers were washed with brine, dried over Na$_2$SO$_4$, filtered, and concentrated to give C33 (9.1 g, 87%), which was used in the next step without further purification. LCMS m/z 214.06 [M+H]$^+$ Step 2. Synthesis of 1,3-dichloro-7-(methoxymethoxy)isoquinoline (S19)

To a solution of C33 (3.0 g, 14.02 mmol) in dichloromethane (100 mL) was added DIPEA (15 mL, 86.12 mmol) and chloro(methoxy)methane (8 mL, 105.3 mmol). The reaction was stirred at room temperature for 1 hours. After complete conversion, the mixture was evaporated and purified by silica gel chromatography, eluting with 0% to 100% EtOAc in heptane to give S19 (2.93 g, 72%). LCMS m/z 258.05 [M+H]$^+$ Preparation of S20

1-(4-aza-1-azoniabicyclo[2.2.2]octan-1-yl)-7-benzyloxy-4-(2-methyl-4-pyridyl)-3-tetrahydropyran-4-yl-isoquinoline (S20)

S11

C34

-continued

S20

Step 1. Synthesis of 7-benzyloxy-4-(2-methyl-4-pyridyl)-2-oxido-3-tetrahydropyran-4-yl-isoquinolin-2-ium (C34)

A suspension of S11 (2.97 g, 7.169 mmol), (2-methyl-4-pyridyl)boronic acid (1.83 g, 13.36 mmol) and aqueous solution of Na$_2$CO$_3$ (7 mL of 2M, 14.0 mmol) in DMSO (60 mL) was sparged with N$_2$ for 5 min. Pd(dppf) Cl2·dichloromethane (400 mg, 0.4898 mmol) was added and the reaction was sparged with N$_2$ for another 5 minutes. The resulting mixture was heated at 100° C. and stirred for 3 hours. After completion of the reaction, the reaction mixture was cooled to room temperature, diluted with water and extracted with EtOAc three times. The combined organic layers were dried over anhydrous Na$_2$SO$_4$, filtered, and concentrated under reduced pressure to give C34 (2.6 g, 85%) as a tan solid. $^1$H NMR (300 MHz, DMSO-d$_6$) δ 8.92 (s, 1H), 8.65 (dd, J=5.0, 0.8 Hz, 1H), 7.54-7.33 (m, 6H), 7.31-7.26 (m, 1H), 7.24-7.17 (m, 2H), 6.92 (d, J=9.2 Hz, 1H), 5.22 (s, 2H), 3.82 (dd, J=11.1, 3.7 Hz, 2H), 3.06 (t, J=11.5 Hz, 3H), 2.82-2.59 (m, 2H), 2.57 (s, 3H), 1.42-1.27 (m, 2H). LCMS m/z 427.3 [M+H]$^+$ Step 2. Synthesis of 1-(4-aza-1-azoniabicyclo[2.2.2] octan-1-yl)-7-benzyloxy-4-(2-methyl-4-pyridyl)-3-tetrahydropyran-4-yl-isoquinoline (S20)

A solution of C34 (513 mg, 1.203 mmol) and DABCO (500 mg, 4.457 mmol) in dichloromethane (10 mL) was cooled to 0° C., and to this was added TFAA (450 μL, 3.237 mmol). The resulting mixture was allowed to warm to room temperature and stirred for another 1 h and then concentrated to dryness. The residue was dissolved in minimum of DMSO and purified by reverse phase chromatography (C18, eluting from 10% to 100% CH$_3$CN in water with 0.1% TFA modifier) to give S20 bistrifluoroacetate salt (930 mg, 99%) as an off-white solid. LCMS m/z 521.35 [M+H]$^+$ Preparation of S21

7-benzyloxy-2-chloro-4-(4-fluorophenyl)-3-tetrahydropyran-4-yl-quinoline (S21)

C35

-continued

C36

C37

C38

C39

C40

-continued

S21

Step 1. Synthesis of 4-benzyloxy-2-nitro-benzonitrile (C36)

CuCN (4.6507 g, 51.926 mmol) was added to a stirred solution of C35 (8.0 g, 25.963 mmol) in DMF (100 mL). The resulting mixture was heated at 150° C. and stirred for 3 hours. After completion of reaction, the mixture was cooled to room temperature. The reaction mixture was diluted with water (200 mL) and extracted with EtOAc (2×100 mL). The combined organic layers were washed with brine, dried over anhydrous $Na_2SO_4$, filtered, and concentrated to give a crude C36 (6 g, 91%) as a light grey solid, which was used in the next step without further purification. $^1$H NMR (400 MHz, DMSO-$d_6$) δ 8.1 (d, J=8.6 Hz, 1H), 7.97 (d, J=2.44, 1H), 7.61 (dd, J=2.48, 8.68 Hz, 1H), 7.49 (d, J=7.04 Hz, 2H), 7.44-7.35 (m, 3H), 5.34 (s, 2H).

Step 2. Synthesis of 2-amino-4-benzyloxy-benzonitrile (C37)

A solution of C36 (3 g, 11.800 mmol) in acetic acid (13 mL) was cooled 0° C., and to this Fe powder (13.179 g, 236.00 mmol) was added. The reaction was allowed to warm up to room temperature and stirred for 2 hours. After completion of reaction, the reaction mixture was filtered through celite. The residue was diluted with $Na_2CO_3$ solution and extracted with EtOAc (3×50 mL). The combined organic layers were washed with brine, dried over $Na_2SO_4$, and concentrated to give crude C37 (2.3 g, 87%) as a white solid, which was used in the next step without further purification. $^1$H NMR (400 MHz, Chloroform-d) δ 7.37-7.25 (m, 6H), 6.38 (dd, J=8.7, 2.2 Hz, 1H), 6.27 (d, J=2.3 Hz, 1H), 5.04 (s, 2H), 4.37 (s, 2H).

Step 3. Synthesis of (2-amino-4-benzyloxy-phenyl)-(4-fluorophenyl)methanone (C38)

To a stirred solution of C37 (16 g, 71.346 mmol) and (4-fluorophenyl)boronic acid (19.965 g, 142.69 mmol) in 2-MeTHF (160 mL) and water (80 mL) was added 5,5'-Dimethyl-2,2'-dipyridyl (1.3145 g, 7.1346 mmol), Pd(TFA)$_2$ (1.1860 g, 3.5673 mmol) and methanesulfonic acid (46.298 mL, 713.46 mmol) under $N_2$ at room temperature. The resulting mixture was heated at 80° C. and stirred for 30 hours. After completion of reaction, the reaction mixture was quenched with $Na_2CO_3$ solution and extracted with EtOAc (2×200 mL). The combined organic layers were washed with water (100 mL) and brine (100 mL), dried over anhydrous $Na_2SO_4$, filtered, and concentrated. The residue was purified with silica gel chromatography, eluting with 0% to 10% EtOAc in heptane to give C38 (18.375 g, 80%) as a white solid. $^1$H NMR (400 MHz, DMSO-$d_6$) δ 7.61-7.52 (m, 2H), 7.48-7.36 (m, 4H), 7.39-7.26 (m, 6H), 7.25-7.17 (m, 1H), 5.75 (s, 1H), 5.10 (s, 2H).

Step 4. Synthesis of N-[5-benzyloxy-2-(4-fluo-robenzoyl)phenyl]-2-tetrahydropyran-4-yl-acetamide (C39)

A catalytic amount of DMF was added to a mixture of $SOCl_2$ (4.6649 g, 2.8601 mL, 39.210 mmol) and 2-tetrahy-dropyran-4-ylacetic acid (3.3917 g, 23.526 mmol). The resulting mixture was refluxed for 1 hours. After complete formation of acid chloride, the reaction mixture was evaporated and then dissolved in dichloromethane (30 mL). This suspension was added to the mixture of C38 (6.3 g, 19.605 mmol) and pyridine (7.7538 g, 7.9282 mL, 98.025 mmol) in dichloromethane (147 ml) at 0° C. The reaction mixture was stirred at room temperature for 1 hours. The reaction was quenched with 1 N HCl and extracted with dichloromethane (100 mL). The organic layer was dried over anhydrous $Na_2SO_4$ and evaporated to dryness. The residue was purified by silica gel chromatography, eluting 0% to 20% EtOAc in heptane to give C39 (7.4 g, 84%) as a light yellow solid. $^1H$ NMR (400 MHz, Chloroform-d) δ 11.50 (s, 1H), 8.53 (d, J=2.6 Hz, 1H), 7.70-7.61 (m, 2H), 7.53-7.30 (m, 6H), 7.20-7.10 (m, 2H), 6.64 (dd, J=8.8, 2.6 Hz, 1H), 5.16 (s, 2H), 4.00-3.91 (m, 2H), 3.43 (td, J=11.8, 2.1 Hz, 2H), 2.39 (d, J=7.1 Hz, 2H), 2.17 (dp, J=11.6, 4.0 Hz, 1H), 1.75-1.67 (m, 2H), 1.44 (dd, J=12.2, 4.4 Hz, 1H), 1.43-1.34 (m, 1H). LCMS m/z 448.3 $[M+H]^+$

Step 5. Synthesis of 7-benzyloxy-4-(4-fluorophe-nyl)-3-tetrahydropyran-4-yl-quinolin-2-ol (C40)

To a stirred solution of C39 (6 g, 13.408 mmol) in toluene (125 mL) was added NaOtBu (3.8657 g, 40.224 mmol). The reaction mixture was refluxed for 16 hours. After completion of the reaction, the reaction mixture was evaporated. The residue was diluted with dichloromethane (300 mL) and washed with water. The organic layer was dried over anhydrous $Na_2SO_4$, filtered, and concentrated. The residue was purified by silica gel chromatography, eluting with 30% EtOAc in hexane to give C40 (3.2 g, 49%) as an off-white solid. $^1H$ NMR (400 MHz, DMSO-d6) δ 11.74 (s, 1H), 7.45-7.27 (m, 8H), 6.92 (d, J=2.28 Hz, 1H), 6.73 (dd, J=9, 2.4 Hz, 1H), 6.65 (d, J=8.92 Hz, 1H), 5.12 (s, 2H), 3.78 (d, J=9.64 Hz, 2H), 2.99 (t, J=11.24 Hz, 2H), 2.50 (d, J=21.4, 3H) 1.22 (d, J=8.68 Hz, 2H). LCMS m/z 430.0 $[M+H]^+$

Step 6. Synthesis of 7-benzyloxy-2-chloro-4-(4-fluorophenyl)-3-tetrahydropyran-4-yl-quinoline (S21)

A solution of C40 (300 mg, 0.6985 mmol) in toluene (1.5 mL) was cooled to 0° C., and to this was added $SOCl_2$ (831.01 mg, 0.5095 mL, 6.9850 mmol) followed by a catalytic amount of DMF. The resulting mixture was heated to 80° C. and stirred for 3 hours. After completion of the reaction, the reaction mixture was evaporated. The residue was diluted with dichloromethane (20 mL) and washed with sat. $NaHCO_3$ solution (10 mL) and water (10 mL). The organic layer was dried over anhydrous $Na_2SO_4$ and concentrated. The residue was purified by silica gel chromatography, eluting with 20% EtOAc in hexane to obtain S21 (300 mg, 89%) as a light yellow solid. $^1H$ NMR (400 MHz, DMSO-d6) δ 7.49-7.33 (m, 10H), 7.26-7.23 (m, 1H), 7.03 (d, J=9.4 Hz, 1H), 5.76 (s, 1H), 5.30 (s, 2H), 3.85 (d, J=10.8

Hz, 2H), 3.62 (d, J=12.6 Hz, 1H), 3.07 (s, 4H), 1.44 (d, J=13.1 Hz, 2H). LCMS m/z 448.0 $[M+H]^+$

Preparation of S22

Synthesis of 2-chloro-4-(4-fluorophenyl)-3-isopropyl-7-methoxy-quinoline (S22)

S18

C41

C42

C43

-continued

S22

Step 1. Synthesis of 4-(4-fluorophenyl)-3-isopropenyl-7-methoxy-quinoline (C41)

A suspension of S18 (3 g, 12.581 mmol), (4-fluorophenyl) boronic acid (2.1124 g, 15.097 mmol), $K_2CO_3$ (3.4775 g, 25.162 mmol) in 1,4-dioxane (40 mL) and water (8 mL) was sparged with $N_2$ for 30 minutes. $PCy_3$ (352.81 mg, 1.2581 mmol) and $Pd(PPh_3)_4$ (1.0177 g, 0.8807 mmol) were added under $N_2$ and the reaction was heated at 100° C. and stirred for 18 hours. After completion of the reaction, the reaction mixture was filtered through celite, washed with EtOAc (80 mL) and concentrated. The residue was purified by silica gel chromatography, eluting with 0% to 100% EtOAc in hexane to afford C41 (4 g, 95%) as an off-white solid. $^1$H NMR (400 MHz, Chloroform-d) δ 8.76 (s, 1H), 7.52-7.43 (m, 2H), 7.35-7.25 (m, 2H), 7.19-7.13 (m, 2H), 7.12-7.08 (m, 1H), 5.20-5.14 (m, 1H), 5.05-4.96 (m, 1H), 3.95 (s, 3H), 1.63 (s, 3H). LCMS m/z 294.0 [M+H]$^+$

Step 2. Synthesis of 4-(4-fluorophenyl)-3-isopropyl-7-methoxy-quinoline (C42)

Pd (50 mg, 0.4698 mmol) was added to a solution of S18 (1.3 g, 4.432 mmol) in EtOH (20 mL) under $N_2$. The resulting mixture was stirred at room temperature under a $H_2$ balloon for 18 hours. The reaction mixture was filtered through a plug of Celite and concentrated under reduced pressure to give C42(1.26 g, 92%) LCMS m/z 295.32 [M+H]$^+$

Step 3. Synthesis of 4-(4-fluorophenyl)-3-isopropyl-7-methoxy-1-oxido-quinolin-1-ium (C43)

To a solution of C42 (1.36 g, 4.370 mmol) in dichloromethane (10 mL) was added m-CPBA (1.54 g, 8.924 mmol). The reaction mixture was stirred at room temperature for 2 hours. The reaction mixture was diluted with dichloromethane and washed with sat. NaHCO$_3$ solution. The organic layer was dried over MgSO$_4$, filtered and concentrated under reduced pressure. The residue was purified by silica gel chromatography eluting with 0% to 20% MeOH in dichloromethane to give C43 (1.05 g, 69%) $^1$H NMR (400 MHz, Chloroform-d) δ 8.53 (s, 1H), 8.04 (d, J=2.6 Hz, 1H), 7.19-7.13 (m, 5H), 7.06 (dd, J=9.2, 2.7 Hz, 1H), 3.94 (s, 3H), 2.80 (hept, J=7.0 Hz, 1H), 1.13 (d, J=7.0 Hz, 6H). $^{19}$F NMR (376 MHz, Chloroform-d) δ −113.33. LCMS m/z 312.49 [M+H]$^+$

Step 4. Synthesis of 2-chloro-4-(4-fluorophenyl)-3-isopropyl-7-methoxy-quinoline (S22)

POCl$_3$ (600 μL, 6.437 mmol) and DMF (150 μL, 1.937 mmol) were successively added in a dropwise manner to a solution of C43 (0.731 g, 2.113 mmol) in dichloromethane (10 mL) at 0° C. The resulting mixture was allowed to warm up to room temperature and stirred for 18 hours. The reaction mixture was diluted with aqueous solution of Na$_2$CO$_3$ and extracted with dichloromethane. The organic layer was dried over MgSO$_4$, filtered and concentrated under reduced pressure to give S22 (695.4 mg, 85%) as an off-white solid. $^1$H NMR (300 MHz, Chloroform-d) δ 7.28 (dd, J=2.3, 0.8 Hz, 1H), 7.17-7.08 (m, 4H), 6.99-6.94 (m, 2H), 3.85 (s, 3H), 3.22-2.98 (m, 1H), 1.25 (d, J=7.2 Hz, 6H). 19 F NMR (282 MHz, Chloroform-d) δ −113.52. LCMS m/z 329.66 [M+H]$^+$

Preparation of S23

7-benzyloxy-2-chloro-4-(4-fluoro-3-methyl-phenyl)-3-isopropyl-quinoline (S23)

-continued

C47

C48

S23

Step 1. Synthesis of 4-(4-fluoro-3-methyl-phenyl)-3-isopropenyl-7-methoxy-quinolin (C44)

A suspension of S18 (3.22 g, 13.78 mmol), (4-fluoro-3-methyl-phenyl)boronic acid (5.3 g, 34.43 mmol, and $Na_2CO_3$ (5.9 g, 55.67 mmol) in DMF (30 mL) was sparged with $N_2$ for 2 minutes. $Pd(PPh_3)_4$ (811 mg, 0.7018 mmol) was added and the resulting mixture was heated at 120° C. and stirred for 12 hours. The reaction mixture was cooled to room temperature, diluted with EtOAc (200 mL) and washed with water (200 mL) and brine (200 mL). The organic layer was dried over anhydrous $Na_2SO_4$, filtered and concentrated under reduced pressure. The residue was purified by silica gel chromatography eluting with 10% to 90% EtOAc in hexane to give C44 (3.6 g, 66%). LCMS m/z 307.34 [M+H]$^+$

Step 2. Synthesis of 4-(4-fluoro-3-methyl-phenyl)-3-isopropyl-7-methoxy-quinoline (C45)

Pd (131.57 mg, 1.2363 mmol) was added to a stirred solution of C44 (380 mg, 1.2363 mmol) in EtOH (7 mL) under $N_2$. The resulting mixture was stirred at room temperature under a $H_2$ balloon for 12 hours. The reaction mixture was filtered through celite, washed with EtOH and concentrated under reduced pressure to give C45 (380 mg, 99%), which was used in the next step without further purification. LCMS m/z 310.2 [M+H]$^+$

Step 3. Synthesis of 4-(4-fluoro-3-methyl-phenyl)-3-isopropyl-quinolin-7-ol (C46)

A solution of $BBr_3$ (56.566 mL of 1M in dichloromethane, 56.566 mmol) was added dropwise to a solution of C45 (2.5 g, 8.0808 mmol) in dichloromethane (25 mL) at 0° C. The resulting mixture was heated at 60° C. for 4 hours. The reaction mixture was concentrated, neutralized with sat. $NaHCO_3$ solution and extracted with dichloromethane (2×50 mL). The combined organic layers were washed with brine, dried over anhydrous $Na_2SO_4$, filtered, and concentrated under reduced pressure. The residue was purified by silica gel chromatography eluting with 0% to 70% EtOAc in hexane to give C46 (1.8 g, 63%). LCMS m/z 296.1 [M+H]$^+$

Step 4. Synthesis of 7-benzyloxy-4-(4-fluoro-3-methyl-phenyl)-3-isopropyl-quinoline (C47)

To a stirred solution of C46 (2 g, 6.7716 mmol) in DMF (10 mL) was added $K_2CO_3$ (2.3397 g, 16.929 mmol) followed by benzyl chloride (1.0286 g, 0.9351 mL, 8.1259 mmol) at room temperature. The resulting mixture was stirred for 18 h at room temperature. The mixture was quenched with sat. $NaHCO_3$ solution (10 ml) and extracted with EtOAc. The organic layer was washed with brine, dried over anhydrous $Na_2SO_4$ and concentrated under reduced pressure. The residue was purified with silica gel chromatography, eluting with 0% to 20% EtOAc in hexane to give C47 (1.65 g, 62%) as a white solid. LCMS m/z 387.6 [M+H]$^+$

Step 5. Synthesis of 7-benzyloxy-4-(4-fluoro-methyl-phenyl)-3-isopropyl-1-oxido-quinolin-1-ium (C48)

To a solution of C47 (650 mg, 1.6862 mmol) in dichloromethane (15 mL) was added m-CPBA (581.96 mg, 3.3724 mmol). The resulting mixture was stirred at room temperature for 18 hours. The reaction mixture was diluted with EtOAc and washed with a sat. $NaHCO_3$ solution. The organic layer was dried over anhydrous $Na_2SO_4$, filtered and concentrated under reduced pressure. The residue was then triturated with 10% dichloromethane in pentane and concentrated to afford C48 (550 mg, 69%) as an off-white solid. LCMS m/z 386.2 [M+H]$^+$

Step 6. Synthesis of 7-benzyloxy-2-chloro-4-(4-fluoro-3-methyl-phenyl)-3-isopropyl-quinoline (S23)

$POCl_3$ (840.25 mg, 0.5108 mL, 5.4800 mmol) and DMF (100.14 mg, 0.1061 mL, 1.3700 mmol) were successively added in a dropwise manner to a solution of C48 (550 mg, 1.3700 mmol) in dichloromethane (6 mL) at 0° C. The resulting mixture was allowed to warm up to room temperature and stirred at this temperature for 18 hours. After completion of the reaction, solvent was evaporated under reduced pressure and the residue was washed with sat. $Na_2CO_3$ solution (10 mL) and extracted with EtOAc (2×10 mL). The combined organic layers were dried over anhydrous $Na_2SO_4$, filtered and concentrated under reduced pressure. The residue was purified by silica gel chromatography, eluting with 5% to 10% EtOAc in hexane to afford S23 (500 mg, 81%) as an off-white solid. LCMS m/z 420.49 [M+H]$^+$

Preparation of S24

4-chloro-3-isopropyl-2-methyl-quinolin-7-ol (S24)

C42 m-CPBA →

C49

POCl₃ →

S24

Step 1. Synthesis of 4-(4-fluoro-3-methyl-phenyl)-3-isopropyl-7-methoxy-1-oxido-quinolin-1-ium (C49)

To a solution of C42 (85 mg, 0.2747 mmol) in dichloromethane (5 mL) was added m-CPBA (185 mg, 0.8255 mmol). The resulting mixture was stirred at room temperature for 2 hours. After completion of the reaction, the reaction was quenched with sat. NaHCO₃ solution and extracted with dichloromethane. The organic layer was dried over anhydrous Na₂SO₄, filtered, and concentrated. The residue was purified by silica gel chromatography, eluting with 0% to 10% MeOH in dichloromethane to give C49 (85 mg, 95%). $^1$H NMR (300 MHz, Chloroform-d) δ 8.61 (s, 1H), 8.12 (d, J=2.6 Hz, 1H), 7.28 (d, J=9.2 Hz, 1H), 7.22-6.99 (m, 4H), 4.02 (s, 3H), 2.90 (p, J=6.9 Hz, 1H), 2.37 (d, J=2.0 Hz, 3H), 1.21 (dd, J=6.9, 3.8 Hz, 6H) ppm. LCMS m/z 326.59 [M+H]⁺

Step 2. Synthesis of 2-chloro-4-(4-fluoro-3-methyl-phenyl)-3-isopropyl-7-methoxy-quinoline (S24)

A mixture of C49 (80 mg, 0.2459 mmol) and POCl₃ (1120 µL, 1.287 mmol) in CHCl₃ (1.5 mL) was microwaved at 80°

C. for 3 hours. After completion of the reaction, the reaction mixture was quenched with water. Then sat. NaHCO₃ aqueous solution was added and the mixture was extracted with dichloromethane (2×10 mL). The combined organic layers were dried over anhydrous Na₂SO₄, filtered, and concentrated to give S24 (70 mg, 83%). $^1$H NMR (300 MHz, Chloroform-d) δ 7.40 (d, J=2.4 Hz, 1H), 7.23-6.97 (m, 5H), 3.95 (s, 3H), 3.22 (s, 1H), 2.38 (d, J=2.0 Hz, 3H), 1.45-1.29 (m, 6H) ppm. LCMS m/z 344.55 [M+H]⁺

Preparation of S25

4-chloro-3-isopropyl-2-methylquinolin-7-ol (S25)

C50

SOCl₂ →

C51

BBr₃ →

S25

Step 1. Synthesis of 4-chloro-3-isopropyl-7-methoxy-2-methyl-quinoline (C51)

A mixture of C50 (1.0 g, 4.324 mmol) and SOCl₂ (10 mL, 137.1 mmol) in DMF (500 µL, 6.457 mmol) was microwaved at 80° C. for 2 hours. After completion of the reaction, the reaction mixture was concentrated. The residue was diluted with cold water and sat. NaHCO₃ solution until precipitate formed. The solid was filtered, washed with water, and dried to afford C51 (1.0 g, 93%) $^1$H NMR (300 MHz, Chloroform-d) δ 8.12 (d, J=9.3 Hz, 1H), 7.32 (d, J=2.6 Hz, 1H), 7.21 (dd, J=9.2, 2.6 Hz, 1H), 3.96 (s, 3H), 2.82 (s, 3H), 1.50 (d, J=7.2 Hz, 6H) ppm. LCMS m/z 250.23 [M+H]⁺

Step 2. Synthesis of 4-chloro-3-isopropyl-2-methyl-quinolin-7-ol (S25)

A solution of BBr₃ (15 mL of 1 M in dichloromethane, 15.00 mmol) was added in a dropwise manner to a solution of C51 (900 mg, 3.604 mmol) in anhydrous dichloromethane (50 mL) at 0° C. under N₂. The resulting mixture was allowed to warm up to room temperature and stirred for 60 hours. After completion of the reaction, the mixture was cooled down to 0° C., quenched with cold water and evaporated to remove dichloromethane. Water was added and the mixture was extracted with EtOAc. The organic layer was washed with brine, dried over Na$_2$SO$_4$, filtered, and concentrated to give S25 (650 mg, 75%). $^1$H NMR (300 MHz, DMSO-d6) δ 11.51 (s, 1H), 8.29 (d, J=9.3 Hz, 1H), 7.57-7.31 (m, 2H), 3.69 (s, 1H), 2.92 (s, 3H), 1.45 (d, J=7.2 Hz, 6H) ppm. LCMS m/z 236.19 [M+H]$^+$ Preparation of S26

7-benzyloxy-2-chloro-4-(4-fluorophenyl)-3-(2-methoxy-1-methyl-ethyl)quinoline (S26)

216

-continued

Step 1. Synthesis of 5-[(3-benzyloxyanilino)methyl-ene]-2,2-dimethyl-1,3-dioxane-4,6-dione (C53)

To a suspension of C52 (30 g, 150.57 mmol) and Meldrum's acid (25.607 g, 177.67 mmol) in EtOH (30 mL) was added trimethyl orthoformate (18.854 g, 177.67 mmol). The resulting mixture was heated to reflux for 1 hour. The reaction mixture was cooled down to room temperature and stirring was continued for another 2 hours. The suspension was filtered, and the solid residue was stirred in anhydrous EtOH (150 mL) for 2 hours. The solid residue was collected by filtration and dried in vacuo to give C53 (50 g, 92%). $^1$H NMR (400 MHz, DMSO-$d_6$) δ 11.21 (d, J=14.4 Hz, 1H), 8.61 (d, J=14.5 Hz, 1H), 7.47 (d, J=7.4 Hz, 2H), 7.40 (t, J=7.4 Hz, 2H), 7.37-7.29 (m, 3H), 7.12 (dd, J=8.2, 2.1 Hz, 1H), 6.91 (dd, J=8.2, 2.4 Hz, 1H), 5.16 (s, 2H), 1.68 (s, 6H). LCMS m/z 354.0 [M+H]$^+$

Step 2. Synthesis of 7-benzyloxy-1H-quinolin-4-one (C54)

A stirred mixture of C53 (50 g, 141.50 mmol) and Dowtherm A (100 mL) was heated at 220° C. for 30 min. The reaction mixture was cooled to RT and diluted with hexane (50 mL) until precipitation formed. The solid residue was collected by filtration and washed with hexane to give C54 (30 g, 79%) as a white solid. LCMS m/z 252.0 [M+H]$^+$

Step 3. Synthesis of 7-benzyloxy-3-bromo-1H-quinolin-4-one (C55)

To a suspension of C54 (1 g, 3.9796 mmol) in anhydrous DMF (4 mL) was added pyridine (978 mg, 1.00 mL, 12.364 mmol). The mixture was cooled to −16° C. and pyridinium tribromide (905 mg, 2.8297 mmol) was added within 5 minutes. After stirring for 1 hour, at which the temperature rose from −16° C. to −8° C., more pyridinium tribromide (249 mg, 0.7786 mmol) was added. After another 1 hour, more pyridinium tribromide (220 mg, 0.6879 mmol) was added again when the temperature rose from −8° C. to −6° C. The resulting mixture was stirred for another 1 hour. NaOAc (1.35 g, 16.457 mmol) was added followed by water (40 mL). The mixture was stirred for 10 min at 0° C., and then the solid was filtered, washed with water (5×10 mL) and dried under vacuum to afford C55 (1.3 g, 96%) as yellow solid. $^1$H NMR (300 MHz, DMSO-$d_6$): δ 5.21 (s, 2H), 7.01-7.11 (m, 2H), 7.30-7.45 (m, 3H), 7.46-7.53 (m, 2H), 8.00-8.07 (m, 1H), 8.38 (d, J=6.1 Hz, 1H), 12.01-12.12 (m, 1H); LCMS m/z 330.0 [M+H]$^+$

Step 4. Synthesis of 7-benzyloxy-3-bromo-4-chloro-quinoline (C56)

To a suspension of C55 (11.59 g, 33.347 mmol) in SOCl$_2$ (97.860 g, 60 mL, 822.55 mmol) was added DMF (28.320 mg, 0.03 mL, 0.3874 mmol). The mixture was heated to 70° C. and stirred for 1.5 hours. After completion of the reaction, SOCl$_2$ was co-evaporated with addition of toluene (2×75 ml). The residue was diluted with sat. NaHCO$_3$ solution (3×150 mL) and extracted with dichloromethane (3×100 mL). The combined organic layers were washed with brine (2×100 mL), dried over Na$_2$SO$_4$, filtered, and concentrated. The residue was triturated in CH$_3$CN (50 mL) at stirred at room temperature for 3 hours. The residue was filtered off, washed with MTBE (2×5 mL) and dried in vacuo to afford C56 (10.91 g, 91%) as beige solid. $^1$H NMR (300 MHz, DMSO-$d_6$) δ 5.33 (s, 2H), 7.31-7.46 (m, 3H), 7.47-7.55 (m, 3H), 7.56-7.63 m, 1H), 8.15 (d, J=9.2 Hz, 1H), 8.98 (s, 1H); LCMS m/z 348.0 [M+H]$^+$

Step 5

Synthesis of 7-benzyloxy-4-chloro-3-isopropenyl-quinoline (C57)

A suspension of C56 (6 g, 15.490 mmol), potassium trifluoro(isopropenyl)borate (2.5214 g, 17.039 mmol), K$_2$CO$_3$ (6.4224 g, 46.470 mmol) in 1,4-dioxane (50 mL) and water (10 mL) was sparged with N$_2$ for 30 minutes. Pd(dppf) Cl$_2$·dichloromethane (1.2650 g, 1.5490 mmol) was added and the reaction was heated at 100° C. for 18 hours. The reaction mixture was cooled to room temperature, filtered through Celite®, washed with EtOAc and concentrated under reduced pressure. The residue was purified by silica gel chromatography eluting with 0% to 10% EtOAc in hexane to give C57 (4.3 g, 84%) as a white solid. LCMS m/z 310.0 [M+H]$^+$

Step 6. Synthesis of 7-benzyloxy-4-(4-fluorophe-nyl)-3-isopropenyl-quinoline (C58)

A mixture of C57 (6 g, 19.368 mmol), (4-fluorophenyl) boronic acid (3.2520 g, 23.242 mmol), and K$_2$CO$_3$ (5.3535 g, 38.736 mmol) in 1,4-dioxane (60 mL) and H$_2$O (10 mL) was sparged with N$_2$ for 10 minutes. Pd(PPh$_3$)$_4$ (1.5667 g, 1.3558 mmol) and PCy$_3$ (543.13 mg, 1.9368 mmol) were successively added under N$_2$ and the reaction was heated at 90° C. for 18 hours. The reaction mixture was cooled to room temperature, filtered through celite, washed with EtOAc and concentrated under reduced pressure. The residue was purified by silica gel chromatography eluting with 0% to 20% EtOAc in hexane to give C58 (6 g, 79%) as a white solid. LCMS m/z 370.3 [M+H]$^+$

Step 7. Synthesis of 2-[7-benzyloxy-4-(4-fluorophe-nyl)-3-quinolyl]propan-1-ol (C59)

9-BBN (54.192 mL of 0.5M, 27.096 mmol) was added dropwise to a solution of C58 (4.4 g, 7.7416 mmol) in THF (44.000 mL) at 0° C. After 1 hours, more 9-BBN (23.224 mL of 0.5M, 11.612 mmol) was added in a dropwise manner at 0° C. Stirring was continued for another 1 hours at room temperature, at which another lot of 9-BBN (30.966 mL of 0.5 M, 15.483 mmol) was added at 0° C. The resulting mixture was stirred at room temperature for 18 hours. After completion of the reaction, the reaction mixture was cooled to 0° C. An aqueous solution of NaOH (10.529 mL of 1 M, 10.529 mmol) and H$_2$O$_2$ (26.333 g, 23.723 mL, 232.25 mmol) were successively added in a dropwise manner. The reaction mixture was allowed to warm to room temperature and stirred for 2 hours. The reaction mixture was diluted with EtOAc (100 mL), washed with water (3×25 mL). The organic layer was washed with brine (25 mL), dried over anhydrous Na$_2$SO$_4$ and concentrated. This residue was purified by silica gel chromatography, eluting with 60% EtOAc in hexane to afford C59 (2.8 g, 90%) as sticky light-yellow gum. LCMS m/z 388.0 [M+H]$^+$

Step 8. Synthesis of 7-benzyloxy-4-(4-fluorophe-nyl)-3-(2-methoxy-1-methyl-ethyl)quinoline (C60)

NaH (891.91 mg, 60% w/w, 22.300 mmol) was added to a stirred solution of C59 (1.8 g, 4.4600 mmol) in THF (40 mL) at 0° C. The resulting mixture was stirred at this temperature for 30 min and then CH₃I (2.5322 g, 1.1106 mL, 17.840 mmol) was added. The resulting mixture was stirred at RT for 2 hours. After completion, the mixture was diluted with sat. NH₄Cl solution (10 mL) and extracted with dichloromethane (20 mL). The organic layer was dried over Na₂SO₄, filtered, concentrated under reduced pressure. The residue was purified by silica gel column chromatography, eluting with 30% EtOAc in hexane to obtain pure C60 (1.1 g, 61%) as sticky yellow gum. ¹H NMR (400 MHz, DMSO-d₆) δ 8.91 (s, 1H), 7.54-7.47 (m, 3H), 7.37 (dt, J=27.9, 7.4 Hz, 7H), 7.23 (dd, J=9.4, 2.5 Hz, 1H), 7.15 (d, J=9.2 Hz, 1H), 5.29 (s, 2H), 3.54 (t, J=8.5 Hz, 1H), 3.45 (dd, J=9.5, 6.7 Hz, 1H), 3.12 (s, 3H),1.18 (d, J=6.9 Hz, 3H). LCMS m/z 402.0 [M+H]⁺

Step 9. Synthesis of 7-benzyloxy-4-(4-fluorophenyl)-3-(2-methoxy-1-methyl-ethyl)-1-oxido-quinolin-1-ium (C61)

To a solution of C60 (1.1 g, 2.7399 mmol) in dichloromethane (30 mL) was added m-CPBA (709.21 mg, 4.1098 mmol) at 0° C. The resulting mixture was stirred at RT for 3 h. The reaction mixture was diluted with dichloromethane (10 mL), washed with sat. Na₂CO₃ solution (25 mL), water (25 mL) and brine (25 mL). The organic layer was dried over Na₂SO₄, filtered and concentrated under reduced pressure to give C61 (1 g, 83%), which was used in the next step without further purification. ¹H NMR (400 MHz, DMSO-d₆) δ 8.71 (s, 1H), 8.07 (d, J=2.7 Hz, 1H), 7.51 (d, J=7.1 Hz, 2H), 7.45-7.37 (m, 4H), 7.41-7.31 (m, 4H), 7.23 (d, J=9.2 Hz, 1H), 5.33 (s, 2H), 3.52 (dd, J=9.6, 7.7 Hz, 1H), 3.41 (dd, J=9.6, 6.3 Hz, 1H), 3.13 (s, 3H), 1.14 (d, J=7.0 Hz, 3H). LCMS m/z 418.0 [M+H]⁺

Step 10. Synthesis of 7-benzyloxy-2-chloro-4-(4-fluorophenyl)-3-(2-methoxy-1-methyl-ethyl)quinoline (S26)

POCl₃ (293.81 mg, 0.1786 mL, 1.9162 mmol) and catalytic amount of DMF were successively added in a dropwise manner to a stirred solution of C61 (400 mg, 0.9581 mmol) in toluene (4 mL). The resulting mixture was heated at 80° C. and stirred for 2 hours.

After completion of the reaction, reaction mixture was evaporated, diluted with EtOAc (50 mL) and washed with sat. NaHCO₃ (20 mL) solution. The organic layer was dried over anhydrous Na₂SO₄, filtered, and concentrated. The residue was purified by column chromatography, eluting with 10% EtOAc in hexane to give S26 (350 mg, 82%) as a yellow gum. ¹H NMR (400 MHz, DMSO-d₆) δ 7.53-7.30 (m, 10H), 7.25 (dd, J=9.3, 2.6 Hz, 1H), 7.03 (d, J=9.3 Hz, 1H), 5.30 (s, 2H), 3.78 (s, 1H), 3.51 (s, 1H), 3.10 (s, 3H), 1.23 (s, 3H). LCMS m/z 436.0 [M+H]⁺

Preparation of S27

4-(4-fluoro-3-methyl-phenyl)-7-methoxy-2-methyl-quinoline (S27)

C62

-continued

S27

To a solution of C62 (150 mg, 0.5950 mmol) and (4-fluoro-3-methyl-phenyl)boronic acid (140 mg, 0.9094 mmol) in DMF (3 mL), Pd(dppf)Cl₂ (25 mg, 0.03061 mmol) was added under nitrogen. Then, an aqueous solution of Na₂CO₃ (600 μL of 2M, 1.2 mmol) was added and the reaction was heated in a microwave reactor at 110° C. for 30 minutes. The reaction mixture was diluted with water (30 mL) and filtered. Purification by silica gel chromatography (10-60% EtOAc in heptane) afforded S27 (149 mg, 88%) ¹H NMR (300 MHz, Chloroform-d) δ 7.73 (d, J=9.2 Hz, 1H), 7.44 (d, J=2.6 Hz, 1H), 7.34-7.29 (m, 1H), 7.28-7.24 (m, 1H), 7.20-7.05 (m, 3H), 3.98 (s, 3H), 2.75 (s, 3H), 2.39 (d, J=2.0 Hz, 3H). LCMS m/z 281.93 [M+H]⁺

Preparation of S28

2-[7-benzyloxy-4-(4-fluoro-3-methyl-phenyl)-1-oxido-quinolin-1-ium-3-yl]propan-1-ol (S28)

C57

C63

-continued

C64

S28

Step 1. 7-benzyloxy-4-(4-fluoro-3-methyl-phenyl)-3-isopropenyl-quinoline (C63)

To a solution of C57 (3.5 g, 9.3209 mmol) in 1,4-dioxane (50 mL) were added (4-fluoro-3-methyl-phenyl)boronic acid (1.7219 g, 11.185 mmol) and a solution of $K_2CO_3$ (2.5764 g, 18.642 mmol) in water (10 mL). The reaction mixture was degassed with argon for 30 minutes, and $PCy_3$ (261.39 mg, 0.9321 mmol) and $Pd(PPh_3)_4$ (754.00 mg, 0.6525 mmol) were added. The reaction was heated at 100° C. for 18 hours. The mixture was filtered through a Celite plug, washed with EtOAc (150 mL) and concentrated. Purification by silica gel chromatography (15% EtOAc in hexanes) afforded C63 (2.9 g, 68%) as an off white solid. $^1H$ NMR (400 MHz, Chloroform-d) δ 8.74 (s, 1H), 7.56-7.44 (m, 4H), 7.44-7.29 (m, 3H), 7.21-7.12 (m, 1H), 7.16-7.03 (m, 2H), 5.22 (s, 2H), 5.16 (s, 1H), 4.98 (s, 1H), 2.33 (s, 3H), 1.65 (s, 3H). LCMS m/z 384.0 [M+H]$^+$

Step 2. 2-[7-benzyloxy-4-(4-fluoro-3-methyl-phenyl)-3-quinolyl]propan-1-ol (C64)

To a solution of C68 (2.9 g, 6.383 mmol) in dry THF (30 mL), a solution of 9-BBN (44.680 mL of 0.5M, 22.34 mmol) in THF was added drop wise at 0° C. The reaction mixture was stirred at room temperature for 1 hour, followed by drop wise addition of another amount of a solution of 9-BBN (19.149 mL of 0.5M, 9.5745 mmol) in THF at 0° C. The reaction mixture was stirred at room temperature for 1 hour more, and another portion of a solution of 9-BBN (25.532 mL of 0.5 M, 12.766 mmol) in THF was added at 0° C. The reaction was stirred at room temperature for additional 18 hours. The reaction mixture was cooled to 0° C. and an aqueous solution of NaOH (8.7 mL of 1M, 8.7000 mmol) was added drop wise, followed by drop wise addition of $H_2O_2$ (5.8442 g, 17.55 mL, 51.544 mmol). The reaction mixture was stirred at 0° C. for 45 minutes, warmed to room temperature and stirred for 1 hour more. The mixture was diluted with EtOAc (100 mL), washed successively with water (100 mL) and brine (100 mL), dried over $Na_2SO_4$ and concentrated. Purification by silica gel chromatography (60% EtOAc in hexanes) afforded C64 (4 g, 94%) as a light yellow solid. LCMS m/z 402.0 [M+H]$^+$

Step 3. 2-[7-benzyloxy-4-(4-fluoro-3-methyl-phenyl)-1-oxido-quinolin-1-ium-3-yl]propan-1-ol (S28)

To a solution of C64 (4 g, 5.9780 mmol) in dichloromethane (100 mL) was added m-CPBA (1.4737 g, 6.5758 mmol) at 0° C. The reaction mixture was stirred at room temperature for 3 hours. The reaction mixture was diluted with dichloromethane (50 ml), washed successively with an aqueous saturated solution of $NaHCO_3$ (40 ml), water (40 ml) and brine (40 ml). The organic phase was dried over $Na_2SO_4$ and concentrated to afford S28 (2.2 g, 84%) as a light brown solid which was advanced without further purification. 1H NMR (400 MHz, DMSO-$d_6$) δ 8.65 (s, 1H), 8.06 (d, J=2.7 Hz, 1H), 7.92-7.86 (m, 1H), 7.59-7.47 (m, 2H), 7.45-7.12 (m, 8H), 5.32 (s, 2H), 4.73-4.68 (m, 1H), 3.57-3.40 (m, 1H), 2.80-2.71 (m, 1H), 2.31 (s, 3H), 1.21-1.09 (m, 3H). LCMS m/z 418.0 [M+H]$^+$

Preparation of S29

7-benzyloxy-4-(4-fluoro-3-methyl-phenyl)-1-oxido-3-tetrahydropyran-4-yl-quinolin-1-ium (S29)

C56

C65

C66

-continued

C67

C68

S29

Step 1. 7-benzyloxy-4-chloro-3-(3,6-dihydro-2H-pyran-4-yl)quinoline (C65)

To a solution of K$_3$PO$_4$ (9.74 g, 45.886 mmol) in water (9 mL), was added toluene (100 mL) and the mixture was degassed with nitrogen for 15 minutes. Then, C56 (8 g, 22.259 mmol), 2-(3,6-dihydro-2H-pyran-4-yl)-4,4,5,5-tetramethyl-1,3,2-dioxaborolane (5.5 g, 26.181 mmol), PCy$_3$ (1.26 g, 4.4931 mmol) and Pd(OAc)$_2$ (575 mg, 2.5612 mmol) were successively added. The reaction was heated at 95° C. for 18 hours. The mixture was cooled to room temperature, diluted with EtOAc (600 mL), washed successively with an aqueous solution of 5% NaHCO$_3$ (150 mL×3) and brine (150 mL×2), dried over Na$_2$SO$_4$, filtered and concentrated. The residue was triturated with heptane (50 mL) and acetonitrile (30 mL), filtered and dried. Purification by silica gel chromatography (0-50% EtOAc in dichloromethane) afforded C65 (5.7 g, 73%) as a beige solid. $^1$H NMR (300 MHz, Chloroform-d) δ 2.45-2.62 (m, 2H), 3.98 (t, J=5.2 Hz, 2H), 4.37 (q, J=2.6 Hz, 2H), 5.22 (s, 2H), 5.85-5.94 (m, 1H), 7.29-7.58 (m, 7H), 8.18 (d, J=9.2 Hz, 1H), 8.60 (s, 1H). LCMS m/z 352.1 [M+H]$^+$

Step 2. 7-benzyloxy-3-(3,6-dihydro-2H-pyran-4-yl)-4-(4-fluoro-3-methyl-phenyl)quinoline (C66)

A suspension of C65 (2.9 g, 8.2427 mmol), (4-fluoro-3-methyl-phenyl)boronic acid (1.5227 g, 9.8912 mmol), K$_2$CO$_3$ (2.2783 g, 16.485 mmol), PCy$_3$ (231.16 mg, 0.8243 mmol) in 1,4-dioxane (26 mL) and water (3.7 mL) was degassed with nitrogen for 10 minutes. Then, Pd(PPh$_3$)$_4$ (666.76 mg, 0.5770 mmol) was added and the reaction mixture was heated at 100° C. for 12 hours. The mixture was filtered through a Celite® plug and washed with EtOAc. The solution was concentrated and purification by silica gel chromatography (20-30% EtOAc in hexanes) afforded C66 (2.5 g, 68%) as a white solid. LCMS m/z 426.0 [M+H]$^+$

Step 3. 4-(4-fluoro-3-methyl-phenyl)-3-tetrahydro-pyran-4-yl-quinolin-7-ol (C67)

A solution of C66 (1 g, 2.3502 mmol) in EtOH (20 mL) was degassed with nitrogen for 5 minutes and 10% palladium on carbon (2 g, 50% w/w, 9.396 mmol) was added. The container was purged with hydrogen and the reaction mixture stirred at room temperature for 2 hours. The mixture was filtered through a Celite® plug, washed with methanol (150 mL) and concentrated to afford C67 (600 mg, 72%) as a yellow solid. LCMS m/z 337.9 [M+H]$^+$

Step 4. 7-benzyloxy-4-(4-fluoro-3-methyl-phenyl)-3-tetrahydropyran-4-yl-quinoline (C68)

To a solution of C67 (3.4 g, 10.08 mmol) in DMF (45 mL), K$_2$CO$_3$ (3.4818 g, 25.193 mmol) was added. Then, the mixture was cooled to 0° C. and benzyl chloride (1.531 g, 1.39 mL, 12.09 mmol) was added drop wise. The reaction was stirred at room temperature for 12 hours. An additional 1 equiv. of benzyl chloride and 2.5 equiv. of K$_2$CO$_3$ were added at 0° C., and the reaction was warmed to room temperature for another 12 h. The mixture was diluted with EtOAc (250 mL), washed with ice cold water (30 mL×4), dried over Na$_2$SO$_4$ and concentrated. Purification by silica gel chromatography (50% EtOAc in hexanes) afforded C68 (2.5 g, 51%) as an off-white solid. $^1$H NMR (400 MHz, DMSO-d$_6$) δ 8.92 (s, 1H), 7.50 (dd, J=5.0, 2.3 Hz, 3H), 7.40 (dd, J=8.2, 6.5 Hz, 2H), 7.33 (td, J=9.5, 8.4, 3.9 Hz, 2H), 7.23 (dt, J=9.3, 2.6 Hz, 2H), 7.16 (d, J=9.1 Hz, 2H), 5.29 (s, 2H), 3.88 (t, J=5.8 Hz, 2H), 3.16 (t, J=11.5 Hz, 2H), 2.67-2.61 (m, 1H), 2.31 (s, 3H), 2.01-1.84 (m, 2H), 1.56 (d, J=13.0 Hz, 2H). LCMS m/z 427.9 [M+H]$^+$

Step 5. 7-benzyloxy-4-(4-fluoro-3-methyl-phenyl)-1-oxido-3-tetrahydropyran-4-yl-quinolin-1-ium (S29)

To a solution of C68 (2.7 g, 6.315 mmol) in dichloromethane (25 mL) was added m-CPBA (1.35 g, 7.831 mmol) at 0° C. The reaction was stirred at room temperature for 12 hours. The mixture was diluted with dichloromethane (200 mL), washed with an aqueous saturated solution of NaHCO$_3$ (30 mL) and concentrated. Purification by silica gel chromatography (5% MeOH in dichloromethane) afforded S29 (2.6 g, 84%) as a yellow solid. LCMS m/z 444.1 [M+H]$^+$

Preparation of S30

7-benzyloxy-2-chloro-4-(4-fluoro-3-methyl-phenyl)-
3-tetrahydropyran-4-yl-quinoline (S30)

S29

→ POCl₃, DMF

S30

To a solution of S29 (2.7 g, 6.089 mmol) in dichlorometh-ane (25 mL), POCl₃ (3.7338 g, 2.27 mL, 24.351 mmol) was added dropwise while in an ice bath, followed by DMF (472.0 mg, 0.5 mL, 6.457 mmol). The reaction was stirred at room temperature for 18 hours. The solvent was evapo-rated and a saturated aqueous solution of Na₂CO₃ (30 mL) was added. The mixture was extracted with EtOAc (100 mL×2), the organic phases were combined, dried over Na₂SO₄ and concentrated. Purification by silica gel chroma-tography (15% EtOAc in hexanes) afforded S30 (2.5 g, 89%) as a white solid. $^{1}$H NMR (400 MHz, DMSO-d₆) δ 7.50-7.30 (m, 8H), 7.25 (dd, J=9.2, 2.7 Hz, 2H), 7.06 (d, J=9.2 Hz, 1H), 5.76 (s, 1H), 5.29 (s, 2H), 4.03 (q, J=7.0 Hz, 1H), 3.85 (d, J=10.9 Hz, 2H), 3.07 (s, 4H), 2.32 (d, J=2.0 Hz, 4H), 1.99 (s, 1H), 1.44 (d, J=12.6 Hz, 2H), 1.26-1.13 (m, 1H). LCMS m/z 462.1 [M+H]$^{+}$

Preparation of S31

7-benzyloxy-4-chloro-3-(3,6-dihydro-2H-pyran-4-
yl)-1-oxido-quinolin-1-ium (S31)

C65

→ m-CPBA

-continued

S31

To a solution of C65 (1 g, 2.8423 mmol) in dichlorometh-ane (15 mL) was added m-CPBA (589 mg, 3.410 mmol), and the mixture was stirred at RT for 6 h. An aqueous saturated solution of Na₂CO₃ (20 mL) was added. The mixture was extracted with dichloromethane (30 mL×2), the organic phases were combined, dried over Na₂SO₄ and concentrated. The crude compound was washed with 20% EtOAc in hexanes to afford S31 (810 mg, 72%) as a white solid. LCMS m/z 368.0 [M+H]$^{+}$

Preparation of S32

7-benzyloxy-4-(4-fluorophenyl)-3-isopropenyl-1-
oxido-quinolin-1-ium (S32)

C57

→ Pd(PPh₃)₄, PCy₃ / K₂CO₃

C69

→ m-CPBA

S32

Step 1. 7-benzyloxy-4-(4-fluorophenyl)-3-isopropenyl-quinoline (C69)

C57 (6.0 g, 19.368 mmol), (4-fluorophenyl)boronic acid (3.252 g, 23.242 mmol), and $K_2CO_3$ (5.354 g, 38.736 mmol) were suspended in a mixture of 1,4-dioxane (60 mL) and water (10 mL). The suspension was degassed for 10 minutes and $Pd(PPh_3)_4$ (1.567 g, 1.3558 mmol) and $PCy_3$ (543 mg, 1.9368 mmol) were added. The reaction was heated at 90° C. for 18 hours. The mixture was filtered through a plug of Celite, washed with EtOAc and concentrated. Purification by silica gel chromatography (10-20% EtOAc in hexanes) afforded C69 as white solid. LCMS m/z 370.3 $[M+H]^+$

Step 2. 7-benzyloxy-4-(4-fluorophenyl)-3-isopropenyl-1-oxido-quinolin-1-ium (S32)

To a solution of C69 (6.0 g, 16.241 mmol) in dichloromethane (80 mL), m-CPBA (3.3631 g, 19.489 mmol) was added and the reaction was stirred at room temperature for 6 hours. The mixture was concentrated and a saturated aqueous solution of $NaHCO_3$ was added. The resulting suspension was stirred for 15 minutes, the solids were filtered and dried to afford S32 (5.2 g, 83%). LCMS m/z 386.3 $[M+H]^+$

Preparation of S33

8-benzyloxy-1-chloro-4-(4-fluorophenyl)-3-tetrahydropyran-4-yl-isoquinoline (S33)

C70

C71

C72

C73

C74

-continued

C75

C76

C77

S33

Step 1. trimethyl(2-tetrahydropyran-4-ylethynyl)silane (C71)

To a mixture of ethylmagnesium bromide (120 mL of 3M, 360.0 mmol) solution in $Et_2O$ and THF (200 mL), ethynyltrimethylsilane (50 mL, 353.8 mmol) was added dropwise and while in an ice bath. The reaction was heated to reflux for 1 hour. The mixture was cooled to room temperature and NMP (300 mL), 4-iodotetrahydropyran (C70) (50 g of 97% w/w, 228.7 mmol), and $FeBr_2$ (5 g, 23.19 mmol) were added successively. The mixture was placed under nitrogen and stirred at 30° C. for 4 hours. MTBE and aqueous saturated ammonium chloride (1:1, 800 mL) were added to the reaction mixture. The mixture was extracted with MTBE (20 mL×2), the organic phases were combined, dried over $Na_2SO_4$, filtered through a silica gel plug and rinse with MTBE to afford C71 (29.5 g, 70%) as an amber oil. $^1$H NMR (300 MHz, Chloroform-d) δ 3.88 (m, 2H), 3.48 (m, 2H), 2.64 (tt, J=8.4, 4.1 Hz, 1H), 1.87-1.74 (m, 2H), 1.72-1.57 (m, 2H), 0.15 (s, 9H).

Step 2. 2-benzyloxy-6-bromo-benzaldehyde (C73)

To a solution of C72 (5.25 g, 26.12 mmol) and bromomethylbenzene (3.2 mL, 26.90 mmol) in DMF (50 mL), K$_2$CO$_3$ (4.97 g, 35.96 mmol) was added. The mixture was stirred at room temperature for 3 hours. The reaction was diluted with EtOAc, washed successively with water (3×) and brine, dried over Na$_2$SO$_4$, filtered and concentrated to give C73 (7.35 g, 97%) as an off-white solid. $^1$H NMR (300 MHz, Chloroform-d) δ 10.50 (s, 1H), 7.54-7.23 (m, 7H), 7.02 (dd, J=7.5, 2.0 Hz, 1H), 5.21 (s, 2H). LCMS m/z 290.8 [M+H]$^+$

Step 3. 2-benzyloxy-6-(2-tetrahydropyran-4-ylethynyl)benzaldehyde (C74)

To a mixture of C71 (25 g, 85.87 mmol) and C73 (25 g, 137.1 mmol) in 1,4-dioxane (170 mL), N-isopropylpropan-2-amine (75 mL, 535.1 mmol), CuI (840 mg, 4.411 mmol), Pd(PPh$_3$)$_2$Cl$_2$ (2.5 g, 3.562 mmol) and TBAF dihydrate (40 g, 126.8 mmol) were added successively. The reaction was heated at 50° C. for 2 hours. The mixture was cooled to room temperature, poured into a mixture of water (50 mL), a saturated aqueous NH4Cl solution (100 mL) and ethyl acetate (500 mL), and stirred for 10 minutes. The organic phase was washed successively with an aqueous solution of HCl 1 M (100 mL×2) and brine (100 mL), dried over MgSO$_4$, filtered and concentrated. Purification by silica gel chromatography (0-70% EtOAc in heptane) afforded C74 (25 g, 91%) as a yellow viscous oil. $^1$H NMR (300 MHz, Chloroform-d) δ 10.65 (s, 1H), 7.50-7.30 (m, 6H), 7.11 (dd, J=7.7, 0.9 Hz, 1H), 6.96 (dd, J=8.5, 0.9 Hz, 1H), 5.20 (s, 2H), 3.97 (ddd, J=11.6, 5.9, 3.6 Hz, 2H), 3.58 (ddd, J=11.5, 8.2, 3.1 Hz, 2H), 2.94 (dt, J=8.3, 4.1 Hz, 1H), 2.02-1.87 (m, 2H), 1.80 (dtd, J=13.5, 8.2, 3.6 Hz, 2H). LCMS m/z 321.25 [M+H]$^+$.

Step 4. (1E)-2-benzyloxy-6-(2-tetrahydropyran-4-ylethynyl)benzaldehyde oxime (C75)

A mixture of hydroxylamine chlorohydrate (35 g, 503.7 mmol) in pyridine (130 mL, 1.607 mol) was stirred for 30 minutes at room temperature and a solution of C74 (50 g, 156.1 mmol) in acetonitrile (500 mL) was added over 20 minutes. The suspension was stirred at room temperature for 2 hours. The reaction was concentrated, and dichloromethane (600 mL) and a cold aqueous solution of HCl 1M (100 mL) were added to the residue. The mixture was stirred for 20 minutes and the organic layer was separated, washed successively with an aqueous solution of HCl 1 M (100 mL×2), water (100 mL), brine (100 mL), dried over MgSO$_4$, filtered and concentrated. The residue was triturated with MTBE (200 mL) and dried to afford C75 (40 g, 76%) as a white solid. $^1$H NMR (300 MHz, Chloroform-d) δ 9.21 (s, 1H), 8.63 (s, 1H), 7.48-7.28 (m, 5H), 7.22-7.11 (m, 1H), 7.08 (dd, J=7.7, 1.2 Hz, 1H), 6.88 (dd, J=8.2, 1.2 Hz, 1H), 5.22 (s, 2H), 3.95 (ddd, J=11.6, 6.0, 3.6 Hz, 2H), 3.56 (ddd, J=11.4, 8.1, 3.1 Hz, 2H), 2.91 (dq, J=8.3, 4.1 Hz, 1H), 2.00-1.85 (m, 2H), 1.85-1.67 (m, 2H). LCMS m/z 336.08 [M+H]$^+$

Step 5. 8-benzyloxy-4-bromo-2-oxido-3-tetrahydropyran-4-yl-isoquinolin-2-ium (C76)

To a solution of C75 (6.53 g, 19.470 mmol) in DMA (50 mL), CuBr (10.86 g, 48.622 mmol) was added and the mixture was heated at 60° C. for 1 hour. The reaction was cooled to 0° C., and a mixture of an aqueous solution of NH$_4$OH and water (2:1, 50 mL) were slowly added in 5 minutes. The suspension was stirred at room temperature for 30 minutes, the solids were filtered and washed with water. The solid was dissolved in dichloromethane, dried over Na$_2$SO$_4$, filtered, concentrated and dried. The residue was triturated with MTBE (35 mL), filtered, washed with heptane and dried to afford C76 (5.8 g, 69%) as tan solid. $^1$H NMR (300 MHz, DMSO-d$_6$) δ 8.84 (s, 1H), 7.69-7.62 (m, 2H), 7.60-7.50 (m, 2H), 7.49-7.33 (m, 3H), 7.32-7.22 (m, 1H), 5.36 (s, 2H), 4.08-3.83 (m, 3H), 3.43 (t, J=11.2 Hz, 2H), 3.07-2.78 (m, 2H), 1.43 (d, J=12.3 Hz, 2H). LCMS m/z 414.1 [M+H]$^+$

Step 6. 8-benzyloxy-4-(4-fluorophenyl)-2-oxido-3-tetrahydropyran-4-yl-isoquinolin-2-ium (C77)

To a solution of C76 (2.0 g, 4.828 mmol) and (4-fluorophenyl)boronic acid (1.008 g, 7.204 mmol) in DMSO (20 mL), an aqueous solution of Na$_2$CO$_3$ (7.25 mL of 2M, 14.50 mmol) was added and the suspension was degassed with nitrogen for 5 minutes. Then, Pd(dppf)Cl$_2$·dichloromethane (150 mg, 0.2460 mmol) was added and the solution was degassed again with nitrogen for 5 min. The mixture was heated to 100° C. for 3 hours. Water was added to the reaction, and the mixture was extracted with EtOAc (150 mL×3). The product precipitated in EtOAc, the organic phase was filtered and washed with cold EtOAc to afford C77 (1.552 g, 64%). $^1$H NMR (300 MHz, Chloroform-d) δ 9.30 (s, 1H), 7.52-7.37 (m, 8H), 7.32 (d, J=8.1 Hz, 1H), 7.27-7.23 (m, 5H), 6.92 (d, J=7.6 Hz, 1H), 6.68 (d, J=8.6 Hz, 1H), 5.27 (s, 2H), 3.98 (dd, J=11.0, 4.0 Hz, 3H), 3.28 (t, J=10.8 Hz, 1H), 1.43 (dd, J=11.4, 2.6 Hz, 1H). LCMS m/z 430.56 [M+H]$^+$

Step 7. 8-benzyloxy-1-chloro-4-(4-fluorophenyl)-3-tetrahydropyran-4-yl-isoquinoline (S33)

To a solution of C77 (1.2 g, 2.403 mmol) and DIEA (1.45 mL, 8.325 mmol) in dichloromethane (14 mL), and oxalyl chloride (2.7 mL of 2M, 5.4 mmol) was added drop wise while at −78° C. The reaction was stirred for 4 hours and was allowed to warm to 0° C. MeOH (6 mL) was added and the mixture was stirred for 10 minutes. The suspension was concentrated, MeOH (5 mL) were added and the mixture was cooled down to 0° C. for 1 h. The solids were filtered and washed with cold MeOH to afford S33 (639 mg, 58%) as a white solid. $^1$H NMR (300 MHz, Chloroform-d) δ 7.60 (d, J=7.4 Hz, 2H), 7.48-7.32 (m, 4H), 7.25-7.19 (m, 4H), 7.00 (d, J=7.9 Hz, 1H), 6.85 (dd, J=8.5, 0.9 Hz, 1H), 5.32 (s, 2H), 4.00 (dd, J=11.4, 4.3 Hz, 2H), 3.30 (t, J=12.1 Hz, 2H), 2.80-2.65 (m, 1H), 2.25 (qd, J=12.5, 4.4 Hz, 2H), 1.49 (d, J=13.4 Hz, 2H). LCMS m/z 448.47 [M+H]$^+$ Preparation of S34

8-benzyloxy-4-(3,4-difluorophenyl)-2-oxido-3-tetra-hydropyran-4-yl-isoquinolin-2-ium (S34)

Preparation of S35

8-benzyloxy-1-chloro-4-(3,4-difluorophenyl)-3-tet-rahydropyran-4-yl-isoquinoline (S35)

C76

S34

S34

To a suspension of C76 (5.0 g, 11.83 mmol) and (3,4-difluorophenyl)boronic acid (2.47 g, 15.64 mmol) in DMSO (62 mL), water (11.0 mL) and Na$_2$CO$_3$ (3.76 g, 35.48 mmol) were added. The mixture was degassed with of nitrogen for 5 minutes, and Pd(dppf)Cl$_2$ was added (386.4 mg, 0.473 mmol). The suspension was degassed again with nitrogen for 5 minutes. The reaction was heated at 100° C. for 2 hours. The reaction mixture was cooled to room temperature and poured into ice-cold brine and was extracted with EtOAc (100 mL×3). The combined organic phases were washed with brine (100 mL), dried, filtered, and concentrated. The solid was triturated with MTBE and filtered to provide S34 (4.62 g, 78%) as a brown solid. $^1$H NMR (300 MHz, Chloroform-d) δ 9.28 (d, J=0.9 Hz, 1H), 7.50-7.27 (m, 8H), 7.10 (ddd, J=10.4, 7.4, 2.1 Hz, 1H), 7.00 (ddd, J=8.6, 4.3, 1.8 Hz, 1H), 6.91 (dd, J=7.9, 0.7 Hz, 1H), 6.64 (dt, J=8.5, 0.9 Hz, 1H), 5.25 (s, 2H), 4.06-3.91 (m, 2H), 3.29 (q, J=11.4, 10.4 Hz, 3H), 2.67 (d, J=31.8 Hz, 1H), 1.44 (s, 2H), 1.31-1.22 (m, 1H). LCMS m/z 448.42 [M+H]$^+$

S35

To a solution of S34 (599 mg, 1.34 mmol) and DIPEA (725 4.162 mmol) in dry dichloromethane (7 mL), oxalyl dichloride (1.42 mL of 2M, 2.84 mmol) was added while at −78° C. The reaction was allowed to warm to 0° C. for 2 hours. Then, MeOH (2 mL) was added and the mixture was stirred for 10 minutes. The reaction was concentrated, MeOH was added (5 mL), the solids were filtered, washed with cold MeOH and dried to afford S35 (335 mg, 54%) $^1$H NMR (400 MHz, Chloroform-d) δ 7.60 (ddt, J=7.5, 1.3, 0.7 Hz, 2H), 7.49-7.41 (m, 3H), 7.41-7.31 (m, 2H), 7.09 (ddd, J=10.5, 7.5, 2.1 Hz, 1H), 7.05-6.96 (m, 2H), 6.84 (dd, J=8.5, 0.9 Hz, 1H), 4.08-3.96 (m, 2H), 3.40-3.27 (m, 2H), 2.72 (tt, J=11.7, 3.8 Hz, 1H), 2.35-2.19 (m, 2H), 1.49 (dd, J=12.7, 3.5 Hz, 2H). LCMS m/z 466.38 [M+H]$^+$ Preparation of S36

8-benzyloxy-4-(4-fluoro-3-methyl-phenyl)-3-isopro-penyl-1-oxido-quinolin-1-ium (S36)

C78

-continued

C79

C80

C81

C82

C83

C84

S36

Step 1. 5-[(2-benzyloxyanilino)methylene]-2,2-dim-ethyl-1,3-dioxane-4,6-dione (C79)

To a solution of C78 (25.0 g, 22.9 mL, 119.2 mmol) in EtOH (150 mL), 2,2-dimethyl-1,3-dioxane-4,6-dione (20.616 g, 143.04 mmol) and trimethyl orthoformate (20.492 g, 21.17 mL, 193.10 mmol) were added. The reaction was heated at 100° C. for 2 hours. The mixture was stirred at room temperature for 1 hour, the solids were filtered, washed with EtOH and dried to give C79 (39.0 g, 88%) as an off-white solid. LCMS m/z 354.0 [M+H]$^+$

Step 2: 8-benzyloxy-1H-quinolin-4-one (C80)

Dowtherm A (150 mL) was heated at 220° C. for 10 minutes and C79 (35.0 g, 99.047 mmol) was added portion wise. The mixture was stirred for 30 min. The reaction was cooled to room temperature and stirred for 20 minutes. Then, hexanes were added, the solids were filtered, washed with hexanes and dried to afford C80 (22 g, 78%) as a brown solid. LCMS m/z 252.0 [M+H]$^+$

Step 3. 8-benzyloxy-3-bromo-1H-quinolin-4-one (C81)

To a solution of C80 (18.8 g, 65.839 mmol) in DMF (150.40 mL), NBS (12.890 g, 72.423 mmol) was added while in an ice bath. The reaction was stirred for 3 hours at room temperature. Cold water was added to the mixture; the solids were filtered, washed with water and dried to afford C81 (20 g, 88%) as brown solid. LCMS m/z 331.0 [M+H]$^+$

Step 4. 8-benzyloxy-3-bromo-4-chloro-quinoline (C82)

To a solution of C81 (20 g, 60.574 mmol) in toluene (150 mL), thionyl chloride (72.065 g, 44.212 mL, 605.74 mmol) was added and the reaction was refluxed for 2 hours. The mixture was concentrated, and dichloromethane and an aqueous solution of NaHCO$_3$ were added. The mixture was extracted with dichloromethane, the organic phases were combined, washed with brine, dried over Na$_2$SO$_4$ and concentrated. Purification by silica gel chromatography (10-50% EtOAc in hexanes) afforded C82 (19 g, 85%). LCMS m/z 349.0 [M+H]$^+$

Step 5. 8-benzyloxy-4-chloro-3-isopropenyl-quinoline (C83)

To a solution of C82 (14 g, 40.158 mmol) in 1,4-dioxane (120 mL) and water (30 mL), potassium isopropenyltrifluo-roborate (5.9424 g, 40.158 mmol) and K$_2$CO$_3$ (16.650 g, 120.47 mmol) were added. The mixture was degassed under nitrogen and Pd(dppf)Cl$_2$·dichloromethane (3.3199 g, 4.0158 mmol) was added. The reaction was heated at 90° C. for 16 hours. The reaction mixture was diluted with EtOAc and water was added. The mixture was extracted with dichloromethane, the organic phases were combined, washed with brine, dried over Na$_2$SO$_4$ and concentrated. Purification by silica gel chromatography (0-50% EtOAc in hexanes) afforded C83 (8.5 g, 65%) as a brown solid. LCMS m/z 310.0 [M+H]$^+$

Step 6. 8-benzyloxy-4-(4-fluoro-3-methyl-phenyl)-3-isopropenyl-quinoline (C84)

To a solution of C83 (4.35 g, 10.856 mmol) in 1,4-dioxane (40 mL) and water (8.70 mL), (4-fluoro-3-methyl-phenyl)

boronic acid (2.5069 g, 16.284 mmol) and $K_2CO_3$ (4.5011 g, 32.568 mmol) were added. Then, the mixture was degassed under $N_2$ and $Pd(PPh_3)_4$ (1.25 g, 1.08 mmol), $PCy_3$ (304.43 mg, 1.0856 mmol) were added. The reaction was heated at 90° C. for 16 hours. The reaction mixture was diluted with EtOAc and water was added. The mixture was extracted with dichloromethane, the organic phases were combined, washed with brine, dried over $Na_2SO_4$ and concentrated. Purification by silica gel chromatography (10-50% EtOAc in hexanes) afforded C84 (4.1 g, 90%). LCMS m/z 384.0 [M+H]$^+$

Step 7. 8-benzyloxy-4-(4-fluoro-3-methyl-phenyl)-3-isopropenyl-1-oxido-quinolin-1-ium (S36)

To a solution of C84 (2.5 g, 6.52 mmol) in dichloromethane (25 mL), m-CPBA (1.91 g, 11.08 mmol) was added. The mixture was stirred at room temperature for 7 hours. An aqueous saturated solution of $Na_2CO_3$ (10 mL) was added. The mixture was extracted with dichloromethane (10 mL×3), the organic phases were combined and concentrated. Purification by trituration with hexanes afforded S36 (1.5 g, 51%) as a light yellow solid. LCMS m/z 400.0 [M+H]$^+$

Compound 1

(2S)-2-[[4-(4-fluorophenyl)-7-hydroxy-3-(2-methoxy-1,1-dimethyl-ethyl)-1-isoquinolyl]oxy]propanoic acid (1)

S1

C85

-continued

1

Step 1. Synthesis of benzyl (2S)-2-[[7-benzyloxy-4-(4-fluorophenyl)-3-(2-methoxy-1,1-dimethyl-ethyl)-1-isoquinolyl]oxy]propanoate (C85)

To a solution of S1 (120 mg, 0.2746 mmol) and benzyl (2R)-2-(p-tolylsulfonyloxy)propanoate (140 mg, 0.4187 mmol) in DMF (2 mL) was added CsF (200 mg, 1.317 mmol) and the resulting solution was stirred at 50° C. for 15 hours. The mixture was extracted with EtOAc and the organic layer was washed with $NaHCO_3$ solution, dried. After evaporation, purification by silica gel chromatography (Gradient: 0-50% EtOAc in heptane) yielded the product as a colorless oil. benzyl (2S)-2-[[7-benzyloxy-4-(4-fluorophenyl)-3-(2-methoxy-1,1-dimethyl-ethyl)-1-isoquinolyl]oxy]propanoate (50.2 mg, 31%). $^1$H NMR (400 MHz, Chloroform-d) δ 7.60 (d, J=2.7 Hz, 1H), 7.46-7.36 (m, 2H), 7.36-7.30 (m, 2H), 7.30-7.26 (m, 1H), 7.26-7.18 (m, 6H), 7.18-7.12 (m, 2H), 7.12-6.99 (m, 3H), 6.84 (d, J=9.3 Hz, 1H), 5.47 (q, J=7.0 Hz, 1H), 5.24-5.03 (m, 5H), 3.35 (d, J=8.7 Hz, 1H), 3.08 (d, J=2.1 Hz, 4H), 1.70 (d, J=7.0 Hz, 3H), 1.03 (s, 3H), 0.97 (s, 3H). LCMS m/z 594.4 [M+H]$^+$

Step 2. Synthesis of (2S)-2-[[4-(4-fluorophenyl)-7-hydroxy-3-(2-methoxy-1,1-dimethyl-ethyl)-1-isoquinolyl]oxy]propanoic acid (1)

To a solution of C85 (50 mg, 0.084 mmol) in MeOH (2 mL) and EtOAc (1 mL) was added Pd/C (8.9 mg, 0.08363 mmol) and a 1 atm balloon of $H_2$. The reaction mixture was stirred for 1 hour and filtered through a pad of Celite®, the clear solution was concentrated give 1 as a white solid (33.2 mg, 95%). $^1$H NMR (400 MHz, Chloroform-d) δ 7.37-6.90 (m, 6H), 6.82-6.69 (m, 1H), 6.63 (d, J=9.5 Hz, 1H), 5.28 (q, J=6.8 Hz, 1H), 3.48-3.29 (m, 2H), 3.22 (s, 3H), 1.58 (d, J=6.4 Hz, 3H), 1.00 (d, J=8.8 Hz, 6H). ESI-MS m/z calc. 413.16385, found 414.27 (M+1)$^+$; Retention time: 0.49 minutes

238

Compounds 2 and 3

(2S)-2-[[4-(4-fluorophenyl)-7-hydroxy-3-(2-hy-droxy-1,1-dimethyl-ethyl)-1-isoquinolyl]oxy]pro-panoic acid (2) and 4-(4-fluorophenyl)-7-hydroxy-3-(1-hydroxy-2-methylpropan-2-yl)isoquinolin-1 (2H)-one (3)

3.34 (p, J=2.5 Hz, 1H), 2.36 (s, 6H). LCMS m/z 400.36 [M+H]$^+$ and 3 (4.7 mg, 34%) $^1$H NMR (400 MHz, Methanol-d$_4$/acetonitrile-d$_3$) δ 8.97 (d, J=2.8 Hz, 1H), 8.69-8.52 (m, 5H), 8.42 (dd, J=8.9, 2.8 Hz, 1H), 8.08 (d, J=8.9 Hz, 1H), 4.64 (p, J=1.6 Hz, 2H), 3.34 (p, J=2.5 Hz, 1H), 2.36 (s, 6H). LCMS m/z 328.1 [M+H]$^+$ Compounds 4 and 5

3-[[4-(4-fluorophenyl)-7-hydroxy-3-(2-methoxy-1,1-dimethyl-ethyl)-1-isoquinolyl]oxy]cyclobutanecar-boxylic acid (4) and 3-[[4-(4-fluorophenyl)-7-hy-droxy-3-(2-methoxy-1,1-dimethyl-ethyl)-1-isoquinolyl]oxy]cyclobutanecarboxylic acid (5)

1

2 (major)

3 (minor)

S1

C86

4

To a solution of 1 (16 mg, 0.03870 mmol) in dichloromethane (0.5 mL) was added BBr$_3$ (80 μL of 1 M, 0.08000 mmol) in dichloromethane at 0° C. and the resulting solution was allowed to warm to room temperature. After stirring for 2 hour, additional BBr$_3$ (80 μL of 1 M, 0.08000 mmol) was added and the reaction was stirred for 12 hours and quenched with ice and extracted with dichloromethane (3×2 mL).The combined organic phase was concentrated and purified by HPLC: 0-70% ACN in Water (FA modifier) to give 2 (8 mg, 52%). $^1$H NMR (400 MHz, Methanol-d$_4$) δ 8.97 (d, J=2.8 Hz, 1H), 8.69-8.52 (m, 5H), 8.42 (dd, J=8.9, 2.8 Hz, 1H), 8.08 (d, J=8.9 Hz, 1H), 4.64 (p, J=1.6 Hz, 2H), -continued

Step 1. Synthesis of benzyl 3-[[7-benzyloxy-4-(4-fluorophenyl)-3-(2-methoxy-1,1-dimethyl-ethyl)-1-isoquinolyl]oxy]cyclobutanecarboxylate (C86)

To a solution of S1 (120 mg, 0.2746 mmol) and benzyl 3-(p-tolylsulfonyloxy)cyclobutanecarboxylate (150 mg, 0.4129 mmol) in DMF (2 mL) was added CsF (200 mg, 1.317 mmol) and the reaction mixture was stirred at 50° C. for 15 hours. The mixture was extracted with EtOAc and the organic layer was washed with NaHCO$_3$ solution, dried. After evaporation, purification by silica gel chromatography (Gradient: 0-50% EtOAc in heptane) yielded C86 as a colorless oil. (56 mg, 33%). $^1$H NMR (400 MHz, Chloroform-d) δ 7.50 (d, J=2.6 Hz, 1H), 7.40 (ddd, J=8.1, 4.1, 1.4 Hz, 2H), 7.36-7.20 (m, 9H), 7.21-7.13 (m, 2H), 7.10-7.00 (m, 3H), 6.82 (dd, J=9.2, 4.0 Hz, 1H), 5.57 (ttd, J=7.4, 6.4, 1.1 Hz, 1H), 5.31 (tt, J=8.2, 7.0 Hz, 0H), 5.14 (s, 2H), 5.09 (d, J=1.5 Hz, 2H), 3.28 (s, 2H), 3.27-3.16 (m, 1H), 3.10 (d, J=4.7 Hz, 3H), 2.85 (dddd, J=11.5, 7.3, 4.4, 2.3 Hz, 2H), 2.62-2.47 (m, 2H), 1.04 (s, 5H). LCMS m/z 642.38 [M+H]$^+$ Step 2. Synthesis of 3-[[4-(4-fluorophenyl)-7-hydroxy-3-(2-methoxy-1,1-dimethyl-ethyl)-1-isoquinolyl]oxy]cyclobutanecarboxylic acid (4) and 3-[[4-(4-fluorophenyl)-7-hydroxy-3-(2-methoxy-1,1-dimethyl-ethyl)-1-isoquinolyl]oxy]cyclobutanecarboxylic acid (5)

To a solution of C86 (55 mg, 0.08834 mmol) in MeOH (1 μL) and EtOAc (3 mL) was added Pd/C (10 mg of 10% w/w, 0.009397 mmol) and a 1 atm H$_2$ balloon (50 mg, 24.80 mmol) for 1 hour. The reaction mixture was stirred for 1 hour and filtered through a pad of Celite®, the clear solution was concentrated give a white solid which was purified by reverse phase chromatography 40-85% acetonitrile (0.1% TFA) on C18 to give 4 (36 mg, 91%) $^1$H NMR (400 MHz, Chloroform-d) δ 7.52 (s, 1H), 7.26 (dd, J=5.8, 2.6 Hz, 2H), 7.18 (t, J=8.6 Hz, 2H), 7.11 (dd, J=9.2, 2.6 Hz, 1H), 6.88 (d, J=9.1 Hz, 1H), 5.61 (q, J=6.7 Hz, 1H), 3.56 (s, 2H), 3.46 (s, 3H), 3.34 (t, J=10.0 Hz, 1H), 2.97 (t, J=5.5 Hz, 2H), 2.72 (q, J=12.2, 10.4 Hz, 2H), 1.13 (s, 6H). LCMS m/z 440.19 [M+H]$^+$ and 5 (3.3 mg, 8%) $^1$H NMR (400 MHz, Chloroform-d) δ 7.48 (d, J=2.6 Hz, 1H), 7.28-7.21 (m, 2H), 7.17 (t, J=8.6 Hz, 2H), 7.07 (dd, J=9.1, 2.6 Hz, 1H), 6.84 (d, J=9.2 Hz, 1H), 5.39 (q, J=6.9 Hz, 1H), 3.53 (s, 2H), 3.43 (s, 3H), 2.99 (dt, J=22.8, 8.4 Hz, 3H), 2.61 (t, J=9.7 Hz, 2H), 1.14 (s, 6H). LCMS m/z 440.24 [M+H]$^+$ Compound 6

3-[[4-(4-(4-fluorophenyl)-7-hydroxy-3-(2-hydroxy-1,1-dimethyl-ethyl)-1-isoquinolyl]oxy]cyclobutan-ecarboxylic acid (6)

Step 1. Synthesis of 3-[[4-(4-fluorophenyl)-7-hydroxy-3-(2-hydroxy-1,1-dimethyl-ethyl)-1-isoquinolyl]oxy]cyclobutanecarboxylic acid (6)

To a solution of 4 (11 mg, 0.02444 mmol) in dichloromethane (0.5 mL) was added BBr$_3$ (50 μL of 1 M, 0.05 mmol) at 0° C. in a dropwise fashion. The reaction was warmed to room temperature and additional BBr$_3$ (50 μL of 1 M, 0.05 mmol) was added at room temperature and stirred for another 2 hours. The reaction was quenched with ice and the mixture was evaporated to dryness. The residue was purified by reverse phase MPLC 0-70% ACN in Water (0.2% Formic Acid modifier) to give 6 (6.5 mg, 63%). $^1$H NMR (400 MHz, Methanol-d$_4$) δ 7.53-7.44 (m, 1H), 7.27 (t, J=6.8 Hz, 2H), 7.19 (t, J=8.5 Hz, 2H), 7.07 (dt, J=9.2, 1.9 Hz, 1H), 6.85 (d, J=9.1 Hz, 1H), 5.57 (p, J=6.8 Hz, 1H), 3.71 (s, 2H), 3.23 (dq, J=9.7, 4.8, 4.3 Hz, 1H), 2.96-2.81 (m, 2H), 2.62 (td, J=12.8, 11.6, 7.7 Hz, 2H), 1.07 (s, 6H). LCMS m/z 426.19 [M+H]$^+$

Compound 7

Synthesis of (2S)-2-[[8-fluoro-4-(4-fluorophenyl)-7-hydroxy-3-isopropyl-1-isoquinolyl]oxy]propanoic acid (7)

S2

7

Step 1: Synthesis of (2S)-2-[[8-fluoro-4-(4-fluoro-phenyl)-7-hydroxy-3-isopropyl-1-isoquinolyl]oxy]propanoic acid (7)

To a solution of S2 (45 mg, 0.06 mmol) in DMF (2 mL) was added NaH (30 mg, 0.75 mmol) at room temperature. The reaction was stirred for 15 hours at room temperature and was quenched by addition of MeOH (4 mL). At this point, Pd/C (10 mg, 0.0094 mmol) was added and a balloon of $H_2$ (1 atm) was fitted to the reaction mixture. The reaction was stirred for 2 hours and filtered through a pad of Celite® and the residue was purified by reverse MPLC: 40 g C18 column, eluting with 10-100% ACN in water with 0.1% FA to provide 7 (11.6 mg, 44%) $^1$H NMR (400 MHz, Methanol-$d_4$) δ 7.22 (d, J=7.2 Hz, 4H), 6.83 (dd, J=9.1, 1.5 Hz, 1H), 5.35 (q, J=7.0 Hz, 1H), 2.76 (p, J=6.7 Hz, 1H), 1.71 (d, J=7.0 Hz, 3H), 1.14 (dd, J=20.3, 6.7 Hz, 6H). LCMS m/z 388.2 $[M+H]^+$

Compounds 8-18

Compounds 8-18 (Table 1) were prepared from intermediate S2 according to the method described for 7. Any modifications to methods are noted in Table 1 and accompanying footnotes.

TABLE 1

Method of preparation, structure and physicochemical data for compounds 8-18

| Compound | Method/Product | Alcohol | $^1$HNMR; LCMS m/z [M + H]$^+$ |
|---|---|---|---|
| 8 | Compound 7[1] from S2 | | 1H NMR (400 MHz, Methanol-$d_4$) δ 7.26-7.15 (m, 5H), 6.82 (dd, J = 9.1, 1.5 Hz, 1H), 5.42-5.30 (m, 1H), 3.02-2.82 (m, 3H), 2.86-2.73 (m, 1H), 2.51-2.39 (m, 2H), 1.17 (d, J = 6.7 Hz, 6H). LCMS m/z 414.49 [M + H]$^+$ |

TABLE 1-continued

Method of preparation, structure and physicochemical data for compounds 8-18

| Compound | Method/Product | Alcohol | $^1$HNMR; LCMS m/z [M + H]$^+$ |
|---|---|---|---|
| 9 | Compound 7$^1$ from S2 | | $^1$H NMR (400 MHz, Methanol-d$_4$) δ 7.26-7.15 (m, 5H), 6.82 (dd, J = 9.1, 1.4 Hz, IH), 5.60 (p, J = 6.9 Hz, 1H), 3.27-3.14 (m, 1H), 2.86 (dddd, J = 11.1, 7.3, 3.6, 2.4 Hz, 2H), 2.78 (p, J = 6.7 Hz, IH), 2.64-2.51 (m, 2H), 1.16 (d, J = 6.7 Hz, 6H). LCMS m/z 414.49 [M + H]$^+$ |
| 10 | Compound 7$^2$ from S2 | | $^1$H NMR (400 MHz, Methanol-d$_4$) δ 7.26-7.15 (m, 5H), 6.82 (dd, J = 9.1, 1.4 Hz, IH), 5.48 (p, J = 7.0 Hz, IH), 3.15-3.05 (m, 2H), 2.78 (p, J = 6.7 Hz, 1H), 2.25-2.15 (m, 2H), 1.50 (s, 3H), 1.15 (d, J = 6.7 Hz, 6H). LCMS m/z 428.49 [M + H]$^+$ |
| 11 | Compound 7$^2$ from S2 | | $^1$H NMR (400 MHz, Methanol-d$_4$) δ 7.26-7.14(m, 5H), 6.82 (dd, J = 9.1, 1.5 Hz, 1H), 5.47 (p, J = 7.3 Hz, 1H), 2.79 (p, J = 6.7 Hz, 1H), 2.73-2.63 (m, 2H), 2.62-2.51 (m, 2H), 1.53 (s, 3H), 1.17 (d, J = 6.7 Hz, 6H). LCMS m/z 428.49 [M + H]$^+$ |

TABLE 1-continued

Method of preparation, structure and physicochemical data for compounds 8-18

| Compound | Method/Product | Alcohol | $^1$HNMR; LCMS m/z [M + H]$^+$ |
|---|---|---|---|
| 12 | Compound 7 from S2 | | $^1$H NMR (400 MHz, Methanol-d$_4$) δ 7.27-7.14 (m, 5H), 6.82 (dd, J = 9.1, 1.5 Hz, IH), 4.80 (t, J = 6.4 Hz, 2H), 2.90 (t, J = 6.5 Hz, 2H), 2.80 (h, J = 6.9 Hz, 1H), 1.19 (d, J = 6.7 Hz, 6H). LCMS m/z 388.16 [M + H]$^+$ |
| 13 | Compound 7 from S2 | | $^1$H NMR (400 MHz, Methanol-d$_4$) δ 7.21 (dd, J = 10.0, 7.5 Hz, 5H), 6.83 (dd, J = 9.1, 1.5 Hz, 1H), 5.35 (q, J = 7.0 Hz, IH), 2.76 (hept, J = 6.7 Hz, IH), 1.71 (d, J = 7.0 Hz, 3H), 1.14 (dd, J = 20.4, 6.7 Hz, 6H). LCMS m/z 388.2 [M + H]$^+$ |
| 14 | Compound 7 from S2 | | $^1$H NMR (400 MHz, Methanol-d$_4$) δ 7.23 (d, J = 7.2 Hz, 3H), 7.19-7.02 (m, 1H), 6.82 (dd, J = 9.1, 1.5 Hz, 1H), 5.84-5.75 (m, 1H), 3.19-3.09 (m, 1H), 2.86-2.74 (m, 1H), 2.40-2.15 (m, 4H), 2.10-1.90 (m, 3H), 1.18 (dt, J = 6.8, 1.5 Hz, 6H). LCMS m/z 428.18 [M + H]$^+$ |

TABLE 1-continued

| Compound | Method/Product | Alcohol | $^{1}$HNMR; LCMS m/z [M + H]$^{+}$ |
|---|---|---|---|

Method of preparation, structure and physicochemical data for compounds 8-18

| 15 | Compound 7 from S2 | | $^{1}$H NMR (400 MHz, Methanol-d$_4$) δ 7.27-7.21 (m, 3H), 7.17 (dd, J = 9.1, 8.0 Hz, 1H), 6.81 (dd, J = 9.0, 1.4 Hz, 1H), 5.72-5.64 (m, 1H), 2.98-2.87 (m, 1H), 2.79 (p, J = 6.7 Hz, 1H), 2.55 (ddd, J = 14.8, 9.3, 6.3 Hz, 1H), 2.29-1.97 (m, 6H), 1.18 (dd, J = 6.7, 2.7 Hz, 6H). LCMS m/z 428.22 [M + H]$^{+}$ |
| 16 | Compound 7 from S2 | | $^{1}$H NMR (400 MHz, Methanol-d$_4$) δ 8.71 (dd, J = 17.0, 2.5 Hz, 1H), 8.29 (d, J = 8.6 Hz, IH), 7.96 (ddd, J = 17.1, 8.6, 2.6 Hz, IH), 7.38-7.15 (m, 5H), 6.96 (dd, J = 9.1, 1.4 Hz, IH), 2.78 (dq, J = 13.4, 6.9 Hz, IH), 1.01 (dd, J = 9.4, 6.7 Hz, 6H). LCMS m/z 437.18 [M + H]$^{+}$ |
| 17 | Compound 7 from S2 | | $^{1}$H NMR (400 MHz, Methanol-d$_4$) δ 7.21 (dd, J = 16.9, 7.6 Hz, 5H), 6.83 (dd, J = 9.1, 1.4 Hz, IH), 6.10-5.99 (m, IH), 4.85 (d, J = 3.3 Hz, 1H), 2.80 (h, J = 6.6 Hz, 1H), 2.14 (s, 3H), 1.55 (d, J = 6.4 Hz, 3H), 1.19 (dd, J = 6.7, 2.0 Hz, 6H). LCMS m/z 459.23 [M + H]$^{+}$ |

TABLE 1-continued

Method of preparation, structure and physicochemical data for compounds 8-18

| Compound | Method/Product | Alcohol | $^1$HNMR; LCMS m/z [M + H]$^+$ |
|---|---|---|---|
| 18 | Compound 7 from S2 | | $^1$H NMR (400 MHz, Methanol-d$_4$) δ 7.30-7.23 (m, 4H), 6.88 (dd, J = 9.1, 1.4 Hz, 1H), 5.83 (q, J = 7.3 Hz, 1H), 2.79 (p, J = 6.7 Hz, 1H), 1.15 (dd, J = 23.1, 6.7 Hz, 6H). LCMS m/z 442.17 [M + H]$^+$ |

Compound 19

2-[2-[[4-(4-fluorophenyl)-7-hydroxy-3-isopropyl-1-isoquinolyl]oxy]-6-azaspiro[3.4]octan-6-yl]acetic acid (19)

-continued

251

-continued

C90

19

Step 1: Synthesis of tert-butyl 2-[[7-benzyloxy-4-(4-fluorophenyl)-3-isopropyl-1-isoquinolyl]oxy]-6-azaspiro[3.4]octane-6-carboxylate (C87)

To a mixture of S7 isoquinoline (200 mg, 0.4927 mmol) and tert-butyl 2-hydroxy-6-azaspiro[3.4]octane-6-carboxylate (672 mg, 2.956 mmol) in dry DMF (12.00 mL) was slowly added NaH (130 mg of 60% w/w, 3.250 mmol) at room temperature. The reaction mixture was microwaved at 85° C. under $N_2$ for 2 hours. The reaction mixture was quenched with water (1 mL) and HCl (1 M; ~3 mL/pH=6). The desired product was extracted with EtOAc, washed with water, sat. NaCl and dried over sodium sulfate. Purification by silica gel chromatography led to C87 (116 mg, 39%) LCMS m/z 597.37 [M+H]$^+$

Step 2: Synthesis of 1-(6-azaspiro[3.4]octan-2-yloxy)-7-benzyloxy-4-(4-fluorophenyl)-3-isopropyl-isoquinoline (C88)

To a solution of C87 (116 mg, 0.1944 mmol) in dichloromethane (2 mL) was added TFA (1 mL, 12.98 mmol). The reaction mixture was stirred for 18 hours at room temperature and the excess solvent was removed to give C88 (Trifluoroacetate salt) (110 mg, 93%) which was used without further purification; LCMS m/z 497.12 [M+H]$^+$

Step 3. Synthesis of ethyl 2-[2-[[7-benzyloxy-4-(4-fluorophenyl)-3-isopropyl-1-isoquinolyl]oxy]-6-azaspiro[3.4]octan-6-yl]acetate (C89)

To a solution of C88 (110 mg, 0.1801 mmol), ethyl 2-oxoacetate (220.7 mg of 50% w/w, 1.081 mmol) and acetic acid (10.25 μL, 0.1802 mmol) in dichloromethane (4 mL) was added triacetoxy-hydrido-boron (Sodium salt) (305.4 mg, 1.441 mmol). The resulting mixture was stirred for 6 hours. The reaction was diluted with dichloromethane and slowly quenched with MeOH and sat. NaHCO$_3$ (50 mL). After separation, the organic layer was washed with water, sat. NaCl and dried over sodium sulfate. Evaporation led to C89 (100 mg, 95%) which was used without further purification; LCMS m/z 583.47 [M+H]$^+$

Step 4. Synthesis of ethyl 2-[2-[[4-(4-fluorophenyl)-7-hydroxy-3-isopropyl-1-isoquinolyl]oxy]-6-azaspiro[3.4]octan-6-y]acetate (C90)

A solution of palladium (30 mg of 10% w/w, 0.02819 mmol) and C89 (100 mg, 0.1716 mmol) in MeOH (20 mL) and EtOAc (40 mL) was stirred under H$_2$ (1 atm) at room temperature for 18 hours. The mixture was filtered through a pad of Celite® and concentrated to dryness. The residue was purified by silica gel chromatography 0-10% of MeOH in dichloromethane) to give C90 (84 mg, 99%). LCMS m/z 493.52 [M+H]$^+$.

Step 5. Synthesis of 2-[2-[[4-(4-fluorophenyl)-7-hydroxy-3-isopropyl-1-isoquinolyl]oxy]-6-azaspiro[3.4]octan-6-y]acetic acid (19)

A solution of C90 (84 mg, 0.1705 mmol) and LiOH·H$_2$O (63 mg, 1.501 mmol) in water (1.5 mL) and THF (1.5 mL) was stirred at room temperature for 3 hours after which the reaction mixture was treated with HCl (1 N) until pH=7. The excess solvent was removed HPLC purification gave 19 (43 mg, 52%) $^1$H NMR (300 MHz, Methanol-d$_4$) δ 7.53 (dd, J=2.5, 0.6 Hz, 1H), 7.35-6.93 (m, 6H), 5.54 (p, J=6.8 Hz, 1H), 4.24-4.02 (m, 2H), 4.02-3.77 (m, 2H), 3.30 (d, J=12.2 Hz, 2H), 3.00-2.70 (m, 3H), 2.65-2.20 (m, 4H), 1.18 (d, J=6.7 Hz, 6H). LCMS m/z 465.19 [M+H]$^+$ Compounds 20-30

Compounds 20-30 (Table 2) were prepared from intermediate C91 and C92 according to the method described in Table 2. Any modifications to methods are noted in Table 2 and accompanying footnotes.

C89

NaHCO₃, I₂

C92

C91

+

Step 1. Synthesis of ethyl 2-[2-[[7-benzyloxy-4-(4-fluorophenyl)-3-isopropyl-1-isoquinolyl]oxy]-5-oxo-6-azaspiro[3.4]octan-6-yl]acetate (C91) and ethyl 2-[2-[[7-benzyloxy-4-(4-fluorophenyl)-3-isopropyl-1-isoquinolyl]oxy]-7-oxo-6-azaspiro[3.4]octan-6-yl]acetate (C92)

To a solution of C89 (200 mg, 0.3432 mmol) and NaHCO₃ (3.75 mL of 1 M, 3.750 mmol) in THF (13 mL) was added I₂ (140 μL, 2.719 mmol). The reaction mixture was stirred for 6 hours and quenched by the addition of sat. NaHCO₃ and sat. sodium thiosulfate (10 mL). After extraction of the aqueous phase with EtOAc, the organic phase was dried over sodium sulfate and concentrated to dryness. The residue was purified by silica gel chromatography (0-25-50% of EtOAc in heptane) to give C91 (135 mg, 66%) LCMS m/z 597.57 [M+H]⁺ and C92 (45 mg, 22%) LCMS m/z 597.57 [M+H]⁺

TABLE 2

| | | | $^1$H NMR; LCMS m/z |
|---|---|---|---|
| Compound | Method/Product | Alcohol | [M + H]⁺ |
| 20 | From S7, Hydrogenation of C91 | | $^1$H NMR (300 MHz, Chloroform-d and Methanol-d₄) δ 7.54 (td, J = 2.4, 0.9 Hz, 1H), 7.30-7.02 (m, 6H), 5.69-5.49 (m, 1H), 4.20 (dd, J = 7.1, 4.0 Hz, 2H), 4.10 (d, J = 0.9 Hz, 2H), 3.49 (dt, J = 13.4, 6.8 Hz, 2H), 3.14-2.99 (m, 1H), 2.82 (h, J = 6.6 Hz, 1H), 2.75-2.56 (m, 2H), 2.47-2.25 (m, 3H), 1.31 (dt, J = 7.2, 3.6 Hz, 3H), 1.15 (dd, J = 6.7, 4.8 Hz, 6H). LCMS m/z 507.45 [M + H]⁺ |

Method of preparation, structure and physicochemical data for compounds 20-30

TABLE 2-continued

Method of preparation, structure and physicochemical data for compounds 20-30

| Compound | Method/Product | Alcohol | ¹H NMR; LCMS m/z [M + H]⁺ |
|---|---|---|---|
| 21 | From S7, Hydrogenation and hydrolysis of C91 | | ¹H NMR (300 MHz, DMSO-d₆) δ 9.98 (s, 1H), 7.44 (d, J = 2.5 Hz, 1H), 7.40-7.24 (m, 4H), 7.16 (dd, J = 9.0, 2.6 Hz, 1H), 7.00 (d, J = 9.0 Hz, 1H), 5.48 (dt, J = 9.5, 7.2 Hz, 1H), 3.94 (d, J = 3.2 Hz, 2H), 2.93-2.65 (m, 2H), 2.62-2.52 (m, 1H), 2.49-2.36 (m, 2H), 2.35-2.09 (m, 4H), 1.16-1.06 (m, 6H). LCMS m/z 479.47 [M + H]⁺ |
| 22 | Prepared from 21 by HPLC purification | | ¹H NMR (300 MHz, Methanol-d₄) δ 7.55 (dd, J = 2.3, 0.9 Hz, 1H), 7.33-6.95 (m, 6H), 5.69-5.53 (m, 1H), 4.08 (s, 2H), 3.48 (t, J = 6.9 Hz, 2H), 3.06 (ddd, J = 10.4, 7.3, 2.5 Hz, 2H), 2.81 (p, J = 6.6 Hz, 1H), 2.34 (qd, J = 6.4, 3.1 Hz, 4H), 1.14 (d, J = 6.7 Hz, 6H). LCMS m/z 479.0 [M + H]⁺ |
| 23 | Prepared from 21 by HPLC purification | | ¹H NMR (300 MHz, Methanol-d₄) δ 7.54 (dd, J = 2.3, 0.9 Hz, 1H), 7.35-6.88 (m, 6H), 5.57 (p, J = 7.7 Hz, 1H), 4.07 (s, 2H), 3.52 (t, J = 6.8 Hz, 2H), 2.83 (p, J = 6.6 Hz, 1H), 2.77-2.49 (m, 4H), 2.41 (t, J = 6.8 Hz, 2H), 1.15 (d, J = 6.7 Hz, 6H). LCMS m/z 479.17 [M + H]⁺ |

TABLE 2-continued

Method of preparation, structure and physicochemical data for compounds 20-30

| Compound | Method/Product | Alcohol | $^1$H NMR; LCMS m/z<br>[M + H]$^+$ |
|---|---|---|---|
| 24 | From S7, Hydrolysis of<br>C92 | | $^1$H NMR (300 MHz,<br>Methanol-d$_4$) δ 7.55 (ddd,<br>J = 5.6, 2.5, 0.7 Hz, 1H),<br>7.34-6.97 (m, 6H), 5.55<br>(dq, J = 21.1, 6.8 Hz, 1H),<br>4.08 (d, J = 9.1 Hz, 2H),<br>3.69 (d, J = 19.5 Hz, 2H),<br>2.84 (dddd, J = 14.8, 10.3,<br>8.3, 4.8 Hz, 3H), 2.68 (d, J =<br>16.3 Hz, 2H), 2.49-2.33<br>(m, 2H), 1.18 (dd, J = 6.8,<br>2.6 Hz, 6H). LCMS m/z<br>479.17 [M + H]$^+$ |
| 25 | From S7 | | $^1$H NMR (300 MHz,<br>Methanol-d$_4$) δ 7.63-7.53<br>(m, 1H), 7.30-7.01 (m,<br>6H), 5.75 (s, 1H), 4.10 (s,<br>2H), 3.65 (s, 4H), 2.87 (p,<br>J = 6.6 Hz, 1H), 2.47 (s,<br>4H), 1.16 (d, J = 6.7 Hz,<br>6H). LCMS m/z 439.42<br>[M + H]$^+$ |
| 26 | From S7, same as<br>compound 20 | | $^1$H NMR (300 MHz,<br>Chloroform-d and<br>Methanol-d$_4$) δ 7.50 (d, J =<br>2.2 Hz, 1H), 7.30-6.95<br>(m, 6H), 5.32 (p, J = 6.9<br>Hz, 1H), 4.22 (dd, J =<br>13.5, 6.4 Hz, 2H), 3.57 (s,<br>2H), 3.49 (s, 2H), 3.34(s,<br>2H), 2.95-2.71 (m, 3H),<br>2.51-2.33 (m, 2H), 1.31<br>(d, J = 7.1 Hz, 3H), 1.15<br>(d, J = 6.7 Hz, 6H). LCMS<br>m/z 479.47 [M + H]$^+$ |

TABLE 2-continued

Method of preparation, structure and physicochemical data for compounds 20-30

| Compound | Method/Product | Alcohol | ${}^1$H NMR; LCMS m/z [M + H]$^+$ |
|---|---|---|---|
| 27 | From S7, same as compound 19 | | 1H NMR (300 MHz, Chloroform-d and Methanol-d$_4$) δ 7.50-7.46 (m, 1H), 7.33-7.00 (m, 6H), 5.42 (q, J = 6.6 Hz, 1H), 4.46 (s, 2H), 4.38-4.17 (m, 2H), 4.11 (s, 2H), 3.21-2.79 (m, 3H), 2.76-2.47 (m, 2H), 1.17 (dd, J = 6.7, 1.3 Hz, 6H). LCMS m/z 451.18 [M + H]$^+$ |
| 28 | From S7 | | ${}^1$H NMR (300 MHz, Chloroform-d) δ 7.54 (t, J = 1.7 Hz, 1H), 7.26-7.02 (m, 5H), 5.39 (s, 1H), 5.10 (d, J = 37.1 Hz, 1H), 4.19 (m, 2H), 3.36 (d, J = 14.8 Hz, 1H), 2.99 (s, 1H), 2.81 (p, J = 6.6 Hz, 1H), 2.45-2.22 (m, 1H), 2.06-1.71 (m, 2H), 1.51 (s, 9H), 1.13 (t, J = 7.0 Hz, 6H). ESI-MS m/z calc. 524.23224, found 525.45 [M + H] |
| 29 | From S7 | | ${}^1$H NMR (300 MHz, Chloroform-d) δ 7.59 (dd, J = 2.4, 0.8 Hz, 1H), 7.20 (s, 2H), 7.18 (d, J = 1.4 Hz, 2H), 7.13-7.08 (m, 2H), 6.11 (s, 1H), 5.49 (dqd, J = 13.2, 6.6, 5.9, 3.9 Hz, 2H), 4.05-3.90 (m, 2H), 2.87 (h, J = 6.7 Hz, 1H), 1.51 (d, J = 6.5 Hz, 3H), 1.19 (dd, J = 7.7, 6.8 Hz, 6H) ppm. LCMS m/z 356.6 [M + H]$^+$ |

TABLE 2-continued

Method of preparation, structure and physicochemical data for compounds 20-30

| Compound | Method/Product | Alcohol | $^1$H NMR; LCMS m/z [M + H]$^+$ |
|---|---|---|---|
| 30 | From S7 | | $^1$H NMR (400 MHz, Chloroform-d) δ 7.55 (dd, J = 2.6, 0.6 Hz, 1H), 7.25-7.17 (m, 4H), 7.13 (dd, J = 9.1, 2.6 Hz, 1H), 7.06 (dd, J = 9.0, 0.5 Hz, 1H), 4.72 (dd, J = 12.1, 2.0 Hz, 1H), 4.57 (dd, J = 12.1, 7.0 Hz, 1H), 4.45 (pd, J = 6.5, 1.9 Hz, 1H), 2.90 (p, J = 6.8 Hz, 1H), 1.40 (d, J = 6.5 Hz, 3H), 1.22 (dd, J = 6.8, 2.8 Hz, 6H). LCMS m/z 356.17 [M + H]$^+$ |

Compounds 31-33

Step 1: Synthesis of ethyl 2-[[7-benzyloxy-4-(4-fluorophenyl)-3-isopropyl-1-isoquinolyl]oxy]acetate (C93)

To a solution of S5 (744 mg, 1.920 mmol) in DMF (8 mL) was added Cs$_2$CO$_3$ (1.30 g, 3.990 mmol) followed by ethyl 2-bromoacetate (385 μL, 3.472 mmol). The reaction was held at 90° C. for 90 minutes. The solvent was removed by rotary evaporation. The resulting crude material was purified by silica gel chromatography (0-60% EtOAc in heptane) to afford C93 (644 mg, 69%) LCMS m/z 473.17 [M+H]$^+$, which was used directly in the next step.

Step 2: To a solution of 4-(4-fluorophenyl)-3-isopropyl-7-methoxy-1-[(3S)-pyrrolidin-3-yl]oxy-isoquinoline (Trifluoroacetate salt) (50 mg, 0.1011 mmol) and 2-cyanoacetic acid (12 mg, 0.1411 mmol) in DMF (1 mL) was added TEA (50 μL, 0.3587 mmol) followed by HATU (58 mg, 0.1525 mmol). The reaction was stirred at room temperature for 3 hours and was quenched by addition of water. The aqueous phase was extracted with EtOAc (3×5 mL). The combined organic fractions were washed with brine, dried over sodium sulfate and concentrated to dryness. The residue was purified by silica gel chromatography eluting with 0-10% MeOH in dichloromethane to provide the desired product as white solid C94 (34 mg, 75%) $^1$H NMR (400 MHz, Chloroform-d) δ 7.42 (d, J=2.3 Hz, 1H), 7.24-7.10 (m, 6H), 5.94 (dtt, J=11.3, 4.6, 2.1 Hz, 1H), 4.09-3.99 (m, 1H), 3.93 (s, 3H), 3.91-3.70 (m, 3H), 3.53 (s, 1H), 3.46 (s, 1H), 2.87 (h, J=6.7 Hz, 1H), 2.67-2.27 (m, 2H), 1.17 (dt, J=6.7, 1.8 Hz, 6H). LCMS m/z 448.25 [M+H]$^+$ 44: $^1$H NMR (400 MHz, Chloroform-d) δ 7.44 (dt, J=4.6, 1.6 Hz, 1H), 7.18-7.08 (m, 4H), 7.06 (dd, J=4.8, 1.5 Hz, 2H), 5.87 (dd, J=28.9, 24.0 Hz, 2H), 4.15-3.89 (m, 2H), 3.87-3.70 (m, 2H), 2.86-2.72 (m, 1H), 2.55-2.16 (m, 2H), 1.12-1.05 (m, 6H). LCMS m/z 434.3 [M+H]$^+$ Compounds 31-42

Compounds 31-42 (Table 3) were prepared from intermediates indicated in Table 3.

TABLE 3

| | Method of preparation, structure, physicochemical data for compounds 31-42 | | |
|---|---|---|---|
| Compound | Method/Product | Intermediate | $^1$H NMR; LCMS m/z [M + H]$^+$ |
| 31 | Hydrogenation of S5 | N/A | $^1$H NMR (400 MHz, DMSO-d$_6$) δ 10.95 (s, 1H), 9.89 (s, 1H), 7.56 (d, J = 2.6 Hz, 1H), 7.37-7.22 (m, 3H), 7.06 (dd, J = 8.9, 2.7 Hz, 1H), 6.74 (d, J = 8.8 Hz, 1H), 2.67-2.54 (m, 1H), 1.15 (d, J = 7.0 Hz, 6H). ESI-MS m/z calc. 297.11652, found 298.22 (M + 1)$^+$ |
| 32 | From S5, Hydrogenation of C93 | N/A | $^1$H NMR (400 MHz, Acetone-d$_6$) δ 8.91 (s, 1H), 7.63 (dd, J = 2.7, 0.6 Hz, 1H), 7.35-7.27 (m, 4H), 7.24 (dd, J = 9.1, 2.6 Hz, 1H), 7.12 (dd, J = 9.0, 0.6 Hz, 1H), 5.09 (s, 2H), 4.21 (q, J = 7.1 Hz, 2H), 2.83 (p, J = 6.7 Hz, 1H), 1.26 (t, J = 7.1 Hz, 3H), 1.13 (d, J = 6.7 Hz, 6H). ESI-MS m/z calc. 383.1533, found 384.27 (M + 1)$^+$ |
| 33 | From S5, Hydrolysis and hydrogenation of C93 | N/A | $^1$H NMR (400 MHz, DMSO-d$_6$) δ 12.84 (s, 1H), 10.05 (s, 1H), 7.46 (t, J = 2.5 Hz, 1H), 7.40-7.25 (m, 4H), 7.19 (dd, J = 9.1, 2.6 Hz, 1H), 7.03 (d, J = 9.1 Hz, 1H), 5.00 (s, 2H), 2.73 (p, J = 6.6 Hz, 1H), 1.09 (d, J = 6.6 Hz, 6H). ESI-MS m/z calc. 355.12198, found 356.22 (M + 1)$^+$ |

TABLE 3-continued

Method of preparation, structure, physicochemical data for compounds 31-42

| Compound | Method/Product | Intermediate | $^1$H NMR; LCMS m/z [M + H]$^+$ |
|---|---|---|---|
| 34 | From S6 and hydrogenation | | $^1$H NMR (300 MHz, Chloroform-d) δ 7.62 (dd, J = 2.0, 1.2 Hz, 1H), 7.27-7.12 (m, 6H), 5.49 (q, J = 6.9 Hz, 1H), 2.89 (p, J = 6.8 Hz, 1H), 1.81 (d, J = 6.9 Hz, 3H), 1.20 (d, J = 6.7 Hz, 3H), 1.16 (d, J = 6.8 Hz, 3H). $^{19}$F NMR (282 MHz, Chloroform-d ) δ −114.78. ESI-MS m/z calc. 369.13763, found 370.36 (M + 1)$^+$ |
| 35 | From S3, Cs$_2$CO$_3$ and AlBr$_3$ | | $^1$H NMR (400 MHz, Chloroform-d) δ 7.50 (dd, J = 2.2, 1.0 Hz, 1H), 7.18-7.07 (m, 6H), 2.81 (h, J = 6.8 Hz, 1H), 1.75 (s, 6H), 1.11 (d, J = 6.8 Hz, 6H). ESI-MS m/z calc. 383.1533, found 384.29 (M + 1)$^+$ |
| 36 | From S3, CsF and AlBr$_3$ | | $^1$H NMR (400 MHz, Chloroform-d) δ 7.51 (dd, J = 2.4, 0.8 Hz, 1H), 7.17-7.02 (m, 6H), 5.38 (q, J = 7.0 Hz, 1H), 3.87 (s, 3H), 3.69 (s, 3H), 2.74 (hept, J = 6.7 Hz, 1H), 1.70 (d, J = 7.0 Hz, 3H), 1.07 (d, J = 6.7 Hz, 3H), 1.00 (d, J = 6.6 Hz, 3H). ESI-MS m/z calc. 397.16895, found 398.29 (M + 1)$^+$ |

TABLE 3-continued

| | | | |
|---|---|---|---|
| | Method of preparation, structure, physicochemical data for compounds 31-42 | | |
| Compound | Method/Product | Intermediate | ¹H NMR; LCMS m/z [M + H]⁺ |
| 37 | From S3, CsF and AlBr₃ | | ¹H NMR (400 MHz, Acetonitrile-d₃) δ 7.53 (dd, J = 2.6, 0.6 Hz, 1H), 7.32-7.21 (m, 4H), 7.17 (dd, J = 9.1, 2.6 Hz, 1H), 7.10 (dd, J = 9.0, 0.6 Hz, 1H), 5.71-5.49 (m, 1H), 3.23 (ttd, J = 10.1, 4.0, 1.1 Hz, 1H), 2.92-2.79 (m, 3H), 2.64-2.52 (m, 2H), 1.17 (d, J = 6.7 Hz, 9H). ESI-MS m/z calc. 395.1533, found 396.21 (M + 1)⁺ |
| 38 | From S3, CsF and AlBr₃ | | ¹H NMR (400 MHz, Chloroform-d) δ 7.62 (dd, J = 2.2, 1.0 Hz, 1H), 7.27-7.12 (m, 6H), 5.50 (q, J = 6.8 Hz, 1H), 2.89 (h, J = 6.8 Hz, 1H), 1.82 (d, J = 6.9 Hz, 3H), 1.21 (d, J = 6.7 Hz, 3H), 1.16 (d, J = 6.8 Hz, 3H). ESI-MS m/z calc. 369.13763, found 370.15 (M + 1)+ |
| 39 | From S3, CsF and AlBr₃ | | 1H NMR (400 MHz, Chloroform-d) δ 7.55 (s, 1H), 7.24-7.07 (m, 6H), 5.41 (q, J = 7.2 Hz, 1H), 2.96 (q, J = 9.0 Hz, 3H), 2.83 (p, J = 6.7 Hz, 1H), 2.68-2.51 (m, 2H), 1.15 (d, J = 6.7 Hz, 6H). ESI-MS m/z calc. 395.1533, found 396.21 (M + 1)⁺ |

TABLE 3-continued

Method of preparation, structure, physicochemical data for compounds 31-42

| Compound | Method/Product | Intermediate | $^1$H NMR; LCMS m/z [M + H]$^+$ |
|---|---|---|---|
| 40 | From S3, CsF and BBr$_3$ | | $^1$H NMR (400 MHz, Methanol-d$_4$) δ 8.50 (s, 2H), 7.49 (d, J = 2.5 Hz, 1H), 7.30-7.20 (m, 4H), 7.14 (dd, J = 9.1, 2.5 Hz, 1H), 7.08 (d, J = 8.9 Hz, 1H), 5.93 (t, J = 2.4 Hz, 1H), 3.82-3.67 (m, 2H), 3.68-3.49 (m, 2H), 2.86 (p, J = 6.7 Hz, 1H), 2.61-2.45 (m, 2H), 1.20 (d, J = 6.7 Hz, 6H). ESI-MS m/z calc. 366.17435, found 367.18 (M + 1)+ |
| 41 | From S5, Cs$_2$CO$_3$ and hydrogenation | MeI | $^1$H NMR (400 MHz, Acetone-d$_6$) δ 8.83 (s, 1H), 7.57 (dd, J = 2.6, 0.6 Hz, 1H), 7.35-7.27 (m, 4H), 7.21 (dd, J = 9.0, 2.6 Hz, 1H), 7.09 (dd, J = 9.0, 0.6 Hz, 1H), 4.13 (s, 3H), 2.86 (p, J = 6.7 Hz, 1H), 1.20 (d, J = 6.7 Hz, 6H). ESI-MS m/z calc. 311.13217, found 312.61 (M + 1)$^+$ |
| 42 | From S3, Cs$_2$CO$_3$, LiAlH$_4$ reduction and BBr$_3$ | | $^1$H NMR (400 MHz, Chloroform-d) δ 7.51 (dd, J = 2.5, 0.8 Hz, 1H), 7.16-6.99 (m, 6H), 5.96 (s, 1H), 5.43 (d, J = 8.9 Hz, 1H), 5.38 (qd, J = 6.7, 3.0 Hz, 1H), 3.87 (d, J = 7.4 Hz, 2H), 2.79 (hept, J = 6.7 Hz, 1H), 1.42 (d, J = 6.5 Hz, 3H), 1.10 (dd, J = 11.6, 6.8 Hz, 6H). ESI-MS m/z calc. 355.1584, found 355.99 (M + 1)$^+$ |

Compounds 43 and 44

2-Step procedure: Synthesis of ethyl 2-[[7-benzy-loxy-4-(4-fluorophenyl)-3-isopropyl-1-isoquinolyl]oxy]acetate (C94)

Step 1: To a solution tert-butyl (3S)-3-[[4-(4-fluorophe-nyl)-3-isopropyl-7-methoxy-1-isoquinolyl]oxy]pyrrolidine-1-carboxylate (146 mg, 0.3034 mmol) in DCM (1 mL) was added TFA (250 μL, 3.245 mmol) at room temperature and the solution was stirred for 1 hour. Evaporation of the crude reaction mixture led to the isolation of a white solid ESI-MS m/z calc. 380.19, found 381.22 (M+1)$^+$; Retention time: 0.45 minutes, which was used directly in the next step.

Step 2: To a solution of 4-(4-fluorophenyl)-3-isopropyl-7-methoxy-1-[(3S)-pyrrolidin-3-yl]oxy-isoquinoline (Trif-luoroacetate salt) (50 mg, 0.1011 mmol) and 2-cyanoacetic acid (12 mg, 0.1411 mmol) in DMF (1 mL) was added TEA (50 μL, 0.3587 mmol) followed by HATU (58 mg, 0.1525 mmol). The reaction was stirred at room temperature for 3 hours and was quenched by addition of water. The aqueous phase was extracted with EtOAc (3×5 mL). The combined organic fractions were washed with brine, dried over sodium sulfate and concentrated to dryness. The residue was purified by silica gel chromatography eluting with 0-10% MeOH in dichloromethane to provide the desired product as white solid C94 (34 mg, 75%) $^1$H NMR (400 MHz, Chloroform-d) δ 7.42 (d, J=2.3 Hz, 1H), 7.24-7.10 (m, 6H), 5.94 (dtt, J=11.3, 4.6, 2.1 Hz, 1H), 4.09-3.99 (m, 1H), 3.93 (s, 3H), 3.91-3.70 (m, 3H), 3.53 (s, 1H), 3.46 (s, 1H), 2.87 (h, J=6.7 Hz, 1H), 2.67-2.27 (m, 2H), 1.17 (dt, J=6.7, 1.8 Hz, 6H). LCMS m/z 448.25 [M+H]$^+$ 1)$^+$ Compounds 43 and 44 were isolated following general procedure 2 (GP2) using BBr$_3$ as Lewis acid.

43: $^1$H NMR (400 MHz, Chloroform-d) δ 7.45 (d, J=3.1 Hz, 1H), 7.26-7.01 (m, 6H), 5.93 (d, J=10.1 Hz, 1H), 4.21-3.65 (m, 4H), 3.44-3.22 (m, 2H), 2.92-2.75 (m, 1H), 2.48 (d, J=14.5 Hz, 1H), 2.34 (ddt, J=35.9, 9.4, 4.7 Hz, 1H), 1.17 (d, J=6.7 Hz, 6H). ESI-MS m/z calc. 451.19073, found 452.26 (M+1)$^+$; Retention time: 0.44 minutes 44: $^1$H NMR (400 MHz, Chloroform-d) δ 7.44 (dt, J=4.6, 1.6 Hz, 1H), 7.18-7.08 (m, 4H), 7.06 (dd, J=4.8, 1.5 Hz, 2H), 5.87 (dd, J=28.9, 24.0 Hz, 2H), 4.15-3.89 (m, 2H), 3.87-3.70 (m, 2H), 2.86-2.72 (m, 1H), 2.55-2.16 (m, 2H), 1.12-1.05 (m, 6H). LCMS m/z 434.3 [M+H]$^+$ <table>
<tr><td>273</td><td>274</td></tr>
</table>

Compound 45

-continued 3-((4-(4-fluoro-3-methylphenyl)-7-hydroxy-3-iso-
propylisoquinolin-1-yl)oxy)-1-methylcyclobutane-1-
carboxylic acid (45)

S10

45

Step 1: To a solution of S10 (Trifluoroacetate salt) (60 mg, 0.098 mmol) and methyl 3-hydroxy-1-methyl-cyclobutan-ecarboxylate (35.4 mg, 0.245 mmol) in DMF (1 mL) was added NaH (7.8 mg, 0.196 mmol) at 0° C., the solution was stirred at this temperature for 1 hours and then 4 hours at room temperature. After this time, LCMS shows complete consumption of starting material. This reaction mixture was directly carried forward to the next step.

Step 2: To the previous reaction mixture was added MeOH (1 mL) and the reaction mixture was filtered through a Celite® plug to remove precipitates. To this solution was added dihydroxypalladium (6.9 mg, 0.01 mmol) and the solution was placed in a Parr vessel. The vessel was brought to 25 psi under hydrogen atmosphere and was stirred for 4 hours by which time the reaction mixture was filtered through a 0.2 micron filter, and then concentrated in vacuo to remove MeOH. The crude mixture in DMF was carried directly in the next step.

Step 3: To the previous DMF mixture was added KOH (98 µL of 10M solution) at RT and the reaction mixture was stirred for 6 h and then diluted with $H_2O$ (3 mL) and flash frozen in a dry ice/acetone bath. The frozen solution was concentrated via lyophilization and the crude residue filtered through a Celite® pad adding DMF to a final volume of 2 mL. The sample was purified by automated reverse phase HPLC purification (CAPER, formic acid modifier) to provide 45. $^1$H NMR (400 MHz, DMSO-$d_6$) δ 7.44 (d, J=2.6 Hz, 1H), 7.33-7.04 (m, 4H), 7.01 (d, J=9.0 Hz, 1H), 5.38 (p, J=7.0 Hz, 1H), 3.05-2.98 (m, 2H), 2.75 (td, J=12.7, 12.1, 6.1 Hz, 1H), 2.37-2.25 (m, 3H), 2.20-2.03 (m, 2H), 1.43 (s, 3H), 1.20-0.89 (m, 6H). LCMS m/z 424.24 [M+H]$^+$.

Compounds 46-59

Compounds 46-59 (Table 4) were prepared from intermediates indicated in Table 4.

TABLE 4

Method of preparation, structure and physicochemical data for compounds 46-59

| Compound | Method/Product | Alcohol | $^1$H NMR; LCMS m/z [M + H]$^+$ |
|---|---|---|---|
| 46 | From S10, Using the procedures for 45 | | $^1$H NMR (400 MHz, DMSO-d$_6$) δ 7.39 (d, J = 2.5 Hz, 1H), 7.27 (dd, J = 9.8, 8.3 Hz, 1H), 7.24-7.17 (m, 2H), 7.16-7.08 (m, 1H), 7.05 (d, J = 9.1 Hz, 1H), 3.03 (d, J = 22.1 Hz, 5H), 2.77 (p, J = 6.6 Hz, 1H), 2.34-2.25 (m, 3H), 1.09 (dd, J = 6.7, 4.2 Hz, 6H). LCMS m/z 478.21 [M + H]$^+$ |
| 47 | From S10, Using the procedures for 45 | | $^1$H NMR (400 MHz, DMSO-d$_6$) δ 7.43 (d, J = 2.6 Hz, 1H), 7.26 (dd, J = 9.8, 8.3 Hz, 1H), 7.21-7.12 (m, 2H), 7.09 (td, J = 5.4, 2.6 Hz, 1H), 7.01 (d, J = 9.0 Hz, 1H), 5.50 (p, J = 7.2 Hz, 1H), 3.16-3.08 (m, 1H), 2.75 (qd, J = 7.9, 7.4, 4.5 Hz, 3H), 2.47 (d, J = 3.1 Hz, 2H), 2.36-2.20 (m, 3H), 1.11 (dd, J = 6.7, 4.4 Hz, 6H). LCMS m/z 410.23 [M + H]$^+$ |
| 48 | From S10, Using the procedures for 45 | | $^1$H NMR (400 MHz, DMSO-d$_6$) δ 7.41 (d, J = 2.6 Hz, 1H), 7.26 (dd, J = 9.8, 8.3 Hz, 1H), 7.22-7.05 (m, 3H), 7.01 (d, J = 9.0 Hz, 1H), 5.66 (dt, J = 5.9, 3.0 Hz, 1H), 3.05-2.99 (m, 1H), 2.78 (p, J = 6.6 Hz, 1H), 2.30 (d, J = 1.9 Hz, 3H), 2.16 (dtd, J = 44.1, 13.2, 12.6, 8.0 Hz, 4H), 1.87 (tq, J = 15.0, 8.3, 7.5 Hz, 2H), 1.14 (ddd, J = 6.4, 4.4, 1.6 Hz, 6H). LCMS m/z 424.24 [M + H]$^+$ |

TABLE 4-continued

Method of preparation, structure and physicochemical data for compounds 46-59

| Compound | Method/Product | Alcohol | $^1$H NMR; LCMS m/z [M + H]$^+$ |
|---|---|---|---|
| 49 | From S10, Using the procedures for 45 | | $^1$H NMR (400 MHz, DMSO-d$_6$) δ 7.48 (d, J = 2.5 Hz, 1H), 7.26 (dd, J = 9.8, 8.3 Hz, 1H), 7.22-7.14 (m, 2H), 7.10 (ddd, J = 13.1, 8.2, 5.5 Hz, 1H), 7.01 (d, J = 9.0 Hz, 1H), 5.31 (t, J = 7.0 Hz, 1H), 2.83-2.67 (m, 3H), 2.30 (s, 3H), 2.28-2.21 (m, 1H), 1.26 (d, J = 4.7 Hz, 6H), 1.12 (td, J = 6.7, 4.8 Hz, 6H). LCMS m/z 438.25 [M + H]$^+$ |
| 50 | From S10, Using the procedures for 45 | | $^1$H NMR (400 MHz, DMSO-d$_6$) δ 7.37 (d, J = 2.6 Hz, 1H), 7.27 (dd, J = 9.9, 8.3 Hz, 1H), 7.22-7.12 (m, 2H), 7.12-7.05 (m, 1H), 7.01 (d, J = 9.0 Hz, 1H), 4.73 (s, 2H), 2.79 (p, J = 6.6 Hz, 1H), 2.45 (dd, J = 9.7, 6.9 Hz, 2H), 2.30 (d, J = 1.9 Hz, 3H), 2.12 (ddt, J = 24.3, 17.5, 8.9 Hz, 3H), 1.93 (dt, J = 10.1, 4.8 Hz, 1H), 1.28-1.05 (m, 6H). LCMS m/z 424.24 [M + H]$^+$ |
| 51 | From S10, Using the procedures for 45 | | $^1$H NMR (400 MHz, DMSO-d$_6$) δ 7.42 (d, J = 2.6 Hz, 1H), 7.26 (dd, J = 9.8, 8.3 Hz, 1H), 7.17 (td, J = 8.9, 2.4 Hz, 2H), 7.10 (td, J = 6.0, 5.4, 2.7 Hz, 1H), 7.01 (d, J = 9.0 Hz, 1H), 5.30 (p, J = 7.4 Hz, 1H), 2.90 (p, J = 8.8 Hz, 1H), 2.85-2.70 (m, 3H), 2.42-2.19 (m, 5H), 1.13 (dd, J = 6.7, 4.1 Hz, 6H). LCMS m/z 410.23 [M + H]$^+$ |

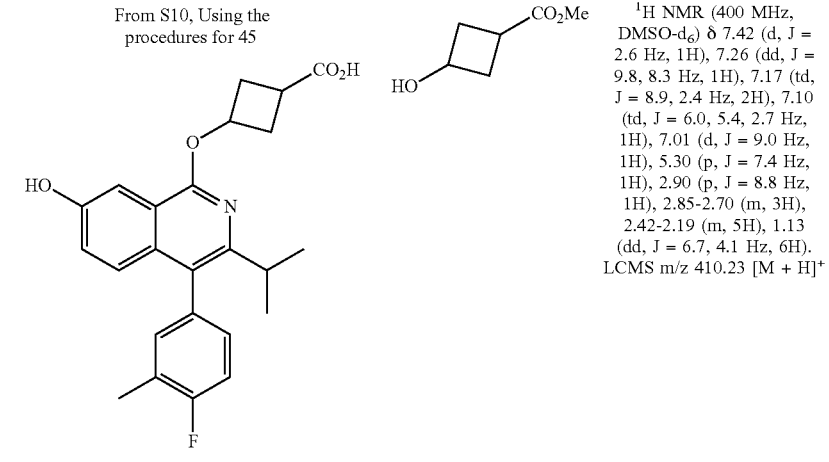

TABLE 4-continued

Method of preparation, structure and physicochemical data for compounds 46-59

| Compound | Method/Product | Alcohol | ¹H NMR; LCMS m/z [M + H]⁺ |
|----------|----------------|---------|---------------------------|
| 52 | From S10, Using the procedures for 45 | | LCMS m/z 424.24 [M + H]⁺ |
| 53 | From S10, Using the procedures for 45 | | ¹H NMR (400 MHz, DMSO-d₆) δ 7.45 (d, J = 2.6 Hz, 1H), 7.28-7.07 (m, 4H), 7.00 (d, J = 9.0 Hz, 1H), 5.28-5.19 (m, 1H), 2.77 (q, J = 6.6 Hz, 1H), 2.66 (dd, J = 10.3, 7.7 Hz, 1H), 2.47 (s, 1H), 2.40-2.28 (m, 4H), 1.43 (s, 3H), 1.14 (ddd, J = 9.9, 6.7, 4.5 Hz, 6H), 1.05 (s, 3H). LCMS m/z 438.25 [M + H]⁺ |
| 54 | From S10, Using the procedures for 45 | | ¹H NMR (400 MHz, DMSO-d₆) δ 7.42 (d, J = 2.6 Hz, 1H), 7.26 (dd, J = 9.8, 8.3 Hz, 1H), 7.17 (ddd, J = 11.6, 8.3, 2.4 Hz, 2H), 7.09 (ddd, J = 7.8, 5.0, 2.2 Hz, 1H), 7.01 (d, J = 9.0 Hz, 1H), 5.42 (p, J = 1.2 Hz, 1H), 2.77 (p, J = 6.6 Hz, 1H), 2.58 (s, 2H), 2.47 (s, 2H), 2.35-2.26 (m, 3H), 1.45 (s, 3H), 1.12 (dd, J = 6.6, 4.3 Hz, 6H). LCMS m/z 424.24 [M + H]⁺ |

TABLE 4-continued

Method of preparation, structure and physicochemical data for compounds 46-59

| Compound | Method/Product | Alcohol | $^1$H NMR; LCMS m/z [M + H]$^+$ |
|---|---|---|---|
| 55 | From S10, Using the procedures for 45 | | $^1$H NMR (300 MHz, DMSO-d$_6$) δ 9.92 (s, 1H), 7.46 (s, 1H), 7.34-6.96 (m, 5H), 4.55 (s, 2H), 2.77 (s, 1H), 2.30 (s, 3H), 2.03 (d, J = 4.9 Hz, 6H), 1.12 (dd, J = 6.4, 3.4 Hz, 6H). LCMS m/z 436.41 [M + H]$^+$ |
| 56 | From S10, Using the procedures for 45 | | $^1$H NMR (400 MHz, DMSO-d$_6$) δ 7.88 (d, J = 2.2 Hz, 1H), 7.82 (dt, J = 6.9, 1.8 Hz, 1H), 7.58 (q, J = 3.4, 2.8 Hz, 3H), 7.31-7.21 (m, 3H), 7.16-7.08 (m, 2H), 2.73 (p, J = 6.5 Hz, 1H), 2.31 (d, J = 1.9 Hz, 3H), 0.94 (dd, J = 6.1, 2.2 Hz, 6H). LCMS m/z 432.27 [M + H]$^+$ |
| 57 | From S10, Using the procedures for 45 | | $^1$H NMR (400 MHz, DMSO-d$_6$) δ 7.70-7.62 (m, 2H), 7.57 (d, J = 2.5 Hz, 1H), 7.36 (d, J = 8.1 Hz, 1H), 7.30-7.22 (m, 2H), 7.20 (dd, J = 7.9, 2.0 Hz, 1H), 7.14-7.08 (m, 2H), 3.77 (s, 3H), 2.69 (dd, J = 14.1, 7.5 Hz, 1H), 2.30 (d, J = 1.8 Hz, 3H), 0.85 (dd, J = 6.7, 1.9 Hz, 6H). LCMS m/z 462.26 [M + H]$^+$ |

TABLE 4-continued

Method of preparation, structure and physicochemical data for compounds 46-59

| Compound | Method/Product | Alcohol | $^1$H NMR; LCMS m/z [M + H]$^+$ |
|---|---|---|---|
| 58 | From S10, Using the procedures for 45 | | $^1$H NMR (400 MHz, DMSO-d$_6$) δ 8.76 (d, J = 2.7 Hz, 1H), 8.19 (d, J = 8.6 Hz, 1H), 7.96 (dd, J= 8.6, 2.7 Hz, 1H), 7.60 (d, J = 2.5 Hz, 1H), 7.34-7.25 (m, 2H), 7.22 (dd, J = 7.5, 2.1 Hz, 1H), 7.13 (dd, J = 9.6, 5.7 Hz, 2H), 2.75 (dt, J = 14.1, 7.0 Hz, 1H), 2.36-2.26 (m, 3H), 0.96 (dd, J = 6.8, 2.3 Hz, 6H). LCMS m/z 433.28 [M + H]$^+$ |
| 59 | From S10, Using the procedures for 45 | | $^1$H NMR (400 MHz, DMSO-d$_6$) δ 10.35 (s, 1H), 7.51 (d, J = 2.5 Hz, 1H), 7.35-7.20 (m, 4H), 7.15 (dd, J = 10.3, 5.1 Hz, 2H), 2.80 (p, J = 6.6 Hz, 1H), 2.36-2.25 (m, 3H), 1.17-0.97 (m, 6H). LCMS m/z 422.91 [M + H]$^+$ |

Compounds 60 and 61

2-((4-(4-fluoro-3-methylphenyl)-7-hydroxy-3-iso-propylisoquinolin-1-yl)oxy)-N-(methylsulfonyl)acet-amide (60) and 2-((4-(4-fluoro-3-methylphenyl)-7-hydroxy isopropylisoquinolin-1-yl)oxy)acetic acid (61)

285 286

-continued

C96 + C97 → H₂, Pd/C, NaOH → 61

↓ methanesulfonamide (H₂N-SO₂-CH₃) / DMAP, EDCI

C98 → H₂, Pd/C → 60

Compound 60

Step 1: To a solution of S8 (1.03 g, 2.477 mmol) and benzyl 2-hydroxyacetate (510 µL, 3.594 mmol) in THF (15.45 mL) was added KOtBu (3.6 mL of 1M, 3.600 mmol) in THF. The solution was stirred for 30 minutes and additional benzyl 2-hydroxyacetate (510 µL, 3.594 mmol) was added followed by the addition of KOtBu (3.6 mL of 1M, 3.60 mmol) in THF. The solution was stirred for another 30 minutes and was diluted with aq. NH₄Cl and the aqueous phase was extracted with EtOAc. The combined organic phases were dried over Na₂SO₄, filtered and concentrated in vacuo. The resulting residue was purified by silica gel chromatography (40 g ISCO column) using 0-50% EtOAc/heptanes gradient to afford C95 (1.03 g, 76%) LCMS m/z 542.32 [M+H]$^+$ Step 2: A solution of C95 (200 mg, 0.3638 mmol), 2-isopropenyl-4,4,5,5-tetramethyl-1,3,2-dioxaborolane (127 mg, 0.7558 mmol) and Na₂CO₃ (570 µL of 2M, 1.140 mmol) in 1,4-dioxane (3 mL) and water (600 µL) was bubbled with N₂ for 5 min. Then, Pd(OAc)₂ (5 mg, 0.02227 mmol) and dicyclohexyl-[2-(2,4,6-triisopropylphenyl)phenyl]phosphane (23 mg, 0.04825 mmol) were added and the solution was microwaved at 130° C. for 30 minutes. HCl (600 µL of 2M) was added to acidify the solution and EtOAc (10 mL) was added. After the extraction of aqueous phase with additional EtOAc (2×3 mL), the combined organic layer was washed with brine (2×2 mL) and dried over MgSO₄, filtered and concentrated. The residue was purified by MPLC: 0-20% MeOH in dichloromethane to give C97 (96 mg, 48%) $^1$H NMR (400 MHz, Chloroform-d) δ 7.66 (d, J=2.6 Hz, 1H), 7.45-7.37 (m, 2H), 7.33 (ddt, J=8.7, 6.4, 1.1 Hz, 2H), 7.30-7.25 (m, 2H), 7.19 (dd, J=9.2, 2.6 Hz, 2H), 7.03-6.89 (m, 3H), 5.16 (s, 2H), 5.11 (s, 2H), 5.06 (s, 2H), 4.94 (p, J=1.6 Hz, 1H), 4.66 (dt, J=1.9, 0.9 Hz, 1H), 2.23 (d, J=2.0 Hz, 3H), 1.81 (dd, J=1.5, 0.9 Hz, 3H). LCMS m/z 548.36 [M+H]$^+$; and C96 (94 mg, 53%) LCMS m/z 458.29 [M+H]$^+$ Step 3: To a solution of C96 (95 mg, 0.1956 mmol), methanesulfonamide (22 mg, 0.2313 mmol), DMAP (30 mg, 0.2456 mmol) and TEA (55 µL, 0.3946 mmol) in dry dichloromethane (2 mL) cooled to 0° C. was added EDCI (52 mg, 0.2713 mmol). The reaction mixture was warmed to room temperature and stirred for 15 hours. The reaction mixture was then diluted with water, extracted with EtOAc, dried over sodium sulfate, filtered, and concentrated to dryness. The residue was purified by MPLC: 12 g column, eluting with 0-50% EtOAc in dichloromethane to give C98 (60 mg, 56%) $^1$H NMR (400 MHz, Chloroform-d) δ 7.54 (d, J=2.6 Hz, 1H), 7.41 (d, J=7.5 Hz, 2H), 7.28 (ddt, J=33.7, 10.5, 7.7 Hz, 6H), 7.06-6.91 (m, 3H), 6.51 (d, J=8.3 Hz, 1H), 5.14 (s, 2H), 4.99 (d, J=5.1 Hz, 2H), 4.74 (s, 1H), 3.60 (s, 2H), 3.19 (s, 3H), 2.24 (d, J=2.0 Hz, 3H), 1.85 (s, 3H). LCMS m/z 535.3 [M+H]$^+$ Step 4: To a solution of C98 (60 mg, 0.1098 mmol) in MeOH (2 mL) was added Pd/C (10 mg of 10% w/w, 0.00939 mmol) and a hydrogen balloon (1 atm) was fitted to the reaction vial and the reaction mixture was stirred for 24 hours after which the solution was filtered through a Celite® pad and concentrated to dryness. The residue was purified by silica gel chromatography (12 g ISCO column) using 0-50% MeOH/dichloromethane gradient to afford 60 (14.2 mg, 28%) $^1$H NMR (400 MHz, Chloroform-d) δ 7.53 (d, J=2.1 Hz, 1H), 7.19 (s, 1H), 7.14-7.00 (m, 3H), 7.01-6.88 (m, 3H), 5.03 (s, 2H), 3.26 (s, 3H), 2.81 (p, J=6.7 Hz, 1H), 2.26 (s, 4H), 1.20 (q, J=6.4, 5.2 Hz, 6H). LCMS m/z 447.26 [M+H]$^+$;

Compound 61

To a solution of C97 (95 mg, 0.1710 mmol) in MeOH (2 mL) and EtOAc (2 mL) was added the wetted Pd/C (20 mg of 10% w/w, 0.01879 mmol) and a hydrogen balloon (1 atm) was fitted to the reaction vial and the reaction mixture was stirred for 48 hours by which time the reaction was incomplete. The solution was transferred into a Parr shaker and the hydrogen pressure was adjusted to 50 psi and the stirring was continued for 15 hours. The solution was then filtered and washed with MeOH (5 mL), then NaOH (500 μL of 1 M, 0.5000 mmol) was added and the solution was stirred for 1 hour at room temperature and 30 minutes at 50° C. The solution was then neutralized to pH 4, extracted with EtOAc (2×10 mL). The combined organic layers were washed with brine, dried over MgSO$_4$ and then concentrated to give 61 (60.2 mg, 95%) $^1$H NMR (400 MHz, Chloroform-d) δ 7.51 (s, 1H), 7.11-6.69 (m, 6H), 5.01 (s, 2H), 2.78 (hept, J=6.7 Hz, 1H), 2.24 (d, J=1.9 Hz, 3H), 1.30-1.10 (m, 3H), 0.88-0.74 (m, 3H). LCMS m/z 371.68 [M+H]$^+$;

Compounds 62 and 63

4-(4-fluoro-3-methylphenyl)-7-hydroxy-3-isopropylisoquinoline-1-carboxylic acid (62) and 4-(4-fluoro-3-methylphenyl)-7-hydroxy-3-isopropylisoquinoline-1-carboxamide (63)

62

-continued

63

To a solution of TMSCN (1.25 g, 12.60 mmol) and S9 (3000 mg, 7.345 mmol) in THF (60 mL) was added DBU (3.3 mL, 22.07 mmol) and the resulting solution was stirred at 50° C. for 15 hours. The solution was cooled to room temperature and then diluted with EtOAc and aqueous bicarbonate solution. The two phases were separated, and the organic phase was concentrated to dryness, triturated with MeOH and the solid was taken in acetonitrile and filtered. The solid was added to KOH/EtOAc (30 mL) and the solution was stirred at 70° C. for 1 hour, cooled down to room temperature, acidified to pH 2 and extracted with dichloromethane (500 mL). The organic phase was dried over anhydrous sodium sulfate and concentrated. The residue was taken into a solution of dichloromethane/MeOH/EtOAc (1:1:4, 30 mL) and Pd(OH)$_2$ (1 g, 1.424 mmol) was added. The solution was stirred for 15 hours and then filtered over a Celite® pad. After evaporation, the residue was purified by reverse phase flash chromatography (ISCO, C18 column, 30 g) eluting with CH$_3$CN/water (0-100%, 0.1% TFA) to afford 62 (684 mg, 27%) $^1$H NMR (400 MHz, DMSO-d$_6$) δ 7.61 (s, 1H), 7.27 (m, 1H), 7.17 (m, 1H), 7.07 (m, 2H), 6.97 (m, 1H), 2.92-2.73 (m, 1H), 2.32 (s, 3H), 1.12 (m, 6H) and 63 (2 mg, side product) $^1$H NMR (400 MHz, DMSO-d$_6$) δ 10.16 (s, 1H), 8.47 (d, J=2.5 Hz, 1H), 8.12 (s, 1H), 7.70 (s, 1H), 7.33-7.03 (m, 4H), 2.88 (m, 1H), 2.32 (m, 3H), 1.19 (m, 6H).

Compound 64

(4-(4-fluoro-3-methylphenyl)-7-hydroxy-3-isopropylisoquinoline-1-carbonyl)alanine (64)

62

-continued

64

To a solution of 62 (50 mg, 0.1473 mmol), ethyl 2-aminopropanoate (HCl salt) (35 mg, 0.2279 mmol) in DMF (2 mL) was added T3P (95 mg, 0.2986 mmol) and DIPEA (80 µL, 0.4593 mmol) at room temperature. The resulting solution was stirred for 15 hours and KOH (150 µL of 10 M, 1.500 mmol) was added and the solution was stirred further for 15 hours. The solution was then filtered with a syringe filter and submitted for prep-LCMS purification (C18 ACN/Water with HCl modifier) to yield 64 (16.1 mg, 25%). LCMS m/z 411.39 $[M+H]^+$.

Compounds 65-78

Compounds 65-78 (Table 5) were prepared from intermediates indicated in Table 5. Any modifications to methods are noted in Table 5 and accompanying footnotes.

TABLE 5

Method of preparation, structure and physicochemical data for compounds 65-78

| Compound | Method/Product | Amine | $^1$H NMR; LCMS m/z $[M + H]^+$ |
|---|---|---|---|
| 65 | [a]From S9 using the procedure for compound 64 | | $^1$H NMR (400 MHz, DMSO-d$_6$) δ 10.18 (s, 1H), 8.83 (d, J = 8.1 Hz, 1H), 8.17 (d, J = 2.4 Hz, 1H), 7.36-7.09 (m, 5H), 4.48 (h, J = 8.3 Hz, 1H), 3.00 (s, 1H), 2.98-2.80 (m, 2H), 2.38-2.25 (m, 6H), 1.20 (dd, J = 6.7, 4.8 Hz, 6H). LCMS m/z 437.18 $[M + H]^+$ |
| 66 | [a]From S9 using the procedure for compound 64 | | $^1$H NMR (400 MHz, DMSO-d$_6$) δ 10.17 (s, 1H), 7.34-7.12 (m, 6H), 4.33 (d, J = 2.0 Hz, 1H), 4.08 (s, 1H), 2.88 (d, J = 8.5 Hz, 3H), 2.38-2.19 (m, 4H), 1.19-0.98 (m, 6H). LCMS m/z 411.39 $[M + H]^+$ |

TABLE 5-continued

Method of preparation, structure and physicochemical data for compounds 65-78

| Compound | Method/Product | Amine | $^1$H NMR; LCMS m/z $[M + H]^+$ |
|---|---|---|---|
| 67 | $^a$From S9 using the procedure for compound 64 | | $^1$H NMR (400 MHz, DMSO-d$_6$) δ 10.89 (s, 1H), 10.30 (s, 1H), 8.14 (d, J = 2.5 Hz, 1H), 8.01 (s, 4H), 7.42-7.10 (m, 5H), 3.03-2.87 (m, 2H), 2.40-2.27 (m, 3H), 1.24 (dd, J = 6.7, 4.7 Hz, 6H). LCMS m/z 459.14 [M + H]$^+$ |
| 68 | $^a$From S9 using the procedure for compound 64 | | $^1$H NMR (400 MHz, DMSO-d$_6$) δ 10.78 (s, 1H), 8.56 (s, 1H), 8.16 (d, J = 2.4 Hz, 1H), 8.07 (d, J = 7.9 Hz, 1H), 7.75 (d, J = 7.7 Hz, 1H), 7.56 (t, J = 7.9 Hz, 1H), 7.41-7.13 (m, 5H), 2.94 (q, J = 6.7 Hz, 1H), 2.37-2.31 (m, 3H), 1.25 (dd, J = 6.8, 4.8 Hz, 6H). LCMS m/z 459.14 [M + H]$^+$ |
| 69 | $^a$From S9 using the procedure for compound 64 | | LCMS m/z 460.18 [M + H]$^+$ |

TABLE 5-continued

Method of preparation, structure and physicochemical data for compounds 65-78

| Compound | Method/Product | Amine | $^1$H NMR; LCMS m/z [M + H]$^+$ |
|---|---|---|---|
| 70 | From S9 using the procedure for compound 64 | | LCMS m/z 465.24 [M + H]$^+$ |
| 71 | From S9 using the procedure for compound 64 | | LCMS m/z 437.25 [M + H]$^+$ |
| 72 | From S9 using the procedure for compound 64 | | LCMS m/z 451.20 [M + H]$^+$ |

TABLE 5-continued

Method of preparation, structure and physicochemical data for compounds 65-78

| Compound | Method/Product | Amine | $^1$H NMR; LCMS m/z [M + H]$^+$ |
|---|---|---|---|
| 73 | From S9 using the procedure for compound 64 | | $^1$H NMR (400 MHz, DMSO-d$_6$) δ 9.05 (s, 1H), 8.29 (d, J = 2.5 Hz, 1H), 7.33 (d, J = 8.9 Hz, 1H), 7.27-7.18 (m, 2H), 7.14 (dd, J = 8.5, 4.4 Hz, 2H), 2.88 (p, J = 6.8 Hz, 1H), 2.37-2.26 (m, 9H), 1.24-1.16 (m, 6H). LCMS m/z 449.26 [M + H]$^+$ |
| 74 | From S9 using the procedure for compound 64 | | $^1$H NMR (400 MHz, DMSO-d$_6$) δ 10.24 (s, 1H), 9.02 (d, J = 7.9 Hz, 1H), 8.76 (d, J = 2.4 Hz, 1H), 7.34 (t, J = 9.0 Hz, 1H), 7.26 (dd, J = 9.2, 2.6 Hz, 2H), 7.18 (d, J = 9.2 Hz, 2H), 4.57 (dt, J = 7.6, 3.7 Hz, 1H), 4.03-3.81 (m, 2H), 2.94-2.89 (m, 1H), 2.37-2.27 (m, 3H), 1.21 (dd, J = 6.7, 4.9 Hz, 6H). LCMS m/z 427.18 [M + H]$^+$ |
| 75 | From S9 using the procedure for compound 64 | | $^1$H NMR (400 MHz, DMSO-d$_6$) δ 10.19 (s, 1H), 8.72 (m, 1H), 8.53 (d, J = 2.6 Hz, 1H), 7.33 (dd, J = 9.9, 8.3 Hz, 1H), 7.24 (dd, J = 9.2, 2.6 Hz, 2H), 7.15 (d, J = 9.2 Hz, 2H), 3.76-3.37 (m, 4H), 2.90 (p, J = 6.4 Hz, 1H), 2.33 (d, J = 1.9 Hz, 3H), 1.20 (m, 6H). LCMS m/z 383.38 [M + H]$^+$ |

TABLE 5-continued

Method of preparation, structure and physicochemical data for compounds 65-78

| Compound | Method/Product | Amine | $^{1}$H NMR; LCMS m/z [M + H]$^{+}$ |
|---|---|---|---|
| 76 | From S9 using the procedure for compound 64 | | $^{1}$H NMR (400 MHz, DMSO-d$_{6}$) δ 10.23 (s, 1H), 9.56 (s, 1H), 8.97 (t, J = 6.1 Hz, 1H), 8.58 (d, J = 2.5 Hz, 1H), 7.40-7.11 (m, 5H), 3.76 (m, 2H), 3.37 (d, J = 5.7 Hz, 2H), 2.91 (d, J = 4.5 Hz, 7H), 2.33 (d, J = 1.9 Hz, 3H), 1.22 (m, 6H). LCMS m/z 383.38 [M + H]$^{+}$ |
| 77 | From S9 using the procedure for compound 64 | | $^{1}$H NMR (400 MHz, DMSO-d$_{6}$) δ 10.18 (s, 1H), 8.76 (t, J = 5.8 Hz, 1H), 8.43 (d, J = 2.5 Hz, 1H), 7.32 (t, J = 9.1 Hz, 1H), 7.25-7.21 (m, 2H), 7.19-7.12 (m, 2H), 3.45 (m, 6H), 2.88 (p, J = 6.7 Hz, 1H), 2.32 (d, J = 1.9 Hz, 3H), 2.22 (t, J = 8.0 Hz, 2H), 1.95 (p, J = 7.4 Hz, 2H), 1.28-1.16 (m, 6H). LCMS m/z 450.39 [M + H]$^{+}$ |
| 78 | From S9 using the procedure for compound 64 | | $^{1}$H NMR (400 MHz, DMSO-d$_{6}$) δ 10.20 (s, 1H), 8.84 (m, 1H), 8.40 (d, J = 2.5 Hz, 1H), 7.32 (m, 1H), 7.24 (m, 2H), 7.18-7.09 (m, 2H), 3.23 (dd, J = 9.5, 6.4 Hz, 2H), 3.01 (s, 3H), 2.89 (p, J = 6.7 Hz, 1H), 2.33 (d, J = 1.9 Hz, 3H), 2.05 (t, J = 7.8 Hz, 2H), 1.21 (dd, J = 6.8, 4.9 Hz, 6H) LCMS m/z 459.35 [M + H]$^{+}$ |

$^{a}$HATU was used instead of 3TP for the preparation if this compound.

Compound 79

3-(4-(4-fluoro-3-methylphenyl)-7-hydroxy-3-isopro-
pylisoquinolin-1-yl)propanoic acid (79)

S9

C99

C100

C101

-continued

79

4-Step procedure: Synthesis of 3-[4-(4-fluoro-3-
methyl-phenyl)-7-hydroxy-3-isopropyl-1-isoqui-
nolyl]propanoic acid (79)

Step 1: (COCl)₂ (2 mL of 2 M in dichloromethane, 4.000 mmol) was added to a solution of S9 (800 mg, 1.993 mmol) and DIEA (800 µL, 4.593 mmol) in dichloromethane (9 mL) at −78° C. The reaction was slowly warmed to 0° C. over 2 hours and was quenched by the addition of MeOH (2 mL) and after stirring for 10 minutes, the mixture was concentrated to dryness. MeOH (3 mL) was added and the resulting solid was filtered and washed with cold MeOH and dried under high vacuum to afford C99 (620 mg, 74%) ¹H NMR (300 MHz, Chloroform-d) δ 7.71-7.65 (m, 1H), 7.57-7.49 (m, 2H), 7.48-7.32 (m, 3H), 7.30 (d, J=2.4 Hz, 1H), 7.27 (d, J=0.7 Hz, 1H), 7.26-7.00 (m, 3H), 5.25 (s, 2H), 2.95 (p, J=6.8 Hz, 1H), 2.37 (d, J=2.0 Hz, 3H), 1.24 (dd, J=6.7, 3.8 Hz, 6H) ppm. LCMS m/z 419.94 [M+H]⁺

Step 2: To a solution of C99 (350 mg, 0.8335 mmol) and Pd(PPh₃)₄ (78 mg, 0.06750 mmol) in THF (7 mL) was slowly added bromo-(3-ethoxy-3-oxo-propyl)zinc (7 mL of 0.5M 3.500 mmol) under N₂ atmosphere. The solution was then stirred at 80° C. for 8 hours. The solvent was evaporated, and the residue was dissolved in dichloromethane. The organic phase was washed with NaOH (0.5 M, 6 mL), water, brine and dried over sodium sulfate. After filtration and concentration to dryness, the residue was purified by silica gel chromatography (12 g ISCO column) using 0-50% EtOAc/heptanes gradient to afford C100 (310 mg, 77%) LCMS m/z 485.87 [M+H]⁺;

Step 3: A suspension of Pd/C (100 mg of 10% w/w, 0.09397 mmol) and C100 (310 mg, 0.6384 mmol) in MeOH/EtOAc (1:1) (100 mL) was stirred under H₂ (balloon, 1 atm) for 3 hour at room temperature. The suspension was then filtered through a Celite® pad the concentrated to dryness to afford C101 (250 mg, 99%) 1H NMR (300 MHz, Chloroform-d) δ 7.43 (d, J=2.5 Hz, 1H), 7.27-6.90 (m, 5H), 5.49 (s, 1H), 4.22 (q, J=7.1 Hz, 2H), 3.59 (t, J=6.8 Hz, 2H), 3.08 (t, J=6.8 Hz, 2H), 2.92 (p, J=6.7 Hz, 1H), 2.35 (d, J=1.9 Hz, 3H), 1.32 (t, J=7.1 Hz, 3H), 1.19 (dd, J=6.7, 3.8 Hz, 6H) ppm. LCMS m/z 396.24 [M+H]⁺;

Step 4: A solution of C101 (240 mg, 0.6069 mmol) and LiOH·H₂O (380 mg, 9.055 mmol) in THF/water (2:1) (15 mL) was stirred for 6 hours. The reaction mixture was then acidified with HCl (10 mL of 1M, 10.00 mmol) and extracted with EtOAc. The organic layer was washed with water, sat. NaCl, dried over sodium sulfate and concentrated to dryness to give 79 (hydrochloride salt) (215 mg, 83%) ¹H NMR (300 MHz, DMSO-d$_6$) δ 12.03 (s, 1H), 10.02 (s, 1H), 7.39 (d, J=2.3 Hz, 1H), 7.28 (dd, J=9.9, 8.3 Hz, 1H), 7.22-7.15 (m, 2H), 7.14-7.03 (m, 2H), 3.40 (dd, J=7.3, 5.8 Hz, 2H), 2.84 (dp, J=20.0, 6.7, 6.2 Hz, 3H), 2.30 (d, J=1.9 Hz, 3H), 1.14 (dd, J=6.7, 3.8 Hz, 6H) ppm. LCMS m/z 368.01 [M+H]$^+$.

Compounds 80-86

Compounds 80-86 (Table 6) were prepared from intermediates indicated in Table 6. Any modifications to methods are noted in Table 6 and accompanying footnotes.

TABLE 6

Method of preparation, structure and physicochemical data for compounds 80-86

| Compound | Method/Product | Alkyl halide or Zn reagent | $^1$H NMR; LCMS m/z [M + H]$^+$ |
|---|---|---|---|
| 80 | From S9 using the procedure for compound 79 | CO$_2$Et, CO$_2$H, ZnBr | $^1$H NMR (300 MHz, Chloroform-d) δ 7.88 (s, 1H), 7.38-7.29 (m, 1H), 7.26 (s, 1H), 7.20-6.96 (m, 3H), 3.61 (s, 2H), 3.04 (p, J = 7.0 Hz, 1H), 2.50 (d, J = 7.1 Hz, 2H), 2.36 (d, J = 1.8 Hz, 3H), 2.28 (d, J = 6.6 Hz, 2H), 1.41-1.29 (m, 6H). LCMS m/z 382.09 [M + H]$^+$ |
| 81 | From S9 using the procedure for compound 79 | CO$_2$Me, CO$_2$H, ZnBr | $^1$H NMR (300 MHz, DMSO-d$_6$) δ 12.03 (s, 1H), 7.39 (s, 1H), 7.34-7.05 (m, 5H), 3.51 (d, J = 11.9 Hz, 1H), 3.19 (d, J = 14.9 Hz, 2H), 2.81 (s, 1H), 2.31 (s, 3H), 1.28 (d, J = 6.4 Hz, 3H), 1.15 (d, J = 9.8 Hz, 6H). LCMS m/z 382.41 [M + H]$^+$ |
| 82 | $^a$From S9 using the procedure for compound 79 | CO$_2$Me, CO$_2$H, ZnBr | $^1$H NMR (300 MHz, Chloroform-d) δ 7.89 (s, 1H), 7.36 (d, J = 9.4 Hz, 1H), 7.27-6.86 (m, 4H), 3.65 (d, J = 58.9 Hz, 2H), 3.06 (p, J = 7.0 Hz, 1H), 2.56 (s, 1H), 2.36 (dd, J = 3.6, 1.9 Hz, 3H), 2.13 (d, J = 21.9 Hz, 2H), 1.35 (d, J = 5.6 Hz, 6H), 1.17 (d, J = 6.6 Hz, 3H). LCMS m/z 396.36 [M + H]$^+$ |

TABLE 6-continued

Method of preparation, structure and physicochemical data for compounds 80-86

| Compound | Method/Product | Alkyl halide or Zn reagent | $^1$H NMR; LCMS m/z [M + H]$^+$ |
|---|---|---|---|
| 83 | From S9 using the procedure for compound 79 | CO$_2$Me ZnBr | $^1$H NMR (300 MHz, DMSO-d$_6$) δ 12.03 (s, 1H), 10.00 (s, 1H), 7.52-6.95 (m, 6H), 3.64-3.43 (m, 1H), 3.19 (d, J = 15.0 Hz, 2H), 2.94-2.70 (m, IH), 2.30 (s, 3H), 1.41-0.97 (m, 9H). LCMS m/z 381.96 [M + H]$^+$ |
| 84 | $^{b,c}$From S9 using the procedure for compound 79 | CO$_2$Et I | $^1$H NMR (300 MHz, Chloroform-d) δ 7.82 (s, 1H), 7.38 (dd, J = 9.3, 2.0 Hz, 1H), 7.21 (d, J = 9.2 Hz, 1H), 7.08 (t, J = 8.7 Hz, 1H), 6.95 (td, J = 8.6, 3.7 Hz, 2H), 4.66 (s, 1H), 3.44-3.24 (m, 1H), 3.04 (dd, J = 13.9, 6.8 Hz, 3H), 2.59 (s, 2H), 2.26 (d, J = 1.9 Hz, 3H), 1.37-1.28 (m, 6H). LCMS m/z 393.93 [M + H]$^+$ |
| 85 | $^{b,c}$From S9 using the procedure for compound 79 | CO$_2$Et I | $^1$H NMR (300 MHz, Chloroform-d) δ 7.46 (s, 1H), 7.24-6.95 (m, 5H), 4.72 (s, 1H), 3.40 (s, 1H), 3.03 (s, 5H), 2.46-2.23 (m, 3H), 1.40-1.27 (m, 6H). LCMS m/z 394.33 [M + H]$^+$ |

TABLE 6-continued

Method of preparation, structure and physicochemical data for compounds 80-86

| Compound | Method/Product | Alkyl halide or Zn reagent | $^1$H NMR; LCMS m/z [M + H]$^+$ |
|---|---|---|---|
| 86 | $^b$From S9 using the procedure for compound 79 | | $^1$H NMR (300 MHz, Methanol-d$_4$) δ 7.53 (dd, J = 2.3, 0.7 Hz, 1H), 7.27-6.98 (m, 5H), 3.32-3.16 (m, 2H), 2.96 (p, J = 6.8 Hz, 1H), 2.35 (d, J = 1.9 Hz, 3H), 2.16-1.99 (m, 2H), 1.22 (dd, J = 6.8, 3.2 Hz, 6H). LCMS m/z 410.04 [M + H]$^+$ |

$^a$The cyclopropyl group opened to the ethyl group during the hydrogenation step $^b$The Zn reagent was generated in-situ using ZnCu (3 eq. for 1 eq. of alkyl halide) in toluene/DMA at 85° C. in microwave (0.165 M).

$^c$The cis and trans isomer were separated using SFC after the Negishi coupling step

Compounds 87 and 88

(E)-3-(4-(4-fluoro-3-methylphenyl)-7-hydroxy-3-isopropylisoquinolin-1-yl)but-2-enoic acid (87) and 3-(4-(4-fluoro-3-methylphenyl)-7-hydroxy-3-isopropylisoquinolin-1-yl)butanoic acid (88)

C102

C103

-continued

C104

87

-continued

88

Step 1: To solution of C102 (100 mg, 0.2381 mmol), tert-butyl 4-(4,4,5,5-tetramethyl-1,3,2-dioxaborolan-2-yl) benzoate (110 mg, 0.3616 mmol), Pd(PPh₃)₄ (25 mg, 0.02163 mmol) in DMF (3.5 mL) was added Na₂CO₃ (550 μL of 2M, 1.100 mmol) under an atmosphere of N₂. The reaction mixture was then microwaved at 130° C. for 1 hour. The reaction was then diluted with water and the aqueous phase was extracted with EtOAc. The organic layer was washed with water, brine and dried over sodium sulfate. After concentration to dryness, the residue was purified by silica gel chromatography (40 g ISCO column) using 0-60% EtOAc/heptanes gradient to afford C103 (127 mg, 95%) LCMS m/z 562.41 [M+H]⁺

Step 2: A suspension of Pd/C (35 mg of 10% w/w, 0.03289 mmol) and C103 (100 mg, 0.2010 mmol) in MeOH/ EtOAc (1:1) (34 mL) was stirred under H₂ (balloon, 1 atm) for 3 hours at room temperature. The suspension was then filtered through a Celite® pad the concentrated to dryness to afford C104. ¹H NMR (300 MHz, Chloroform-d) δ 7.46 (d, J=2.5 Hz, 1H), 7.32 (s, 1H), 7.21-7.02 (m, 4H), 6.14 (d, J=1.5 Hz, 1H), 5.57 (s, 1H), 4.29 (q, J=7.1 Hz, 2H), 3.00 (h, J=6.6 Hz, 1H), 2.75 (d, J=1.5 Hz, 3H), 2.38 (d, J=1.9 Hz, 3H), 1.36 (t, J=7.1 Hz, 3H), 1.23 (dd, J=6.7, 3.7 Hz, 6H). LCMS m/z 408.55 [M+H]⁺

Step 3: A solution of C104 (48 mg, 0.1178 mmol) and LiOH·H₂O (60 mg, 1.430 mmol) in THF/water (2:1) (3 mL) was stirred for 2 hours at room temperature. The reaction mixture was then acidified with HCl (1.5 mL of 1M, 1.5 mmol) and extracted with EtOAc. The organic layer was washed with water, sat. NaCl, dried over sodium sulfate and concentrated to dryness to give a residue which was purified by silica gel chromatography (4 g ISCO column) using 0-25% MeOH/dichloromethane gradient to afford 87 (45 mg, 92%) ¹H NMR (300 MHz, Chloroform-d and MeOH-d₄) δ 7.39 (s, 1H), 7.32-7.00 (m, 5H), 6.11 (s, 1H), 3.36 (s, 2H), 3.11-2.91 (m, 1H), 2.68 (s, 3H), 2.36 (s, 3H), 1.22 (d, J=3.1 Hz, 6H). LCMS m/z 380.43 [M+H]⁺

Step 4: A suspension of Pd/C (30 mg of 10% w/w, 0.02819 mmol) and 87 (45 mg, 0.1082 mmol) in MeOH/ EtOAc (1:1) (16 mL) was stirred under H₂ (balloon, 1 atm) for 3 hours at room temperature. The suspension was then filtered through a Celite® pad the concentrated to dryness to give a residue which was purified by silica gel chromatography (12 g ISCO column) using 0-25% MeOH/dichloromethane gradient to afford 88 (25 mg, 53%) ¹H NMR (300 MHz, Methanol-d₄) δ 7.52 (t, J=3.4 Hz, 1H), 7.30 (s, 2H), 7.26-6.90 (m, 3H), 4.16 (dt, J=14.4, 7.4 Hz, 1H), 3.58-3.26

(m, 2H), 2.98 (d, J=16.4 Hz, 1H), 2.37 (s, 3H), 1.58 (d, J=7.2 Hz, 3H), 1.30 (dq, J=6.5, 3.3 Hz, 6H) ppm. LCMS m/z 382.05 [M+H]⁺

Compound 89

3-(4-(4-fluoro-3-methylphenyl)-7-hydroxy-3-isopropylisoquinolin-1-yl)bicyclo[1.1.1]pentane-1-carboxylic acid (89)

C15

C105

C106

C107

C108

-continued

89

Step 1: MgSO₄ (3.123 g, 25.945 mmol) was added to a solution of C15 (8.9 g, 27.179 mmol) and tert-butylamine (10.440 g, 15 mL, 142.75 mmol) in dichloromethane (70 mL). After 4 h, the reaction was monitored by $^1$H NMR and showed complete conversion. The reaction mixture was filtered over Celite® and washed with dichloromethane. The filtrate was concentrated under reduced pressure to yield C105 (10.38 g, 97%) as an orange solid. $^1$H NMR (300 MHz, Chloroform-d) δ 1.03-1.46 (m, 15H), 2.83 (dt, J=13.7, 6.7 Hz, 1H), 5.12 (s, 2H), 6.83-7.02 (m, 1H), 7.29-7.54 (m, 6H), 7.65 (d, J=2.6 Hz, 1H), 8.78 (s, 1H).

Step 2: AgNO₃ (1.063 g, 6.2576 mmol) and LiCO₃ (2.540 g, 34.375 mmol) were added to a solution of C105 (10.387 g, 26.476 mmol) in dry DMA (130 mL). The reaction was stirred 2 minutes at room temperature and NBS (7.617 g, 42.796 mmol) was added. The reaction was stirred for 2 hours at room temperature and was filtered and the solid washed with EtOAc (50 mL). The filtrate was diluted with EtOAc (100 mL) and washed with a 10% aq. solution of Na₂S₂O₃ (100 mL). The aqueous layer was extracted with EtOAc (20 mL). The combined organic layers were washed with water (4×60 mL), brine (60 mL), dried over anhydrous sodium sulfate, filtered and concentrated under reduced pressure. The crude product was purified by silica gel chromatography (using 0-85% EtOAc/Heptane) to yield C106 (7.71 g, 82%) $^1$H NMR (300 MHz, Chloroform-d) δ 1.36 (d, J=6.8 Hz, 6H), 3.84 (dquin, J=13.5, 6.7 Hz, 1H), 5.22 (s, 2H), 7.27-7.57 (m, 7H), 8.15 (d, J=9.4 Hz, 1H), 9.04 (s, 1H). LCMS m/z 356.1 [M+H]⁺

Step 3: A solution of C106 (7.711 g, 21.645 mmol), (4-fluoro-3-methyl-phenyl)boronic acid (4.60 g, 29.913 mmol) and Na₂CO₃ (21 mL of 2 M in water, 42.000 mmol) in DMSO (77 mL) was heated to 100° C. and sparged with N₂ for 15 min. PdCl₂(dppf)•dichloromethane (1.22 g, 1.4939 mmol) was added and the reaction was sparged for 2 min. The reaction was stirred at 100° C. for 4 hours and cooled to room temperature. An aqueous solution of pH 7 0.1M potassium phosphate buffer (150 mL) was added and the resulting precipitate was filtered and washed with water (2×200 mL). The solid was dissolved in dichloromethane (200 mL), dried over Na₂SO₄, filtered over Celite®, washed with dichloromethane and concentrated under reduced pressure. The crude product was purified by chromatography on a silica plug eluted with Heptane (100%) then Heptane/EtOAc (5:1) to yield C107 (7.71 g, 91%). $^1$H NMR (300 MHz, Chloroform-d) δ 1.25 (m, 6H), 2.36 (s, 3H), 2.92-3.11 (m, 1H), 5.21 (s, 2H), 7.00-7.54 (m, 11H), 9.18 (s, 1H). $^{19}$F NMR (282 MHz, Chloroform-d) δ −119.3 (s, 1F). LCMS m/z 386.2 [M+H]⁺

Step 4: A clear vial was charged with C107 (50 mg, 0.1282 mmol), O3-(1,3-dioxoisoindolin-2-yl) O1-methyl bicyclo[1.1.1]pentane-1,3-dicarboxylate (66 mg, 0.1916 mmol), (Ir[dF(CF₃)ppy]₂(dtbpy))PF₆ (3 mg, 0.00267 mmol) and the vial was purged 3 times with N₂. Then, DMA (1.5 mL) and TFA (20 µL, 0.259 mmol) and the mixture was stirred under argon and irradiated with two blue LED Kessil lamps. After 2 hours, the reaction was quenched with DIPEA (0.1 mL), diluted with water (10 mL) and EtOAc (10 mL). The aqueous layer was extracted with EtOAc, dried with sodium sulfate, filtered, and concentrated. The residue was purified by silica gel chromatography (0-25% EtOAc: Heptane gradient) to yield C108 (26 mg, 39%). $^1$H NMR (400 MHz, Chloroform-d) δ 7.51 (dd, J=2.3, 0.8 Hz, 1H), 7.43-7.37 (m, 2H), 7.37-7.31 (m, 2H), 7.31-7.24 (m, 1H), 7.18 (d, J=0.8 Hz, 1H), 7.17-7.14 (m, 1H), 7.04 (dd, J=9.6, 8.2 Hz, 1H), 7.00-6.91 (m, 2H), 5.15 (s, 2H), 3.70 (s, 3H), 2.83 (h, J=6.7 Hz, 1H), 2.50 (d, J=8.5 Hz, 6H), 2.26 (d, J=1.9 Hz, 3H), 1.11 (dd, J=6.7, 5.1 Hz, 6H). LCMS m/z 510.26 [M+H]⁺

Steps 5 and 6 were conducted in the same fashion as Steps 3 and 4 for compounds 87 and 88 to yield 89 (9 mg, 43%). $^1$H NMR (400 MHz, Methanol-d₄) δ 7.66 (d, J=2.3 Hz, 1H), 7.20-7.13 (m, 2H), 7.13-7.07 (m, 2H), 7.04 (ddd, J=7.8, 5.0, 2.2 Hz, 1H), 2.90 (p, J=6.7 Hz, 1H), 2.65 (s, 6H), 2.34 (d, J=2.0 Hz, 3H), 1.19 (dd, J=6.7, 3.5 Hz, 6H). LCMS m/z 406.35 [M+H]⁺

Compound 90

4-(4-(4-fluoro-3-methylphenyl)-7-hydroxy-3-isopropylisoquinolin-1-yl)benzoic acid (90)

C102

311

-continued

CO₂t-Bu

C108

$$\xrightarrow{\text{1. H}_2\text{, Pd/C} \atop \text{2. HCl dioxane}}$$

CO₂H

90

Step 1: A solution of C102 (100 mg, 0.2381 mmol), tert-butyl 4-(4,4,5,5-tetramethyl-1,3,2-dioxaborolan-2-yl) benzoate (110 mg, 0.3616 mmol) and Pd(PPh₃)₄ (25 mg, 0.0216 mmol) and Na₂CO₃ (550 μL of 2 M, 1.100 mmol) in DMF (3.5 mL) was microwaved at 130° C. for 1 hour. The reaction was then diluted with water and the aqueous phase was extracted with EtOAc. The organic layer was washed with water, brine and dried over sodium sulfate. After concentration to dryness, the residue was purified by silica gel chromatography (12 g ISCO column) using 0-50% EtOAc/heptanes gradient to afford C109 (127 mg, 95%) LCMS m/z 562.41 [M+H]⁺.

Step 2: The hydrogenation reaction (H₂, Pd/C) was carried in the same fashion as for compound 89.

Step 3: To the product formed in Step 2 (105 mg, 0.2227 mmol) was added HCl (5 mL of 4M, 20.0 mmol) in dioxane. The reaction mixture was microwaved at 100° C. for 30 minutes. Concentration to dryness afforded 90 (hydrochloride salt) (95 mg, 85%). ¹H NMR (300 MHz, DMSO-d₆) δ 10.13 (d, J=1.8 Hz, 1H), 8.36-6.86 (m, 10H), 2.94 (d, J=8.6 Hz, 1H), 2.34 (s, 3H), 1.21 (q, J=6.6, 4.5 Hz, 6H) ppm. LCMS m/z 416.38 [M+H]⁺

312

Compound 91

(4-(4-fluoro-3-methylphenyl)-7-hydroxy-3-(tetra-hydro-2H-pyran-4-yl)isoquinoline-1-carbonyl)serine (91)

S11

$$\xrightarrow{\text{PdCl}_2\text{(dppf)•DCM} \atop \text{Na}_2\text{CO}_3}$$

$$\xrightarrow{\text{1. TMSCN, TEA} \atop \text{2. Pd(OH)}_2\text{, KOH}}$$

C110

CO₂H

C111

$$\xrightarrow{\text{T3P, DIEA}}$$

91

Step 1: A solution of S11 (7.66 g, 18.489 mmol), (4-fluoro-3-methyl-phenyl)boronic acid (4.26 g, 27.672 mmol) and Na₂CO₃ (19 mL of 2 M in water, 38.000 mmol) in DMSO (80 mL) was heated to 100° C. and sparged with N₂ for 15 minutes. PdCl₂(dppf)•dichloromethane (789 mg, 0.9662 mmol) was added and the reaction was sparged with N₂ for 2 minutes. The reaction was stirred at 100° C. for 4 hours, cooled to room temperature, diluted with EtOAc (300 mL), washed with a pH 7 0.1 M potassium phosphate buffer (2×150 mL). A solid precipitated and was filtered off, dissolved in dichloromethane, filtered over Celite®, washed with dichloromethane and concentrated under reduced pressure to yield C110 (2.3 g, 28%) as a tan solid. The organic layer was further washed with water (3×100 mL), brine (100 mL), dried over $Na_2SO_4$, filtered and concentrated under reduced pressure. The crude product was purified by silica gel chromatography (ISCO 220 g 0-5% MeOH/dichloromethane). The fractions containing the product were combined and recrystallized in ACN (about 250 mL), filtered and dried under reduced pressure to yield C110 (3.7 g, 45%) as tan crystals. Both batches were combined to yield C110 (6.0 g, 71%). $^{1}$H NMR (300 MHz, Chloroform-d) δ 1.41 (d, J=11.7 Hz, 2H), 2.38 (d, J=1.5 Hz, 3H), 2.51-2.96 (m, 2H), 3.28 (t, J=11.3 Hz, 3H), 3.97 (dd, J=11.0, 3.4 Hz, 2H), 5.18 (s, 2H), 6.93-7.22 (m, 6H), 7.31-7.52 (m, 5H), 8.73 (s, 1H). $^{19}$F NMR (282 MHz, Chloroform-d) δ −117.1 (s, 1F). LCMS m/z 444.2 [M+H]$^{+}$.

Steps 2 and 3: To a solution of C110 in ACN/THF (4:1) (125 mL) (100 mL) was added TMSCN (2.4 mL, 18.00 mmol) and TEA (2.2 mL, 15.78 mmol) under an atmosphere of $N_2$. The solution was then heated to 40° C. for 3 days before concentration to dryness. The residue was purified by silica gel chromatography (220 g ISCO column) using 0-60% EtOAc/heptanes gradient to afford the cyano derivative (2.38 g, 95%) which was dissolved in EtOH and $Pd(OH)_2$ (778.0 mg, 1.108 mmol) was added and the solution was stirred under $H_2$ (balloon, 1 atm) for 30 hours at room temperature. The suspension was then filtered through a Celite® pad the concentrated to dryness to give a residue which was diluted with dichloromethane/1N NaOH (1:1) (50 mL). The aqueous layer was acidified with 2 M HCl and was extracted with EtOAc and dried over sodium sulfate. Concentration to dryness afforded C111 (742 mg, 35%). $^{1}$H NMR (300 MHz, DMSO-$d_6$) δ 7.76 (s, 1H), 7.35-7.06 (m, 5H), 3.87 (m, 2H), 3.17 (s, 2H), 2.32 (m, 3H), 2.18-1.96 (m, 2H), 1.45 (d, J=12.9 Hz, 2H).

Step 4: To a solution of C111 (50 mg, 0.131 mmol), methyl 2-amino-3-hydroxy-propanoate (HCl salt) (33 mg, 0.196 mmol) in DMF (2 mL) was added T3P (83 mg, 0.262 mmol) and DIPEA (68 μL, 0.393 mmol) at room temperature. The resulting solution was stirred for 15 hours and KOH (150 μL of 10M, 1.500 mmol) was added and the solution was stirred further for 15 hours. The solution was then filtered with a syringe filter and submitted for prep-LCMS purification (C18 ACN/Water with HCl modifier) to yield 91 (12.8 mg, 17.8%). $^{1}$H NMR (400 MHz, DMSO-$d_6$) δ 10.29 (s, 1H), 8.95 (d, J=7.9 Hz, 1H), 8.74 (d, J=2.5 Hz, 1H), 7.34 (m, 1H), 7.27 (dd, J=9.1, 2.6 Hz, 2H), 7.18 (dd, J=9.3, 4.6 Hz, 2H), 4.56 (dd, J=7.9, 3.9 Hz, 1H), 4.03-3.79 (m, 4H), 3.21 (m, 2H), 2.87-2.69 (m, 1H), 2.33 (d, J=2.1 Hz, 3H), 2.07 (d, J=12.2 Hz, 3H), 1.54 (d, J=13.1 Hz, 2H). LCMS m/z 469.25 [M+H]$^{+}$;

Compounds 92-96

Compounds 92-96 (Table 7) were prepared from intermediates indicated in Table 7. When the amine coupling partner isn't an ester, the last step (KOH hydrolysis) isn't conducted. Any modifications to methods are noted in Table 7 and accompanying footnotes.

TABLE 7

| Method of preparation, structure and physicochemical data for compounds 92-96 | | | |
|---|---|---|---|
| Compound | Method/Product | Amine | $^{1}$H NMR; LCMS m/z [M + H]$^{+}$ |
| 92 | From S11 using the procedure for compound 91 | $CO_2Et$ $NH_2$ | LCMS m/z 479.19 [M + H]$^{+}$ |

TABLE 7-continued

Method of preparation, structure and physicochemical data for compounds 92-96

| Compound | Method/Product | Amine | ¹H NMR; LCMS m/z [M + H]⁺ |
|---|---|---|---|
| 93 | From S11 using the procedure for compound 91 | | ¹H NMR (400 MHz, DMSO-d₆) δ 10.25 (s, 1H), 9.17 (s, 1H), 8.29 (d, J = 2.5 Hz, 1H), 7.33 (t, J = 9.0 Hz, 1H), 7.24 (dd, J = 9.3, 2.7 Hz, 2H), 7.15 (dd, J = 8.4, 4.8 Hz, 2H), 3.89 (d, J = 11.0 Hz, 2H), 3.19 (t, J = 12.0 Hz, 2H), 2.75 (t, J = 11.5 Hz, 1H), 2.41 (s, 6H), 2.33 (d, J = 1.9 Hz, 3H), 2.15 (dd, J = 15.8, 7.8 Hz, 2H), 1.45 (d, J = 12.8 Hz, 2H). LCMS m/z 491.25 [M + H]⁺ |
| 94 | From S11 using the procedure for compound 91 | | LCMS m/z 479.19 [M + H]⁺ |
| 95 | ᵃFrom S11 using the procedure for compound 91 | | ¹H NMR (400 MHz, DMSO-d₆) δ 10.22 (s, 1H), 8.87 (m, 1H), 8.42 (dd, J = 7.1, 2.5 Hz, 1H), 7.33 (m, 1H), 7.28-7.23 (m, 2H), 7.15 (d, J = 9.1 Hz, 2H), 3.97-3.82 (m, 2H), 3.60-3.49 (m, 2H), 3.22 (dt, J = 16.6, 9.8 Hz, 4H), 3.01 (d, J = 6.2 Hz, 3H), 2.75 (t, J = 12.3 Hz, 1H), 2.33 (d, J = 1.9 Hz, 3H), 2.11 (ddt, J = 50.0, 14.9, 7.3 Hz, 4H), 1.47 (d, J = 13.0 Hz, 2H). LCMS m/z 501.15 [M + H]⁺ |

TABLE 7-continued

| | Method of preparation, structure and physicochemical data for compounds 92-96 | | |
|---|---|---|---|
| Compound | Method/Product | Amine | $^1$H NMR; LCMS m/z [M + H]$^+$ |
| 96 | $^a$From S11 using the procedure for compound 91 <br><br> | | $^1$H NMR (400 MHz, DMSO-d$_6$) δ 10.22 (s, 1H), 8.72 (t, J = 5.9 Hz, 1H), 8.52 (d, J = 2.5 Hz, 1H), 7.33 (t, J = 9.0 Hz, 1H), 7.25 (dd, J = 9.3, 2.7 Hz, 2H), 7.16 (d, J = 9.2 Hz, 2H), 3.88 (dd, J = 11.4, 4.1 Hz, 2H), 3.61 (t, J = 6.1 Hz, 2H), 3.51-3.47 (m, 2H), 3.20 (t, J = 11.9 Hz, 2H), 2.75 (td, J = 11.6, 11.1, 5.9 Hz, 1H), 2.33 (s, 3H), 2.11 (tt, J = 13.4, 8.7 Hz, 2H), 1.48 (d, J = 13.0 Hz, 2H). LCMS m/z 425.19 [M + H]$^+$ |

$^a$The hydrolysis step (KOH) was not conducted

Compound 97

4-((4-(4-fluoro-3-methylphenyl)-7-hydroxy-3-(tetra-hydro-2H-pyran-4-yl)isoquinolin-1-yloxy)benzoic acid (97)

S12

97

Step 1: To a solution of S12 (trifluoroacetate salt) (600 mg, 0.919 mmol) and methyl 4-hydroxybenzoate (416 mg, 2.734 mmol) in DMF (3.33 mL) was added K$_2$CO$_3$ (380 mg, 2.750 mmol) and the reaction was stirred at room temperature for 16 hours. After this time, LCMS showed complete consumption of starting material and the reaction mixture was directly carried forward to the next step.

Step 2: To the DMF reaction mixture was added MeOH (3.33 mL) and the resulting suspension was filtered through a Celite® pad to remove the excess K$_2$CO$_3$. To this solution was added Pd(OH)$_2$ (45 mg of 60% w/w, 0.1923 mmol). A H$_2$ balloon (1 atm) was fitted to the reaction vessel and the reaction was stirred for 4 hours. The reaction mixture was filtered through a 0.2 micron filter, and then concentrated in vacuo to remove MeOH and the crude DMF reaction mixture was taken directly to the next step.

Step 3: To the DMF reaction mixture from the previous step was added KOH (920 μL of 10 M, 9.20 mmol) at room temperature and the reaction was stirred for 3 hours and diluted with water (3 mL) and flash frozen in a dry ice/acetone bath. The frozen solution was concentrated via lyophilization and the crude residue was purified by ISCO reverse phase flash chromatography (50 g C18, 5-95% MeCN in H$_2$O with 0.1% formic acid modifier) to provide 97 (132.5 mg, 30%). $^1$H NMR (300 MHz, Methanol-d$_4$) δ

8.18-8.06 (m, 2H), 7.60 (dd, J=2.1, 1.0 Hz, 1H), 7.43-7.30 (m, 2H), 7.23-7.11 (m, 4H), 7.08 (ddd, J=7.9, 5.1, 2.2 Hz, 1H), 3.84 (dd, J=11.4, 4.0 Hz, 2H), 3.29-3.16 (m, 2H), 2.72 (tt, J=11.6, 3.8 Hz, 1H), 2.34 (d, J=1.9 Hz, 3H), 1.99-1.75 (m, 2H), 1.52-1.35 (m, 2H). LCMS m/z 474.25 [M+H]$^+$

Compounds 99-101

Compounds 98-101 (Table 8) were prepared from intermediates indicated in Table 8. Any modifications to methods are noted in Table 8 and accompanying footnotes.

TABLE 8

Method of preparation, structure and physicochemical data for compounds 98-101

| Compound | Method/Product | Alcohol | $^1$H NMR; LCMS m/z [M + H]$^+$ |
|---|---|---|---|
| 98 | From S12 using the procedure for compound 97 | | LCMS m/z 504.14 [M + H]$^+$ |
| 99 | From S12 using the procedure for compound 97 | | LCMS m/z 474.15 [M + H]$^+$ |

TABLE 8-continued

Method of preparation, structure and physicochemical data for compounds 98-101

| Compound | Method/Product | Alcohol | $^1$H NMR; LCMS m/z [M + H]$^+$ |
|---|---|---|---|
| 100 | From S12 using the procedure for compound 97 | | LCMS m/z 475.15 [M + H]$^+$ |
| 101 | [a,b]From S12 using the procedure for compound 97 | | $^1$H NMR (400 MHz, Chloroform-d) δ 7.53 (s, 1H), 7.30 (s, 1H), 7.17-6.94 (m, 4H), 5.62 (p, J = 6.8 Hz, 1H), 3.98 (d, J = 11.3 Hz, 2H), 3.40-3.19 (m, 3H), 2.93 (ddt, J = 11.8, 7.5, 4.0 Hz, 2H), 2.76-2.68 (m, 2H), 2.58 (ddt, J = 12.6, 9.4, 5.7 Hz, 2H), 2.34 (s, 3H), 2.16 (dd, J = 18.1, 8.2 Hz, 2H), 1.45 (d, J = 13.2 Hz, 2H). LCMS m/z 452.52 [M + H]$^+$ |

[a]For step 1, NaH (21 equiv.) in DMSO (0.06 M) was used instead of K$_2$CO$_3$ in DMF.

[b]Hydrolysis step not conducted.

323

Compound 102

4-(4-(4-fluoro-3-methylphenyl)-7-hydroxy-3-(tetra-hydro-2H-pyran-4-yl)isoquinolin-1-yl)butanoic acid (102)

C110

(COCl)₂, DIEA →

C112

BrZn⏜⏜CO₂Et / Pd(PPh₃)₄ →

C113

H₂, Pd/C →

324

-continued

C114

LiOH →

102

Compounds 102-105

Compounds 102-105 (Table 9) were prepared from intermediates indicated in Table 9. Any modifications to methods are noted in Table 9 and accompanying footnotes.

TABLE 9

| Compound | Product | Zn reagent | ¹H NMR; LCMS m/z [M + H]⁺ |
|---|---|---|---|
| | Method of preparation, structure, physicochemical data for compounds 102-105 | | |
| 102 | From C110 using the procedure for compound 79 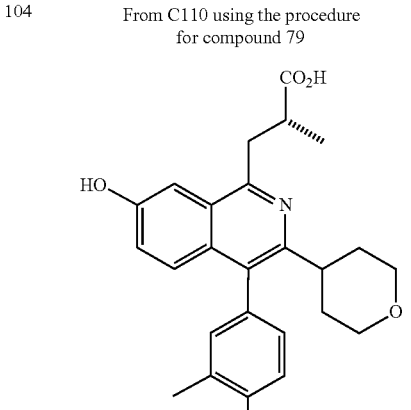 | CO₂Et, ZnBr | ¹H NMR (300 MHz, Chloroform-d) δ 7.79 (s, 1H), 7.28-6.79 (m, 6H), 4.01 (d, J = 11.0 Hz, 2H), 3.61 (s, 2H), 3.32 (t, J = 11.7 Hz, 2H), 2.92 (s, 1H), 2.62 (s, 2H), 2.39-2.24 (m, 7H), 1.55 (d, J = 12.7 Hz, 2H). LCMS m/z 424.48 [M + H]⁺ |
| 103 | From C110 using the procedure for compound 79 | CO₂Me, ZnBr | ¹H NMR (300 MHz, DMSO-d₆) δ 12.07 (s, 1H), 10.04 (s, 1H), 7.40 (d, J = 2.4 Hz, 1H), 7.28 (dd, J = 9.9, 8.3 Hz, 1H), 7.24-7.03 (m, 4H), 3.85 (d, J = 11.3 Hz, 2H), 3.53 (dd, J = 15.8, 6.6 Hz, 1H), 3.29-3.06 (m, 4H), 2.75-2.61 (m, 1H), 2.31 (d, J = 1.8 Hz, 3H), 2.09 (td, J = 12.3, 7.6 Hz, 2H), 1.40 (t, J = 12.0 Hz, 2H), 1.28 (d, J = 6.8 Hz, 3H). LCMS m/z 424.39 [M + H]⁺ |
| 104 | From C110 using the procedure for compound 79 | CO₂Me, ZnBr | ¹H NMR (300 MHz, DMSO-d₆) δ 12.08 (s, 1H), 10.04 (s, 1H), 7.40 (s, 1H), 7.35-7.03 (m, 5H), 3.85 (d, J = 10.9 Hz, 2H), 3.53 (d, J = 15.1 Hz, 1H), 3.19 (d, J = 13.4 Hz, 5H), 2.69 (d, J = 16.1 Hz, 1H), 2.31 (s, 3H), 2.09 (s, 2H), 1.51-1.17 (m, 5H). LCMS m/z 424.39 [M + H]⁺ |

TABLE 9-continued

Method of preparation, structure, physicochemical data for compounds 102-105

| Compound | Product | Zn reagent | $^1$H NMR; LCMS m/z [M + H]$^+$ |
|---|---|---|---|
| 105 | | $^a$N/A | 1H NMR (400 MHz, Methanol-d$_4$) δ 7.74 (d, J = 2.4 Hz, 1H), 7.61 (dd, J = 9.2, 2.4 Hz, 1H), 7.48 (d, J = 9.2 Hz, 1H), 7.33-7.27 (m, 2H), 7.22 (ddd, J = 7.9, 4.9, 2.2 Hz, 1H), 4.02 (dd, J = 11.6, 4.4 Hz, 2H), 3.91 (t, J = 7.1 Hz, 2H), 3.31 (tt, J = 4.1, 2.5 Hz, 3H), 3.09 (tt, J = 13.4, 4.2 Hz, 1H), 3.01 (t, J = 7.1 Hz, 2H), 2.38 (d, J = 2.0 Hz, 3H), 2.20 (dtd, J = 23.6, 11.9, 11.1, 6.8 Hz, 2H), 1.72 (dd, J = 13.8, 3.6 Hz, 2H). LCMS m/z 410.35 [M + H]$^+$ |

$^a$Compound 105 was prepared from S8 using two successive Suzuki reactions (with ethyl (E)-3-(4,4,5,5-tetramethyl-1,3,2-dioxaborolan-2-yl)prop-2-enoate and 2-(3,6-dihydro-2H-pyran-4-yl)-4,4,5,5-tetramethyl-1,3,2-dioxaborolane, respectively) followed by hydrogenation (H$_2$, Pd/C).

Compound 106

4-(4-(4-fluoro-3-methylphenyl)-7-hydroxy-3-(tetra-hydro-2H-pyran-4-yl)isoquinolin-1-yl)benzoic acid (106)

-continued

Compound 106 was prepared using the same procedure as for compound 90. $^1$H NMR (300 MHz, DMSO-d$_6$) δ 10.10 (s, 1H), 8.28-8.06 (m, 2H), 7.90-7.76 (m, 2H), 7.42-7.12 (m, 6H), 3.86 (dd, J=11.3, 4.2 Hz, 2H), 3.75-3.63 (m, 1H), 3.55-3.42 (m, 1H), 2.81 (t, J=11.6 Hz, 1H), 2.34 (d, J=1.8 Hz, 3H), 2.07 (dt, J=12.4, 5.7 Hz, 2H), 1.52 (d, J=13.0 Hz, 2H). LCMS m/z 458.32 [M+H]$^+$

Compound 107

4-(4-fluoro-3-methylphenyl)-7-hydroxy-2-(3-hy-droxypropyl)-3-isopropylisoquinolin-1(2H)-one (107)

-continued

C116

C117

C118

107

Step 1: In a sealed tube, a suspension of C1 (3.05 g, 9.4966 mmol) in TEA (22 mL) was bubbled through with N$_2$ for 10 minutes. Then, PdCl$_2$(PPh$_3$)$_2$ (657 mg, 0.9334 mmol) and CuI (56 mg, 0.2940 mmol) were added and bubbled through with N$_2$ for another 2 min. 3-methylbut-1-yne (1.3986 g, 2.1 mL, 20.532 mmol) was added and the tube was sealed, stirred and heated at 70° C. for 15 hours. The reaction mixture was cooled to room temperature, diluted with EtOAc (100 mL). The organic layer was washed with 3M HCl (2×60 mL), water (60 mL), brine, dried over anhydrous sodium sulfate, filtered, loaded on silica gel and concentrated under reduced pressure. The residue was purified on silica gel chromatography, eluting from 0% to 20% ethyl acetate in heptanes to give C116 (2.7 g, 92%). $^1$H NMR (300 MHz, Chloroform-d) δ 1.29 (d, J=6.8 Hz, 6H), 2.83 (spt, J=6.9 Hz, 1H), 3.93 (s, 3H), 5.09 (s, 2H), 7.04 (dd, J=8.7, 2.8 Hz, 1H), 7.31-7.47 (m, 6H), 7.50 (d, J=2.6 Hz, 1H). LCMS m/z 309.2 [M+H]$^+$ Step 2: To a solution of C116 (2 g, 6.4792 mmol) in anhydrous dichloromethane (40 mL) was added, at room temperature, a solution of 12 (1.88 g, 7.4071 mmol) in anhydrous dichloromethane (50 mL) over 30 minutes. The reaction mixture was stirred at room temperature for an additional 20 min then EtOAc (300 mL) was added. The organic phase was washed with a mixture of 5% aqueous NaHCO$_3$ and brine (3×100 mL, 90/10 ratio) and brine (2×50 mL), dried over sodium sulfate, filtered and the solvent was removed under reduced pressure. The residue was purified by silica gel chromatography eluting with 20-70% dichloromethane in heptanes to afford C117 (2.32 g, 85%) as white solid. $^1$H NMR (300 MHz, DMSO-d$_6$) δ 1.20 (d, J=6.8 Hz, 6H), 3.49 (sept, J=6.8 Hz, 1H), 5.27 (s, 2H), 7.30-7.44 (m, 3H), 7.45-7.51 (m, 2H), 7.59 (dd, J=8.8, 2.8 Hz, 1H), 7.64 (d, J=2.8 Hz, 1H), 7.70 (d, J=8.8 Hz, 1H). LCMS m/z 421.0 [M+H]$^+$ Step 3: In a sealed tube were added water (3.75 mL) and potassium phosphate (2.69 g, 12.673 mmol). The mixture was stirred for 10 minutes at room temperature then toluene (48 mL) was added. Nitrogen was bubbled through the mixture for 15 minutes and C117 (2.6 g, 6.1869 mmol), (4-fluoro-3-methyl-phenyl)boronic acid (1.23 g, 7.9898 mmol) and XPhos Pd G2 (364.3 mg, 0.4630 mmol) were added. The tube was sealed then transferred to a pre-heated oil bath set to 70° C. and stirred at this temperature for 2 hours. The reaction mixture was cooled to room temperature, then diluted with EtOAc (350 mL). The organic phase was washed with 5% aqueous NaHCO$_3$ (3×75 mL) and brine (2×75 mL), dried over sodium sulfate, filtered and concentrated to dryness. The residue was purified by silica gel chromatography eluting with 30-90% dichloromethane in heptanes to afford C118 (2.33 g, 93%) as white solid. $^1$H NMR (300 MHz, DMSO-d$_6$) δ 1.12 (d, J=6.6 Hz, 6H), 2.29 (s, 3H), 2.54-2.67 (m, 1H), 5.25 (s, 2H), 6.84 (d, J=8.8 Hz, 1H), 7.13-7.21 (m, 1H), 7.23-7.51 (m, 8H), 7.70 (d, J=2.7 Hz, 1H); $^{19}$F NMR (282 MHz, DMSO-d$_6$) δ −118.4-118.2 (m, 1F).

Step 4: A solution of C118 (500 mg, 1.241 mmol) and 3-aminopropan-1-ol (2000 μL, 26.18 mmol). was and heated to 180° C. for 90 minutes under microwave irradiation. The mixture was diluted with dichloromethane (60 mL) and water (30 mL) and then 1 M HCl was added (~26 mL) to bring the pH to ~1. At this time, the organic layer was removed and filtered over a phase separator and concentrated. The mixture was dissolved in dichloromethane (10 mL) and MsOH (20 μL, 0.3082 mmol) was added and the mixture was stirred at room temperature for 3.5 hours. The mixture was concentrated and then redissolved in minimal dichloromethane for purification by silica gel chromatography eluting with 0-5% MeOH in dichloromethane to yield 7-benzyloxy-4-(4-fluoro-3-methyl-phenyl)-2-(3-hydroxy-propyl)-3-isopropyl-isoquinolin-1-one (425 mg, 73%). $^1$H NMR (400 MHz, Chloroform-d) δ 7.97 (d, J=2.8 Hz, 1H), 7.55-7.30 (m, 5H), 7.22-6.95 (m, 4H), 6.81 (s, 1H), 5.21 (s, 2H), 4.46 (s, 2H), 3.68 (s, 2H), 3.33 (p, J=7.3 Hz, 1H), 2.40-2.27 (m, 3H), 2.05 (d, J=21.2 Hz, 2H), 1.41-1.27 (m, 3H), 1.07 (s, 3H). LCMS m/z 460.35 [M+H]$^+$ Step 5: To a flask was added 7-benzyloxy-4-(4-fluoro-3-methyl-phenyl)-2-(3-hydroxypropyl)-3-isopropyl-isoquinolin-1-one (250 mg, 0.5440 mmol), Pd/C (100 mg, 0.01879 mmol) and EtOAc (15 mL). The suspension was purged with N$_2$ three times and then with H$_2$ five times and then stirred under H$_2$ (60 psi) for 2 hours, filtered through a pad of Celite® and concentrated to dryness to afford 107 (200 mg, 95%). $^1$H NMR (400 MHz, DMSO-d$_6$) δ 9.89 (s, 1H), 7.58 (d, J=2.6 Hz, 1H), 7.25 (dd, J=9.8, 8.3 Hz, 1H), 7.18 (dd, J=7.7, 2.1 Hz, 1H), 7.10 (dt, J=8.4, 3.9 Hz, 1H), 7.03 (dd, J=8.8, 2.7 Hz, 1H), 6.61 (d, J=8.9 Hz, 1H), 4.68 (t, J=5.1 Hz, 1H), 4.16 (s, 2H), 3.60-3.49 (m, 2H), 3.17 (d, J=5.3 Hz, 1H), 2.29 (d, J=1.8 Hz, 3H), 1.83 (d, J=8.4 Hz, 2H), 1.23 (s, 6H). LCMS m/z 370.3 [M+H]$^+$ Compounds 108-111

Compounds 108-111 (Table 10) were prepared from inter-mediates indicated in Table 10. Any modifications to methods are noted in Table 10 and accompanying footnotes.

TABLE 10

Method of preparation, structure and physicochemical data for compounds 108-111

| Compound | Method/Product | amine | $^1$H NMR; LCMS m/z [M + H]$^+$ |
|---|---|---|---|
| 108 | From C118 using the procedure for compound 107 | | $^1$H NMR (400 MHz, DMSO-d$_6$) δ 9.89 (s, 1H), 7.58 (d, J = 2.6 Hz, 1H), 7.24 (ddd, J = 10.0, 8.3, 2.4 Hz, 1H), 7.16 (dd, J = 7.8, 2.1 Hz, 1H), 7.08 (td, J = 6.3, 5.8, 3.0 Hz, 1H), 7.04 (dt, J = 8.9, 2.2 Hz, 1H), 6.60 (d, J = 8.8 Hz, 1H), 4.84 (d, J = 83.6 Hz, 2H), 4.35 (s, 1H), 4.11-3.86 (m, 2H), 3.44 (d, J = 1.8 Hz, 2H), 2.29 (t, J = 2.3 Hz, 3H), 1.17 (t, J = 7.1 Hz, 6H). LCMS m/z 386.37 [M + H]$^+$ |
| 109 | From C118 using the procedure for compound 107 | | $^1$H NMR (400 MHz, Methanol-d$_4$) δ 7.66-7.63 (m, 1H), 7.20-6.97 (m, 5H), 6.73 (d, J = 8.8 Hz, 1H), 4.38 (t, J = 6.8 Hz, 2H), 3.88 (t, J = 6.8 Hz, 2H), 3.33-3.32 (m, 0H), 2.33 (d, J = 2.0 Hz, 3H), 1.37-1.15 (m, 6H). LCMS m/z 356.35 [M + H]$^+$ |
| 110 | $^a$From C118 using the procedure for compound 107 | | $^1$H NMR (400 MHz, DMSO-d$_6$) δ 12.64 (s, 1H), 10.01 (s, 1H), 7.56 (d, J = 2.7 Hz, 1H), 7.28-7.16 (m, 2H), 7.14-7.01 (m, 2H), 6.58 (d, J = 9.0 Hz, 1H), 5.77 (s, 1H), 4.78 (s, 2H), 3.17 (s, 1H), 2.29 (d, J = 1.8 Hz, 3H), 1.11-0.93 (m, 6H). LCMS m/z 410.31 [M + H]$^+$ |

TABLE 10-continued

Method of preparation, structure and physicochemical data for compounds 108-111

| Compound | Method/Product | amine | ¹H NMR; LCMS m/z [M + H]⁺ |
|---|---|---|---|
| 111 | *From C118 using the procedure for compound 107 | | LCMS m/z 408.9 [M + H]⁺ |

*hydrolysis reacton (LiOH 10 equiv. in MeOH at 80 °C.) was performed after the hydrogenation step.

Compounds 112 and 113

3-(4-(4-fluoro-3-methylphenyl)-7-hydroxy-3-isopropyl-1-oxoisoquinolin-2(1H)-yl)propanoic acid (112) and 3-(4-(4-fluoro-3-methylphenyl)-3-isopropyl-1-oxoisoquinolin-2(1H)-yl)propanamide (113)

-continued

Step 1: To a suspension of C119 (coming from Step 4 of the synthesis of 107) (20 mg, 0.04352 mmol) and NaHCO₃ (9 mg, 0.1071 mmol) in dichloromethane (0.5 mL) was added Dess-Martin periodinane (19 mg, 0.04480 mmol) and the reaction mixture was stirred at room temperature for 1 hour and additional Dess-Martin periodinane (19 mg, 0.04480 mmol) was added and the reaction was stirred for 1 hour. The reaction was quenched with a 1:1 mixture (5 mL) of sat. aq. sodium bicarbonate and sodium thiosulfate for 30 minutes. The product was extracted with dichloromethane and the organic phase was washed with brine, dried with sodium sulfate, filtered, and concentrated to give the aldehyde which was used in the next step with further purification.

Step 2: To a flask was added NaClO$_2$ (20 mg, 0.2211 mmol), NaH$_2$PO$_4$ (55 mg, 0.4546 mmol), and water (2 mL), the mixture was stirred until the solids dissolved. In another flask, the crude aldehyde from the first step was dissolved in THF (1.3 mL) and t-BuOH (2 mL). 2-methylbut-2-ene (450 µL of 2M, 0.900 mmol) as a solution in THF was added and the resulting biphasic mixture was stirred for 1 hour. The mixture was diluted with EtOAc and water, the pH was adjusted with 1 M HCl to pH 2. The organic layer (containing C120) was concentrated and used in the next step without further purification.

Step 3: To a flask was added the solid from the previous step, Pd/C (10 mg, 0.001879 mmol), and EtOAc (2 mL). The suspension was purged with N$_2$ three times and then with H$_2$ five times and then stirred under H$_2$ (60 psi) for 78 h (10:40). The material was filtered over a syringe filter and concentrated to yield 112 (5 mg, 20%). $^1$H NMR (400 MHz, Methanol-d$_4$) δ 7.64 (d, J=2.7 Hz, 1H), 7.19-7.00 (m, 5H), 6.75 (d, J=8.9 Hz, 1H), 4.54-4.40 (m, 2H), 2.84 (t, J=7.9 Hz, 2H), 2.33 (d, J=1.9 Hz, 3H), 2.27-2.15 (m, 1H), 1.29 (s, 6H). LCMS m/z 384.34 [M+H]$^+$ Step 4: The crude residue of a 100 mg scale reaction of step 3 (described above) was added DMF (4 mL), NH$_3$ (2 mL of 0.5M, 1.000 mmol) in dioxane, DIPEA (100 µL, 0.5741 mmol) and HATU (100 mg, 0.2630 mmol) and the reaction mixture was stirred for 5 minutes. The mixture was diluted with water (50 mL) and EtOAc (50 mL), separated, and the organic mixture was washed with brine (2×50 mL). The organic layer was dried with magnesium sulfate, filtered, and concentrated. The crude solid was suspended in ~2 mL dichloromethane and filtered to give 113 (35 mg, 42%) $^1$H NMR (400 MHz, DMSO-d$_6$) δ 9.93 (s, 1H), 7.59 (d, J=2.7 Hz, 1H), 7.47 (s, 1H), 7.26 (dd, J=9.8, 8.3 Hz, 1H), 7.21-7.14 (m, 1H), 7.09 (ddd, J=7.8, 4.9, 2.3 Hz, 1H), 7.04 (dd, J=8.8, 2.7 Hz, 1H), 6.97 (s, 1H), 6.62 (d, J=8.8 Hz, 1H), 4.27 (t, J=8.0 Hz, 2H), 3.25-3.11 (m, 1H), 2.56 (s, 2H), 2.29 (d, J=1.8 Hz, 3H), 1.21 (s, 6H). LCMS m/z 383.4 [M+H]$^+$

Compound 114

2-((4-(4-fluoro-3-methylphenyl)-7-hydroxy-3-(tetrahydro-2H-pyran-4-yl)isoquinolin-1-yl)oxy)acetic acid (114)

Compound 114 was prepared from S8 using the same reaction sequence as for compound 61 with the exception that 2-(3,6-dihydro-2H-pyran-4-yl)-4,4,5,5-tetramethyl-1,3, 2-dioxaborolane was used as the coupling partner in the Suzuki coupling step. $^1$H NMR (400 MHz, Methanol-d$_4$) δ 7.47 (d, J=2.4 Hz, 1H), 7.09-7.03 (m, 1H), 7.03-6.97 (m, 3H), 6.96-6.90 (m, 1H), 4.93 (s, 2H), 3.88-3.78 (m, 2H), 3.17 (d, J=11.8 Hz, 3H), 2.71-2.53 (m, 1H), 2.22 (d, J=1.9 Hz, 2H), 2.14-1.96 (m, 2H), 1.40-1.31 (m, 2H). LCMS m/z 412.38 [M+H]$^+$

Compound 115

(1r,3r)-3-(4-(4-fluoro-3-methylphenyl)-7-hydroxy-1-oxo-3-(tetrahydro-2H-pyran-4-yl)isoquinolin-2(1H)-yl)cyclobutane-1-carboxylic acid (115)

Step 1: To a solution of C1 (5 g, 15.57 mmol) in DMF (31 mL) and TEA (15.8 g, 156.1 mmol) was added CuI (178 mg, 0.9346 mmol), TBAF (6.4 g, 20.28 mmol) and TMS-alkyne (3.7 g, 20.29 mmol). The solution was purged with $N_2$ for 5 minutes and $PdCl_2(PPh_3)_4$ (328 mg, 0.4673 mmol) and the solution was purged for another 5 minutes and then heated at 80° C. for 15 hours. The solution was cooled down to room temperature and the TEA was removed in vacuo. Water (500 mL) was added followed by EtOAc (450 mL). The organic phase was washed with brine and concentrated. The residue was purified by silica gel chromatography (120 g ISCO column) using 0-40% EtOAc/heptanes gradient to afford C121 (2.0 g, 37%). $^1$H NMR (300 MHz, Chloroform-d) δ 7.46-7.23 (m, 8H), 6.97 (dd, J=8.6, 2.8 Hz, 1H), 5.02 (s, 2H), 3.91 (ddd, J=11.5, 5.9, 3.6 Hz, 2H), 3.84 (s, 3H), 3.50 (ddd, J=11.4, 8.2, 3.1 Hz, 2H), 2.83 (tt, J=8.3, 4.1 Hz, 1H), 1.92-1.80 (m, 2H), 1.70 (dtd, J=13.5, 8.3, 3.6 Hz, 2H).

Step 2: To a solution of C121 (500 mg, 1.427 mmol) in THF (1.8 mL), methanol (600 μL) and $H_2O$ (600 μL) was added LiOH (205 mg, 8.560 mmol) at room temperature and the solution was stirred for 15 hours. The reaction was acidified with 1 M HCl and extracted with EtOAc (10 mL). The organic solution was concentrated and the product was triturated with heptane to give the corresponding acid (400 mg, 83%). $^1$H NMR (300 MHz, Acetone-$d_6$) δ 7.70 (d, J=2.7 Hz, 1H), 7.59-7.29 (m, 7H), 6.46 (d, J=0.8 Hz, 1H), 5.27 (s, 2H), 3.98 (ddd, J=11.6, 3.8, 1.9 Hz, 2H), 3.47 (td, J=11.7, 2.2 Hz, 2H), 2.73 (dt, J=11.8, 3.8 Hz, 1H), 1.90 (ddd, J=12.9, 4.1, 2.0 Hz, 2H), 1.72 (dtd, J=13.1, 11.8, 4.5 Hz, 2H).

Step 3: To a solution of the acid obtained above (50 mg, 0.1486 mmol) in acetone (3 mL) was added $AgNO_3$ (7.57 mg, 0.04456 mmol). The reaction mixture was stirred in the dark for 24 hours at room temperature. The reaction was concentrated, and the residue was purified by silica gel chromatography (12 g ISCO column) using 0-40% EtOAc/heptanes gradient to afford C122 (33 mg, 66%). $^1$H NMR (300 MHz, Chloroform-d) δ 7.70 (d, J=2.3 Hz, 1H), 7.46-7.15 (m, 8H), 6.14 (s, 1H), 5.08 (s, 2H), 4.01 (ddd, J=11.5, 4.2, 1.7 Hz, 2H), 3.42 (td, J=11.8, 2.2 Hz, 2H), 2.63 (tt, J=11.8, 3.8 Hz, 1H), 2.00-1.61 (m, 4H), 1.29-1.13 (m, 3H), 0.86-0.75 (m, 2H).

Step 4: To a suspension of C122 (102 mg, 0.3032 mmol), molecular sieves (400 mg), and methyl 3-aminocyclobutanecarboxylate (hydrochloride salt) (375 mg, 2.264 mmol) was added pyridine (2 mL). The suspension was then heated at 140° C. for 15 hours. The reaction was cooled to room temperature and diluted with dichloromethane. The reaction mixture was filtered through a Celite® pad and acidified with 1 M HCl. The organic phase was separated and concentrated. The product was purified by silica gel to afford the corresponding ester (78 mg, 57%). $^1$H NMR (300 MHz, Chloroform-d) δ 7.88 (d, J=2.6 Hz, 1H), 7.54-7.30 (m, 7H), 6.34 (s, 1H), 5.20 (s, 3H), 4.14 (dt, J=11.7, 2.3 Hz, 2H), 3.78 (s, 3H), 3.74-3.47 (m, 5H), 2.93 (td, J=10.5, 5.5 Hz, 1H), 2.55 (ddd, J=12.5, 9.3, 3.8 Hz, 2H), 1.94-1.70 (m, 4H).

Step 5: To a solution of the above ester (114 mg, 0.2547 mmol) in THF (2 mL) was added NB S (59 mg, 0.3315 mmol) at 0° C. The reaction mixture was warmed to room temperature, stirred for 1 hours, quenched with aqueous sat. $NaHCO_3$ and extracted with EtOAc. The organic phase was concentrated, and the residue was purified by silica gel chromatography (0 to 30% EtOAc in Heptane) to afford C123 (84 mg, 63%). $^1$H NMR (300 MHz, Chloroform-d) δ 7.93 (d, J=9.0 Hz, 1H), 7.89 (d, J=2.7 Hz, 1H), 7.53-7.33 (m, 6H), 5.22 (s, 2H), 4.24-4.14 (m, 2H), 3.80 (s, 3H), 3.67-3.40 (m, 5H), 2.61 (t, J=8.9 Hz, 2H), 2.34 (d, J=10.8 Hz, 3H), 1.77 (d, J=13.0 Hz, 2H), 1.59 (s, 2H).

Step 6: In a 20 mL vial were added water (100 μL) and potassium phosphate (57 mg, 0.2685 mmol). The mixture was stirred for 10 minutes at room temperature then toluene (700 μL) was added. $N_2$ was bubbled through the mixture for 15 minutes then C123 (40 mg, 0.07599 mmol), (4-fluoro-3-methyl-phenyl)boronic acid (18 mg, 0.1169 mmol) and dicyclohexyl-[2-(2,6-diisopropoxyphenyl)phenyl]phosphane;methanesulfonate;N-methyl-2-phenyl-aniline Pd (13 mg, 0.01529 mmol) were added. The tube was sealed then transferred to a pre-heated oil bath set to 70° C. and stirred at this temperature for 2 hours. The reaction was quenched with water and extracted with EtOAc. The organic solution was dried with $Na_2SO_4$ and concentrated.

The product was purified by silica gel chromatography to afford the corresponding Suzuki product (35 mg, 67%) LCMS m/z 556.34 [M+H]$^+$.

Step 7: To a 20 mL vial was added Pd/C (1.6 mg, 0.001503 mmol) and the product from the previous step and MeOH (4 mL) was added via syringe. Then, $H_2$ was bubbled for 5 min and the reaction was stirred at RT for 4 h, at which time complete reduction was observed. The reaction mixture was filtered, and product was purified by ISCO to afford the corresponding phenol. LCMS m/z 466.38 [M+H]$^+$.

Step 8: The product from the previous step was dissolved in THF/MeOH/$H_2O$ (3:1:1) (2 mL) and LiCl (10 mg, 0.2359 mmol) was added and the reaction mixture was stirred at room temperature for 4 hours. The reaction mixture was diluted with $H_2O$ and acidified with 1 N HCl. The product was extracted with EtOAc and the organic solution was dried with $Na_2SO_4$ and concentrated to give 115 (8 mg, 22%). $^1$H NMR (300 MHz, Methanol-$d_4$) δ 7.65 (d, J=2.6 Hz, 1H), 7.23-7.08 (m, 2H), 7.04 (dt, J=8.8, 3.3 Hz, 2H), 6.73 (d, J=8.8 Hz, 1H), 5.43 (p, J=8.7 Hz, 1H), 3.95 (dd, J=11.5, 4.4 Hz, 2H), 3.59 (q, J=10.1 Hz, 2H), 3.46-3.33 (m, 1H), 3.08 (dd, J=12.5, 10.0 Hz, 3H), 2.58 (ddd, J=12.4, 9.1, 3.6 Hz, 2H), 2.24-2.06 (m, 2H), 1.60 (d, J=13.1 Hz, 2H). LCMS m/z 452.38 [M+H]$^+$ Compound 116

(R)-2-((4-(4-fluorophenyl)-7-hydroxy-3-(tetrahydro-2H-pyran-4-yl)isoquinolin-1-yl)oxy)propanoic acid (116)

S13

-continued

C124

116

Step 1: (2S)-2-[[7-benzyloxy-4-(4-fluorophenyl)-3-tetrahydropyran-4-yl-1-isoquinolyl]oxy]propanoic acid (C124)

Method A: DABCO-Catalyzed S$_N$Ar Reaction with Alcohols. To a mixture of S13 (170 mg, 0.1961 mmol) and (2S)-2-hydroxypropanoic acid (97 mg, 1.077 mmol) in dry DMF (4 mL) was added NaH (103 mg of 60% w/w, 2.575 mmol) under N$_2$. The reaction mixture was stirred for 18 hours at room temperature. After completion, the reaction mixture was quenched with water and 1 M of HCl (5 mL). The residue was extracted with EtOAc, dried over anhydrous Na$_2$SO$_4$, filtered, and concentrated. The crude product was purified by silica gel chromatography eluting with 0-30% of MeOH in dichloromethane to afford C124 (65 mg, 66%). $^1$H NMR (400 MHz, Chloroform-d) δ 7.71 (d, J=2.6 Hz, 1H), 7.55-7.49 (m, 2H), 7.46-7.41 (m, 2H), 7.38 (d, J=7.2 Hz, 1H), 7.28-7.14 (m, 6H), 5.45 (q, J=7.0 Hz, 1H), 5.22 (d, J=3.5 Hz, 2H), 4.10-3.89 (m, 2H), 3.33 (dddd, J=17.5, 13.2, 11.5, 2.1 Hz, 2H), 2.72 (tt, J=11.7, 3.7 Hz, 1H), 2.26 (qd, J=12.7, 4.5 Hz, 1H), 2.11-2.00 (m, 1H), 1.83 (d, J=7.1 Hz, 3H), 1.49 (d, J=7.0 Hz, 2H). LCMS m/z 501.93 [M+H]$^+$.

Step 2: (2S)-2-[[4-(4-fluorophenyl)-7-hydroxy-3-tetrahydropyran-4-yl-1-isoquinolyl]oxy]propanoic acid (116)

Method B: Pd Catalyzed Transfer Hydrogenation. Pd (16 mg of 10% w/w, 0.01503 mmol) was added to a solution of C124 (63 mg, 0.1256 mmol) in MeOH (10 mL) and EtOAc (10 mL). The resulting mixture was stirred at room temperature under a H$_2$ balloon for 18 hours. The reaction mixture was filtered through a plug of celite and concentrated under reduced pressure. The residue was purified by silica gel chromatography eluting with 20-30% MeOH in dichloromethane to give 116 (35 mg, 63%). $^1$H NMR (400 MHz, Methanol-d4) δ 7.61 (dd, J=2.5, 0.6 Hz, 1H), 7.30-7.00 (m, 6H), 5.45 (q, J=7.0 Hz, 1H), 3.96 (ddd, J=20.5, 11.3, 4.3 Hz, 2H), 3.35-3.22 (m, 2H), 2.69 (tt, J=11.6, 3.7 Hz, 1H), 2.24 (qd, J=12.7, 4.6 Hz, 1H), 2.14-2.03 (m, 1H), 1.75 (d, J=7.0 Hz, 3H), 1.56-1.39 (m, 2H) ppm. LCMS m/z 412.29 [M+H]$^+$.

Compounds 117-142

Compounds 117-142 (Table 11) were prepared in two or three steps from intermediate S13 from the appropriate alcohols according to the method described for compound 116. Any modifications to methods are noted in Table 11 and accompanying footnotes.

TABLE 11

| | | | $^1$H NMR; LCMS m/z |
|---|---|---|---|
| Compound | Method/Product | Alcohols | [M + H]$^+$ |
| 117 | Compound 116 from S13 | | $^1$H NMR (300 MHz, Chloroform-d and Methanol-d$_4$) δ 7.98 (s, 1H), 7.61 (dd, J = 2.5, 0.7 Hz, 1H), 7.25-7.06 (m, 6H), 5.45 (q, J = 7.0 Hz, 1H), 3.95 (td, J = 11.6, 5.9 Hz, 2H), 2.69 (tt, J = 11.6, 3.7 Hz, 1H), 2.35-1.96 (m, 2H), 1.75 (d, J = 7.0 Hz, 3H), 1.47 (t, J = 14.2 Hz, 2H. LCMS m/z 412.38 |

TABLE 11-continued

Method of preparation, structure, physicochemical data for compound 117-142

| Compound | Method/Product | Alcohols | ¹H NMR; LCMS m/z [M + H]⁺ |
|---|---|---|---|
| 118 | Compound 116 from S13 | | ¹H NMR (300 MHz, Chloroform-d and Methanol-d₄) δ 7.56 (dd, J = 2.4, 0.7 Hz, 1H), 7.29-7.01 (m, 6H), 5.62 (ttd, J = 7.3, 6.1, 1.1 Hz, 1H), 4.06-3.89 (m, 2H), 3.36-3.11 (m, 3H), 3.05-2.83 (m, 2H), 2.78-2.50 (m, 3H), 2.16 (qd, J = 12.7, 4.5 Hz, 2H), 1.62-1.37 (m, 2H). LCMS m/z 438.25 |
| 119 | Compound 116 from S13 | | ¹H NMR (400 MHz, DMSO-d₆) δ 10.31 (s, 1H), 8.79 (d, J = 2.5 Hz, 1H), 8.22 (dd, J = 8.6, 2.5 Hz, 1H), 7.97 (dt, J = 8.6, 2.6 Hz, 1H), 7.61 (d, J = 2.5 Hz, 1H), 7.44-7.28 (m, 5H), 7.13 (dd, J = 9.2, 2.4 Hz, 1H), 3.75 (d, J = 11.0 Hz, 2H), 3.08 (t, J = 12.0 Hz, 2H), 2.66-2.58 (m, 1H), 1.64 (q, J = 12.8 Hz, 2H), 1.39 (d, J = 13.0 Hz, 2H). LCMS m/z 461.38 |
| 120 | Compound 116 from S13 | | ¹H NMR (300 MHz, Chloroform-d) δ 8.05 (s, 1H), 7.58 (t, J = 1.6 Hz, 1H), 7.27-7.06 (m, 5H), 5.51-5.35 (m, 1H), 4.04 (dd, J = 11.4, 4.3 Hz, 2H), 3.36 (t, J = 11.9 Hz, 2H), 2.96 (t, J = 6.2 Hz, 3H), 2.83-2.49 (m, 3H), 2.33-2.11 (m, 2H), 1.48 (d, J = 11.8 Hz, 2H). LCMS m/z 438.39 |

TABLE 11-continued

Method of preparation, structure, physicochemical data for compound 117-142

| Compound | Method/Product | Alcohols | $^1$H NMR; LCMS m/z [M + H]$^+$ |
|---|---|---|---|
| 121 | Compound 116 from S13 | | $^1$H NMR (400 MHz, Methanol-d$_4$) δ 7.54 (dd, J = 2.5, 0.6 Hz, 1H), 7.29-7.24 (m, 3H), 7.20-7.09 (m, 2H), 5.93 (q, J = 7.4 Hz, 1H), 3.93 (td, J = 11.6, 4.4 Hz, 2H), 3.25 (dd, J = 4.2, 2.1 Hz, 2H), 2.72 (tt, J = 11.7, 3.7 Hz, 1H), 2.24-2.02 (m, 2H), 1.48 (dd, J = 22.4, 13.5 Hz, 2H). LCMS m/z 466.17 |
| 122 | Compound 116 from S13 | | $^1$H NMR (400 MHz, Methanol-d$_4$) δ 7.47 (dd, J = 2.5, 0.7 Hz, 1H), 7.31-7.19 (m, 4H), 7.14-7.01 (m, 2H), 4.57 (s, 2H), 3.96 (dd, J = 11.5, 4.4 Hz, 2H), 3.34 (d, J = 2.0 Hz, 1H), 3.28 (d, J = 2.0 Hz, 1H), 2.73 (tt, J = 11.6, 3.8 Hz, 1H), 2.22 (qd, J = 12.7, 4.5 Hz, 2H), 1.55-1.46 (m, 2H), 1.41 (s, 6H). LCMS m/z 440.24 |
| 123 | Compound 116 from S13 | | $^1$H NMR (400 MHz, Methanol-d$_4$) δ 7.43 (dd, J = 2.4, 0.7 Hz, 1H), 7.31-7.19 (m, 4H), 7.15-7.04 (m, 2H), 4.00-3.88 (m, 2H), 3.37-3.24 (m, 2H), 2.71 (tt, J = 11.5, 3.7 Hz, 1H), 2.16 (qd, J = 12.7, 4.5 Hz, 2H), 1.74-1.61 (m, 2H), 1.52-1.38 (m, 2H), 1.39-1.26 (m, 2H). LCMS m/z 424.17 |

TABLE 11-continued

Method of preparation, structure, physicochemical data for compound 117-142

| Compound | Method/Product | Alcohols | $^1$H NMR; LCMS m/z [M + H]$^+$ |
|---|---|---|---|
| 124 | Compound 116 from S13 | | $^1$H NMR (300 MHz, Chloroform-d) δ 7.90 (dd, J = 2.5, 0.7 Hz, 1H), 7.26-7.04 (m, 6H), 4.83-4.68 (m, 2H), 4.08-3.87 (m, 6H), 3.81 (s, 4H), 3.43-3.25 (m, 2H), 2.73 (t, J = 5.8 Hz, 3H), 2.24 (qd, J = 12.8, 4.6 Hz, 2H), 1.56-1.37 (m, 2H). LCMS m/z 499.86 |
| 125 | Compound 116 from S13 | | $^1$H NMR (400 MHz, Methanol-d$_4$) δ 7.51 (d, J = 2.4 Hz, 1H), 7.33-7.19 (m, 4H), 7.13-7.01 (m, 2H), 4.74 (s, 2H), 3.95 (dd, J = 11.3, 4.3 Hz, 2H), 2.80-2.63 (m, 2H), 2.19 (qd, J = 12.7, 4.4 Hz, 3H), 1.49 (d, J = 12.9 Hz, 2H), 1.34 (q, J = 4.0 Hz, 2H), 1.13 (q, J = 4.0 Hz, 2H). LCMS m/z 438.3 |
| 126 | Compound 116 from S13 | | $^1$H NMR (400 MHz, Methanol-d$_4$) δ 7.47 (dd, J = 2.5, 0.7 Hz, 1H), 7.31-7.20 (m, 4H), 7.09 (qd, J = 9.1, 1.6 Hz, 2H), 5.04 (d, J = 6.2 Hz, 2H), 5.00 (s, 2H), 4.82 (d, J = 6.2 Hz, 2H), 3.96 (dd, J = 11.4, 4.4 Hz, 2H), 3.34 (d, J = 1.9 Hz, 2H), 2.75 (tt, J = 11.6, 3.8 Hz, 1H), 2.23 (qd, J = 12.8, 4.6 Hz, 2H), 1.52 (dd, J = 13.0, 3.6 Hz, 2H). LCMS m/z 454.28 |

TABLE 11-continued

Method of preparation, structure, physicochemical data for compound 117-142

| Compound | Method/Product | Alcohols | $^1$H NMR; LCMS m/z [M + H]$^+$ |
|---|---|---|---|
| 127 | Compound 116 from S13 | | $^1$H NMR (300 MHz, Methanol-d$_4$) δ 7.53 (dd, J = 2.4, 0.7 Hz, 1H), 7.28-7.01 (m, 6H), 5.35 (p, J = 7.1 Hz, 1H), 4.00 (dd, J = 11.5, 4.1 Hz, 2H), 3.39 (d, J = 1.9 Hz, 1H), 3.34-3.26 (m, 1H), 3.11 (p, J = 8.6 Hz, 1H), 2.88-2.59 (m, 3H), 2.52-2.09 (m, 8H), 1.60-1.39 (m, 2H). LCMS m/z 478.29 |
| 128 | Compound 116 from S13$^1$ | | $^1$H NMR (400 MHz, Chloroform-d and Methanol-d$_4$) δ 7.51-7.43 (m, 1H), 7.18-6.95 (m, 6H), 4.74-4.59 (m, 2H), 4.50 (dt, J = 9.4, 4.8 Hz, 2H), 3.98-3.86 (m, 3H), 3.26-3.18 (m, 1H), 2.60 (dtd, J = 13.4, 9.6, 8.7, 4.8 Hz, 1H), 2.36-2.18 (m, 2H), 2.17-2.01 (m, 3H), 2.00-1.89 (m, 1H), 1.44-1.29 (m, 2H). LCMS m/z 467.99 |
| 129 | Compound 116 from S13 | | $^1$H NMR (400 MHz, DMSO-d$_6$) δ 10.06-9.97 (m, 1H), 7.44 (d, J = 2.6 Hz, 1H), 7.33 (pd, J = 7.5, 6.4, 2.8 Hz, 4H), 7.17 (dt, J = 9.0, 2.6 Hz, 1H), 7.00 (dd, J = 9.0, 2.4 Hz, 1H), 5.25 (d, J = 4.6 Hz, 1H), 5.02-4.88 (m, 1H), 3.99 (d, J = 7.6 Hz, 1H), 3.86 (d, J = 10.3 Hz, 2H), 3.16 (t, J = 12.0 Hz, 2H), 2.98-2.86 (m, 2H), 2.04 (q, J = 16.3, 12.5 Hz, 4H), 1.43 (d, J = 12.9 Hz, 2H). LCMS m/z 410.18 |

TABLE 11-continued

Method of preparation, structure, physicochemical data for compound 117-142

| Compound | Method/Product | Alcohols | $^1$H NMR; LCMS m/z [M + H]$^+$ |
|---|---|---|---|
| 130 | Compound 116 from S13 | | $^1$H NMR (300 MHz, Chloroform-d) δ 7.58 (t, J = 1.6 Hz, 1H), 7.27-6.94 (m, 6H), 6.24 (s, 1H), 5.02 (dd, J = 8.0, 6.1 Hz, 2H), 4.90-4.67 (m, 4H), 4.02 (dd, J = 11.4, 4.4 Hz, 2H), 3.65 (tt, J = 8.0, 6.2 Hz, 1H), 3.45-3.22 (m, 2H), 2.74 (tt, J = 11.6, 3.8 Hz, 1H), 2.24 (qd, J = 12.7, 4.5 Hz, 2H), 1.50 (dd, J = 13.4, 3.6 Hz, 2H). LCMS m/z 410.35 |
| 131 | Compound 116 from S13 | | LCMS m/z 592.29 |
| 132 | Compound 116 from S13[2] | | $^1$H NMR (400 MHz, DMSO-d$_6$) δ 10.05-9.98 (m, 1H), 7.54-7.46 (m, 1H), 7.41-7.25 (m, 4H), 7.17 (dt, J = 9.1, 2.8 Hz, 1H), 7.00 (dd, J = 8.9, 2.7 Hz, 1H), 5.04 (d, J = 4.6 Hz, 1H), 4.74 (s, 1H), 4.52 (dt, J = 10.8, 3.5 Hz, 1H), 4.46-4.37 (m, 1H), 3.97 (s, 1H), 3.86 (d, J = 11.3 Hz, 2H), 3.57 (d, J = 5.6 Hz, 2H), 3.17 (t, J = 11.9 Hz, 2H), 2.61 (d, J = 13.6 Hz, 1H), 2.11-1.97 (m, 2H), 1.44 (d, J = 13.0 Hz, 2H). LCMS m/z 414.18 |

TABLE 11-continued

Method of preparation, structure, physicochemical data for compound 117-142

| Compound | Method/Product | Alcohols | ¹H NMR; LCMS m/z [M + H]⁺ |
|---|---|---|---|
| 133 | Compound 116 from S13 | | ¹H NMR (400 MHz, Methanol-d₄) δ 7.51 (dd, J = 2.6, 0.6 Hz, 1H), 7.31-7.18 (m, 4H), 7.16-7.02 (m, 2H), 5.77 (t, J = 8.3 Hz, 1H), 3.94 (dd, J = 10.2, 3.9 Hz, 2H), 3.60-3.44 (m, 2H), 3.32 (d, J = 2.8 Hz, 1H), 3.26 (d, J = 2.1 Hz, 1H), 2.99-2.88 (m, 1H), 2.73 (tt, J = 11.6, 3.7 Hz, 1H), 2.32-2.07 (m, 3H), 1.50 (d, J = 12.2 Hz, 2H). LCMS m/z 423.22 |
| 134 | Compound 116 from S13 | | ¹H NMR (300 MHz, Chloroform-d and Methanol-d₄) δ 7.57 (dd, J = 2.3, 0.9 Hz, 1H), 7.30-6.99 (m, 6H), 5.50 (p, J = 6.8 Hz, 1H), 3.98 (dd, J = 11.3, 4.3 Hz, 2H), 3.74 (d, J = 7.0 Hz, 2H), 3.39 (s, 1H), 3.33 (d, J = 10.8 Hz, 2H), 2.84-2.34 (m, 6H), 2.18 (qd, J = 12.8, 4.6 Hz, 2H), 1.48 (d, J = 12.5 Hz, 2H). LCMS m/z 424.22 |
| 135 | Compound 116 from S13 | | ¹H NMR (300 MHz, Chloroform-d) δ 7.53 (dd, J = 2.1, 1.1 Hz, 1H), 7.25-7.07 (m, 6H), 5.52 (s, 1H), 5.38-5.24 (m, 1H), 4.87 (s, 2H), 4.77 (s, 2H), 4.02 (dd, J = 11.5, 4.4 Hz, 2H), 3.34 (t, J = 11.6 Hz, 2H), 2.98 (ddd, J = 10.5, 7.1, 3.0 Hz, 2H), 2.70 (ddt, J = 11.7, 7.6, 3.8 Hz, 1H), 2.56-2.41 (m, 2H), 2.19 (qd, J = 12.7, 4.5 Hz, 2H), 1.53-1.41 (m, 2H). LCMS m/z 436.36 |

TABLE 11-continued

Method of preparation, structure, physicochemical data for compound 117-142

| Compound | Method/Product | Alcohols | [sup]1[/sup]H NMR; LCMS m/z [M + H][sup]+[/sup] |
|---|---|---|---|
| 136 | Compound 116 from S13[2] | | [sup]1[/sup]H NMR (400 MHz, DMSO-d[sub]6[/sub]) δ 7.53 (dt, J = 30.0, 2.6 Hz, 1H), 7.40-7.25 (m, 3H), 7.21-7.06 (m, 1H), 7.06-6.70 (m, 2H), 4.88 (d, J = 87.2 Hz, 1H), 4.65-4.44 (m, 2H), 4.08-3.89 (m, 1H), 3.89-3.78 (m, 2H), 3.68 (s, 1H), 3.52-3.42 (m, 1H), 3.17 (t, J = 12.0 Hz, 1H), 3.11-2.96 (m, 1H), 2.63 (s, 1H), 2.05 (d, J = 12.5 Hz, 2H), 1.54-1.28 (m, 2H). LCMS m/z 444.19 |
| 137 | Compound 116 from S13 | | [sup]1[/sup]H NMR (300 MHz, Chloroform-d) δ 7.53 (dd, J = 2.2, 1.1 Hz, 1H), 7.26-7.01 (m, 6H), 5.42 (s, 1H), 4.78 (d, J = 24.6 Hz, 4H), 4.49 (d, J = 6.5 Hz, 2H), 4.01 (dd, J = 11.4, 4.3 Hz, 2H), 3.35 (t, J = 11.9 Hz, 2H), 2.82-2.63 (m, 2H), 2.59-2.43 (m, 2H), 2.25 (td, J = 11.7, 4.9 Hz, 4H), 1.48 (d, J = 13.2 Hz, 2H). LCMS m/z 450.36 |
| 138 | Compound 116 from S13 | | [sup]1[/sup]H NMR (300 MHz, Methanol-d[sub]4[/sub]) δ 7.34 (d, J = 2.5 Hz, 1H), 7.29-7.16 (m, 4H), 7.04 (dd, J = 9.0, 2.5 Hz, 1H), 6.93 (d, J = 9.0 Hz, 1H), 4.70 (dd, J = 11.6, 5.5 Hz, 1H), 4.60 (dd, J = 11.6, 5.0 Hz, 1H), 4.39-4.22 (m, 3H), 3.95 (dd, J = 11.4, 4.3 Hz, 2H), 3.58-3.47 (m, 2H), 3.35 (s, 2H), 2.70 (ddt, J = 11.5, 7.5, 3.8 Hz, 1H), 2.26-2.11 (m, 2H), 1.54-1.45 (m, 2H). LCMS m/z 453.33 |

TABLE 11-continued

Method of preparation, structure, physicochemical data for compound 117-142

| Compound | Method/Product | Alcohols | $^1$H NMR; LCMS m/z [M + H]$^+$ |
|---|---|---|---|
| 139 | Compound 116 from S13 | | $^1$H NMR (300 MHz, Methanol-d$_4$) δ 7.49 (dd, J = 2.5, 0.7 Hz, 1H), 7.31-7.19 (m, 4H), 7.11 (dd, J = 9.0, 2.5 Hz, 1H), 7.05 (dd, J = 9.1, 0.7 Hz, 1H), 4.72 (t, J = 6.2 Hz, 2H), 3.95 (dd, J = 11.3, 4.3 Hz, 2H), 3.40-3.32 (m, 4H), 2.73 (ddt, J = 11.5, 7.6, 3.8 Hz, 1H), 2.51-2.38 (m, 2H), 2.29-2.12 (m, 2H), 1.57-1.44 (m, 2H). LCMS m/z 461.29 |
| 140 | Compound 116 from S13 | | $^1$H NMR (300 MHz, Methanol-d$_4$) δ 7.55 (dd, J = 2.4, 0.7 Hz, 1H), 7.26 (s, 2H), 7.24 (d, J = 1.4 Hz, 2H), 7.16-7.04 (m, 2H), 4.68 (t, J = 5.7 Hz, 2H), 3.95 (dd, J = 11.3, 4.4 Hz, 2H), 3.64 (t, J = 5.7 Hz, 2H), 3.37-3.24 (m, 2H), 3.00 (s, 3H), 2.74 (ddt, J = 11.6, 7.5, 3.9 Hz, 1H), 2.30-2.12 (m, 2H), 1.56-1.47 (m, 2H). LCMS m/z 461.25 |

TABLE 11-continued

| | Method of preparation, structure, physicochemical data for compound 117-142 | | |
|---|---|---|---|
| Compound | Method/Product | Alcohols | $^1$H NMR; LCMS m/z [M + H]$^+$ |
| 141 | Compound 116 from S13[2] 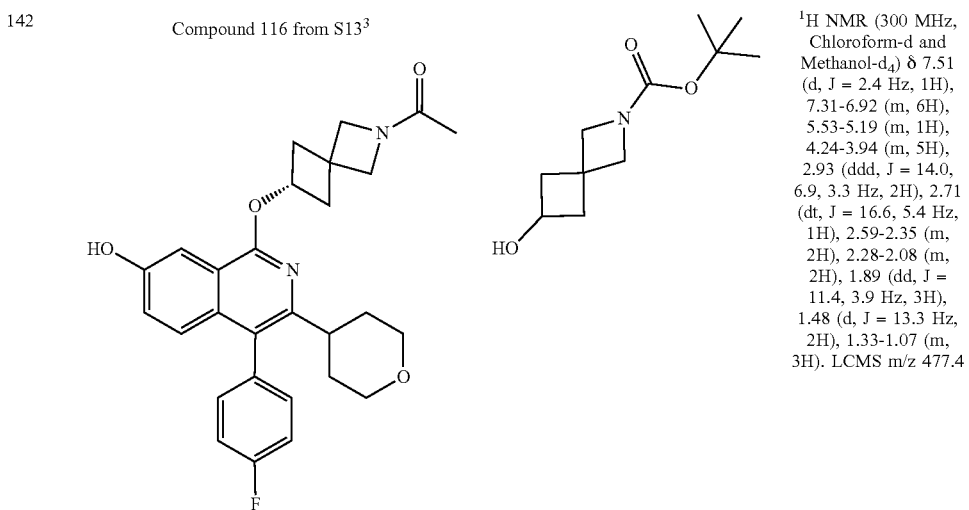 | | $^1$H NMR (400 MHz, DMSO-d$_6$) δ 7.58-7.47 (m, 1H), 7.47-7.26 (m, 4H), 7.18 (dt, J = 9.2, 2.4 Hz, 1H), 7.01 (dd, J = 9.1, 2.4 Hz, 1H), 6.40 (s, 1H), 5.05 (s, 2H), 4.67 (dd, J = 26.9, 11.7 Hz, 1H), 4.54-4.39 (m, 1H), 4.16 (s, 2H), 3.87 (d, J = 11.4 Hz, 2H), 3.76 (s, 1H), 3.17 (t, J = 12.0 Hz, 2H), 2.05 (d, J = 13.3 Hz, 2H), 1.45 (d, J = 13.1 Hz, 2H). LCMS m/z 472.14 |
| 142 | Compound 116 from S13[3] | | $^1$H NMR (300 MHz, Chloroform-d and Methanol-d$_4$) δ 7.51 (d, J = 2.4 Hz, 1H), 7.31-6.92 (m, 6H), 5.53-5.19 (m, 1H), 4.24-3.94 (m, 5H), 2.93 (ddd, J = 14.0, 6.9, 3.3 Hz, 2H), 2.71 (dt, J = 16.6, 5.4 Hz, 1H), 2.59-2.35 (m, 2H), 2.28-2.08 (m, 2H), 1.89 (dd, J = 11.4, 3.9 Hz, 3H), 1.48 (d, J = 13.3 Hz, 2H), 1.33-1.07 (m, 3H). LCMS m/z 477.4 |

[1]Standard method D using KOH was carried out after standard method B using Pd(OH)$_2$.

[2]Additional treatment with HCl to remove the acetal groups was carried out after standard method B using Pd(OH)$_2$.

[3]TFA deprotection followed by standard method E using acetic anhydride and DIPEA were carried out before standard method B.

Compound 143

3-[4-(4-fluorophenyl)-7-hydroxy-3-tetrahydropyran-
4-yl-1-isoquinolyl]propanoic acid (143)

C29

C125

C126

-continued

C127

143

Step 1: 7-benzyloxy-4-(4-fluorophenyl)-2-oxido-3-
tetrahydropyran-4-yl-isoquinolin-2-ium (C29)

Method C-1: Suzuki Coupling Method. A suspension of S11 (14.41 g, 34.782 mmol), (4-fluorophenyl)boronic acid (7.29 g, 52.101 mmol) and aq. solution of $Na_2CO_3$ (35 mL of 2 M in water, 70.000 mmol) in DMSO (140 mL) was purged with $N_2$ for 30 minutes. Pd(dppf) $Cl_2$·dichloromethane (1.42 g, 1.7388 mmol) was added and the reaction was purged with $N_2$ for another 5 minutes. The reaction was heated to 100° C. for 2 hours, cooled to room temperature, cooled to 0° C., diluted with water (280 mL) and filtered. The residue was then dissolved with dichloromethane (through filter paper). The filtrate was decanted, dried over anhydrous $Na_2SO_4$, filtered and concentrated under reduced pressure. The brown solid was triturated in ACN (50 mL), filtered and washed with ACN. The residue was triturated again in a mixture of dichloromethane (10 mL) and ACN (25 mL), the solid was filtered and washed with minimum dichloromethane to give C29 (9.19 g, 59%) as tan solid. $^1$H NMR (300 MHz, CDCl3) δ 1.40 (d, J=11.7 Hz, 2H), 2.67 (br. s., 2H), 3.11-3.37 (m, 3H), 3.95 (dd, J=11.0, 3.7 Hz, 2H), 5.17 (s, 2H), 6.94-7.18 (m, 3H), 7.19-7.29 (m, 4H), 7.31-7.51 (m, 5H), 8.73 (s, 1H). $^{19}$F NMR (282 MHz, Chloroform-d) δ −113.2-112.2 (m, 1F). LCMS m/z calc. 430.2 [M+H]+.

Step 1: 7-benzyloxy-1-chloro-4-(4-fluorophenyl)-3-tetrahydropyran-4-yl-isoquinoline (C125)

Method C-2: Halogenation of Isoquinoline N-Oxide with Oxalyl Chloride. Oxalyl dichloride (6 mL of 2M in dichloromethane, 12.00 mmol) was added to a solution of C29 (3 g, 6.985 mmol) and DIPEA (3 mL, 17.22 mmol) in dry dichloromethane (25 mL) at −78° C. The reaction was allowed to warm to 0° C. over 2 hours, and the dark reaction was quenched by the addition of MeOH (2 mL). After stirring for 10 minutes, the mixture was concentrated in vacuo. MeOH (5 mL) was added and the resulting solid was filtered and washed with cold MeOH and dried under high vacuum to afford C125 (2.73 g, 87%) as a colorless solid. $^{1}$H NMR (300 MHz, Chloroform-d) δ 7.72-7.30 (m, 7H), 7.27-7.20 (m, 5H), 5.26 (s, 2H), 4.01 (dd, J=11.4, 4.4 Hz, 2H), 3.32 (t, J=11.4 Hz, 2H), 2.55-2.45 (m, 1H), 2.34-2.11 (m, 2H), 1.50 (m, 2H).

Steps 2-3: ethyl 3-[4-(4-fluorophenyl)-7-hydroxy-3-tetrahydropyran-4-yl-1-isoquinolyl]propanoate (C126)

The transformation of intermediate C125 to C127 was accomplished via standard Suzuki protocol using ethyl Pd(PPh$_3$)$_4$ in DMF stirred at 130° C. for 2 hours, followed by standard hydrogenation using method B.

Step 4: 3-[4-(4-fluorophenyl)-7-hydroxy-3-tetrahydropyran-4-yl-1-isoquinolyl]propanoic acid (143)

Method D: Ester hydrolysis with LiOH. A solution of C127 (70 mg, 0.1653 mmol) dissolved in a mixture of THF (3 mL) and H$_2$O (1.5 mL) was treated with LiOH(100 mg, 2.383 mmol), and the reaction mixture was stirred for 18 hours at room temperature. The reaction mixture was acidified with HCl (2.5 mL of 1 M, 2.500 mmol) and extracted with EtOAc. Organic layer was dried over anhydrous Na$_2$SO$_4$, filtered and concentrated to give 143 (65 mg, 87%). $^{1}$H NMR (300 MHz, Chloroform-d) δ 7.58 (s, 1H), 7.28-7.13 (m, 7H), 4.06-3.98 (m, 2H), 3.68 (d, J=6.4 Hz, 2H), 3.31 (t, J=11.7 Hz, 2H), 3.08 (t, J=6.1 Hz, 2H), 2.85 (t, J=12.0 Hz, 1H), 2.32-2.18 (m, 2H), 1.60-1.49 (m, 2H). LCMS m/z 396.13 [M+H]$^{+}$.

Compound 144

1-[[4-(4-fluorophenyl)-7-hydroxy-3-tetrahydropyran-4-yl-isoquinoline-1-carbonyl]amino]cyclopropanecarboxylic acid (144)

S11

-continued

C128

C129

144

Step 1: 7-benzyloxy-4-bromo-3-tetrahydropyran-4-yl-isoquinoline-1-carbonitrile (C128)

To a mixture of S11 (10 g, 23.73 mmol) in ACN (150 mL) and THF (100 mL) was added TEA (8.25 mL, 59.19 mmol) and TMSCN (10 mL, 75.00 mmol) under N$_2$. The reaction was heated to 55° C. for 18 hours. More TMSCN (10 mL, 75.00 mmol) was added and the reaction was stirred for another 2 days. After completion of the reaction, the mixture was concentrated to dryness. MeOH (30 mL) was added and the solid was filtered off to yield C128 (1400 mg, 14%). $^{1}$H NMR (300 MHz, Chloroform-d) δ 8.26 (d, J=10.0 Hz, 1H), 7.65-7.34 (m, 7H), 5.30 (s, 2H), 4.15 (dd, J=11.5, 4.3 Hz, 2H), 3.73-3.57 (m, 2H), 2.24-2.08 (m, 1H), 1.78 (d, J=13.4 Hz, 2H), 1.28 (s, 1H). LCMS m/z 423.22 [M+H]$^{+}$.

Steps 2-4: 4-(4-fluorophenyl)-7-hydroxy-3-tetrahy-
dropyran-4-yl-isoquinoline-1-carboxylic acid
(C129)

The transformation of intermediate C128 to C129 was
accomplished via standard method C, standard method B
using Pd(OH)$_2$ and standard method D using NaOH, respec-
tively.

Step 5: 1-[[[4-(4-fluorophenyl)-7-hydroxy-3-tetrahy-
dropyran-4-yl-isoquinoline-1-carbonyl]amino]
methyl]cyclopropanecarboxylic acid (144)

Method E: Amide Coupling Method. To a mixture of
C129 (40 mg, 0.1089 mmol) in DMF (2 mL) was added
ethyl 1-(aminomethyl)cyclopropanecarboxylate (approxi-
mately 23.38 mg, 0.1634 mmol), T3P (approximately 138.6

μL of 50% w/v, 0.2178 mmol) and DIPEA (approximately
42.22 mg, 56.90 μL, 0.3267 mmol). The reaction was stirred
at room temperature for 18 hours. After completion of
reaction, the mixture was concentrated to dryness and dis-
solved in minimal amount of DMSO. Purification by
reversed-phase HPLC. Method: C18 Waters Sunfire column
(30×150 mm, 5 micron). Gradient: MeCN in H$_2$O with 5
mM HCl afforded 144 (HCl salt) (5.80 mg, 11%). LCMS
m/z 465.19 [M+H]$^+$.

Compounds 145-155

Compounds 145-155 (Table 12) were prepared in five or
six steps from intermediate S11 from the appropriate amines
according to the method described for compound 144. Any
modifications to methods are noted in Table 12 and accom-
panying footnotes.

TABLE 12

| | Method of preparation, structure, physicochemical data for compounds 145-155 | | |
|---|---|---|---|
| Compound | Method/Product | Amines | $^1$H NMR; LCMS m/z [M + H]$^+$ |
| 145 | Compound 144 from S11[1] | | $^1$H NMR (400 MHz, DMSO-d$_6$) δ 10.29 (s, 1H), 8.96 (m, 1H), 8.66 (d, J = 2.6 Hz, 1H), 7.39 (m, 4H), 7.26 (dd, J = 9.2, 2.5 Hz, 1H), 7.15 (d, J = 9.2 Hz, 1H), 3.88 (dd, J = 11.0, 4.3 Hz, 2H), 3.62 (d, J = 6.4 Hz, 2H), 3.18 (m, 3H), 2.78-2.66 (m, 1H), 2.03 (m, 2H), 1.51 (d, J = 13.1 Hz, 2H), 1.11 (m, 2H), 1.02 (m, 2H). LCMS m/z 495.16 |
| 146 | Compound 144 from S11[1] | | $^1$H NMR (400 MHz, DMSO-d$_6$) δ 9.13 (s, 1H), 8.39 (d, J = 2.5 Hz, 1H), 7.45-7.32 (m, 4H), 7.25 (dd, J = 9.2, 2.6 Hz, 1H), 7.13 (d, J = 9.2 Hz, 1H), 3.88 (dd, J = 11.2, 4.3 Hz, 3H), 3.17 (t, J = 11.8 Hz, 3H), 2.70 (d, J = 12.1 Hz, 1H), 2.24-2.07 (m, 2H), 1.54-1.42 (m, 4H), 1.26 (q, J = 4.7 Hz, 2H). LCMS m/z 453.18 |

TABLE 12-continued

Method of preparation, structure, physicochemical data for compounds 145-155

| Compound | Method/Product | Amines | $^{1}$H NMR; LCMS m/z [M + H]$^{+}$ |
|---|---|---|---|
| 147 | Compound 144 from S11[1] | | $^{1}$H NMR (400 MHz, DMSO-d$_6$) δ 10.27 (s, 1H), 8.80 (t, J = 6.5 Hz, 1H), 8.66 (d, J = 2.5 Hz, 1H), 7.40 (dd, J = 7.4, 3.4 Hz, 4H), 7.26 (dd, J = 9.2, 2.5 Hz, 1H), 7.15 (d, J = 9.2 Hz, 1H), 3.87 (dd, J = 11.0, 4.2 Hz, 2H), 3.54 (d, J = 6.4 Hz, 2H), 3.18 (t, J = 11.8 Hz, 2H), 2.80-2.65 (m, 1H), 2.11-1.95 (m, 2H), 1.58-1.46 (m, 2H), 1.21 (s, 6H). LCMS m/z 467.21 |
| 148 | Compound 144 from S11[1] | | $^{1}$H NMR (400 MHz, DMSO-d$_6$) δ 10.30 (s, 1H), 9.11 (d, J = 9.1 Hz, 1H), 8.82 (d, J = 2.5 Hz, 1H), 7.47-7.35 (m, 3H), 7.33-7.26 (m, 1H), 7.16 (d, J = 9.2 Hz, 1H), 4.45 (d, J = 8.7 Hz, 1H), 3.96-3.77 (m, 4H), 3.68-3.51 (m, 2H), 3.18 (t, J = 11.8 Hz, 2H), 3.01 (d, J = 5.1 Hz, 1H), 2.75 (m, 1H), 2.00 (m, 3H), 1.80 (d, J = 13.8 Hz, 1H), 1.53 (d, J = 12.9 Hz, 2H). LCMS m/z 495.23 |
| 149 | Compound 144 from S11[1] | | $^{1}$H NMR (400 MHz, DMSO-d$_6$) δ 10.25 (s, 1H), 8.88 (t, J = 6.1 Hz, 1H), 8.55 (d, J = 2.5 Hz, 1H), 7.44-7.34 (m, 4H), 7.25 (dd, J = 9.2, 2.5 Hz, 1H), 7.14 (d, J = 9.2 Hz, 1H), 3.88 (dd, J = 10.8, 4.2 Hz, 2H), 3.62 (t, J = 6.6 Hz, 2H), 3.18 (t, J = 11.8 Hz, 2H), 2.78-2.66 (m, 1H), 2.62 (d, J = 6.9 Hz, 1H), 2.19-2.00 (m, 2H), 1.51-1.43 (m, 2H). LCMS m/z 439.17 |

TABLE 12-continued

Method of preparation, structure, physicochemical data for compounds 145-155

| Compound | Method/Product | Amines | $^1$H NMR; LCMS m/z [M + H]$^+$ |
|---|---|---|---|
| 150 | Compound 144 from S11[1] | | $^1$H NMR (400 MHz, DMSO-d$_6$) δ 10.23 (s, 1H), 8.88 (d, J = 8.1 Hz, 1H), 8.16 (d, J = 2.5 Hz, 1H), 7.46-7.33 (m, 4H), 7.24 (dd, J = 9.2, 2.5 Hz, 1H), 7.13 (d, J = 9.2 Hz, 1H), 4.71 (h, J = 8.2 Hz, 1H), 3.97-3.84 (m, 2H), 3.18 (t, J = 11.8 Hz, 2H), 3.01 (dt, J = 9.5, 5.2 Hz, 1H), 2.78-2.67 (m, 1H), 2.60-2.41 (m, 3H), 2.24-2.07 (m, 2H), 1.47 (d, J = 13.0 Hz, 2H). LCMS m/z 465.19 |
| 151 | Compound 144 from S11[1] | | $^1$H NMR (400 MHz, DMSO-d$_6$) δ 8.74 (t, J = 5.9 Hz, 1H), 8.58 (d, J = 2.5 Hz, 1H), 7.47-7.35 (m, 4H), 7.26 (dd, J = 9.2, 2.6 Hz, 1H), 7.14 (d, J = 9.2 Hz, 1H), 3.88 (dd, J = 11.5, 3.9 Hz, 2H), 3.71 (p, J = 5.7 Hz, 1H), 3.41-3.33 (m, 2H), 3.18 (t, J = 11.8 Hz, 2H), 2.78-2.68 (m, 1H), 2.08 (dd, J = 17.6, 8.1 Hz, 2H), 1.55-1.44 (m, 3H). LCMS m/z 441.19 |

TABLE 12-continued

Method of preparation, structure, physicochemical data for compounds 145-155

| Compound | Method/Product | Amines | ¹H NMR; LCMS m/z [M + H]⁺ |
|---|---|---|---|
| 152 | Compound 144 from S11 | | ¹H NMR (400 MHz, DMSO-d₆) δ 9.06 (t, J = 6.0 Hz, 1H), 8.50 (d, J = 2.5 Hz, 1H), 7.44-7.32 (m, 3H), 7.30-7.24 (m, 2H), 7.15-7.09 (m, 2H), 4.00-3.75 (m, 4H), 3.17 (m, 3H), 3.00 (p, J = 6.3 Hz, 1H), 2.67 (s, 3H), 2.16 (q, J = 12.7 Hz, 2H), 1.45 (d, J = 13.1 Hz, 2H). LCMS m/z 457.15 |
| 153 | Compound 144 from S11 | | ¹H NMR (400 MHz, DMSO-d₆) δ 11.72 (s, 1H), 10.84 (s, 1H), 10.55 (s, 1H), 8.87 (d, J = 2.5 Hz, 1H), 8.38 (d, J = 6.0 Hz, 1H), 7.42 (d, J = 7.4 Hz, 4H), 7.36-7.16 (m, 2H), 3.89 (dd, J = 11.0, 4.4 Hz, 2H), 3.20 (m, 2H), 2.78 (dd, J = 13.8, 10.1 Hz, 1H), 2.05 (tt, J = 13.1, 6.6 Hz, 2H), 1.63-1.51 (m, 2H). LCMS m/z 477.12 |

TABLE 12-continued

Method of preparation, structure, physicochemical data for compounds 145-155

| Compound | Method/Product | Amines | $^1$H NMR; LCMS m/z [M + H]+ |
|---|---|---|---|
| 154 | Compound 144 from S11 | | $^1$H NMR (400 MHz, DMSO-d$_6$) δ 8.81 (t, J = 6.0 Hz, 1H), 8.43 (d, J = 2.5 Hz, 1H), 7.45-7.35 (m, 4H), 7.25 (dd, J = 9.2, 2.6 Hz, 1H), 7.14 (d, J = 9.2 Hz, 1H), 3.88 (dd, J = 11.3, 4.2 Hz, 2H) 3.60-3.30 (m, 4H), 3.34-3.14 (m, 5H), 2.79-2.67 (m, 1H), 2.14 (qd, J = 12.6, 4.4 Hz, 2H), 1.52-1.41 (m, 3H). LCMS m/z 479.23 |
| 155 | Compound 144 from S11 | | $^1$H NMR (400 MHz, DMSO-d$_6$) δ 10.30 (s, 1H), 9.02 (d, J = 8.1 Hz, 1H), 8.33 (d, J = 2.5 Hz, 1H), 7.45-7.36 (m, 3H), 7.26 (dd, J = 9.2, 2.6 Hz, 1H), 7.15 (d, J = 9.2 Hz, 1H), 4.87 (h, J = 8.1 Hz, 1H), 3.89 (dd, J = 11.3, 4.1 Hz, 3H), 3.36-3.16 (m, 4H), 2.83-2.67 (m, 1H), 2.42-2.30 (m, 1H), 2.14 (m, 2H), 1.47 (t, J = 8.3 Hz, 3H), 1.02-0.94 (m, 1H). LCMS m/z 485.33 |

[1]KOH was added before submitting for purification by reversed-phase HPLC. Method C: C18 Waters Sunfire column (30 × 150 mm, 5 micron). Gradient: 10-100% MeCN in H$_2$O with 0.2% formic acid.

Compound 156

4-[[4-(4-fluorophenyl)-7-hydroxy-1-oxo-3-tetrahy-dropyran-4-yl-2-isoquinolyl]methyl]cyclohexanecar-boxylic acid (156)

C1

C130

C131

C132

-continued

C133

156

Step 1: methyl 5-benzyloxy-2-bromo-benzoate (C1)

Method F: $S_N2$ reaction using Alkyl Bromide. To a solution of methyl 2-bromo-5-hydroxybenzoate (5.34 g, 23.113 mmol) in anhydrous DMF (60 mL) was added $K_2CO_3$ (6.45 g, 46.669 mmol) followed by benzyl bromide (4.6735 g, 3.25 mL, 27.325 mmol). The mixture was stirred at room temperature for 6 hours and then diluted with EtOAc (650 mL). The organic phase was washed with 5% aqueous $NaHCO_3$ (5×100 mL) and brine (2×100 mL), dried over $Na_2SO_4$, filtered and concentrated under reduced pressure. The residue was purified by silica gel chromatography (Column: 120 g Combiflash ISCO. Gradient: 0-20% EtOAc in heptane) to afford C1 (7.32 g, 98%) as white solid. $^1$H NMR (300 MHz, DMSO-$d_6$) δ 3.85 (s, 3H), 5.15 (s, 2H), 7.15 (dd, J=8.8, 3.1 Hz, 1H), 7.26-7.50 (m, 6H), 7.53 (d, J=8.8 Hz, 1H). LCMS m/z 321.0 [M+H]$^+$.

Step 2: methyl 5-benzyloxy-2-(2-tetrahydropyran-4-ylethynyl)benzoate (C130)

Sonogashira Coupling Method. To a mixture of C1 (8 g, 24.91 mmol) and TEA (35 mL, 251.1 mmol) in DMF (50 mL) was added CuI (474 mg, 2.489 mmol), TBAF·3H$_2$O (12 mL, 34.34 mmol), and TMS-alkyne (C71) (5.94 g, 32.58 mmol). The mixture was purged with N$_2$ for 5 minutes, and then PdCl$_2$(PPh$_3$)$_4$ (873 mg, 1.244 mmol) was added. The mixture was purged again with N$_2$ for 5 minutes and then heated to 80° C. for 18 hours. The reaction mixture was cooled down to room temperature, concentrated, diluted with water (500 mL), and extracted with EtOAc (450 mL). The organic layer was washed with brine, dried over anhydrous Na$_2$SO$_4$, filtered, and concentrated. The residue was purified by silica gel chromatography (Column: 120 g Combiflash ISCO. Gradient: 0-40% EtOAc in heptane) to yield C130 (6 g, 69%). $^1$H NMR (300 MHz, Chloroform-d) δ 7.56-7.31 (m, 7H), 7.06 (dd, J=8.6, 2.8 Hz, 1H), 5.11 (s, 2H), 4.00 (ddd, J=11.5, 5.9, 3.6 Hz, 2H), 3.93 (s, 3H), 3.59 (ddd, J=11.5, 8.2, 3.1 Hz, 2H), 2.93 (tt, J=8.3, 4.1 Hz, 1H), 1.95 (ddt, J=13.4, 6.5, 3.7 Hz, 2H), 1.88-1.73 (m, 2H).

Step 3: 7-benzyloxy-4-iodo-3-tetrahydropyran-4-yl-isochromen-1-one (C131)

Electrophilic Cyclization of Alkyne (12-promoted). To a solution of C130 (1.54 g, 4.390 mmol) in anhydrous dichloromethane (20 mL) was added slowly a solution of I$_2$ (1.23 g, 4.846 mmol) in anhydrous dichloromethane (24 mL) over a course of 30 min at RT. The reaction mixture was stirred at room temperature for an additional 20 minutes, and then EtOAc (100 mL) was added. The organic phase was washed with a mixture of 5% aqueous NaHCO$_3$, brine (3×100 mL, 90/10 ratio), followed with more brine (2×50 mL), dried over anhydrous Na$_2$SO$_4$, filtered and concentrated under reduced pressure, in which a white precipitate formed. The precipitate was filtered off to afford C131 (1.76 g, 87%) as a white solid. $^1$H NMR (300 MHz, Chloroform-d) δ 7.79 (d, J=2.7 Hz, 1H), 7.71 (d, J=8.9 Hz, 1H), 7.52-7.33 (m, 7H), 5.20 (s, 2H), 4.11 (dd, J=11.7, 4.3 Hz, 2H), 3.61-3.34 (m, 3H), 2.24-1.95 (m, 2H), 1.75 (dq, J=12.9, 1.9 Hz, 2H).

Steps 4-6: 4-[[4-(4-fluorophenyl)-7-hydroxy-1-oxo-3-tetrahydropyran-4-yl-2-isoquinolyl]methyl]cyclo-hexanecarboxylic acid (156)

The transformation of C131 to C133 was accomplished via standard method C using RuPhos Pd G4 and K$_3$PO$_4$ in toluene stirred at 70° C. for 2 hours, followed by standard method D using NaOH on C132. C133 was subjected to standard method E using HATU and DIPEA in DMF followed by MsOH-mediated cyclization in dichloromethane, and then standard method B and standard method D using LiCl, respectively to form 156. $^1$H NMR (300 MHz, Methanol-d$_4$) δ 7.57 (d, J=2.7 Hz, 1H), 7.24-7.10 (m, 4H), 6.94 (dd, J=8.9, 2.7 Hz, 1H), 6.58 (d, J=9.0 Hz, 1H), 3.76 (d, J=11.5 Hz, 2H), 3.04 (s, 2H), 2.28-2.09 (m, 1H), 1.67 (dd, J=41.7, 31.8 Hz, 7H), 1.29-1.18 (m, 5H). LCMS m/z 480.47 [M+H]$^+$

Compounds 157-159

Compounds 157-159 (Table 13) were prepared four steps from intermediate C133 using appropriate amines according to the method described for compound 156. Any modifications to methods are noted in Table 13 and accompanying footnotes.

TABLE 13

| | Method of preparation, structure, physicochemical data for compounds 157-159 | | |
|---|---|---|---|
| Compound | Method/Product | Amines | $^1$H NMR; LCMS m/z [M + H]$^+$ |
| 157 | Compound 156 from C133 | | $^1$H NMR (400 MHz, Methanol-d$_4$) δ 8.20-8.10 (m, 2H), 7.56 (d, J = 2.6 Hz, 1H), 7.44-7.38 (m, 2H), 7.32-7.24 (m, 2H), 7.23-7.14 (m, 2H), 7.01 (dd, J = 8.9, 2.7 Hz, 1H), 6.67 (d, J = 8.9 Hz, 1H), 3.58-3.47 (m, 2H), 2.71-2.61 (m, 2H), 2.52 (t, J = 11.9 Hz, 1H), 1.44 (d, J = 12.8 Hz, 2H). LCMS m/z 460.39 |
| 158 | Compound 156 from C133 | | $^1$H NMR (400 MHz, Methanol-d$_4$) δ 7.68 (d, J = 2.6 Hz, 1H), 7.28 (d, J = 7.1 Hz, 5H), 7.06 (dd, J = 8.8, 2.7 Hz, 1H), 6.73 (d, J = 8.8 Hz, 1H), 5.33-5.21 (m, 1H), 3.97 (dd, J = 11.5, 4.4 Hz, 2H), 3.73 (d, J = 6.1 Hz, 2H), 3.42 (dd, J = 20.4, 10.1 Hz, 1H), 3.18-3.06 (m, 4H), 2.77 (s, 2H), 2.25-2.10 (m, 5H), 1.62 (d, J = 13.4 Hz, 2H). LCMS m/z 424.39 |

TABLE 13-continued

Method of preparation, structure, physicochemical data for compounds 157-159

| Compound | Method/Product | Amines | $^1$H NMR; LCMS m/z [M + H]$^+$ |
|---|---|---|---|
| 159 | Compound 156 from C133 | | $^1$H NMR (300 MHz, Methanol-d$_4$) δ 7.54 (d, J = 2.6 Hz, 1H), 7.16 (d, J = 7.1 Hz, 4H), 6.93 (dd, J = 8.8, 2.7 Hz, 1H), 6.60 (d, J = 8.8 Hz, 1H), 4.90 (p, J = 8.0 Hz, 1H), 3.86 (dd, J = 11.5, 4.4 Hz, 2H), 3.68-3.57 (m, 1H), 3.10-2.92 (m, 4H), 2.50-2.20 (m, 5H), 1.52 (d, J = 12.7 Hz, 2H). LCMS m/z 478.39 |

Compound 160

4-(4-fluorophenyl)-7-hydroxy-2-(3-hydroxypropyl)-
3-tetrahydropyran-4-yl-isoquinolin-1-one (160)

C132

-continued

160

Compound 160 was obtained directly from a reaction of C132 with 3-aminopropanol followed by MsOH-mediated cyclization and finally standard method B and standard method D. $^1$H NMR (300 MHz, DMSO-d$_6$) δ 9.94 (s, 1H), 7.59 (d, J=2.7 Hz, 1H), 7.40-7.24 (m, 4H), 7.03 (dd, J=8.8, 2.8 Hz, 1H), 6.56 (s, 1H), 4.73 (s, 1H), 4.23 (s, 2H), 3.56 (d, J=5.4 Hz, 2H), 1.85 (s, 2H), 1.56 (d, J=12.4 Hz, 2H). LCMS m/z found 398.38 [M+H]$^+$.

Compounds 161-165

Compounds 161-165 (Table 14) were prepared in three to five steps from intermediate C132 using appropriate amines according to the method described for compound 160. Any modifications to methods are noted in Table 14 and accompanying footnotes.

TABLE 14

Method of preparation, structure, physicochemical data for compounds 161-165

| Compound | Method/Product | Amines | $^1$H NMR; LCMS m/z [M + H]$^+$ |
|---|---|---|---|
| 161 | Compound 160 from C132 | | $^1$H NMR (300 MHz, Methanol-d$_4$) δ 7.62 (d, J = 2.7 Hz, 1H), 7.35-7.18 (m, 4H), 7.03 (dd, J = 8.9, 2.7 Hz, 1H), 6.73-6.61 (m, 1H), 4.98 (s, 2H), 3.80 (d, J = 11.0 Hz, 2H), 3.26 (q, J = 13.2, 10.8 Hz, 5H), 1.69-1.55 (m, 3H), 1.24 (tdd, J = 10.7, 7.7, 3.6 Hz, 4H), 1.06-0.72 (m, 3H). LCMS m/z 438.34 |
| 162 | Compound 160$^1$ | | $^1$H NMR (300 MHz, Methanol-d$_4$) δ 7.66 (d, J = 2.6 Hz, 1H), 7.32-7.20 (m, 5H), 7.04 (dd, J = 8.9, 2.7 Hz, 1H), 6.71 (d, J = 8.9 Hz, 1H), 4.62-4.44 (m, 2H), 3.87 (d, J = 11.1 Hz, 3H), 3.26-3.09 (m, 1H), 2.79-2.66 (m, 3H), 1.63 (d, J = 12.3 Hz, 3H). |
| 163 | Compound 160$^2$ | | $^1$H NMR (300 MHz, Methanol-d$_4$) δ 7.68-7.61 (m, 1H), 7.26 (d, J = 7.9 Hz, 4H), 7.03 (dd, J = 8.9, 2.7 Hz, 1H), 6.71 (s, 1H), 4.28 (t, J = 8.2 Hz, 2H), 4.02 (s, 2H), 3.87 (s, 2H), 3.70 (t, J = 6.3 Hz, 2H), 3.34 (s, 2H), 3.08 (s, 3H), 2.20-2.05 (m, 1H), 2.11 (s, 2H), 1.61 (d, J = 12.0 Hz, 2H). |

TABLE 14-continued

Method of preparation, structure, physicochemical data for compounds 161-165

| Compound | Method/Product | Amines | $^1$H NMR; LCMS m/z [M + H]$^+$ |
|---|---|---|---|
| 164 | Compound 160 from C132 | | $^1$H NMR (300 MHz, Methanol-d$_4$) δ 7.66 (d, J = 2.6 Hz, 1H), 7.25 (d, J = 7.1 Hz, 3H), 7.04 (dd, J = 8.8, 2.7 Hz, 1H), 6.72 (d, J = 8.9 Hz, 1H), 5.52-5.34 (m, 1H), 3.95 (dd, J = 11.3, 4.3 Hz, 2H), 3.72-3.51 (m, 2H), 3.39 (dd, J = 24.2, 3.7 Hz, 0H), 3.39 (s, 1H), 3.07 (td, J = 11.6, 2.3 Hz, 3H), 2.58 (s, 1H), 2.65-2.50 (m, 1H), 2.15 (qd, J = 12.5, 4.4 Hz, 2H), 1.66-1.55 (m, 2H). LCMS m/z 438.39 |
| 165 | Compound 160 from C132 | | $^1$H NMR (300 MHz, Methanol-d$_4$) δ 7.64 (d, J = 2.6 Hz, 1H), 7.34-7.18 (m, 4H), 7.02 (dd, J = 8.9, 2.7 Hz, 1H), 6.65 (d, J = 8.9 Hz, 1H), 5.49 (s, 0H), 4.87 (s, 9H), 4.10 (q, J = 7.1 Hz, 1H), 3.79 (d, J = 11.2 Hz, 2H), 3.49 (s, 2H), 2.01 (s, 1H), 1.61 (d, J = 12.3 Hz, 2H), 1.24 (t, J = 7.1 Hz, 1H), 0.46 (s, 4H). LCMS m/z 424.39 |

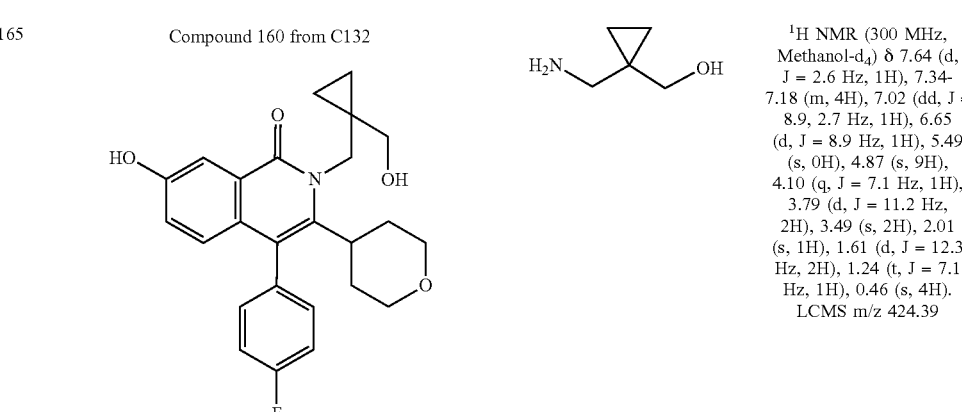

[1]Oxidation to aldehyde was performed with Dess-Martin periodinane and NaHCO$_3$. Further oxidation to carboxylic acid was achieved via treatment with NaClO$_2$ and 2-methylbut-2-ene and Na$_3$PO$_4$. The product was obtained via standard method E using NH$_3$, HATU, and DIPEA before continuing to standard method B.

[2]Additional Mitsunobu reaction with the appropriate amine, PPh$_3$, and ethyl N-ethoxycarbonyliminocarbamate was carried out before continuing to standard method B.

Compounds 166-167

Compounds 166-167 (Table 15) were prepared in two steps from intermediate S14 using appropriate alcohols according to the method described for compound 116. Any modifications to methods are noted in Table 15 and accompanying footnotes.

TABLE 15

Method of preparation, structure, physicochemical data for compounds 166-167

| Compound | Method/Product | Alcohols | $^1$H NMR; LCMS m/z [M + H]$^+$ |
|---|---|---|---|
| 166 | Compound 116 from S14 | | $^1$H NMR (300 MHz, Methanol-d$_4$) δ 7.54 (dd, J = 2.2, 0.9 Hz, 1H), 7.50-7.43 (m, 2H), 7.28-6.87 (m, 4H), 5.71-5.51 (m, 1H), 3.31-3.14 (m, 1H), 3.01-2.72 (m, 3H), 2.70-2.48 (m, 2H), 1.14 (d, J = 6.7 Hz, 6H). LCMS m/z 412.13 |
| 167 | Compound 116 from S14 | | $^1$H NMR (400 MHz, DMSO-d$_6$) δ 7.61-7.54 (m, 2H), 7.50 (d, J = 2.5 Hz, 1H), 7.33-7.23 (m, 2H), 7.16 (dd, J = 9.0, 2.6 Hz, 1H), 6.98 (d, J = 9.0 Hz, 1H), 5.34 (q, J = 6.9 Hz, 1H), 2.69 (p, J = 6.6 Hz, 1H), 1.60 (d, J = 7.0 Hz, 3H), 1.08 (dd, J = 18.8, 6.7 Hz, 6H). LCMS m/z 386.14 |

Compound 168

Methyl (S)-2-((3-ethyl-4-(4-fluorophenyl)-7-hy-
droxyisoquinolin-1-yl)oxy)propanoate (168)

S15

N≡══─P¹

LDA

LiHMDS

P¹ = Et

C134

LG¹

Q¹

O

O

CsF

P¹ = Et

Q¹ = Me

LG¹ = Ts

C135

P¹ = Et

Q¹ = Me

AlBr₃

168

P¹ = Et

Q¹ = Me

Step 1: 3-ethyl-4-(4-fluorophenyl)-7-methoxy-2H-
isoquinolin-1-one (C134)

Isoquinolinones formation using nitriles. LDA (300 μL of
2 M, 0.6000 mmol) was added dropwise to a solution of S15
(126 mg, 0.3995 mmol) in THF (3 mL) at 0° C. The clear
colorless solution turned red and stirred at the same tem-
perature for 1 hours until the temperature warmed up to 0°
C. To this, propanenitrile (50 μL, 0.7008 mmol) was added
dropwise and the reaction was allowed to warm up to room
temperature and stirred for 18 hours. The reaction was
quenched with 1N HCl (200 μL) and solvent was removed
under reduced pressure. The crude product was purified by
silica gel chromatography (Column: 4 g Combiflash ISCO.
Gradient: 10-100% EtOAc in hexane to yield C134 (34 mg,
29%) as an off-white solid. $^1$H NMR (400 MHz, Chloro-
form-d) δ 7.77 (d, J=2.8 Hz, 1H), 7.19-7.14 (m, 2H),
7.14-7.03 (m, 3H), 6.92 (d, J=8.9 Hz, 1H), 3.86 (s, 3H), 2.37
(q, J=7.6 Hz, 2H), 1.14 (t, J=7.6 Hz, 3H). LCMS m/z 298.12
[M+H]$^+$.

Step 2: methyl (2S)-2-[[3-ethyl-4-(4-fluorophenyl)-
7-methoxy-1-isoquinolyl]oxy]-propanoate (C135)

CsF-mediated substitution using tosylates. In a round
bottom flask, CsF (60 mg, 0.3950 mmol) was heated at 200°
C. in vacuo for 15 minutes. The flask was then cooled down
to room temperature and purged with N₂. To this flask was
sequentially added C134 (35 mg, 0.1174 mmol) and DMF (1
mL). After the mixture was stirred for 5 minutes, methyl
(2R)-2-(p-tolylsulfonyloxy)propanoate (33 mg, 0.1278
mmol) was added. The reaction mixture was heated at 50°
C. and stirred for 12 hours. The mixture was quenched with
ice-water and dried with air. The solid was purified by silica
gel chromatography (Column: 4 g Combiflash ISCO. Gra-
dient: 0-50% EtOAc in hexane) to yield as C135 (17 mg,
33%) a colorless clear oil. $^1$H NMR (400 MHz, Chloroform-
d) δ 7.52 (t, J=1.6 Hz, 1H), 7.16-7.05 (m, 6H), 5.42 (q, J=7.0
Hz, 1H), 3.88 (s, 3H), 3.69 (s, 3H), 2.47-2.31 (m, 2H), 1.69
(d, J=7.1 Hz, 3H), 1.05 (t, J=7.5 Hz, 3H). LCMS m/z 714.03
[M+H]$^+$.

Step 3: (2S)-2-[[3-ethyl-4-(4-fluorophenyl)-7-hydroxy-1-isoquinolyl]oxy]propanoic acid (168)

Method G: Demethylation reaction. To a solution of C135 (17 mg, 0.04434 mmol) in EtSH (250 μL) was added AlBr$_3$ (70 mg, 0.2625 mmol) at 0° C. The reaction was stirred for 1 hour. More AlBr$_3$ (70 mg, 0.2625 mmol) were added to push the reaction to completion. After another 1 hour, the reaction was dried under air and the crude product was dissolved in minimal amount of ACN (0.5 mL). The residue was purified by reverse-phase HPLC. Method: C18 Waters Sunfire column (30×150 mm, 5 micron). Gradient: 0-70% MeCN in H$_2$O with 0.2% formic acid to yield 168 (3 mg, 19%). $^1$H NMR (400 MHz, Chloroform-d) δ 7.73-7.66 (m, 0H), 7.63-7.57 (m, 1H), 7.24-7.14 (m, 6H), 5.53-5.41 (m, 1H), 3.22 (q, J=7.1 Hz, 1H), 2.60-2.43 (m, 2H), 1.79 (dd, J=6.9, 5.6 Hz, 3H), 1.16 (td, J=7.5, 1.8 Hz, 3H). LCMS m/z 356.19 [M+H]$^+$.

Compounds 169-172

Compounds 169-172 (Table 16) were prepared in three steps from intermediate S15 using appropriate nitriles and alcohols according to the method described for compound 168. Any modifications to methods are noted in Table 16 and accompanying footnotes.

TABLE 16

| | | | | | $^1$H NMR; LCMS m/z |
|---|---|---|---|---|---|
| Compound | Method/Product | P$^1$ | Q$^1$ | LG$^1$ | [M + H]$^+$ |
| 169 | Compound 168 from S15 | | H | Br | $^1$H NMR (400 MHz, Acetonitrile-d$_3$) δ 7.58 (dd, J = 2.5, 0.7 Hz, 1H), 7.32-7.24 (m, 4H), 7.24-7.14 (m, 2H), 5.16 (s, 2H), 3.51-3.39 (m, 1H), 2.50-2.37 (m, 2H), 1.95 (s, 2H), 1.90-1.77 (m, 2H). LCMS m/z 368.3 |
| 170 | Compound 168 from S15 | CF$_3$ | CH$_3$ | Ts | $^1$H NMR (400 MHz, Chloroform-d) δ 7.61 (d, J = 2.5 Hz, 1H), 7.18-7.03 (m, 6H), 5.55 (q, J = 6.9 Hz, 1H), 1.74 (d, J = 7.0 Hz, 3H). LCMS m/z 396.08 |

TABLE 16-continued

Method of preparation, structure, physicochemical data for compounds 169-172

| Compound | Method/Product | P¹ | Q¹ | LG¹ | ¹H NMR; LCMS m/z [M + H]⁺ |
|---|---|---|---|---|---|

| 171 | Compound 168 from S15 | CF₃ | CH₃ | Ts | ¹H NMR (400 MHz, Chloroform-d) δ 7.57 (dd, J = 2.2, 1.0 Hz, 1H), 7.23-7.14 (m, 3H), 7.13-7.06 (m, 3H), 5.56 (q, J = 7.0 Hz, 1H), 3.91 (s, 3H), 1.76 (d, J = 7.0 Hz, 3H). LCMS m/z 410.17 |

| 172 | Compound 168 from S15 | (3,3-difluorocyclobutyl) | CH₃ | Ts | ¹H NMR (400 MHz, Chloroform-d) δ 7.69-7.54 (m, 1H), 7.17-6.98 (m, 7H), 5.47 (dd, J = 7.1, 4.5 Hz, 1H), 3.22-2.94 (m, 2H), 2.80 (dp, J = 23.2, 12.0, 11.5 Hz, 1H), 2.55 (dtd, J = 16.4, 8.2, 7.2, 3.8 Hz, 2H), 1.77 (d, J = 7.1 Hz, 3H). LCMS m/z 418.14 |

| 173 | Compound 168 from S15¹ | (3,3-difluorocyclobutyl) | — | — | ¹H NMR (400 MHz, Chloroform-d) δ 7.59 (d, J = 2.5 Hz, 1H), 7.24-7.10 (m, 6H), 5.74-5.61 (m, 1H), 3.34 (dp, J = 14.2, 4.6 Hz, 1H), 3.20 (pd, J = 8.4, 3.4 Hz, 1H), 3.09-2.86 (m, 4H), 2.74-2.52 (m, 4H). LCMS m/z 444.2 |

TABLE 16-continued

Method of preparation, structure, physicochemical data for compounds 169-172

| Compound | Method/Product | P¹ | Q¹ | LG¹ | ¹H NMR; LCMS m/z [M + H]⁺ |
|---|---|---|---|---|---|
| 174 | Compound 168 from S15 | | (CH₃)₂ | Br | ¹H NMR (400 MHz, Chloroform-d) δ 7.45 (d, J = 2.6 Hz, 1H), 3.27 (dd, J = 3.3, 1.7 Hz, 2H), 2.58-2.42 (m, 3H), 2.42-2.30 (m, 1H), 2.00 (dtd, J = 23.7, 12.1, 6.1 Hz, 2H), 1.78 (d, J = 14.2 Hz, 2H), 1.70 (s, 6H). LCMS m/z 442.17 |

¹benzyl 3-(p-tolylsulfonyloxy)cyclobutanecarboxylate was used as the reactant in the second step.

Compound 175

4-(4-fluorophenyl)-7-hydroxy-3-isopropyl-isoquino-line-1-carbonitrile (175)

-continued

Step 1: 7-benzyloxy-4-(4-fluorophenyl)-3-isopropyl-iso-quinoline-1-carbonitrile (C136)

DBU (85 µL, 0.5684 mmol) and TMSCN (42 µL, 0.3150 mmol) were added to a suspension of C21 (100 mg, 0.2581 mmol) in dry THF (1.5 mL) at room temperature. The mixture was heated at 50° C. and after stirring for 15 minutes, the mixture became homogeneous. After stirring for 3 hours, a precipitate formed, and the reaction mixture was diluted with EtOAc and washed with 1M HCl. The organic layer was washed with NH₄OH and brine, dried over anhydrous Na₂SO₄, filtered and concentrated. The residue was purified by silica gel chromatography (Column: 4 g Combiflash ISCO. Gradient: 0-20% EtOAc in heptane) to afford C136 (40 mg, 39%) as a colorless solid. ¹H NMR (300 MHz, Chloroform-d) δ 7.63 (dd, J=2.3, 0.8 Hz, 1H), 7.58-7.49 (m, 2H), 7.49-7.31 (m, 5H), 7.25 (m, 4H), 5.29 (s, 2H), 3.00 (hept, J=6.8 Hz, 1H), 1.24 (d, J=6.7 Hz, 6H).

Step 2: 4-(4-fluorophenyl)-7-hydroxy-3-isopropyl-isoquinoline-1-carbonitrile (175)

Compound C136 was subjected to standard method B to furnish 175. ¹H NMR (300 MHz, Chloroform-d) δ 7.68 (dd, J=2.4, 0.7 Hz, 1H), 7.44-7.16 (m, 6H), 6.40 (s, 1H), 3.00 (h, J=6.7 Hz, 1H), 1.24 (d, J=6.8 Hz, 6H). LCMS m/z 307.58 [M+H]⁺.

Compound 176

2-[[3-(dimethylamino)-4-(4-fluorophenyl)-7-methoxy-1-isoquinolyl]oxy]acetic acid (176)

C22

C137

C138

C139

-continued

176

Step 1: methyl 2-[(3-chloro-7-methoxy-1-isoquinolyl)oxy]acetate (C137)

Method H: Nucleophilic Substitution Using Alcohols. To a mixture of C22 (5.09 g, 22.32 mmol) and methyl 2-hydroxyacetate (1.8 mL, 23.32 mmol), in THF (100 mL) was added dropwise KOtBu (25 mL of 1 M, 25.00 mmol) at 0° C. The reaction mixture was warmed to room temperature and stirred for 2 hours. More methyl 2-hydroxyacetate (1.8 mL, 23.32 mmol) and KOtBu (25 mL of 1M, 25.00 mmol) were added to push the reaction to completion. sat. NH₄Cl was added to the reaction mixture and extracted with dichloromethane (3×50 mL). The combined organic layers were washed with brine (1×50 mL), water (2×50 mL), dried over anhydrous Na₂SO₄, filtered, and concentrated to dryness. The residue was purified by silica gel chromatography (Column: 120 g gold Combiflash ISCO. Gradient: 0-100% EtOAc in heptane) to give C137 (3560 mg, 55%). ¹H NMR (400 MHz, Chloroform-d) δ 7.61-7.50 (m, 2H), 7.33 (dt, J=9.0, 1.9 Hz, 1H), 7.24 (s, 1H), 5.12 (d, J=1.4 Hz, 2H), 3.95 (d, J=1.4 Hz, 3H), 3.82 (d, J=1.4 Hz, 3H). LCMS m/z 282.18 [M+H]⁺.

Step 2: methyl 2-[[3-(dimethylamino)-7-methoxy-1-isoquinolyl]oxy]acetate (C138)

Method I: Buchwald Coupling Method. A suspension of C137 (70 mg, 0.2401 mmol), N-methylmethanamine (HCl salt) (25 μL, 0.2876 mmol), Cs₂CO₃ (300 mg, 0.9208 mmol), and dioxane (3 mL) was purged under N₂ for 5 minutes. To this, was added RuPhos Pd G2 (10 mg, 0.01287 mmol), and the mixture was purged again under N₂ for another 5 minutes. The reaction mixture was heated to 80° C. and stirred for 2 hours. The reaction mixture was filtered and concentrated under reduce pressure. The residue was dissolved in minimal amount of DMSO (2 mL) and purified by reverse-phase HPLC. Method: C18 Waters Sunfire column (30×150 mm, 5 micron). Gradient: 2-98% MeCN in H₂O with 0.2% formic acid to yield C138 (32 mg, 41%). LCMS m/z 290.91 [M+H]⁺.

Step 3-5: 2-[[3-(dimethylamino)-4-(4-fluorophenyl)-7-methoxy-1-isoquinolyl]oxy]acetic acid (C139)

Compound C138 was then subjected to bromination with NBS in dichloromethane. Further transformation to C139 was accomplished according to standard method B using 4-fluorophenyl boronic acid followed by standard method D with NaOH.

Step 6: 2-[[3-(dimethylamino)-4-(4-fluorophenyl)-7-methoxy-1-isoquinolyl]oxy]acetic acid (176)

Compound 176 was obtained according to standard method G. $^1$H NMR (400 MHz, Methanol-d4) δ 8.09 (s, 2H), 7.54 (d, J=2.5 Hz, 1H), 7.41-7.34 (m, 2H), 7.30-7.23

(m, 2H), 7.20 (d, J=9.1 Hz, 1H), 7.13 (dd, J=9.1, 2.6 Hz, 1H), 5.04 (s, 2H), 2.80 (s, 6H). LCMS m/z 357.27 [M+H]$^+$.

Compounds 177-181

Compounds 177-181 (Table 17) were prepared in five steps from intermediate C137 using appropriate amines according to the method described for compound 176. Any modifications to methods are noted in Table 17 and accompanying footnotes.

TABLE 17

| Compound | Method/Product | Amines | $^1$H NMR; LCMS m/z [M + H]$^+$ |
|---|---|---|---|
| | Method of preparation, structure, physicochemical data for compounds 177-181 | | |
| 177 | Compound 176 from C137 | | $^1$H NMR (400 MHz, Methanol-d$_4$) δ 7.53 (d, J = 2.5 Hz, 1H), 7.41 (dd, J = 8.3, 5.5 Hz, 2H), 7.27 (q, J = 9.2, 8.5 Hz, 3H), 7.15 (dd, J = 9.1, 2.6 Hz, 1H), 5.05 (s, 2H), 3.62 (s, 4H), 3.14 (s, 4H). LCMS m/z 399.1 |
| 178 | Compound 176 from C137[1] | | $^1$H NMR (400 MHz, Methanol-d$_4$) δ 7.56 (t, J = 1.6 Hz, 1H), 7.30-7.15 (m, 5H), 5.06 (s, 2H), 2.96 (s, 6H), 2.33 (d, J = 1.9 Hz, 3H). LCMS m/z 371.32 |

TABLE 17-continued

Method of preparation, structure, physicochemical data for compounds 177-181

| Compound | Method/Product | Amines | $^1$H NMR; LCMS m/z [M + H][+] |
|---|---|---|---|
| 179 | Compound 176 from C137[1,2] | | $^1$H NMR (400 MHz, Methanol-d[4]) δ 7.65 (d, J = 2.5 Hz, 1H), 7.37-7.16 (m, 5H), 5.13 (s, 2H), 3.36-3.31 (m, 2H), 3.22 (d, J = 2.7 Hz, 3H), 3.13 (d, J = 3.3 Hz, 3H), 2.74 (d, J = 65.3 Hz, 2H), 2.39 (d, J = 1.9 Hz, 3H). LCMS m/z 415.21 |
| 180 | Compound 176 from C137[1] | | $^1$H NMR (400 MHz, Methanol-d[4]) δ 8.07 (d, J = 6.7 Hz, 1H), 7.54-7.50 (m, 1H), 7.30 (d, J = 9.1 Hz, 1H), 7.28 -7.23 (m, 1H), 7.21-7.16 (m, 2H), 7.14 (dd, J = 9.2, 2.6 Hz, 1H), 5.04 (d, J = 1.0 Hz, 2H), 3.75 (d, J = 11.5 Hz, 1H), 3.56 (d, J = 11.4 Hz, 2H), 3.27-2.99 (m, 3H), 2.76 (s, 1H), 2.38-2.29 (m, 3H), 1.06 (d, J = 6.3 Hz, 3H). LCMS m/z 427.36 |
| 181 | Compound 176 from C137[1,3] | | $^1$H NMR (400 MHz, Methanol-d[4]) δ 7.40 (d, J = 2.5 Hz, 1H), 7.09 (d, J = 9.2 Hz, 4H), 6.98 (dd, J = 9.2, 2.6 Hz, 1H), 4.96 (d, J = 2.4 Hz, 2H), 4.47 (s, 1H), 3.73-3.62 (m, 1H), 3.45 (d, J =12.5 Hz, 1H), 3.32 (s, 1H), 3.14 (s, 1H), 2.20 (qd, J = 8.4, 4.2 Hz, 1H), 2.01 (d, J = 0.9 Hz, 4H). LCMS m/z 475.3 |

[1](4-fluoro-3-methyl-phenyl)boronic acid was used in the fourth step.

[2]MOM deprotection was accomplished using HCl instead of standard method G.

[3]The reaction with BBr[3] resulted in F displacement to form the product.

Compounds 182-184

Compounds 182-184 (Table 18) were prepared in two or three steps from intermediate S16 using 3-hydroxycyclobutanecarboxylic acid according to the method described for compound 116. Any modifications to methods are noted in Table 18 and accompanying footnotes.

TABLE 18

| | | | |
|---|---|---|---|
| Method of preparation, structure, physicochemical data for compounds 182-184 | | | |
| Compound | Product | Method | $^1$H NMR; LCMS m/z [M + H]$^+$ |
| 182 | | Compound 116 from S16 | $^1$H NMR (400 MHz, Methanol-d$_4$) δ 7.49 (d, J = 2.5 Hz, 1H), 7.40 (dt, J = 10.7, 8.4 Hz, 1H), 7.21-7.10 (m, 2H), 7.08-7.01 (m, 2H), 5.68-5.54 (m, 1H), 3.96 (dt, J = 10.3, 4.2 Hz, 2H), 3.38-3.27 (m, 2H), 3.21 (ttd, J = 10.2, 4.1, 1.1 Hz, 1H), 2.88 (dddd, J = 11.3, 7.3, 4.1, 2.7 Hz, 2H), 2.69 (tt, J = 11.6, 3.7 Hz, 1H), 2.58 (tdd, J = 10.1, 6.6, 2.8 Hz, 2H), 2.16 (qt, J = 12.7, 4.6 Hz, 2H), 1.55-1.44 (m, 2H). LCMS m/z 456.22 |
| 183 | | Compound 116 from S16$^1$ | $^1$H NMR (400 MHz, Methanol-d$_4$) δ 7.49 (d, J = 2.5 Hz, 1H), 7.40 (dt, J = 10.8, 8.4 Hz, 1H), 7.22-7.10 (m, 2H), 7.08-7.00 (m, 2H), 5.65-5.54 (m, 1H), 4.01-3.90 (m, 2H), 3.76 (s, 3H), 3.39-3.21 (m, 4H), 2.94-2.82 (m, 2H), 2.69 (tt, J = 11.7, 3.8 Hz, 1H), 2.64-2.53 (m, 2H), 2.15 (qt, J = 12.7, 4.6 Hz, 2H), 1.56-1.42 (m, 2H). LCMS m/z 470.22 |
| 184 | | Compound 116 from S16$^2$ | $^1$H NMR (400 MHz, Chloroform-d) δ 7.54 (d, J = 2.5 Hz, 1H), 7.32 (d, J = 1.2 Hz, 1H), 7.31-7.24 (m, 1H), 7.14 (dd, J = 9.0, 2.5 Hz, 1H), 7.11-7.02 (m, 2H), 6.98 (d, J = 4.1 Hz, 1H), 5.54 (p, J = 6.5 Hz, 1H), 3.98 (dd, J = 10.7, 5.0 Hz, 2H), 3.44-3.28 (m, 2H), 3.23 (dt, J = 9.9, 4.9 Hz, 1H), 2.90 (ddd, J = 14.6, 7.2, 4.6 Hz, 2H), 2.72-2.52 (m, 3H), 2.25-2.07 (m, 2H), 1.44 (d, J = 13.9 Hz, 2H). LCMS m/z 455.03 |

$^1$Pd-Catalyzed transfer hydrogenation reaction of compound 182 in MeOH also resulted in the formation of compound 179.

$^2$Compound 184 was synthesized from further treatment of compound 182 with NH$_4$Cl, HATU, and DIPEA according to standard method E.

Compound 185

3-[[7-hydroxy-4-(2-methyl-4-pyridyl)-3-tetrahydro-
pyran-4-yl-1-isoquinolyl]oxy]cyclobutanecarboxylic
acid (185)

S11

C34

C34

C140

-continued

185

Step 1: 7-benzyloxy-4-(2-methyl-4-pyridyl)-2-oxido-3-tetrahydropyran-4-yl-isoquinolin-2-ium (C34)

C34 was synthesized according to standard method C.

Step 2: 1-(4-aza-1-azoniabicyclo[2.2.2]octan-1-yl)-7-benzyloxy-4-(2-methyl-4-pyridyl)-3-tetrahydropy-ran-4-yl-isoquinoline (S20)

Method J: Amination of N-oxide using TFAA and DABCO. A solution of C34 (513 mg, 1.203 mmol) and DABCO in dichloromethane (10 mL) was cooled to 0° C., and to it was added TFAA (450 µL, 3.237 mmol). The mixture was allowed to warm to room temperature and then stirred for 1 hour. The reaction mixture was concentrated, dissolved in minimal amount of DMSO, and purified by reverse-phase HPLC. (C18, 10-100% MeCN in H$_2$O with 0.1% trifluoroacetic acid) to yield S20 (Trifluoroacetic Acid salt) as an off-white solid (930 mg, 99%). LCMS m/z 521.35 [M+H]$^+$.

Steps 3 & 4: 3-[[7-hydroxy-4-(2-methyl-4-pyridyl)-3-tetrahydropyran-4-yl-1-isoquinolyl]oxy]cyclobu-tanecarboxylic acid (185)

S20 was then subjected to standard method A followed by standard method B to form 185. $^1$H NMR (300 MHz, Chloroform-d and Methanol-d$_4$) δ 8.54 (dd, J=5.2, 0.8 Hz, 1H), 7.57 (dd, J=2.6, 0.5 Hz, 1H), 7.20-6.98 (m, 4H), 5.71-5.56 (m, 1H), 3.99 (d, J=11.1 Hz, 2H), 3.35-3.09 (m, 2H), 3.00-2.86 (m, 2H), 2.73-2.49 (m, 6H), 2.36-1.97 (m, 3H), 1.48 (d, J=13.0 Hz, 2H). LCMS m/z 435.37 [M+H]$^+$.

Compounds 186-190

Compounds 186-190 (Table 19) were prepared in four or five steps from intermediate S11 using appropriate boronic acids or esters according to the method described for compound 185. Any modifications to methods are noted in Table 19 and accompanying footnotes.

TABLE 19

Method of preparation, structure, physicochemical data for compounds 186-190

| Compound | Method/Product | Boronic acids or esters | ¹H NMR; LCMS m/z [M + H]⁺ |
|---|---|---|---|
| 186 | Compound 185 from S11 | | ¹H NMR (400 MHz, Methanol-d₄) δ 7.80 (d, J = 9.1 Hz, 1H), 7.45 (d, J = 2.6 Hz, 1H), 7.25 (dd, J = 9.1, 2.7 Hz, 1H), 5.53 (p, J = 6.9 Hz, 1H), 4.05 (dd, J = 11.1, 4.3 Hz, 2H), 3.71-3.54 (m, 2H), 3.31-3.10 (m, 2H), 2.84 (ddd, J = 13.6, 7.0, 3.5 Hz, 2H), 2.52 (dtd, J = 10.7, 7.4, 7.0, 3.4 Hz, 2H), 2.46 (s, 3H), 2.13 (qd, J = 12.6, 4.5 Hz, 2H), 1.67-1.51 (m, 2H). LCMS m/z 358.22 |
| 187 | Compound 185 from S11 | | ¹H NMR (400 MHz, Acetonitrile-d₃) δ 7.60 (dd, J = 9.0, 0.6 Hz, 1H), 7.48 (dd, J = 2.7, 0.5 Hz, 1H), 7.27 (dd, J = 9.0, 2.6 Hz, 1H), 5.62-5.55 (m, 1H), 5.54 (s, 1H), 4.00 (td, J = 10.9, 4.4 Hz, 2H), 3.54-3.37 (m, 2H), 3.28-3.15 (m, 1H), 3.01 (tt, J = 11.6, 3.7 Hz, 1H), 2.89-2.72 (m, 4H), 2.62-2.37 (m, 4H), 2.35-2.08 (m, 4H), 1.57-1.42 (m, 2H). LCMS m/z 460.22 |
| 188 | Compound 185 from S11 | | ¹H NMR (400 MHz, Methanol-d₄) δ 7.49 (d, J = 2.5 Hz, 1H), 7.42-7.34 (m, 2H), 7.20 (ddd, J = 8.4, 4.6, 2.2 Hz, 1H), 7.14 (dd, J = 9.0, 2.6 Hz, 1H), 7.04 (d, J = 9.0 Hz, 1H), 5.66-5.55 (m, 1H), 3.96 (dt, J = 10.3, 4.5 Hz, 2H), 3.39-3.32 (m, 2H), 3.26-3.16 (m, 1H), 2.94-2.84 (m, 2H), 2.74-2.65 (m, 1H), 2.64-2.53 (m, 2H), 2.17 (ddt, J = 16.3, 12.8, 6.3 Hz, 2H), 1.50 (d, J = 13.2 Hz, 2H). LCMS m/z 472.1 |

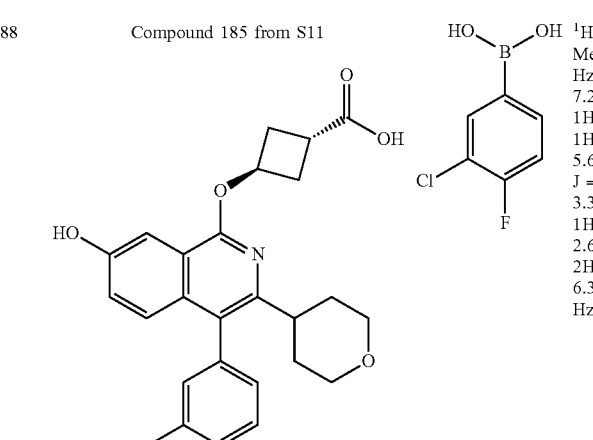

TABLE 19-continued

Method of preparation, structure, physicochemical data for compounds 186-190

| Compound | Method/Product | Boronic acids or esters | $^1$H NMR; LCMS m/z [M + H]$^+$ |
|---|---|---|---|
| 189 | Compound 185 from S11 | | LCMS m/z 472.2 |
| | | | |
| 190 | Compound 185 from S11 | | $^1$H NMR (400 MHz, Methanol-d$_4$) δ 7.69 (dd, J = 9.2, 8.4 Hz, 1H), 7.55-7.46 (m, 1H), 7.31 (dd, J = 8.3, 3.8 Hz, 1H), 7.14 (dd, J = 9.0, 2.6 Hz, 1H), 6.99 (dd, J = 9.0, 0.5 Hz, 1H), 5.69-5.57 (m, 1H), 3.95 (dd, J = 11.6, 4.2 Hz, 2H), 3.31 (p, J = 1.7 Hz, 2H), 3.26-3.16 (m, 1H), 2.89 (dddd, J = 11.3, 7.3, 4.1, 2.7 Hz, 2H), 2.64-2.48 (m, 6H), 2.25-2.08 (m, 2H), 1.64-1.46 (m, 2H). LCMS m/z 453.14 |
| | | | |

Compound 191

3-[(4-cyclopropyl-7-hydroxy-3-tetrahydropyran-4-yl-1-isoquinolyl)oxy]cyclobutanecarboxylic acid (191)

S11

C141

C142

C143

-continued

191

Steps 1 & 2: 3-[(7-benzyloxy-4-bromo-3-tetrahydropyran-4-yl-1-isoquinolyl)oxy]cyclobutanecarboxylic acid (C142)

C142 was synthesized according to standard method J with S11 followed by standard method A on C141.

Step 3: 3-[(7-benzyloxy-4-cyclopropyl-3-tetrahydropyran-4-yl-1-isoquinolyl)oxy]cyclobutanecarboxylic acid (C143)

Negishi Coupling Method. A suspension of C142 (20 mg, 0.03751 mmol), bromo(cyclopropyl)zinc (400 μL of 0.5M, 0.200 mmol), and THF (1 mL) was purged under $N_2$ for 5 minutes. To this was added Cphos Pd G3 (10 mg, 0.0124 mmol) and DavePhos (5 mg, 0.01271 mmol), and the mixture was stirred at room temperature for 2 hours. The reaction was quenched with water and concentrated under reduced pressure. The residue was purified by reversed-phase HPLC. (100 g C18, 10-100% MeCN in $H_2O$ with 0.1% trifluoroacetic acid) to yield C143 (10 mg, 55%). LCMS m/z 474.31 $[M+H]^+$.

Step 4: 3-[(4-cyclopropyl-7-hydroxy-3-tetrahydropyran-4-yl-1-isoquinolyl)oxy]cyclobutanecarboxylic acid (191)

Compound 191 was synthesized according to standard method B. $^1$H NMR (400 MHz, Methanol-$d_4$) δ 8.24 (d, J=9.1 Hz, 1H), 7.43 (d, J=2.6 Hz, 1H), 7.23 (dd, J=9.1, 2.7 Hz, 1H), 5.58-5.46 (m, 1H), 4.06 (dd, J=11.4, 4.3 Hz, 2H), 3.76 (tt, J=11.6, 3.7 Hz, 1H), 3.61 (ddd, J=13.1, 11.4, 1.9 Hz, 2H), 3.24-3.11 (m, 1H), 2.84 (dddd, J=11.4, 7.3, 4.1, 2.5 Hz, 2H), 2.52 (dtd, J=13.5, 6.6, 2.8 Hz, 2H), 2.16 (qd, J=12.8, 4.5 Hz, 2H), 1.88 (tt, J=8.3, 5.6 Hz, 1H), 1.53 (ddd, J=12.9, 3.9, 1.8 Hz, 2H), 1.25-1.15 (m, 2H), 0.53 (td, J=5.9, 4.1 Hz, 2H). LCMS m/z 384.24 $[M+H]^+$.

Compounds 192-194

Compounds 192-194 (Table 20) were prepared in three or four steps from intermediate S11 using appropriate alkyl zinc reagent or amines according to the method described for compound 191 or. Any modifications to methods are noted in Table 20 and accompanying footnotes.

TABLE 20

| Compound | Method/Product | Alkyl ZnBr or amines | ¹H NMR; LCMS m/z [M + H]⁺ |
|---|---|---|---|
| | Method of preparation, structure, physicochemical data for compounds 192-194 | | |
| 192 | Compound 191 from S11 | | ¹H NMR (400 MHz, Methanol-d₄) δ 8.00 (d, J = 9.2 Hz, 1H), 7.45 (d, J = 2.7 Hz, 1H), 7.19 (dd, J = 9.2, 2.7 Hz, 1H), 5.58-5.46 (m, 1H), 4.25 (p, J = 9.2 Hz, 1H), 4.09-4.00 (m, 2H), 3.59 (ddd, J = 13.1, 11.3, 1.9 Hz, 2H), 3.30 (s, 2H), 3.30-3.12 (m, 1H), 2.85 (ddt, J = 14.1, 7.3, 3.3 Hz, 2H), 2.68-2.39 (m, 5H), 2.26-2.09 (m, 3H), 2.01 (dd, J = 11.1, 8.5 Hz, 1H), 1.55 (d, J = 13.3 Hz, 2H). LCMS m/z 398.24 |
| 193 | Compound 191 from S11[1] | | ¹H NMR (400 MHz, Methanol-d₄) δ 7.97 (d, J = 9.1 Hz, 1H), 7.47 (d, J = 2.5 Hz, 1H), 7.28 (dd, J = 9.1, 2.6 Hz, 1H), 5.57-5.47 (m, 1H), 4.41 (t, J = 12.8 Hz, 4H), 4.07 (dd, J = 11.5, 4.3 Hz, 2H), 3.63 (ddd, J = 13.1, 11.4, 1.9 Hz, 2H), 3.55 (tt, J = 11.7, 3.7 Hz, 1H), 3.23-3.11 (m, 1H), 2.84 (dddd, J = 11.3, 7.3, 4.0, 2.5 Hz, 2H), 2.52 (dtd, J = 13.5, 6.5, 2.8 Hz, 2H), 2.13 (qd, J = 12.7, 4.5 Hz, 2H), 1.56 (ddd, J = 13.1, 4.0, 1.8 Hz, 2H). LCMS m/z 435.2 |
| 194 | Compound 191 from S11 | N/A | ¹H NMR(400 MHz, Methanol-d₄) δ 7.99 (d, J = 9.1 Hz, 1H), 7.45 (d, J = 2.5 Hz, 1H), 7.32 (dd, J = 9.1, 2.6 Hz, 1H), 5.60-5.48 (m, 1H), 4.11-4.02 (m, 2H), 3.67-3.52 (m, 3H), 3.25-3.13 (m, 1H), 2.85 (dddd, J = 11.3, 7.3, 4.0, 2.5 Hz, 2H), 2.55 (dtd, J = 13.4, 6.6, 2.8 Hz, 2H), 2.15-2.04 (m, 2H), 1.68 (ddd, J = 13.0, 4.0, 1.9 Hz, 2H). LCMS m/z |

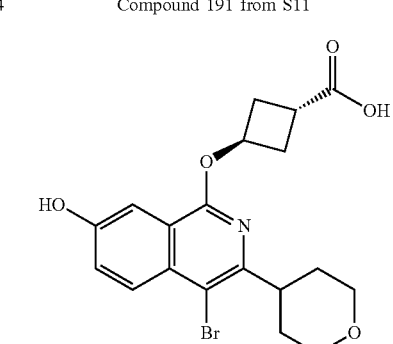

---

[1]Coupling of the amine was performed according to standard method I using tBuXPhos Pd G1 and NaOtBu.

Compound 195

2-[[3-chloro-4-(4-fluoro-3-methyl-phenyl)-7-hy-
droxy-1-isoquinolyl]oxy]acetic acid (195)

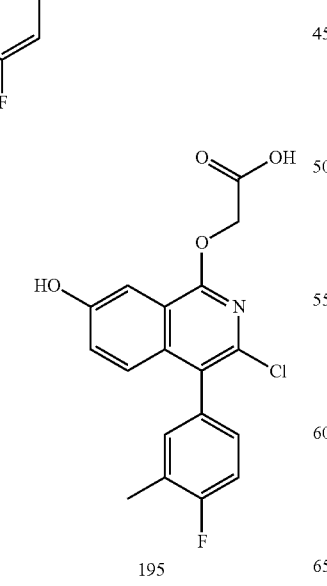

S17

C24

C144

195

Step 1: 1,3-dichloro-4-(4-fluoro-3-methyl-phenyl)-
7-methoxy-isoquinoline (C24)

Compound C24 was synthesized according to standard
method C. ¹H MR (400 MHz, Chloroform-d) δ 7.57 (d,
J=2.5 Hz, 1H), 7.42 (dd, J=9.3, 0.5 Hz, 1H), 7.33 (dd, J=9.2,
2.6 Hz, 1H), 7.21-7.09 (m, 3H), 4.02 (s, 3H), 2.38 (d, J=1.9
Hz, 3H). LCMS m/z 336.1 [M+H]⁺.

Step 2: 2-[[3-chloro-4-(4-fluoro-3-methyl-phenyl)-
7-methoxy-1-isoquinolyl]oxy]acetic acid (C144)

Compound C144 was synthesized according to standard
method H using NaH. ¹H NMR (400 MHz, Chloroform-d)
δ 7.63-7.58 (m, 1H), 7.27 (dd, J=9.3, 0.6 Hz, 1H), 7.21 (dd,
J=9.2, 2.6 Hz, 1H), 7.17-7.06 (m, 3H), 5.16 (s, 2H), 3.94 (s,
3H), 2.39-2.27 (m, 3H). LCMS m/z 376.21 [M+H]⁺.

Step 3: 2-[[3-chloro-4-(4-fluoro-3-methyl-phenyl)-
7-hydroxy-1-isoquinolyl]oxy]acetic acid (195)

Compound 195 was synthesized according to standard
method G using BBr₃. ¹H NMR (400 MHz, Methanol-d₄) δ
7.45 (dd, J=2.0, 1.2 Hz, 1H), 7.12-7.07 (m, 2H), 7.07-7.01
(m, 2H), 6.98 (ddd, J=8.0, 5.1, 1.9 Hz, 1H), 4.97 (s, 2H),
2.22 (d, J=2.0 Hz, 3H). LCMS m/z 362.17 [M+H]⁺.

Compound 196

2-[[4-(4-fluoro-3-methyl-phenyl)-7-hydroxy-3-(2-
hydroxy-1-methyl-ethyl)-1-isoquinolyl]oxy]acetic
acid (196)

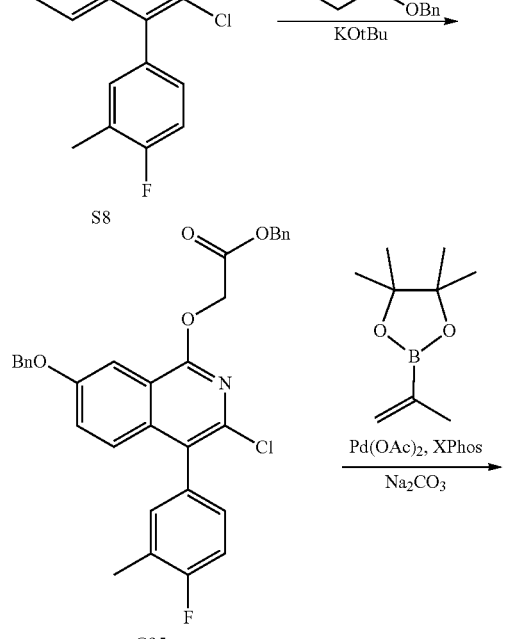

S8

C95

413

-continued

C97

414

Step 1: benzyl 2-[[7-benzyloxy-3-chloro-4-(4-fluoro-3-methyl-phenyl)-1-isoquinolyl]oxy]acetate (C95)

S8 was subjected to standard method H to form C95. LCMS m/z 542.32 [M+H]$^+$.

Step 2: benzyl 2-[[7-benzyloxy-4-(4-fluoro-3-methyl-phenyl)-3-isopropenyl-1-isoquinolyl]oxy] acetate (C97)

C97 was synthesized according to standard method B using Pd(OAc)$_2$ and XPhos.

Step 3: benzyl 2-[[7-benzyloxy-4-(4-fluoro-3-methyl-phenyl)-3-(2-hydroxy-1-methyl-ethyl)-1-isoquinolyl]oxy]acetate (C145)

To a suspension of C97 (100 mg, 0.1826 mmol) in THF (2 mL) was added BH$_3$ (100 of 1M in THF, 0.1000 mmol) at 0° C. The reaction was allowed to stir at room temperature for 2 hours and then cooled back to 0° C. To this was added NaBO$_3$·4H$_2$O (30 mg, 0.1950 mmol) in water (2 mL), and the reaction mixture was stirred for 18 hours. The reaction was quenched with 1 M NaS$_2$O$_3$ solution (5 mL) and stirred for 30 minutes. The solution was extracted with EtOAc (3×5 mL). The combined organic layers were washed with brine, dried over anhydrous MgSO$_4$ and concentrated. The crude product was purified by silica gel chromatography (Column: 4 g Combiflash ISCO. Gradient: 0-70% EtOAc in hexane) to give C145 (25 mg, 21%) as a light yellow solid. $^1$H NMR (400 MHz, Chloroform-d) δ 7.64 (d, J=2.6 Hz, 1H), 7.46-7.38 (m, 2H), 7.37-7.24 (m, 9H), 7.23-7.17 (m, 2H), 7.13 (dd, J=9.2, 2.0 Hz, 1H), 7.06-6.89 (m, 3H), 5.19 (d, J=0.8 Hz, 2H), 5.11 (d, J=8.2 Hz, 2H), 5.08-4.92 (m, 2H), 3.74 (dt, J=10.6, 7.2 Hz, 1H), 3.59 (dt, J=10.6, 3.9 Hz, 1H), 2.89 (tdd, J=7.1, 4.4, 2.7 Hz, 1H), 2.26 (d, J=1.8 Hz, 3H), 2.14 (d, J=27.4 Hz, 1H), 1.23-1.15 (m, 3H). LCMS m/z 566.31 [M+H]$^+$.

Step 4: 2-[[4-(4-fluoro-3-methyl-phenyl)-7-hydroxy-3-(2-hydroxy-1-methyl-ethyl)-1-isoquinolyl]oxy] acetic acid (196)

C145 was then subjected to standard to standard method B to form 196. $^1$H NMR (400 MHz, Acetonitrile-d$_3$) δ 7.42 (dt, J=2.5, 0.7 Hz, 1H), 7.14-6.97 (m, 5H), 5.01-4.85 (m, 2H), 3.73-3.61 (m, 1H), 3.42 (ddd, J=10.3, 5.9, 4.2 Hz, 1H), 2.75 (dddd, J=7.8, 6.8, 5.9, 0.9 Hz, 1H), 2.24 (d, J=2.0 Hz, 3H), 0.97 (dd, J=6.8, 2.9 Hz, 3H). LCMS m/z 386.18 [M+H]$^+$.

Compounds 197-199

Compounds 197-199 (Table 21) were prepared in three to four steps from intermediate S8 using appropriate boronic acids or esters according to the method described for compound 196. Any modifications to methods are noted in Table 21 and accompanying footnotes.

C145

196

TABLE 21

Method of preparation, structure, physicochemical data for compounds 197-199

| Compound | Method/Product | Boronic acids or esters | ¹H NMR; LCMS m/z [M + H]⁺ |
|---|---|---|---|
| 197 | Compound 196 from S8[1] | | ¹H NMR (400 MHz, Acetonitrile-d₃) δ 7.57 (s, 1H), 7.35 (d, J = 1.7 Hz, 1H), 7.30-7.15 (m, 4H), 7.15-7.02 (m, 2H), 6.31 (d, J = 1.8 Hz, 1H), 5.10 (s, 2H), 2.34 (d, J = 2.0 Hz, 3H). LCMS m/z 394.23 |
| 198 | Compound 196 from S8[1] | | ¹H NMR (400 MHz, Acetonitrile-d₃) δ 7.50 (d, J = 2.4 Hz, 1H), 7.20-6.96 (m, 6H), 4.98 (s, 2H), 2.29 (d, J = 2.0 Hz, 3H), 2.28-2.13 (m, 1H), 1.74 (d, J = 33.6 Hz, 6H), 1.58-1.39 (m, 3H). LCMS m/z 396.26 |
| 199 | Compound 196 from S8[1] | | ¹H NMR (400 MHz, Acetonitrile-d₃) δ 7.86-7.58 (m, 1H), 7.54 (d, J = 2.2 Hz, 1H), 7.25-7.16 (m, 4H), 7.16-7.01 (m, 1H), 5.04 (s, 2H), 3.95 (td, J = 8.9, 8.4, 5.9 Hz, 1H), 3.88 (t, J = 7.8 Hz, 1H), 3.79 (tt, J = 7.6, 3.9 Hz, 1H), 3.71 (q, J = 8.1 Hz, 1H), 3.27 (p, J = 8.3 Hz, 1H), 2.34 (q, J = 3.3, 2.3 Hz, 4H), 2.30-2.16 (m, 1H), 1.97 (dt, J = 5.1, 2.7 Hz, 2H). LCMS m/z 398.33 |

[1]Hydroboration step was skipped.

417

Compound 200

418

-continued 4-((7-hydroxy-3-isopropyl-4-(2-methylpyrimidin-5-yl)isoquinolin-1-yl)oxy)benzoic acid (200)

S4

C148

C146

DABCO

TFAA

200

S4 was subjected to standard method C-1 and then standard method H followed by standard method A and finally standard method B to form 200. $^1$H NMR (400 MHz, DMSO-d$_6$) δ 12.96 (s, 1H), 10.28 (s, 1H), 8.70 (s, 2H), 8.14-7.98 (m, 2H), 7.59 (t, J=2.7 Hz, 1H), 7.48-7.38 (m, 2H), 7.31 (dt, J=9.0, 2.1 Hz, 1H), 7.16 (d, J=9.1 Hz, 1H), 2.75 (s, 3H), 2.63 (p, J=6.7 Hz, 1H), 0.97 (d, J=6.6 Hz, 6H). LCMS m/z 416.34 [M+H]$^+$.

C147

NaH

Compounds 201-203

Compounds 201-203 (Table 22) were prepared in five steps from intermediate S4 using appropriate boronic acids or esters according to the method described for compound 200. Any modifications to methods are noted in Table 22 and accompanying footnotes.

TABLE 22

Method of preparation, structure, physicochemical data for compounds 201-203

| Compound | Method/Product | Boronic acids or esters | $^1$H NMR; LCMS m/z [M + H][+] |
|---|---|---|---|
| 201 | Compound 200 from S4 | | $^1$H NMR (400 MHz, DMSO-d6) δ 12.99 (s, 1H), 10.32 (s, 1H), 8.78 (d, J = 5.5 Hz, 1H), 8.10-8.02 (m, 2H), 7.67-7.48 (m, 3H), 7.45-7.39 (m, 2H), 7.31 (dd, J = 9.2, 2.5 Hz, 1H), 7.14 (d, J = 9.1 Hz, 1H), 2.68 (s, 3H), 2.66-2.56 (m, 1H), 0.98 (d, J = 6.6 Hz, 6H). LCMS m/z 415.35 |
| | | | |
| 202 | Compound 200 from S4 | | $^1$H NMR (400 MHz, Methanol-d4) δ 8.62 (d, J = 2.7 Hz, 1H), 8.35 (s, 1H), 8.14-8.08 (m, 2H), 7.68 (ddd, J = 9.1, 2.8, 1.6 Hz, 1H), 7.64 (d, J = 2.5 Hz, 1H), 7.42-7.33 (m, 2H), 7.25 (dd, J = 9.1, 2.5 Hz, 1H), 7.13 (d, J = 9.1 Hz, 1H), 2.70 (hept, J = 6.6 Hz, 1H), 1.04 (dd, J = 6.7, 4.8 Hz, 6H). LCMS m/z 419.35 |
| | | | |
| 203 | Compound 200 from S4[1] | | $^1$H NMR (300 MHz, Methanol-d4) δ 7.51 (dd, J = 9.0, 0.6 Hz, 1H), 7.46 (dd, J = 2.5, 0.6 Hz, 1H), 7.16 (dd, J = 9.0, 2.5 Hz, 1H), 7.01-6.93 (m, 2H), 6.80-6.70 (m, 2H), 5.65-5.51 (m, 1H), 3.25-3.14 (m, 1H), 2.91-2.79 (m, 2H), 2.57 (ddd, J = 13.3, 10.1, 6.6 Hz, 2H), 1.16 (d, J = 6.8 Hz, 6H). |
| | | | |

[1]Ether linkage was synthesized using CuI, 2-(dimethylamino)acetic acid, and Cs2CO3 in the first step.

Compounds 204-205

Compounds 204-205 (Table 23) were prepared in five steps from intermediate S4 using appropriate alcohol according to the method described for compound 200. Any modifications to methods are noted in Table 23 and accompanying footnotes.

TABLE 23

Method of preparation, structure, physicochemical data for compounds 204-205

| Compound | Method/Product | Alcohols | $^1$H NMR; LCMS m/z [M + H]$^+$ |
|---|---|---|---|
| 204 | Compound 200 from S4 | None | $^1$H NMR (400 MHz, Methanol-d$_4$) δ 7.57 (d, J = 8.8 Hz, 1H), 7.41 (dt, J = 2.6, 0.7 Hz, 1H), 7.19 (dd, J = 8.8, 2.5 Hz, 1H), 6.96 (s, 1H), 5.62-5.49 (m, 1H), 3.18 (ttd, J = 10.0, 4.0, 1.1 Hz, 1H), 2.99-2.87 (m, 1H), 2.91-2.77 (m, 2H), 2.60-2.46 (m, 2H), 1.29 (d, J = 6.8 Hz, 6H). LCMS m/z 302.13 |
| 205 | Compound 200 from S4 | | $^1$H NMR (300 MHz, Chloroform-d and Methanol-d$_4$) δ 8.51 (dd, J = 5.1, 0.8 Hz, 1H), 7.56 (d, J = 2.5 Hz, 1H), 7.22-6.91 (m, 4H), 5.79-5.54 (m, 1H), 3.30-3.14 (m, 1H), 2.92 (dddd, J = 11.7, 7.4, 4.5, 2.7 Hz, 2H), 2.74 (p, J = 6.6 Hz, 1H), 2.67-2.39 (m, 5H), 1.16 (dd, J = 6.6, 3.3 Hz, 6H) ppm. LCMS m/z 393.3 |

Compounds 206-211

Compounds 206-211 (Table 24) were prepared in three to four steps from intermediate S20 using appropriate alcohol according to the method described for compound 116. Any modifications to methods are noted in Table 24 and accompanying footnotes.

TABLE 24

Method of preparation, structure, physicochemical data for compounds 206-211

| Compound | Method/Product | Alcohols | $^1$H NMR; LCMS m/z [M + H]$^+$ |
|---|---|---|---|
| 206 | Compound 116 From S20[1] | | $^1$H NMR (400 MHz, Methanol-d$_4$) δ 8.54 (dd, J = 5.1, 0.8 Hz, 1H), 7.61 (d, J = 2.5 Hz, 1H), 7.30-7.22 (m, 1H), 7.21-7.13 (m, 2H), 7.11-7.00 (m, 1H), 5.02 (s, 2H), 3.94 (dd, J = 11.4, 4.4 Hz, 2H), 3.31 (p, J = 1.7 Hz, 2H), 2.71-2.66 (m, 1H), 2.62 (s, 3H), 2.21 (ddq, J = 19.0, 12.5, 6.6, 5.7 Hz, 2H), 1.50 (d, J = 13.4 Hz, 2H). LCMS m/z 394.23 |
| 207 | Compound 116 from S20[2] | | LCMS m/z 406.25 |
| 208 | Compound 116 from S20 | | $^1$H NMR (400 MHz, Methanol-d$_4$) δ 8.81 (d, J = 5.7 Hz, 1H), 7.91 (s, 1H), 7.84 (d, J = 5.4 Hz, 1H), 7.54 (d, J = 2.4 Hz, 1H), 7.20 (dd, J = 8.9, 2.6 Hz, 1H), 7.09 (d, J = 9.0 Hz, 1H), 5.05 (p, J = 7.3 Hz, 1H), 4.20-4.05 (m, 1H), 3.96 (dd, J = 11.2, 4.3 Hz, 2H), 3.50 (d, J = 3.5 Hz, 1H), 3.38 (d, J = 11.9 Hz, 2H), 3.06 (dddt, J = 9.2, 6.8, 5.4, 2.3 Hz, 2H), 2.89 (s, 3H), 2.62 (tq, J = 17.2, 5.9, 5.0 Hz, 1H), 2.31-2.10 (m, 5H), 1.55 (dt, J = 16.5, 8.3 Hz, 2H). LCMS m/z 407.24 |

TABLE 24-continued

Method of preparation, structure, physicochemical data for compounds 206-211

| Compound | Method/Product | Alcohols | ¹H NMR; LCMS m/z [M + H]⁺ |
|---|---|---|---|
| 209 | Compound 116 from S20[2] | | LCMS m/z 411.22 |
| | | | |
| 210 | Compound 116 from S20 | | ¹H NMR (400 MHz, Methanol-d₄) δ 8.55 (dd, J = 5.2, 0.8 Hz, 1H), 8.09 (s, 2H), 7.51 (dd, J = 4.7, 2.5 Hz, 1H), 7.34-7.27 (m, 1H), 7.21 (dd, J = 5.3, 1.6 Hz, 1H), 7.14 (ddd, J = 9.1, 5.1, 2.6 Hz, 1H), 7.03 (dd, J = 9.0, 4.0 Hz, 1H), 5.74-5.57 (m, 1H), 4.63-4.47 (m, 1H), 3.95 (dd, J = 11.5, 4.2 Hz, 2H), 3.33 (d, J = 11.0 Hz, 2H), 2.82-2.67 (m, 1H), 2.64 (s, 3H), 2.59-2.53 (m, 3H), 2.31-1.99 (m, 2H), 1.58-1.44 (m, 2H). LCMS m/z 407.17 |
| | | | |
| 211 | Compound 116 from S20[3] | | ¹H NMR (300 MHz, Chloroform-d and Methanol-d₄) δ 8.55 (dd, J = 5.1, 0.9 Hz, 1H), 7.59 (ddd, J = 7.7, 2.6, 0.5 Hz, 1H), 7.23-6.95 (m, 4H), 5.42 (p, J = 4.7 Hz, 1H), 4.72-4.57 (m, 1H), 4.19 (t, J = 5.3 Hz, 1H), 4.10 (d, J = 4.9 Hz, 1H), 4.04-3.89 (m, 4H), 3.79 (qd, J = 11.5, 5.3 Hz, 1H), 2.65 (s, 4H), 2.19 (tt, J = 12.1, 5.7 Hz, 2H), 1.51 (d, J = 13.3 Hz, 2H). LCMS m/z 411.39 |
| | | | |

[1]Standard method E was carried out using NH₄Cl, HATU, and DIPEA before continuing to standard method B.

[2]Additional treatment with HCl was carried out at the last step.

[3]Additional treatment with HCl was carried out before continuing to standard method B.

427

428

Compound 212

-continued 2-hydroxy-1-(3-((7-hydroxy-4-(2-methylpyridin-4-yl)-3-(tetrahydro-2H-pyran-4-yl)isoquinolin-1-yl)oxy)azetidin-1-yl)ethan-1-one (212)

C149

C150

212

C149 was synthesized according to the method described for compound 206-211. C149 was then treated with HCl to form C150 which underwent further reaction with 2-hydroxyacetic acid according to standard method E using HATU and DIPEA to form 212. $^1$H NMR (400 MHz, Methanol-d$_4$) δ 8.80 (dd, J=6.1, 0.7 Hz, 1H), 7.90 (t, J=2.1 Hz, 1H), 7.82 (dt, J=5.8, 2.2 Hz, 1H), 7.58 (dd, J=2.6, 0.5 Hz, 1H), 7.24 (dd, J=9.1, 2.6 Hz, 1H), 7.12 (dd, J=9.0, 0.5 Hz, 1H), 5.68 (tt, J=6.7, 4.2 Hz, 1H), 4.89-4.84 (m, 1H), 4.68-4.59 (m, 1H), 4.46 (ddd, J=10.4, 4.5, 1.3 Hz, 1H), 4.26-4.13 (m, 3H), 3.96 (d, J=9.7 Hz, 2H), 3.42-3.32 (m, 2H), 2.87 (s, 3H), 2.69-2.56 (m, 1H), 2.27-2.07 (m, 2H), 1.56 (d, J=13.0 Hz, 2H). LCMS m/z 450.28

Compounds 213-215

Compounds 213-215 (Table 25) were prepared according to the method described for compound 212 from either intermediate C149 or compound 207 with appropriate alcohols. Any modifications to methods are noted in Table 25 and accompanying footnotes.

TABLE 25

Method of preparation, structure, physicochemical data for compounds 213-215

| Compound | Method/Product | Alcohols | $^1$H NMR; LCMS m/z [M + H]$^+$ |
|---|---|---|---|
| 213 | Compound 212 from C149 | | $^1$H NMR (400 MHz, Methanol-d$_4$) δ 8.79 (d, J = 6.0 Hz, 1H), 7.89 (s, 1H), 7.81 (d, J = 6.0 Hz, 1H), 7.58 (d, J = 2.5 Hz, 1H), 7.24 (dd, J = 9.1, 2.6 Hz, 1H), 7.12 (d, J = 9.0 Hz, 1H), 5.67 (d, J = 7.4 Hz, 1H), 4.98 (t, J = 8.8 Hz, 1H), 4.71-4.47 (m, 2H), 4.34 (q, J = 6.9 Hz, 1H), 4.18 (d, J = 9.4 Hz, 1H), 4.06-3.88 (m, 2H), 3.36 (d, J =12.1 Hz, 2H), 2.86 (s, 3H), 2.71-2.56 (m, 1H), 2.17 (s, 2H), 1.56 (d, J = 13.3 Hz, 2H), 1.37 (d, J = 6.7 Hz, 3H). LCMS m/z 464.18 |

TABLE 25-continued

Method of preparation, structure, physicochemical data for compounds 213-215

| Compound | Method/Product | Alcohols | ¹H NMR; LCMS m/z [M + H]⁺ |
|---|---|---|---|
| 214 | Compound 212 from 207 | | ¹H NMR (400 MHz, Methanol-d₄) δ 8.81 (d, J = 6.0 Hz, 1H), 7.92 (d, J = 3.7 Hz, 1H), 7.84 (t, J = 5.0 Hz, 1H), 7.50 (d, J = 2.5 Hz, 1H), 7.21 (dd, J = 9.1, 2.6 Hz, 1H), 7.10 (d, J = 9.0 Hz, 1H), 6.05-5.87 (m, 1H), 4.31-4.15 (m, 2H), 4.03-3.65 (m, 6H), 3.36 (t, J = 12.2 Hz, 2H), 2.88 (s, 3H), 2.73-2.59 (m, 1H), 2.54-2.33 (m, 2H), 2.32-2.15 (m, 2H), 1.68-1.52 (m, 2H). LCMS m/z 464.18 |
| 215 | Compound 212 from 207 | | ¹H NMR (400 MHz, Methanol-d₄) δ 8.72 (d, J = 5.7 Hz, 1H), 8.07 (s, 1H), 7.74-7.59 (m, 2H), 7.48 (q, J = 2.7 Hz, 1H), 7.19 (ddd, J = 9.1, 2.6, 1.0 Hz, 1H), 7.15-7.05 (m, 1H), 5.93 (dd, J = 26.8, 4.2 Hz, 1H), 4.60-4.40 (m, 1H), 4.18-3.64 (m, 6H), 3.41-3.33 (m, 2H), 2.79 (d, J = 1.6 Hz, 3H), 2.72-2.61 (m, 1H), 2.55-2.34 (m, 2H), 2.23 (td, J = 8.3, 4.1 Hz, 2H), 1.62-1.52 (m, 2H), 1.40-1.29 (m, 3H) LCMS m/z 478.22 |

Compound 216

3-[[4-(4-fluorophenyl)-7-hydroxy-3-tetrahydropy-
ran-4-yl-2-quinolyl]oxy]cyclobutanecarboxylic acid
(216)

-continued

-continued

C153

C154

216

Step 1: 7-benzyloxy-3-(3,6-dihydro-2H-pyran-4-yl)-4-(4-fluorophenyl)quinoline (C151)

C65 was subjected to standard method C using XPhos Pd G2 to form C151. $^1$H NMR (300 MHz, DMSO-d$_6$) 8.72 (s, 1H), 7.46-7.57 (m, 3H), 7.23-7.45 (m, 9H), 5.73-5.81 (m, 1H), 5.30 (s, 2H), 4.02-4.12 (m, 2H), 3.52 (t, J=5.2 Hz, 2H), 1.76-1.88 (m, 2H). $^{19}$F NMR (282 MHz, DMSO-d$_6$) δ −113.9-113.7 (m, 1F). LCMS m/z 412.2 [M+H]$^+$.

Step 2: 7-benzyloxy-3-(3,6-dihydro-2H-pyran-4-yl)-4-(4-fluorophenyl)-1-oxido-quinolin-1-ium (C152)

Method K: m-CPBA Oxidation to form N-oxide. To a solution of C151 (50 mg, 0.1215 mmol) in dichloromethane (1.5 mL) was added m-CPBA (32 mg, 0.1428 mmol) at 0° C. The mixture was stirred from 0° C. to room temperature over 5 hours then at room temperature for another 3 days. EtOAc (25 mL) was added then the organic layer was washed with 5% aq. solution of NaHCO$_3$ (3×20 mL) and brine (2×20 mL), dried over anhydrous Na$_2$SO$_4$, filtered, and concentrated to give the crude C152 (50 mg).

Step 3: methyl 3-[[7-benzyloxy-3-(3,6-dihydro-2H-pyran-4-yl)-4-(4-fluorophenyl)-2-quinolyl]oxy]cy-clobutanecarboxylate (C153)

To a stirred solution of C152 (200 mg, 0.4679 mmol) in THF (1 mL) was added methyl 3-hydroxycyclobutanecar-boxylate (913.40 mg, 7.0185 mmol) and MsCl (535.99 mg, 0.3622 mL, 4.6790 mmol). The reaction mixture was stirred at room temperature for 4 hours. After completion of the reaction, the reaction mixture was quenched with water (5 mL) and extracted with EtOAc (20 mL). The organic layer was dried over anhydrous Na$_2$SO$_4$ and evaporated. The crude product was purified by silica gel chromatography (Gradient: 0-20% EtOAc in hexane) to give C153 (65 mg, 25%) as colorless gum. $^1$H NMR (400 MHz, DMSO-d$_6$) δ 7.49 (d, J=7.1 Hz, 2H), 7.41 (t, J=7.4 Hz, 2H), 7.37-7.26 (m, 6H), 7.15 (d, J=9.4 Hz, 1H), 7.07 (d, J=9.3 Hz, 1H), 5.29 (d, J=25.5 Hz, 3H), 3.87 (s, 2H), 3.69-3.59 (m, 5H), 2.97-2.67 (m, 4H), 2.24 (d, J=9.2 Hz, 2H), 2.16 (s, 2H). LCMS m/z 540.0 [M+H]$^+$.

Step 4-5: 3-[[4-(4-fluorophenyl)-7-hydroxy-3-tetra-hydropyran-4-yl-2-quinolyl]oxy]cyclobutanecarbox-ylic acid (216)

C153 was subjected to standard method B to afford C154 and D to afford 216. $^1$H NMR (400 MHz, DMSO-d$_6$) δ 9.95 (s, 1H), 7.40-7.28 (m, 4H), 7.00 (s, 1H), 6.84 (d, J=3.4 Hz, 2H), 5.35-5.31 (m, 1H), 3.85-3.83 (m, 2H), 3.04-2.99 (m, 2H), 2.90-2.86 (m, 1H), 2.77-2.76 (m, 2H), 2.32-2.23 (m, 4H), 1.35-1.32 (m, 2H), 1.24-1.20 (m, 1H). LCMS m/z 438.0 [M+H]$^+$.

433

Compound 217

4-[[4-(4-fluorophenyl)-7-hydroxy-3-tetrahydropy-
ran-4-yl-2-quinolyl]oxy]benzoic acid (217)

S21

C155

434

-continued

C156

217

Compound 217 was synthesized according to standard method H using Cs$_2$CO$_3$ to afford C155 followed by standard method B to get to C156 and finally standard method D. $^1$H NMR (400 MHz, DMSO-d$_6$) δ 12.91 (s, 1H), 10.08 (s, 1H), 8.05 (d, J=8.3 Hz, 2H), 7.44-7.32 (m, 6H), 6.97-6.90 (m, 2H), 6.85 (s, 1H), 3.84 (d, J=11.1 Hz, 2H), 3.06 (t, J=11.7 Hz, 2H), 2.74-2.66 (m, 1H), 2.38-2.32 (m, 2H), 1.50 (d, J=12.8 Hz, 2H). LCMS m/z 460.0 [M+H]$^+$.

Compounds 218-221

Compounds 218-221 (Table 26) were prepared in two to three steps from intermediate S21 using appropriate alcohols according to the method described for compound 217. Any modifications to methods are noted in Table 26 and accompanying footnotes.

TABLE 26

| Compound | Method/Product | Alcohols or Amines or Alkyl halides | $^1$H NMR; LCMS m/z [M + H]$^+$ |
|---|---|---|---|

Method of preparation, structure, physicochemical data for compounds 218-221

| 218 | Compound 217 from S21[1] | | $^1$H NMR (400 MHz, DMSO-d$_6$) δ 12.33 (s, 1H), 9.96 (s, 1H), 7.39-7.35 (m, 2H), 7.30-7.27 (m, 2H), 7.04 (s, 1H), 6.86-6.81 (m, 2H), 4.67 (s, 2H), 3.78-3.75 (m, 2H), 2.98 (t, J = 11.6 Hz, 2H), 2.54 (s, 1H), 2.49-2.39 (m, 2H), 2.22-1.90 (m, 6H), 1.29-1.23 (m, 2H). LCMS m/z 452 |
| 219 | Compound 217 from S21[1] | | $^1$H NMR (400 MHz, DMSO-d$_6$) δ 9.96 (s, 1H), 7.38 (t, J = 8.7 Hz, 2H), 7.29 (dd, J = 8.3, 5.6 Hz, 2H), 7.02 (s, 1H), 6.84 (d, J = 2.9 Hz, 2H), 4.60 (t, J = 5.6 Hz, 2H), 3.80 (d, J = 9.1 Hz, 2H), 3.66 (t, J = 5.6 Hz, 2H), 3.52 (t, J = 7.0 Hz, 2H), 3.02 (t, J = 11.7 Hz, 2H), 2.29-2.19 (m, 4H), 1.98-1.90 (m, 2H), 1.34-1.26 (m, 2H). LCMS m/z 451.0 |
| 220 | Compound 217 from S21 | | $^1$H NMR (400 MHz, DMSO-d$_6$) δ 9.92 (s, 1H), 7.38 (t, J = 8.7 Hz, 2H), 7.30 (dd, J = 8.5, 5.6 Hz, 2H), 7.02 (d, J = 2.2 Hz, 1H), 6.88-6.78 (m, 2H), 4.55 (t, J = 7.5 Hz, 2H), 4.45 (s, 1H), 3.82 (d, J = 8.4 Hz, 2H), 3.01 (t, J = 11.6 Hz, 2H), 2.60 (d, J = 12.7 Hz, 1H), 2.40-2.33 (m, 1H), 1.97 (t, J = 7.6 Hz, 2H), 1.31 (d, J= 12.5 Hz, 2H), 1.23 (s, |

TABLE 26-continued

Method of preparation, structure, physicochemical data for compounds 218-221

| Compound | Method/Product | Alcohols or Amines or Alkyl halides | ¹H NMR; LCMS m/z [M + H]⁺ |
|---|---|---|---|
| 221 | Compound 217 from S21[1] | | ¹H NMR (400 MHz, DMSO-d₆) δ 9.93 (s, 1H), 7.38 (t, J = 8.7 Hz, 2H), 7.31-7.27 (m, 2H), 7.01 (d, J = 2.2 Hz, 1H), 6.86-6.80 (m, 2H), 4.49 (t, J = 5.2 Hz, 2H), 3.86-3.78 (m, 4H), 3.02 (t, J = 11.6 Hz, 2H), 2.66-2.57 (m, 1H), 2.45 - 2.37 (m, 2H), 1.30 (d, J = 13.2 Hz, 2H). LCMS 384.0 |

[1]Standard method H was carried out using NaH.

Compound 222

3-[[4-(4-fluorophenyl)-7-hydroxy-3-tetrahydropy-ran-4-yl-2-quinolyl]amino]bicyclo[1.1.1]pentane-1-carboxylic acid (222)

C151

Pd/C, H₂

C157

BnCl / K₂CO₃

C159

-continued

C158 m-CPBA

PyBroP, DIPEA

-continued

C160

C161

222

Steps 1-3: 7-benzyloxy-4-(4-fluorophenyl)-1-oxido-
3-tetrahydropyran-4-yl-quinolin-1-ium (C159)

Compound C159 was synthesized according to standard method B followed by standard method F and standard method K (via the intermediates C157 and C158). $^1$H NMR (300 MHz, Chloroform-d) δ 8.63 (s, 1H), 8.22 (s, 1H), 7.46-7.54 (m, 2H), 7.31-7.45 (m, 3H), 7.13-7.30 (m, 6H), 5.27 (s, 2H), 3.99 (dd, J=11.4, 3.7 Hz, 2H), 3.26 (t, J=11.5 Hz, 2H), 2.70 (tt, J=12.1, 3.5 Hz, 1H), 1.85 (qd, J=12.4, 4.1 Hz, 2H), 1.60 (br d, J=12.4 Hz, 2H); $^{19}$F NMR (282 MHz, Chloroform-d) δ −112.6 (s, 1F). LCMS m/z 430.2 [M+H]$^+$.

Step 4: methyl 3-[[7-benzyloxy-4-(4-fluorophenyl)-
3-tetrahydropyran-4-yl-2-quinolyl]amino]bicyclo
[1.1.1]pentane-1-carboxylate (C160)

A mixture of C159 (150.9 mg, 0.3510 mmol), methyl 3-aminobicyclo[1.1.1]-pentane-1-carboxylate (HCl salt) (116.8 mg, 0.6576 mmol), PyBroP (497.3 mg, 1.067 mmol) and DIPEA (200 μL, 1.148 mmol) in DCE (3 mL) was stirred at 60° C. for 18 hours. The mixture was cooled to room temperature and diluted with dichloromethane. The organic layer was washed with water, dried over MgSO$_4$, filtered, and evaporated. The residue was purified by silica gel chromatography (Column: 4 g Combiflash ISCO. Gradient: 0-70% EtOAc in heptane) to give C160 (135.7 mg, 65%) as a white solid. LCMS m/z 553.4 [M+H]$^+$.

Steps 5-6: 3-[[4-(4-fluorophenyl)-7-hydroxy-3-tetra-
hydropyran-4-yl-2-quinolyl]amino]bicyclo[1.1.1]
pentane-1-carboxylic acid (222)

C160 was then subjected to standard method B to give C161 which was subjected to standard method D to form 222. $^1$H NMR (400 MHz, DMSO-d$_6$) δ 12.38 (s, 1H), 9.65 (s, 1H), 7.35 (d, J=8.8 Hz, 2H), 7.24 (dd, J=8.5, 5.7 Hz, 2H), 6.87 (s, 1H), 6.63-6.56 (m, 2H), 5.76 (s, 1H), 3.74 (d, J=9.6 Hz, 2H), 3.19 (d, J=11.4 Hz, 2H), 2.88 (s, 1H), 2.44 (s, 6H), 1.68 (s, 2H), 1.35 (d, J=13.0 Hz, 2H). LCMS m/z 449.32 (M+H)$^+$.

Compounds 223-230

Compounds 223-230 (Table 27) were prepared in six steps from intermediate C151 using appropriate alcohols according to the method described for compound 222. Any modifications to methods are noted in Table 27 and accompanying footnotes.

TABLE 27

Method of preparation, structure, physicochemical data for compounds 223-230

| Compound | Method/Product | Alcohols or Amines or Alkyl halides | $^1$H NMR; LCMS m/z [M + H]$^+$ |
|---|---|---|---|
| 223 | Compound 222 from C151 | | $^1$H NMR (400 MHz, DMSO-d$_6$) δ 12.20 (s, 1H), 10.75 (s, 1H), 7.47-7.38 (m, 2H), 7.38-7.32 (m, 2H), 7.16 (s, 1H), 6.83 (s, 1H), 6.76 (d, J = 8.8 Hz, 1H), 4.12-3.57 (m, 7H), 3.15 (s, 2H), 2.95 (s, 1H), 2.42 (q, J = 10.6, 9.9 Hz, 2H), 2.07-1.93 (m, 1H), 1.86 (s, 2H), 1.46 (d, J = 12.8 Hz, 2H). LCMS m/z 451.3 |
| 224 | Compound 222 from C151 | | $^1$H NMR (DMSO-d$_6$) δ 12.5 (br, 1H), 9.63 (s, 1H), 7.34 (t, J = 8.8 Hz, 2H), 7.26 (t, J = 5.5 Hz, 2H), 6.83 (s, 1H), 6.62-6.56 (m, 2H), 6.14 (br, 1H), 3.81-3.78 (m, 2H), 3.64-3.62 (m, 2H), 3.08-2.66 (m, 4H), 1.94-1.92 (m, 2H), 1.37-1.34 (m, 2H), 1.14 (d, J = 7.0 Hz, 3H). LCMS m/z 425 |
| 225 | Compound 222 from C151 | | $^1$H NMR (Methanol-d$_4$) δ 7.37-7.29 (m, 5H), 6.92-6.84 (m, 2H), 4.73-4.69 (m, 1H), 3.92-3.89 (m, 2H), 3.30-3.21 (m, 2H), 3.06-2.99 (m, 1H), 2.95-2.84 (m, 2H), 2.02-1.99 (m, 2H), 1.53-1.47 (m, 5H). LCMS m/z 425 |

TABLE 27-continued

| Compound | Method/Product | Alcohols or Amines or Alkyl halides | $^1$H NMR; LCMS m/z [M + H]$^+$ |
|---|---|---|---|
| 226 | Compound 222 from C151 | | $^1$H NMR (DMSO-d$_6$) δ 12.5 (br, 1H), 10.8 (br, 1H), 7.42 (t, J = 8.8 Hz, 2H), 7.34-7.31 (m, 3H), 6.80-6.72 (m, 2H), 3.91-3.90 (m, 2H), 3.79-3.77 (m, 2H), 3.16-3.14 (m, 2H), 2.90-2.88 (m, 1H), 2.77-2.66 (m, 2H), 1.74 (br, 2H), 1.39-1.36 (m, 2H). LCMS m/z 411 |
| 227 | Compound 222 from C151 | | $^1$H NMR (DMSO-d$_6$) δ 13.9 (br, 1H), 9.75 (s, 1H), 7.35 (t, J = 8.5 Hz, 1H), 7.28 (d, J = 7.0 Hz, 1H), 6.85 (s, 1H), 6.65-6.59 (m, 2H), 6.22 (br, 1H), 3.83-3.75 (m, 4H), 3.06-3.04 (m, 2H), 2.80-2.78 (m, 1H), 2.0 (br, 2H), 1.40-1.37 (m, 2H), 1.10-1.07 (m, 4H). LCMS m/z 437 |
| 228 | Compound 222 from C151 | | $^1$H NMR (DMSO-d$_6$) δ 12.4 (br, 1H), 9.64 (s, 1H), 7.34 (t, J = 8.8 Hz, 2H), 7.26 (t, J = 2.8 Hz, 2H), 6.83 (s, 1H), 6.62-6.59 (m, 2H), 5.88 (br, 1H), 4.75-4.71 (m, 1H), 3.80-3.77 (m, 2H), 3.09-3.07 (m, 2H), 2.80-2.65 (m, 3H), 1.89-1.78 (m, 2H), 1.41-1.36 (m, 2H), 1.30 (d, J = 6.56 Hz, 3H). LCMS m/z 425 |

TABLE 27-continued

| | | Alcohols or | |
| | | Amines or Alkyl | $^1$H NMR; LCMS m/z |
| Compound | Method/Product | halides | [M + H]$^+$ |
| --- | --- | --- | --- |

Method of preparation, structure, physicochemical data for compounds 223-230

| 229 | Compound 222 from C151[1] | | $^1$H NMR (DMSO-d$_6$) δ 9.6 (br, 1H), 7.35 (t, J = 8.4 Hz, 2H), 7.28-7.25 (m, 2H), 6.82 (s, 1H), 6.64-6.58 (m, 2H), 6.12 (br, 1H), 4.6 (br, 1H), 3.82 (d, J = 7.76 Hz, 2H), 3.11 (br, 2H), 2.89-2.87 (m, 2H), 2.08 (br, 2H), 1.48 (br, J = 6.95, 3H), 1.43-1.40 (m, 2H). LCMS m/z 411 |
| --- | --- | --- | --- |
| | | | |
| 230 | Compound 222 from C151[2] | | $^1$H NMR (DMSO-d$_6$) δ 12.5 (br, 1H), 9.6 (br, 1H), ), 7.35 (t, J = 8.4 Hz, 2H), 7.27-7.25 (m, 2H), 6.82 (d, J = 1.76 Hz, 1H), 6.64-6.58 (m, 2H), 5.99 (br, 1H), 4.76-4.69 (m, 1H), 3.82-3.80 (m, 2H), 3.12-2.86 (m, 3H), 1.90 (br, 2H), 1.50 (d, J = 7.08 Hz, 3H), 1.40 (d, J = 12.8 Hz, 2H). LCMS m/z 411 |
| | | | |

[1]HCl was used in standard method D

[2]TFA was used in standard method D

Compound 231

(3R)-1-[4-(4-fluorophenyl)-7-hydroxy-3-tetrahydro-
pyran-4-yl-2-quinolyl]pyrrolidine-3-carboxylic acid
(231)

S21

C162

C163

231

Step 1: methyl-(3R)-1-[7-benzyloxy-4-(4-fluorophe-nyl)-3-tetrahydropyran-4-yl-2-quinolyl]pyrrolidine-3-carboxylate (C162)

A mixture of S21 (300 mg, 0.6698 mmol), methyl-(3R)-pyrrolidine-3-carboxylate (HCl salt) (332.79 mg, 2.0094 mmol), $K_2CO_3$ (370.28 mg, 2.6792 mmol) and 1,4 dioxane (5 mL) was purged with $N_2$ for 10 minutes and then P(t-Bu)$_3$ Pd G4 (85.226 mg, 0.1340 mmol) was added. The reaction mixture was heated to 85° C. and stirred for 48 hours. The reaction mixture was filtered through Celite, washed with 10% MeOH in dichloromethane and concentrated. This crude product was purified by silica gel chromatography (Eluent: % EtOAc in hexane) to afford C162 (200 mg, 38%) as an off-white solid. $^1$H NMR (400 MHz, DMSO-d$_6$) δ 7.46 (d, J=7.1 Hz, 2H), 7.43-7.28 (m, 6H), 7.21-7.12 (m, 2H), 7.10-7.03 (m, 1H), 6.91 (ddd, J=9.5, 7.0, 2.6 Hz, 1H), 6.75 (dd, J=18.5, 9.2 Hz, 1H), 5.23 (d, J=3.0 Hz, 2H), 4.13 (q, J=6.9 Hz, 1H), 3.77 (ddd, J=16.4, 12.1, 4.9 Hz, 3H), 3.67 (s, 3H), 3.66-3.54 (m, 2H), 3.45 (dd, J=9.9, 5.6 Hz, 1H), 3.28-3.16 (m, 5H), 2.22 (s, 1H), 2.10 (dd, J=12.3, 7.5 Hz, 1H), 1.67 (d, J=15.4 Hz, 1H), 1.57 (s, 2H), 1.55-1.35 (m, 3H), 1.32-1.13 (m, 1H). LCMS m/z 541.5 [M+H]$^+$.

Steps 2-3: (3R)-1-[4-(4-fluorophenyl)-7-hydroxy-3-tetrahydropyran-4-yl-2-quinolyl]pyrrolidine-3-carboxylic acid (231)

C162 was then subjected to standard method B to afford C163 and standard method D to form 231. $^1$E NMR (DMSO-d$_6$) δ 9.99 (brs, 1H), 7.38-7.31 (m, 4H), 6.95 (d, J=2.28 Hz 1H), 6.74-6.71 (m, 1H,), 6.63 (d, J=9.04 Hz, 1H), 3.75-3.68 (m, 3H), 3.57-3.41 (m, 3H), 3.46-3.18 (m, 4H), 3.11 (t, J=7.24, 1H), 2.18-2.06 (m, 2H), 1.54-1.52 (m, 3H), 1.40-1.37 (m, 1H). LCMS m/z 437.2 (M+H)$^+$.

Compounds 232-234

Compounds 232-234 (Table 28) were prepared in six steps from intermediate S21 using appropriate alcohols according to the method described for compound 231. Any modifications to methods are noted in Table 28 and accompanying footnotes.

TABLE 28

Method of preparation, structure and physicochemical data for compounds 232-234

| Compound | Method/Product | Alcohols or Amines or Alkyl halides | $^1$H NMR; LCMS m/z [M + H]+ |
|---|---|---|---|
| 232 | Compound 222 from C151.[2] | | $^1$H NMR (DMSO-d6) δ 9.99 (brs, 1H), 7.36-7.26 (m, 4H), 6.93 (d, J = 2.16 Hz, 1H), 6.70-6.62 (m, 1H), 6.61 (d, J = 9 Hz, 1H), 4.32-4.24 (m, 4H), 3.71 (d, J = 11 Hz, 2H), 3.52-3.45 (m, 1H), 3.22-3.17 (m, 2H), 2.96 (brs, 1H), 1.44 (brs, 4H). LCMS m/z 423.2 |
| 233 | Compound 216 from S21 | | [1]H (DMSO-d6) δ 9.99 (brs, 1H), 7.37-7.29 (m, 4H), 7.29 (brs, 1H), 6.95 (d, J = 2.16 Hz, 1H), 6.72-6.70 (m, 1H), 6.63 (d, J = 9.08 Hz, 1H), 4.67-4.59 (m, 2H), 4.34-4.27 (m, 2H), 3.71-3.68 (m, 2H), 3.33-3.26 (m, 2H), 2.92 (brs, 1H), 1.45-1.42 (m, 4H). LCMS m/z 441.2 |
| 234 | Compound 216 from S21 | | [1]H (DMSO-d6) δ 7.38-7.31 (m, 4H), 6.95 (d, J = 2.28 Hz, 1H), 6.74-6.71 (m, 1H), 6.63 (d, J = 9.04 Hz, 1H), 3.75-3.68 (m, 3H), 3.57-3.52 (m, 3H), 3.57-3.52 (m, 2H), 3.46-3.41 (m, 1H), 3.21-3.14 (m, 3H), 3.13-3.09 (t, J = 7.28 Hz, 1H), 2.18-2.06 (m, 2H), 1.54-1.49 (m, 3H), 1.40-1.37 (m, 1H). LCMS m/z 437.2 |

451

Compound 235

3-((4-(4-fluorophenyl)-7-hydroxy-2-oxo-3-(tetra-
hydro-2H-pyran-4-yl)quinolin-1(2H)-yl)methyl)
cyclobutane-1-carboxylic acid (235)

C163

C165

235

C165

Compound 235 was synthesized according to standard method F using Cs$_2$CO$_3$ on C164 (coming from S21) to afford C165 followed by standard method B and finally standard method D (via C166). $^1$H (DMSO-d$_6$) δ 12.0 (bs, 1H), 10.21 (bs, 1H), 7.36 (t, J=8.7 Hz, 2H), 7.29 (dd, J=8.4, 5.1 Hz, 2H), 6.83 (d, J=2.9 Hz, 1H), 6.65 (d, J=8.8 Hz, 1H), 6.57 (d, J=8.9 Hz, 1H), 4.41-4.24 (m, 1H), 3.79 (d, J=10.9 Hz, 2H), 2.93 (m, 2H), 2.78 (s, 1H), 2.44 (s, 3H), 2.20-2.08 (m, 5H), 1.20 (bs, 2H). LCMS m/z 452 (M+H)$^+$.

Compound 236

3-(4-(4-fluorophenyl)-7-hydroxy-2-oxo-3-(tetra-
hydro-2H-pyran-4-yl)quinolin-1(2H)-yl)cyclobu-
tane-1-carboxylic acid (236)

Compound 236 (Table 29) was prepared in three steps from intermediate C164 using appropriate alcohol according to the method described for compound 235. Any modifications to methods are noted in Table 29 and accompanying footnotes.

TABLE 29

Method of preparation, structure and physicochemical data for compound 236

| Compound | Method/Product | Alcohols or Amines or Alkyl halides | $^1$H NMR; LCMS m/z [M + H]$^+$ |
|---|---|---|---|
| 236 | Compound 235 from C164$^1$ | | $^1$H NMR (400 MHz, DMSO-d$_6$) δ 12.33 (bs, 1H), 9.93 (s, 1H), 7.40-7.28 (m, 4H), 6.99 (d, J = 2.1 Hz, 1H), 6.84 – 6.83 (m, 2H), 5.52 (t, J = 6.9 Hz, 1H), 3.85 – 3.83 (m, 2H), 3.15 – 2.99 (m, 4H), 2.74 – 2.70 (m, 2H), 2.61 – 2.58 (m, 1H), 2.43 – 2.38 (m, 3H), 1.35 (d, J = 12.6 Hz, 2H). LCMS m/z 438 |

$^1.$ K$_2$CO$_3$ was used in the first step.

Compound 237

4-(4-fluorophenyl)-3-isopropyl-2-methyl-quinolin-7-ol (237)

-continued

237

Step 1: 4-(4-fluorophenyl)-3-isopropyl-7-methoxy-2-methyl-quinoline (C167)

To a solution of C51 (100 mg, 0.4004 mmol), (4-fluorophenyl)boronic acid (123 mg, 0.879 mmol) and Pd(dppf)Cl$_2$ (18 mg, 0.022 mmol) in DMF (3 mL), an aqueous solution of Na$_2$CO$_3$ (610 µL of 2M, 1.22 mmol) was added under N$_2$ and reaction was heated in a microwave reactor at 130° C. for 4 hours. Water was added, the mixture was extracted with EtOAc, the organic phases combined and concentrated. Purification by reverse-phase HPLC (Method: C18 Waters Sunfire column, 30×150 mm, 5 micron. Gradient: MeCN in H$_2$O with 0.1% trifluoroacetic acid) afforded C167 (20 mg, 16%) 1H NMR (300 MHz, Chloroform-d) δ 8.41 (s, 1H), 7.30 (d, J=10.0 Hz, 3H), 7.21 (d, J=9.7 Hz, 3H), 4.08 (s, 3H), 3.30 (s, 3H), 1.27 (d, J=7.0 Hz, 6H). LCMS m/z 310.24 [M+H]$^+$

Step 2: 4-(4-fluorophenyl)-3-isopropyl-2-methyl-quinolin-7-ol (237)

To a solution of C167 (20 mg, 0.06465 mmol) in dry dichloromethane (1 mL), a solution of BBr$_3$ (500 µL of 1M, 0.500 mmol) in dichloromethane was added and the reaction was stirred under nitrogen for 60 hours. Water and ice were added, the mixture was stirred for 1 hours, extracted with dichloromethane. Purification by silica gel chromatography (0-10% of MeOH in dichloromethane) afforded 237 (11 mg, 55%). ¹H NMR (300 MHz, Chloroform-d) δ 7.55 (s, 1H), 7.26-7.06 (m, 4H), 6.85 (d, J=9.1 Hz, 1H), 6.75 (d, J=9.1 Hz, 1H), 3.16 (h, J=7.2 Hz, 1H), 2.87 (s, 3H), 1.23 (d, J=7.3 Hz, 6H). LCMS m/z 296.24 [M+H]⁺

Compound 238

4-[4-(4-fluorophenyl)-7-hydroxy-3-isopropyl-2-qui-nolyl]butanoic acid (238)

S22

C168

-continued

238

Step 1: methyl 4-[4-(4-fluorophenyl)-3-isopropyl-7-methoxy-2-quinolyl]butanoate (C168)

To a mixture of Zn—Cu couple (390.9 mg, 3.032 mmol) in toluene (4 mL) and DMA (1 mL), methyl 4-iodobutanoate (414.8 mg, 1.82 mmol) was added under argon. The reaction was heated at 85° C. for 150 minutes and cooled to room temperature. Then, S22 (100 mg, 0.303 mmol) and Pd(PPh₃)₄ (70 mg, 0.061 mmol) were added and the reaction was heated at 85° C. for 16 hours. The mixture was diluted with EtOAc and filtered. The organic phase was washed successively with water and brine, dried over Na₂SO₄, and concentrated. Purification by silica gel chromatography (0-20% EtOAc in hexanes) afforded C168 (60 mg, 35%). LCMS m/z 396.1 [M+H]⁺

Step 2: 4-[4-(4-fluorophenyl)-7-hydroxy-3-isopro-pyl-2-quinolyl]butanoic acid (238)

To a solution of C168 (60 mg, 0.1517 mmol) in dichloromethane (2 mL), a solution of BBr₃ (1M in dichloromethane) (0.7585 mL of 1M, 0.7585 mmol) was added at −20° C. The reaction was stirred for 8 hours at 25° C. The reaction was concentrated and purified by reverse phase HPLC (Method: C18 YMC Triart Actus column, 20×250 mm, 5 micron. Gradient: acetonitrile in water with 20 mM Ammonium Bicarbonate) to afford 238 (5.5 mg, 10%). ¹H NMR (400 MHz, DMSO-d₆) δ 12.08 (s, 1H), 9.98 (s, 1H), 7.38-7.27 (m, 4H), 7.15 (bs, 1H), 6.95 (d, J=9.08 Hz, 1H), 6.86 (d, J=9.04, 1H), 3.48 (t, J=4.84 Hz, 1H), 3.41 (t, J=5.04 Hz, 1H), 3.08 (bs, 1H), 2.99 (t, J=7.52 Hz, 1H), 2.42 (t, J=7.2 Hz, 2H), 2.02 (t, J=7.44 Hz, 2H), 1.11 (d, J=6.04 Hz, 6H). LCMS m/z 368 [M+H+]

Compounds 239-243

Compounds 239-243 (Table 30) were prepared in two steps from intermediate S22 and the appropriate alkyl iodide or alkyl zincate according to the method described for compound 238. Any modifications to methods are noted in Table 30 and accompanying footnotes.

TABLE 30

Method of preparation, structure, physicochemical data for compounds 239-243

| Compound | Method/Product | Alkyl iodide or zincate | $^1$H NMR; LCMS m/z [M + H]$^+$ |
|---|---|---|---|
| 239 | Compound 238 from S22[1] | | $^1$H NMR (400 MHz, DMSO-d$_6$) δ 7.70 (s, 2H), 7.37 (t, J = 8.8 Hz, 2H), 7.29 (ddd, J = 8.5, 5.4, 2.5 Hz, 2H), 7.18 (d, J = 2.4 Hz, 1H), 6.96 (dd, J = 9.1,2.5 Hz, 1H), 6.85 (d, J = 9.1 Hz, 1H), 3.25 (t, J = 7.0 Hz, 2H), 3.16 (s, 1H), 2.85 (t, J = 7.0 Hz, 2H), 1.17 (d, J = 7.1 Hz, 6H). LCMS m/z 354.17 [M + H+] |
| 240 | Compound 238 from S22 | | $^1$H NMR (400 MHz, DMSO-d$_6$) δ 7.38 (t, J = 8.68 Hz, 2H), 7.30 (t, J = 5.64 Hz, 2H), 7.13 (d, J = 2.32 Hz, 1H), 6.94 – 6.92 (m, 1H), 6.85 (d, J = 9.04 Hz, 1H), 3.38 (m, 2H), 3.14 (bs, 1H), 3.07 – 3.03 (m, 1H), 1.23 (d, J = 6.72 Hz, 3H), 1.15 (s, 6H). LCMS m/z 368 [M + H+] |
| 241 | Compound 238 from S22 | | $^1$H NMR (400 MHz, DMSO-d$_6$) δ 7.38 (t, J = 8.68 Hz, 2H), 7.30 (t, J = 5.64 Hz, 2H), 7.13 (d, J = 2.32 Hz, 1H), 6.94 – 6.92 (m, 1H), 6.85 (d, J = 9.04 Hz, 1H), 3.38 (m, 2H), 3.14 (bs, 1H), 3.07 – 3.03 (m, 1H), 1.23 (d, J = 6.72 Hz, 3H), 1.15 (s, 6H). LCMS m/z 368.1 [M + H+] |
| 242 | Compound 238 from S22 | | $^1$H NMR (400 MHz, DMSO-d$_6$) δ 7.38 – 7.28 (m, 4H), 7.14 (d, J = 2.36 Hz, 1H), 6.94 (dd, J1 = 2.39 Hz, J2 = 9.12 Hz, 1H), 6.86 (d, J = 9.04 Hz, 1H), 3.41 – 3.36 (m, 1H), 3.14 (bs, 1H), 2.22 – 2.17 (m, 1H), 2.15 – 1.91 (m, 3H), 1.28 (d, J = 6.48 Hz, 3H), 1.18 (d, J = 5.28 Hz, 6H). LCMS m/z 382.4 [M + H+] |

TABLE 30-continued

| | | | |
|---|---|---|---|
| | Method of preparation, structure, physicochemical data for compounds 239-243 | | |
| Compound | Method/Product | Alkyl iodide or zincate | $^1$H NMR; LCMS m/z [M + H]$^+$ |
| 243 | Compound 238 from S22 | | $^1$H NMR (400 MHz, DMSO-d$_6$) δ 12.21 (s, 1H), 9.98 (s, 1H), 7.36 (t, J = 8.7 Hz, 2H), 7.29 (t, J = 6.8 Hz, 2H), 7.15 (d, J = 2.4 Hz, 1H), 6.94 (dd, J = 9.0, 2.5 Hz, 1H), 6.85 (d, J = 9.1 Hz, 1H), 3.10 (s, 1H), 3.04 – 2.93 (m, 1H), 2.61 – 2.52 (m, 1H), 1.95 (s, 1H), 1.18 (d, J = 7.0 Hz, 3H), 1.15 (s, 5H). LCMS m/z 382 [M + H+] |

$^1$ The reaction was started with the zincate, no treatment with ZnCu couple was necessary.
THF was used as solvent for the Negishi coupling.

Compound 244

3-[[4-(4-fluorophenyl)-7-hydroxy-3-isopropyl-2-quinolyl]amino]-2-methyl-propanoic acid (244)

S32

C169

C170

244

Step 1: methyl 3-[[7-benzyloxy-4-(4-fluorophenyl)-3-isopropenyl-2-quinolyl]amino]-2-methyl-propanoate (C169)

To a solution of S32 (600 mg, 1.55 mmol), methyl 3-amino-2-methylpropanoate hydrochloride (478.24 mg, 3.11 mmol) in dichloromethane (10 mL), DIEA (1.006 g, 1.39 mL, 7.7835 mmol) was added followed by PyBrop (2.18 g, 4.67 mmol) and the reaction was heated at 45° C. for 18 h. The mixture was diluted with dichloromethane, washed successively with an aqueous solution NaHCO$_3$ (5 mL) and water (10 mL), the organic phase was dried over Na$_2$SO$_4$ and concentrated. Purification by silica gel chromatography (10% EtOAc in hexanes) afforded C169 (350 mg, 43%). LCMS m/z 485.3 [M+H]⁺

Step 2: methyl 3-[[4-(4-fluorophenyl)-7-hydroxy-3-isopropyl-2-quinolyl]amino]-2-methyl-propanoate (C170)

To a solution of C169 (300 mg, 0.6191 mmol) in EtOH (20 mL), Pd/C (250 mg, 2.3492 mmol) was added under argon. The reaction was purged with hydrogen and stirred at room temperature for 18 h. The mixture was filtered and concentrated to afford C170 (190 mg, 62%). LCMS m/z 397.0 [M+H]⁺

Step 3: 3-[[4-(4-fluorophenyl)-7-hydroxy-3-isopropyl-2-quinolyl]amino]-2-methyl-propanoic acid (244)

To a solution of C170 (200 mg, 0.5045 mmol) in THF (2 mL), Methanol (0.5 mL) and water (0.2 mL), LiOH (60 mg, 2.52 mmol) was added and the reaction stirred at room temperature for 18 hours. The mixture was concentrated, diluted with water (5 mL), acidified with a saturated aqueous solution of citric acid and extracted with EtOAc (2 mL×2). The organic phases were combined, dried over Na₂SO₄ and concentrated. Purification by reverse-phase HPLC (Method: C18 YMC Triart Actus column, 20×250 mm, 5 micron. Gradient: acetonitrile in water with 20 mM Ammonium Bicarbonate) afforded 244 (65 mg, 34%) as a white solid. ¹H NMR (400 MHz, DMSO-d₆) δ 9.59 (s, 1H), 7.35-7.31 (t, 2H J=8.76 Hz), 7.26-7.22 (q, 2H), 6.83 (d, 1H J=2.16), 6.61-6.55 (m, 2H,), 5.95 (s, 1H), 3.68-3.60 (m, 2H), 2.96-2.89 (m, 2H), 1.17-1.13 (m, 9H). LCMS m/z 383.2 [M+H+]

Compounds 245-252

Compounds 245-252 (Table 31) were prepared in three steps from intermediate S32 and the appropriate amine according to the method described for compound 244. Any modifications to methods are noted in Table 31 and accompanying footnotes.

TABLE 31

| | Method of preparation, structure, physicochemical data for compounds 244-252 | | |
|---|---|---|---|
| Compound | Method/Product | Amine | ¹H NMR; LCMS m/z [M + H]⁺ |
| 245 | Compound 244 from S32[1,2] | | ¹H NMR (400 MHz, DMSO-d₆) δ 12.25 (brs, 1H), 9.59 (s, 1H), 7.35 – 7.33 (t, 2H J = 8.76 Hz), 7.26 – 7.24 (m, 2H), 6.82 – 6.82 (d, 1H, J = 2.04 Hz), 6.61 – 6.54 (m, 2H,), 5.75 (s, 1H), 4.76 – 4.73 (t, 1H, J = 6.88 Hz), 2.94 – 2.69 (m, 1H), 2.69 – 2.63 (m, 2H), 1.30 – 1.28 (d, 3H, J = 6.52 Hz), 1.18 – 1.13 (t, 6H, J = 8.08 Hz). LCMS m/z 383 [M + H⁺] |
| 246 | Compound 244 from S32[3] | | ¹H NMR (400 MHz, DMSO-d₆) δ 12.86 (bs, 1H), 9.64 (s, 1H), 7.35 (t, J = 8.86 Hz, 2H), 7.26 (t, J = 6.7 Hz, 2H), 6.82 (bs, 1H), 6.65 – 6.58 (m, 2H), 5.86 (bs, 1H), 4.73 (q, 1H), 3.05 – 2.95 (m, 1H), 1.5 (s, 3H), 1.19 (bs, 6H). LCMS m/z 369 [M + H⁺] |

TABLE 31-continued

Method of preparation, structure, physicochemical data for compounds 244-252

| Compound | Method/Product | Amine | ¹H NMR; LCMS m/z [M + H]⁺ |
|---|---|---|---|
| 247 | Compound 244 from S32 | | ¹H NMR (400 MHz, DMSO-d₆) δ 12.82 (bs, 1H), 9.64 (s, 1H), 7.35 (t, J = 8.8 Hz, 2H), 7.26 (t, J = 6.9 Hz, 2H), 6.82 (s, 1H), 6.64-6.58 (m, 2H), 5.83 (bs, 1H), 4.73 (q, 1H), 3.05 – 2.95 (m, 1H), 1.5 (s, 3H), 1.19 (bs, 6H). LCMS m/z 369 (M + H+] |
| 248 | Compound 244 from S32⁴ | | ¹H NMR (400 MHz, DMSO-d₆) δ 12.45 (brs, 1H), 9.60 (s, 1H), 7.34 – 7.32 (d, 2H J = 8.08 Hz), 7.24 (s, 2H), 6.80 (s, 1H), 6.61 – 6.58 (d, 2H, J = 10.96), 6.19 (s, 1H), 4.12 (s, 2H), 3.17 (s, 1H), 2.94 (s, 1H), 1.20 (s, 6H). LCMS m/z 355.42 [M + H⁺] |
| 249 | Compound 244 from S32¹ | | ¹H NMR (400 MHz, DMSO-d₆) δ 9.72 (s, 1H), 7.37 – 7.33 (t, 2H J = 8.88 Hz), 7.28 – 7.25 (t, 2H, J = 6.68), 6.85 (s, 1H), 6.66 – 6.59 (t, 2H, J = 4.76), 6.05 (s, 1H), 3.78 (d, 2H, J = 5.72), 2.96-2.92 (t, 2H, J – 7.68), 1.23 – 1.05 (m, 10H). LCMS m/z 395 [M + H⁺] |

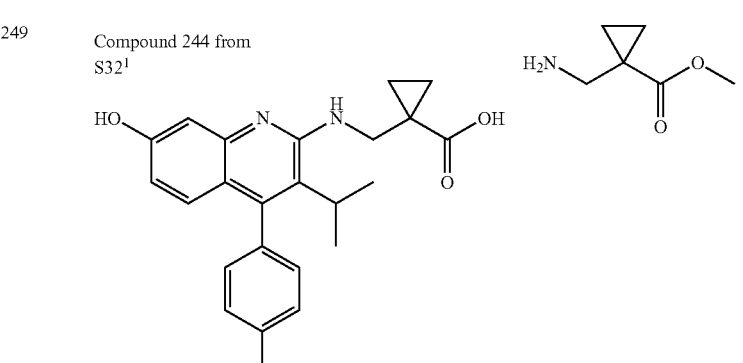

TABLE 31-continued

Method of preparation, structure, physicochemical data for compounds 244-252

| Compound | Method/Product | Amine | ¹H NMR; LCMS m/z [M + H]⁺ |
|---|---|---|---|
| 250 | Compound 244 from S32[1] | | ¹H NMR (400 MHz, DMSO-d₆) δ 9.64 (s, 1H), 7.38 – 7.33 (t, 2H J = 8.88 Hz), 7.26 (s, 2H), 6.80 (s, 1H), 6.66 – 6.59 (q, 2H, J = 10.96), 5.95 (s, 1H), 4.73 (s, 1H), 3.95 – 3.88 (t, 2H), 2.96 (s, 1H), 1.24 (t, 6H, J = 6.44). LCMS m/z 385 [M + H⁺] |
| 251 | Compound 244 from S32[1,5] | | ¹H NMR (400 MHz, DMSO-d₆) δ 9.64 (s, 1H), 7.38 – 7.33 (t, 2H J = 8.88 Hz), 7.26 (s, 2H), 6.80 (s, 1H), 6.66 – 6.59 (q, 2H, J = 10.96), 5.95 (s, 1H), 4.73 (s, 1H), 3.95 – 3.88 (t, 2H), 2.96 (s, 1H), 1.24 (t, 6H, J = 6.44). LCMS m/z 385 [M + H⁺] |
| 252 | Compound 244 from S32[1,5] | | ¹H NMR (400 MHz, DMSO-d₆) δ 12.45 (brs, 1H), 9.58 (s, 1H), 7.36 – 7.31 (t, 2H, J = 8.88 Hz), 7.25 – 7.24 (t, 2H, J = 3.08), 6.83 (s, 1H), 6.62 – 6.56 (q, 2H), 5.78 (s, 1H), 4.77 – 4.74 (t, 1H, J = 6.76), 2.95 – 2.91 (t, 1H, J = 7.32), 2.67 – 2.61 (q, 2H), 1.11 – 1.29 (d, 3H, J = 6.56), 1.17 – 1.13 (t, 6H, J = 8.32). LCMS m/z 383 [M + H⁺] |

[1.] PyBrop amination was performed at room temperature.

[2.] The order of steps was changed; ester hydrolysis was performed before the hydrogenation/benzyl ether deprotection.

[3.] t-Butyl hydrolysis was performed with HCl in dioxane.

[4.] The order of steps was changed; ester hydrolysis was performed before the hydrogenation/benzyl ether deprotection. The ester hydrolysis was performed using NaOH in a mixture of MeOH and water. The then hydrogenation hydrogenation/benzyl ether deprotection was performed with Pt sulfide.

[5.] Benzyl ester was cleaved during the hydrogenation/benzyl ether deprotection procedure Compound 253

1-[[[4-(3,4-difluorophenyl)-7-hydroxy-3-isopropyl-2-quinolyl]amino]methyl]cyclopropanecarboxylic acid (253)

-continued

C174

253

Step 1: 7-benzyloxy-4-(3,4-difluorophenyl)-3-iso-propenyl-quinoline (C171)

To a solution of C57 (5 g, 16.140 mmol) in dioxane (25 mL) and water (3 mL), (3,4-difluorophenyl)boronic acid (5.0974 g, 32.280 mmol) and $K_3PO_4$ (10.278 g, 48.420 mmol) were added. The reaction was purged with nitrogen, $Pd(dppf)Cl_2$ (1.0519 g, 1.614 mmol) was added and the mixture was heated at 90° C. for 16 hours. EtOAc (50 mL) was added and the mixture was stirred for 10 minutes, filtered through Celite plug, washed with EtOAc (50 mL) and concentrated. Purification by silica gel chromatography (30-40% EtOAc in hexanes) afforded C171 (5 g, 69%) as an off white solid. LCMS m/z 388.0 [M+H]$^+$

Step 2: 7-benzyloxy-4-(3,4-difluorophenyl)-3-iso-propenyl-1-oxido-quinolin-1-ium (C172)

To a solution of C171 (3 g, 7.7435 mmol), m-CPBA (1.6035 g, 9.2922 mmol) was added at 0° C. and under argon atmosphere. The reaction was stirred for 5 h. Water (50 mL) was added, the mixture was extracted with EtOAc (100 mL), washed successively with brine and an aqueous saturated solution of $NaHCO_3$, dried over $MgSO_4$ and concentrated. Purification by silica gel chromatography (30-40% EtOAc in hexanes) afforded C172 (2.5 g, 64%) as a yellow oil. LCMS m/z 404.0 [M+H]$^+$

Step 3: methyl 1-[[[7-benzyloxy-4-(3,4-difluorophe-nyl)-3-isopropenyl-2-quinolyl]amino]methyl]cyclo-propanecarboxylate (C173)

To a solution of C172 (335 mg, 0.8304 mmol), methyl 1-(aminomethyl)cyclopropanecarboxylate hydrochloride (412.6 mg, 2.49 mmol) in dichloromethane (10 mL), DIEA (536.6 mg, 0.75 mL, 4.152 mmol) and PyBrop (1.1614 g, 2.4912 mmol) were added. The reaction was heated at 50° C. for 2 days. The mixture was diluted with dichloromethane

---

Reaction scheme (left column)

C57

C171

C172

C173

(20 mL), washed successively with an aqueous solution of NaHCO$_3$ (10 mL) and water (10 mL), dried over Na$_2$SO$_4$ and concentrated. Purification by silica gel chromatography (30-50% EtOAc in hexane) to afford C173 (70 mg, 9%). LCMS m/z 515.0 [M+H]$^+$

Step 4: methyl 1-[[[4-(3,4-difluorophenyl)-7-hy-droxy-3-isopropyl-2-quinolyl]amino]methyl]cyclo-propanecarboxylate (C174)

To a solution of C173 (65 mg, 0.126 mmol) in EtOH (10 mL), Pd/C (100 mg, 0.939 mmol) was added under an argon atmosphere. The reaction was purged with hydrogen and stirred at room temperature for 18 hours. The mixture was filtered through a Celite® plug, washed with EtOAc, and concentrated to afford C174 (30 mg, 31%). LCMS m/z 427.46 [M+H]$^+$

Step 5: 1-[[[4-(3,4-difluorophenyl)-7-hydroxy-3-isopropyl-2-quinolyl]amino]methyl]cyclopropan-ecarboxylic acid (253)

To a solution of C174 (25 mg, 0.058 mmol) in THF (2 mL), Methanol (1 mL) and Water (0.3 mL), LiOH (4.677 mg, 0.195 mmol) was added at 0° C. The reaction was stirred at room temperature for 18 hours. The mixture was concentrated, diluted with water (5 mL), acidified with a saturated aqueous solution of citric acid and extracted with EtOAc (10 mL×2). The organic phases were combined, dried over Na$_2$SO$_4$ and concentrated. Purification by reverse-phase HPLC (Method: C18 YMC Triart Actus column, 20×250 mm, 5 micron. Gradient: acetonitrile in water with 20 mM Ammonium Bicarbonate) afforded 253 (3.5 mg, 14%) as an off white solid. $^1$H NMR (400 MHz, DMSO-d$_6$) δ 13.95 (bs, 1H), 9.73 (bs, 1H), 7.61-7.54 (m, 1H), 7.42 (t, J=8.8 Hz, 1H), 7.09 (bs, 1H), 6.84 (d, J=2.04 Hz, 1H), 6.65-6.59 (m, 2H), 6.07 (bs, 1H), 3.75 (d, J=5.04 Hz, 2H), 2.94-2.89 (m, 1H), 1.33-1.17 (m, 6H), 1.09-0.88 (m, 4H). LCMS m/z 413.4 [M+H]$^+$

Preparation of C176

7-benzyloxy-2-chloro-4-(4-fluorophenyl)-3-isopro-pyl-quinoline (C176)

522

-continued

C175

C176

Step 1: 2-chloro-4-(4-fluorophenyl)-3-isopropyl-quinolin-7-ol (C175)

To a solution of S22 (695 mg, 1.785 mmol) in dichloromethane (4 mL) at 0° C., a solution of BBr$_3$ (4 mL of 1 M, 4.000 mmol) in dichloromethane was added dropwise and the reaction was stirred at room temperature for 3 hours. A cold aqueous solution of NaHCO$_3$ was added, the mixture was extracted with dichloromethane, the organic phases were combined, dried over MgSO$_4$, filtered and concentrated. Purification by silica gel chromatography (0 to 20% EtOAc in heptane) afforded C175 (250 mg, 41%) as a white solid. $^1$H NMR (300 MHz, Chloroform-d) δ 7.35 (dd, J=2.5, 0.6 Hz, 1H), 7.26-7.16 (m, 4H), 7.10 (dd, J=9.2, 0.6 Hz, 1H), 7.03 (dd, J=9.1, 2.5 Hz, 1H), 5.90 (s, 1H), 3.20 (s, 1H), 1.33 (d, J=7.2 Hz, 5H). LCMS m/z 315.67 [M+H]$^+$

Step 2: 7-benzyloxy-2-chloro-4-(4-fluorophenyl)-3-isopropyl-quinoline (C176)

To a solution of C175 (250 mg, 0.7917 mmol) in DMF (8 mL), K$_2$CO$_3$ (235.2 mg, 1.702 mmol) and BnCl (200 µL, 1.738 mmol) were added and the reaction was heated 60° C. for 1 h. Water was added and the mixture was extracted with dichloromethane. The organic phases were combined, dried over MgSO$_4$, filtered and concentrated. Purification by silica gel chromatography (0 to 50% EtOAc in heptane) afforded C176 (210.6 mg, 59%) as a white solid. $^1$H NMR (300 MHz, Chloroform-d) δ 7.42-7.21 (m, 6H), 7.17-7.07 (m, 4H), 7.06-6.95 (m, 2H), 5.12 (s, 2H), 3.11 (s, 1H), 1.24 (d, J=7.2 Hz, 6H). LCMS m/z 406.2 [M+H]$^+$ Compound 254

1-[4-(4-fluorophenyl)-7-hydroxy-3-isopropyl-2-qui-
nolyl]azetidine-3-carboxylic acid (254)

C176

C177

C178

254

Step 1: methyl 1-[7-benzyloxy-4-(4-fluorophenyl)-
3-isopropyl-2-quinolyl]azetidine-3-carboxylate
(C177)

To a solution of C176 (300 mg, 0.7391 mmol) in 1,4-dioxane (4 mL), methyl azetidine-3-carboxylate hydrochloride and K$_2$CO$_3$ (408.59 mg, 2.9564 mmol) were added. The reaction mixture was purged with nitrogen, methanesulfonato(tri-t-butylphosphino)(2'-methylamino-1,1'-biphenyl-2-yl)palladium(II) (94.003 mg, 0.1478 mmol) was added and the reaction mixture was heated at 80° C. for 48 h. The mixture was filtered, washed with EtOAc and the organic phase concentrated. Purification by silica gel chromatography (10-20% EtOAc in hexanes) afforded C177 (40 mg, 10%) as a yellow oil. LCMS m/z 486.24 [M+H]$^+$ Step 2: methyl 1-[4-(4-fluorophenyl)-7-hydroxy-3-isopropyl-2-quinolyl]azetidine-3-carboxylate (C178)

To a solution of C177 (40 mg, 0.083 mmol) in EtOH (2 mL), Pd—C (40 mg, 10% w/w, 0.033 mmol) was added under argon. The reaction was purged with hydrogen and stirred at room temperature for 2 hours. The mixture was filtered through a celite plug, washed with EtOAc and concentrated to afford C178 (30 mg, 86%) as a yellow oil. LCMS m/z 395.13 [M+H]$^+$ Step 3: 1-[4-(4-fluorophenyl)-7-hydroxy-3-isopropyl-2-quinolyl]azetidine-3-carboxylic acid (254)

To a solution of C178 (50 mg, 0.1003 mmol) in a mixture of THF (1.5 mL) and MeOH (0.3 mL), an aqueous solution of aqueous LiOH 1M (0.1003 mL of 1M, 0.1003 mmol) was added and the reaction was stirred for at room temperature for 2 hours. The mixture was concentrated, an aqueous solution of citric acid (5 mL) was added and the mixture was extracted with EtOAc (2×5 mL). The organic phases were combined, dried over Na$_2$SO$_4$ and concentrated. Purification by reverse-phase HPLC (Method: C18 YMC Triart Actus column, 20×250 mm, 5 micron. Gradient: acetonitrile in water with 10 mM AA) afforded 254 (10 mg, 34%) as off-white solid. $^1$H NMR (400 MHz, DMSO-d$_6$) δ 12.65 (bs, 1H), 9.77 (bs, 1H), 7.35-7.27 (m, 4H), 6.93 (s, 1H), 6.70-6.63 (m, 2H), 4.31-4.21 (m, 4H), 3.50-3.43 (m, 1H), 3.50-3.43 (m, 1H), 3.19-3.12 (m, 1H), 0.96 (d, J=7.08 Hz, 6H). LCMS m/z 381.05 [M+H$^+$]

Compounds 255-258

Compounds 255-258 (Table 32) were prepared in three steps from intermediate C176 and the appropriate amine according to the method described for compound 254. Any modifications to methods are noted in Table 32 and accompanying footnotes.

TABLE 32

| | | | ¹H NMR; LCMS m/z |
|---|---|---|---|
| Compound | Method/Product | Amine | [M + H]⁺ |

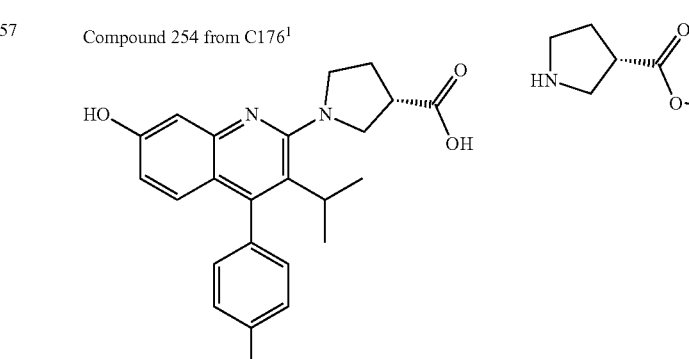

| Compound | Method/Product | Amine | ¹H NMR; LCMS m/z [M + H]⁺ |
|---|---|---|---|
| 255 | Compound 254 from C176 | | ¹H NMR (400 MHz, DMSO-d₆) δ 9.878 (Bs, 1H), 7.34 – 7.25 (m, 4H), 6.90 (s, 1H), 6.67 – 6.61 (m, 2H), 4.24 (t, J = 8.08 Hz, 2H), 3.86 (t, J = 7.2 Hz, 2H), 3.19 – 3.15 (m, 1H), 2.92 – 2.88 (m, 1H), 2.61 (d, J = 7.64 Hz, 1H), 0.94 (d, J = 7.12 Hz, 1H). LCMS m/z 395.11 [M + H⁺] |
| 256 | Compound 254 from C176 | | ¹H NMR (400 MHz, DMSO-d₆) δ 9.82 (bs, 1H), 7.35 – 7.31 (m, 4H), 7.24 (bs, 1H), 6.5 (s, 1H), 6.71 – 6.65 (m, 2H), 4.63 – 4.55 (m, 2H), 4.31 – 4.23 (m, 2H), 3.15 – 3.11 (m, 1H), 0.95 (d, J = 7.04 Hz, 6H). LCMS m/z 399.07 [M + H⁺] |
| 257 | Compound 254 from C176¹ | | ¹H NMR (400 MHz, DMSO-d₆) δ 9.83 (bs, 1H), 7.36 – 7.32 (m, 4H), 6.93 (s, 1H), 6.72 (d, J = 8.46 Hz, 2H), 6.72 (d, J = 8.46 Hz, 1H), 6.66 (d, J = 8.46 Hz, 1H), 3.69 – 3.61 (m, 1H), 3.59 – 3.49 (m, 2H), 3.44 – 3.37 (m, 2H), 3.12 – 3.08 (m, 1H), 2.16 – 2.07 (m, 2H), 0.99 (dd, J = 7.04, Hz, 6H). LCMS m/z 395.14 [M + H⁺] |

TABLE 32-continued

Method of preparation, structure, physicochemical data for compounds 255-258

| Compound | Method/Product | Amine | $^1$H NMR; LCMS m/z [M + H]+ |
|---|---|---|---|
| 258 | Compound 254 from C176[1] | | $^1$H NMR (400 MHz, DMSO-d[6]) δ 9.85 (bs, 1H), 7.36 – 7.31 (m, 4H), 6.95 (s, 1H), 6.73 (d, J = 8.96 Hz, 2H), 6.66 (d, J = 8.46 Hz, 1H), 3.69 – 3.65 (m, 1H), 3.61 – 3.49 (m, 2H), 3.44 – 3.37 (m, 2H), 3.31 – 3.08 (m, 1H), 2.16 – 2.05 (m, 2H), 0.99 (dd, J = 7.04, Hz, 6H). LCMS m/z 395.13 [M + H+] |

[1] 255-258: Buchwald coupling performed at 100° C.

Compound 259

3-[4-(4-fluoro-3-methyl-phenyl)-7-hydroxy-3-iso-propyl-2-quinolyl]bicyclo[1.1.1]pentane-1-carbox-ylic acid (259)

Step 1: methyl 3-[4-(4-fluoro-3-methyl-phenyl)-3-isopropyl-7-methoxy-2-quinolyl]bicyclo[1.1.1]pen-tane-1-carboxylate (C179)

Under inert atmosphere, a suspension of C45, O3-(1,3-dioxoisoindolin-2-yl) O1-methyl bicyclo[1.1.1]pentane-1,3-dicarboxylate (78 mg, 0.2265 mmol), Ir[dF(CF3)ppy]2 (dtbpy))PF6, (4 mg, 0.00356 mmol) and TFA (25 µL, 0.3245 mmol) in DMA (1.5 mL) was stirred and irradiated with two blue LED Kessil lamps for 2 h. DIEA (0.1 mL) was added to the reaction and then diluted with 10 mL of water and 10 mL of EtOAc. The mixture was extracted with EtOAc (2×), dried with Na$_2$SO$_4$, filtered, and concentrated. Purification by silica gel chromatography (0-50% EtOAc in heptane) afforded C179 (35 mg, 51%) as a white solid.

Step 2: 3-[4-(4-fluoro-3-methyl-phenyl)-7-hydroxy-3-isopropyl-2-quinolyl]bicyclo-[1.1.1]pentane-1-carboxylic acid (259)

To a solution of C179 (35 mg, 0.081 mmol) in dichloromethane (2 mL), a solution of BBr$_3$ (200 µL of 1M, 0.20 mmol) in dichloromethane was added while at 0° C. The reaction was stirred at room temperature for 18 hours. Water was added and the organic phase was recovered, dried and concentrated. Purification by reverse phase chromatography (C18 column, 30-100% MeCN:Water, TFA modifier), afforded the desired acid product as well as the ester. Ester containing fractions were concentrated, dissolved in MeOH and LiOH was added and the mixture was heated to 50° C. for 3 hours. The mixture was neutralized with 1 M HCl, extracted with dichloromethane, concentrated, and combined with the isolated acid to afford 259 (7.9 mg, 24%). ¹H NMR (400 MHz, Methanol-d₄) δ 7.31 (dd, J=1.8, 1.1 Hz, 1H), 7.19-7.02 (m, 4H), 6.93-6.86 (m, 2H), 3.87 (t, J=7.4

478

Hz, 1H), 2.52 (s, 6H), 2.34 (d, J=1.9 Hz, 3H), 1.02 (dd, J=7.2, 4.0 Hz, 6H). LCMS m/z 406.35 [M+H]⁺

Compounds 260-262

Compounds 260-262 (Table 33) were prepared in two steps from intermediate S24 and the appropriate alkyl iodide zincate according to the method described for compound 238. Any modifications to methods are noted in Table 33 and accompanying footnotes.

TABLE 33

Method of preparation, structure, physicochemical data for compounds 260-262

| Compound | Method/Product | Alkyl iodide or zincate | ¹H NMR; LCMS m/z [M + H]⁺ |
|---|---|---|---|
| 260 | Compound 238 from S24 | | ¹H NMR (400 MHz, DMSO-d₆) δ 7.30 (t, J = 8.68 Hz, 2H), 7.17 (d, J = 6.96 Hz, 1H), 7.12 (d, J = 2.2 Hz, 1H), 7.07 (bs, 1H), 6.94 (dd, H = 2.28 Hz, J2 = 9.04, 1H) 6.88 (d, J = 9.08 Hz, 1H), 3.38 (m, 2H), 3.14 (bs, 1H), 3.07 – 3.03 (m, 1H), 2.30 (s, 3H) 1.23 (d, J = 6.72 Hz, 3H), 1.17 (s, 6H). LCMS m/z 382 [M + H⁺] |
| 261 | Compound 238 from S24 | | ¹H NMR (400 MHz, DMSO-d₆) δ 7.30 (t, J = 8.68 Hz, 2H), 7.17 (d, J = 6.96 Hz, 1H), 7.12 (d, J = 2.2 Hz, 1H), 7.07 (bs, 1H), 6.94 (dd, J1 = 2.28 Hz, J2 = 9.04, 1H)6.88(d, J = 9.08 Hz, 1H), 3.38 (m, 2H), 3.14 (bs, 1H), 3.07 – 3.03 (m, 1H), 2.30 (s, 3H) 1.23 (d, J = 6.72 Hz, 3H), 1.17 (s, 6H). LCMS m/z 382.2 [M + H⁺] |
| 262 | Compound 238 from S24 | | ¹H NMR (400 MHz, DMSO-d₆) δ 12.22 (s, 1H), 9.97 (s, 1H), 7.30 (t, J = 8.7 Hz, 2H), 7.18 (t, J = 6.68 Hz, 2H), 7.08 (bs, 1H), 6.93 (bs, 1H), 6.89 (bs, 1H), 3.01 (bs, 1H), 2.99 (s, 2H), 2.32 (s, 3H) 2.01 (s, 1H), 1.95 (s, 1H), 1.16 (d, J = 7.0 Hz, 3H), 1.11 (s, 5H). LCMS m/z 396 [M + H⁺] |

Compound 263

4-[4-(4-fluoro-3-methyl-phenyl)-7-hydroxy-3-iso-propyl-2-quinolyl]butanoic acid (263)

Step 1: methyl 4-[7-benzyloxy-4-(4-fluoro-3-methyl-phenyl)-3-isopropyl-2-quinolyl]butanoate (C180)

To a mixture of Zn—Cu couple (153.55 mg, 1.1910 mmol) in Toluene (2 mL) and DMA (0.5 mL), methyl 4-iodobutanoate (162.95 mg, 0.7146 mmol) was added under argon atmosphere and the reaction mixture was heated at 85° C. for 150 min. Then, S23 (50 mg, 0.1191 mmol) and Pd(PPh$_3$)$_4$ (24.729 mg, 0.0214 mmol) were added and the reaction mixture was heated at 85° C. for 16 hours. The mixture was diluted with EtOAc, filtered, washed successively with water and brine, dried over Na$_2$SO$_4$ and concentrated to afford crude C180 (40 mg, 55%). LCMS m/z 486.0 [M+H]$^+$

Step 2: methyl 4-[4-(4-fluoro-3-methyl-phenyl)-7-hydroxy-3-isopropyl-2-quinolyl]butanoate (C181)

To a solution of C180 (40 mg, 0.0824 mmol) in MeOH (3 mL), 10% Pd/C (20 mg, 0.1879 mmol) was added. The reaction was purged with hydrogen and stirred at room temperature for 1 hour. The mixture was filtered through a Celite plug, washed with MeOH and concentrated to afford C181 (20 mg, 55%). LCMS m/z 396.0 [M+H]$^+$

Step 3: 4-[4-(4-fluoro-3-methyl-phenyl)-7-hydroxy-3-isopropyl-2-quinolyl]butanoic acid (263)

To a solution of C181 (20 mg, 0.0506 mmol) in THF (5 mL) and Water (1.5 mL), LiOH (2.4236 mg, 0.1012 mmol) was added and the reaction was stirred for 16 hours. The mixture was concentrated and purified by reverse-phase HPLC (Method: C18 YMC Triart Actus column, 20×250 mm, 5 micron. Gradient: acetonitrile in water with 20 mM Ammonium Bicarbonate) afforded 263 (6.9 mg, 36%). $^1$H NMR (400 MHz, DMSO-d$_6$) δ 7.28 (t, J=8.6 Hz, 1H), 7.18 (m, 1H), 7.14 (d, J=2.3 Hz, 1H), 7.09 (m, 1H), 6.93 (dd, J=9.1, 2.3 Hz, 1H), 6.86 (d, J=9.0 Hz, 1H), 3.01 (m, 1H), 2.99 (t, J=7.7 Hz, 2H), 2.37 (t, J=7.2 Hz, 2H), 2.30 (s, 3H), 2.05 (m, 2H), 1.15 (d, J=6.7 Hz, 1H). LCMS m/z 382 [M+H$^+$]

Compounds 264-270

Compounds 264-270 (Table 34) were prepared in three steps from intermediate S23 and the appropriate amine according to the method described for compound 254. Any modifications to methods are noted in Table 34 and accompanying footnotes.

TABLE 34

| | Method of preparation, structure, physicochemical data for compounds 264-270 | | |
|---|---|---|---|
| Compound | Method/Product | Amine | $^1$H NMR; LCMS m/z [M + H]$^+$ |
| 264 | Compound 254 from S23 | | $^1$H NMR (400 MHz, DMSO-d$_6$) δ 12.60 (bs, 1H), 9.75 (s, 1H), 7.25 (t, J = 8.24 Hz, 1H), 7.17 (d, J = 7.35 Hz, 1H), 7.10 (t, J = 6.56 Hz, 1H), 6.93 (s, 1H), 6.68 (d, J = 7.84 Hz, 2H), 4.3 (t, J = 8.44 Hz, 2H), 4.23 (t, J = 7.22 Hz, 2H), 3.5 – 3.46 (m, 1H), 3.17 – 3.13 (m, 1H), 2.3 (s, 3H), 0.96 (t, J = 6.56 Hz, 2H, 6H). LCMS m/z 395.4 [M + H$^+$] |
| 265 | Compound 254 from S23 | HCl | $^1$H NMR (400 MHz, DMSO-d$_6$) δ 12.20 (bs, 1H), 9.71 (s, 1H), 7.22 (t, J = 7.42 Hz, 1H), 7.15 (d, J = 7.25 Hz, 1H), 7.06 (t, J = 6.24 Hz, 1H), 6.89 (s, 1H), 6.65 (bs, 2H), 4.24 (t, J = 7.84 Hz, 2H), 3.85 (t, J = 6.84 Hz,2H), 3.18 – 3.15 (m, 1H), 2.92 – 2.88 (m, 1H), 2.62 (bs, 2H), 2.29 (s, 3H), 0.95 (t, J = 6.56 Hz, 6H). LCMS m/z 409.43 [M + H$^+$] |
| 266 | Compound 254 from S23 | HCl | $^1$H NMR (400 MHz, DMSO-d$_6$) δ 12.42 (bs, 1H), 9.79 (s, 1H), 7.28 – 7.19 (m, 2H), 7.10 (bs, 1H), 6.96 (bs, 1H), 6.72 (bs, 2H), 3.66 – 3.32 (m, 8H), 2.32 (s, 3H), 2.14-2.09 (bs, 2H), 1.23-0.96 (tt, 6H). LCMS m/z 409.37 [M + H] |
| 267 | Compound 254 from S23 | HCl | $^1$H NMR (400 MHz, DMSO-d$_6$) δ 12.35 (bs, 1H), 9.85 (s, 1H), 7.26 (t, J = 7.64 Hz, 1H), 7.20 (d, J = 6.84 Hz, 1H), 7.18 (t, J = 6.26 Hz, 1H), 6.93 (s, 1H), 6.68 (d, J = 7.24 Hz, 2H), 3.66 – 3.65 (M, 1H), 3.60 – 3.45 (M, 2H), 3.42 – 3.32 (M, 2H), 3.12 – 3.09 (M, 1H), 2.3 (s, 3H), 2.14 – 2.08 (m, 2H), 1.05 – 0.96 (tt, 6H). LCMS m/z 409.37 [M + H$^+$] |

TABLE 34-continued

Method of preparation, structure, physicochemical data for compounds 264-270

| Compound | Method/Product | Amine | $^1$H NMR; LCMS m/z [M + H]$^+$ |
|---|---|---|---|
| 268 | | | $^1$H NMR (400 MHz, DMSO-d$_6$) δ 9.85 (s, 1H), 7.28 – 7.09 (M, 4H), 6.94 (s, 1H), 6.7 (s, 1H), 4.62-4.54 (m, 2H), 4.31 – 4.23 (m, 2H), 3.14 – 3.11 (m, 1H), 2.29 (s, 3H), 0.97 (t, J = 6.26 Hz, 6H). LCMS m/z 413.46 [M + H$^+$] |
| 269 | | | $^1$H NMR (400 MHz, DMSO-d$_6$) δ 9.61 (s, 1H), 7.26 (t, J = 9.02 Hz, 1H), 7.11 (d, J = 7.08 Hz, 1H), 7.03 (t, J = 8.42 Hz, 1H), 6.87 (bs, 1H), 6.65 (d, J = 8.88 Hz, 1H), 6.59 (d, J = 8.72 Hz, 1H), 6.15 (bs, 1H), 3.98 – 3.96 (m, 2H), 3.51 (t, J = 6.36 Hz, 1H), 3.1 (s, 3H), 2.98 – 2.91 (m, 1H), 2.29 (s, 3H), 1.16 (d, J = 8.88 Hz, 1H). LCMS m/z 417.1 [M + H$^+$] |
| 270 | | | $^1$H NMR (400 MHz, DMSO-d$_6$) δ 9.55 (s, 1H), 7.26 (t, J = 9.16 Hz, 1H), 7.1 (d, J = 7.24 Hz, 1H), 7.02 (t, J = 5.62 Hz, 1H), 6.8 (bs, 1H), 6.63 (d, J = 8.84 Hz, 1H), 6.55 (d, J = 8.88 Hz, 1H), 5.93 (bs, 1H), 4.21 (t, J = 7.64 Hz, 2H), 3.7 (t, J = 8.32 Hz, 4H), 3.48 (t, J = 5.8 Hz, 2H), .95 – 2.92 (m, 1H), 2.3 (s, 3H), 1.14 (t, J = 6.84 Hz, 6H). LCMS m/z 424.53 [M + H$^+$] |

$^1$ Saponification was not necessary for these examples.

Compound 271

3-[[4-(4-fluoro-3-methyl-phenyl)-7-hydroxy-3-iso-
propyl-2-quinolyl]amino]propanoic acid (271)

C49

C182

271

Step 1: methyl 3-[[4-(4-fluoro-3-methyl-phenyl)-3-
isopropyl-7-methoxy-2-quinolyl]amino]propanoate
(C182)

To a mixture of C49 (250 mg, 0.7683 mmol), methyl
3-aminopropanoate (160 mg, 1.552 mmol) and PyBrop
(1.12 g, 2.402 mmol) in dichloromethane (3 mL), DIPEA
(400 µL, 2.296 mmol) was added and the reaction was
stirred at room temperature for 18 hours. The mixture was
diluted with dichloromethane (5 mL), washed successively
with water and brine, dried and concentrated. Purification by
silica gel chromatography (10 to 90% EtOAc in hexanes)
afforded C182 (162 mg, 49%). LCMS m/z 410.54 [M+H]$^+$ Step 2: 3-[[4-(4-fluoro-3-methyl-phenyl)-7-hydroxy-
3-isopropyl-2-quinolyl]amino]-propanoic acid (271)

To a solution of C182 (45 mg, 0.1096 mmol) in EtSH (1
mL), AlBr$_3$ (102 mg, 0.3825 mmol) was added and the
reaction was stirred at room temperature for 1 hour. The
mixture was concentrated and 2 ml of DMSO and water
(3020 µL, 167.6 mmol) were added. The mixture was
filtered, the filtrated was recovered and purified by C18
reverse-phase chromatography (10 to 90% acetonitrile in
water, 0.1% formic acid as additive) to afford 271 (30 mg,
66%). $^1$H NMR (400 MHz, Chloroform-d) δ 12.46 (s, 1H),
7.37 (s, 1H), 7.05 (t, J=8.8 Hz, 2H), 6.91-6.74 (m, 2H), 6.67
(q, J=9.1 Hz, 2H), 3.99 (s, 2H), 3.00 (p, J=7.3 Hz, 1H), 2.86
(s, 2H), 2.25 (s, 3H), 1.12 (d, J=7.3 Hz, 6H). LCMS m/z
383.25 [M+H]$^+$

Compounds 272-273

Compounds 272-273 (Table 35) were prepared in two
steps from intermediate C49 and the appropriate amine
according to the method described for compound 271. Any
modifications to methods are noted in Table 35 and accom-
panying footnotes.

TABLE 35

| | Method of preparation, structure, physicochemical data for compounds 272-273 | | | |
|---|---|---|---|---|
| Compound | Product | Amine | Method | $^1$H NMR; LCMS m/z [M + H]$^+$ |
| 272 | Compound 271 from C49 | | Compound 271 from C49 | $^1$H NMR (300 MHz, Methanol-d$_4$) δ 8.38 (s, 1H), 7.27 – 6.99 (m, 4H), 6.84 (d, J = 9.0 Hz, 1H), 6.72 (dd, J = 9.0, 2.4 Hz, 1H), 3.21 – 3.04 (m, 2H), 2.88 – 2.73 (m, 2H), 2.46 (tdd, J = 10.0, 7.5, 2.7 Hz, 2H), 2.35 (d, J = 1.9 Hz, 3H), 1.29 – 1.15 (m, 6H). LCMS m/z 409.21 [M + H$^+$] |
| 273 | Compound 271 from C49 | | Compound 271 from C49 | $^1$H NMR (400 MHz, Methanol-d$_4$) δ 7.20 (dd, J = 9.7, 8.3 Hz, 1H), 7.14 – 7.07 (m, 2H), 7.04 (ddd, J = 7.7, 4.9, 2.3 Hz, 1H), 6.81 (d, J = 8.9 Hz, 1H), 6.69 (dd, J = 9.0, 2.4 Hz, 1H), 4.68 (t, J = 7.8 Hz, 1H), 3.12 (p, J = 7.4 Hz, 1H), 2.97 – 2.78 (m, 3H), 2.39 – 2.22 (m, 5H), 1.28 – 1.18 (m, 6H). LCMS m/z 409.17 (M + H$^+$] |

Preparation of C183

7-(benzyloxy)-4-(4-fluoro-3-methylphenyl)-3-(prop-1-en-2-yl)quinoline 1-oxide (C183)

-continued

C183

To a solution of C63 (6 g, 15.647 mmol) in dichloromethane (50 mL), m-CPBA (3.2401 g, 18.776 mmol) was added and the reaction was stirred at room temperature 12 h. Water and a saturated aqueous solution of NaHCO$_3$ solution (10 mL) were added and the mixture was extracted with dichloromethane (20 mL). The organic phase was washed with brine, dried over Na$_2$SO$_4$ and concentrated to afford C183 (5.8 g, 85%) as a as light brown solid. LCMS m/z 400.0 [M+H]$^+$ Compounds 274-288

Compounds 274-288 (Table 36) were prepared in three steps from intermediate C183 and the appropriate amine according to the method described for compound 244. Any modifications to methods are noted in Table 36 and accompanying footnotes.

TABLE 36

Method of preparation, structure, physicochemical data for compounds 274-288

| Compound | Method/Product | Amine | $^1$H NMR; LCMS m/z [M + H]$^+$ |
|---|---|---|---|
| 274 | Compound 244 from C183 | | $^1$H NMR (400 MHz, DMSO-d$_6$) δ 12.45 (bs, 1H), 9.51 (s, 1H), 7.22 (t, J = 9.04 Hz, 1H), 7.08 (d, J = 6.94 Hz, 1H), 7.03-7.01 (m, 1H), 6.80 (s, 1H), 6.60 (d, J = 8.84 Hz, 1H), 6.54 (d, J = 8.88 Hz, 1H), 5.8 (bs, 1H), 3.67 – 3.60 (m, 1H), 2.94 – 2.88 (m, 1H), 2.26 (s, 3H), 1.2 – 1.11 (m, 9H). LCMS m/z 397.2 [M + H$^+$] |
| 275 | Compound 244 from C183 | | $^1$H NMR (400 MHz, DMSO-d$_6$) δ 12.33 (bs, 1H), 9.58 (s, 1H), 7.26 (t, J = 9.06 Hz, 1H), 7.13 (bs, 1H), 7.05 (bs, 1H), 6.83 (s, 1H), 6.63 (d, J = 8.76 Hz, 1H), 6.57 (d, J = 9.04 Hz, 1H), 5.68 (bs, 1H), 2.97 – 2.93 (m, 1H), 2.69 – 2.61 (m, 2H), 2.28 (s, 3H), 1.3 (s, 3H), 1.16 (t, J = 8.14 Hz, 6H). LCMS m/z 397 [M + H$^+$] |
| 276 | Compound 244 from C183 | | $^1$H NMR (400 MHz, DMSO-d$_6$) δ 12.74 (bs, 1H), 9.65 (s, 1H), 7.25 (t, J = 9.06 Hz, 1H), 7.16 (t. J = 8.86 Hz, 1H), 7.03 – 7.02 (m, 1H), 6.80 (s, 1H), 6.61 (d, J = 8.64 Hz, 1H), 6.54 (d, J = 8.84 Hz, 1H), 6.35 (bs, 1H), 4.67 (q, 1H), 2.97 – 2.91 (m, 1H), 2.29 (s, 3H), 1.27 (s, 3H), 1.18 (t, J = 6.92 Hz, 6H). LCMS m/z 397 [M + H$^+$] |

TABLE 36-continued

Method of preparation, structure, physicochemical data for compounds 274-288

| Compound | Method/Product | Amine | ¹H NMR; LCMS m/z [M + H]⁺ |
|---|---|---|---|
| 277 | Compound 244 from C183 | | ¹H NMR (400 MHz, DMSO-d₆) δ 14.13 (bs, 1H), 9.70 (bs, 1H), 7.27 (t, J = 9.04 Hz, 1H), 7.15 (d, J = 6.12 Hz, 1H), 7.08 – 7.05 (m, 1H), 6.84 (s, 1H), 6.65 (d, J = 8.92 Hz, 1H), 6.60 (d, J = 8.88 Hz, 1H), 6.08 (bs, 1H), 3.76 (d, J = 5.36 Hz, 1H), 2.96 (q, 1H), 2.31 (s, 3H), 1.19 (d, J = 1.48, 6H), 1.09 (s, 2H), 1.04 (s, 2H). LCMS m/z 409 [M + H⁺] |
| 278 | Compound 244 from C183¹ | | ¹H NMR (400 MHz, DMSO-d₆) δ 9.64 (s, 1H), 7.28 (t, J = 8.98 Hz, 1H), 7.14 (t, J = 7.02 Hz, 1H), 7.06 – 7.04 (m, 1H), 6.79 (s, 1H), 6.67 (d, J = 8.88 Hz, 1H), 6.60 (d, J = 8.96 Hz, 1H), 5.88 (bs, 1H), 4.74 (bs, 1H), 3.95 – 3.85 (m, 2H), 3.0 – 2.97 (m, 1H), 2.3 (s, 3H), 1.23 (s, 6H). LCMS m/z 399 [M + H⁺] |
| 279 | Compound 244 from C183² | | ¹H NMR (400 MHz, DMSO-d₆) δ 9.52 (s, 1H), 7.25 (t, J = 9.04 Hz, 1H), 7.16 (t, J = 8.86 Hz, 1H), 7.12 (d, J = 7.4 Hz, 1H), 7.04 (bs, 1H), 6.78 (s, 1H), 6.60 (d, J = 8.84 Hz, 1H), 6.50 (d, J = 9.32 Hz, 1H), 4.2 (bs, 1H), 2.97 – 2.92 (m, 1H), 2.3(s, 3H), 1.4 (s, 3H), 1.21 (t, J = 5.42 Hz, 6H). LCMS m/z 383 [M + H⁺] |

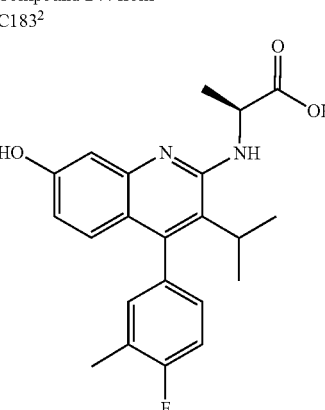

TABLE 36-continued

Method of preparation, structure, physicochemical data for compounds 274-288

| Compound | Method/Product | Amine | $^1$H NMR; LCMS m/z [M + H]$^+$ |
|---|---|---|---|
| 280 | Compound 244 from C183$^2$ 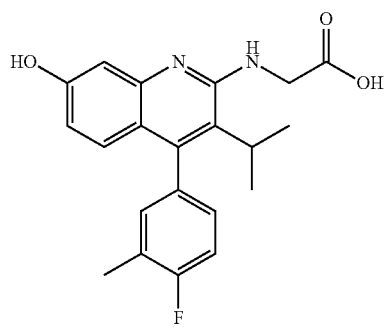 | 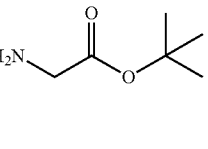 | $^1$H NMR (400 MHz, DMSO-d$_6$) δ 12.85 (bs, 1H), 9.65 (s, 1H), 7.27 (t, J = 9.06 Hz, 1H), 7.16 (d, J = 7.2 Hz, 1H), 7.06 – 7.03 (m, 1H), 6.82 (s, 1H), 6.66 (d, J = 8.88 Hz, 1H), 6.60 (d, J = 8.88 Hz, 1H), 5.8 (bs, 1H), 4.76 – 4.69 (m, 1H), 3.08 – 2.97 (m, 1H), 2.29 (s, 3H), 1.5(s, 3H), 1.18 (t, J = 6.92 Hz, 6H). LCMS m/z 383 [M + H$^+$] |
| 281 | Compound 244 from C183$^2$ | | $^1$H NMR (400 MHz, DMSO-d$_6$) δ 12.52 (bs, 1H), 9.58 (s, 1H), 7.27 (t, J = 8.8 Hz, 1H), 7.12 (d, J = 7.28 Hz, 1H), 7.04 (t, J = 5.56 Hz, 1H), 6.79 (s, 1H), 6.65 (d, J = 8.84 Hz, 1H), 6.58 (d, J = 8.88 Hz, 1H), 6.16 (bs, 1H), 2.98 – 2.94 (m, 1H), 2.23 (s,3H), 1.2 (d, J = 6.52 Hz, 6H). LCMS m/z 369.1 [M + H$^+$] |
| 282 | Compound 244 from C183$^3$ 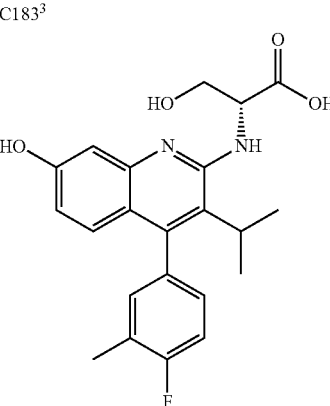 | | $^1$H NMR (400 MHz, DMSO-d$_6$) δ 9.64 (s, 1H), 7.27 (t, J = 9.24 Hz, 1H), 7.14 (t, J = 6.68 Hz, 1H), 7.05 (brs, 1H), 6.79 (s, 1H), 6.68 (d, J = 8.95 Hz, 1H), 6.60 (d, J = 9.04 Hz, 1H), 5.89 (bs, 1H), 4.66 (bs, 1H), 3.94 – 3.83 (m, 2H), 3.0 – 2.96 (m, 1H), 2.3 (s, 3H), 1.24 (s,6H). LCMS m/z 399 [M + H$^+$] |

TABLE 36-continued

Method of preparation, structure, physicochemical data for compounds 274-288

| Compound | Method/Product | Amine | ¹H NMR; LCMS m/z [M + H]⁺ |
|---|---|---|---|
| 283 | Compound 244 from C183[4] 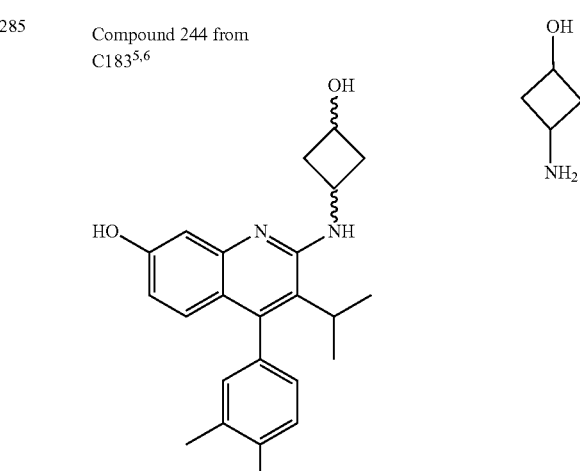 | H₂N ... O ... O | ¹H NMR (400 MHz, DMSO-d₆) δ 12.49 (s, 1H), 9.64 (s, 1H), 7.26 (dd, J = 9.9, 8.3 Hz, 1H), 7.17 – 7.08 (m, 1H), 7.08 – 6.97 (m, 1H), 6.83 (d, J = 2.4 Hz, 1H), 6.63 (d, J = 8.9 Hz, 1H), 6.56 (dd, J = 8.9, 2.4 Hz, 1H), 6.00 (s, 1H), 3.64 (s, 2H), 3.03 – 2.80 (m, 2H), 2.29 (d, J = 1.9 Hz, 3H), 1.23 – 1.08 (m, 9H). LCMS m/z 397.19 [M + H⁺] |
| 284 | Compound 244 from C183[4] | H₂N ... O ... O | ¹H NMR (400 MHz, DMSO-d₆) δ 9.62 (s, 1H), 7.26 (dd, J = 9.9, 8.3 Hz, 1H), 7.12 (dd, J = 7.6, 2.1 Hz, 1H), 7.07 – 6.96 (m, 1H), 6.83 (d, J = 2.4 Hz, 1H), 6.63 (d, J = 8.9 Hz, 1H), 6.56 (dd, J = 8.9, 2.4 Hz, 1H), 6.05 (s, 1H), 3.64 (s, 2H), 3.00 – 2.82 (m, 2H), 2.31 – 2.26(m, 3H), 1.25 – 1.02 (m, 9H). LCMS m/z 397.39 [M + H⁺] |
| 285 | Compound 244 from C183[5,6] | OH ... NH₂ | ¹H NMR (400 MHz, DMSO-d₆) δ 9.54 (s, 1H), 7.25 (t, J = 8.88 Hz, 1H), 7.11 (d, J = 7.20 Hz, 1H), 7.02 (t, J = 6.6 Hz, 1H), 6.80 (bs, 1H), 6.61 (d, J = 8.84 Hz, 1H), 6.56 (d, J = 8.84 Hz, 1H), 5.4 (bs, 1H), 5.01 (d, J = 6.0 Hz, 1H), 4.22 – 4.16 (m, 1H), 3.96 – 3.91 (m, 1H), 3.01 – 2.96 (m, 1H), 2.74 – 2.67 (m, 2H), 2.29 (s,3H), 1.90 – 1.88 (m, 2H), 1.13 (d, J = 6.68 Hz, 6H). LCMS m/z 381.18 [M + H⁺] |

TABLE 36-continued

Method of preparation, structure, physicochemical data for compounds 274-288

| Compound | Method/Product | Amine | ¹H NMR; LCMS m/z [M + H]⁺ |
|----------|---------------|-------|---------------------------|
| 286 | Compound 244 from C183[5,6] 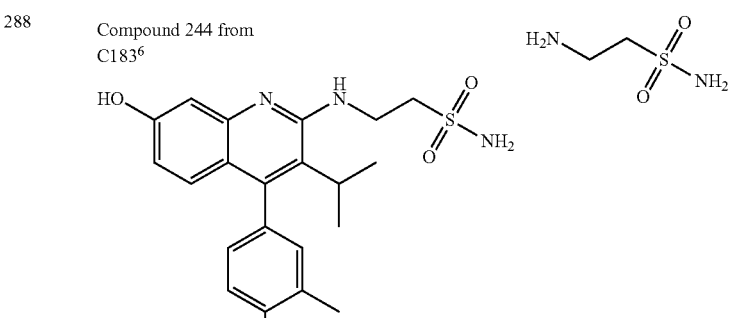 | OH / NH₂ (cyclobutyl) | ¹H NMR (400 MHz, DMSO-d₆) δ 9.54 (s, 1H), 7.25 (t, J = 8.86 Hz, 1H), 7.11 (d, J = 7.40 Hz, 1H), 7.02 (t, J = 6.2 Hz, 1H), 6.80 (bs, 1H), 6.61 (d, J = 8.86 Hz, 1H), 6.56 (d, J = 8.82 Hz, 1H), 5.56 (bs, 1H), 5.02 – 4.98 (m, 1H), 4.75 – 4.73 (m, 1H), 4.33 – 4.31 (m, 1H), 4.20 – 3.92 (m, 1H), 3.1 – 2.97 (m, 1H), 2.72 – 2.66 (m, 1H), 2.32 – 2.24 (m,5H), 1.90 – 1.87 (m, 1H), 1.13 (d, J = 6.68 Hz, 6H). LCMS m/z 381.18 [M + H⁺] |
| 287 | Compound 244 from C183[6] | H₂N—CH₂CH₂—OH | ¹H NMR (400 MHz, DMSO-d₆) δ 9.58 (s, 1H), 7.26 (t, J = 8.96 Hz, 1H), 7.11 (d, J = 6.64 Hz, 1H), 7.02 (t, J = 7.86 Hz, 1H), 6.80 (bs, 1H), 6.63 (d, J = 8.8 Hz, 1H), 6.56 (d, J = 8.76 Hz, 1H), 5.8 (bs, 1H), 5.14 (bs, 1H), 3.64 – 3.62 (m, 4H), 2.97 – 2.93 (m, 1H), 2.29 (s,3H), 1.16 (d, J = 6.6, Hz, 6H). LCMS m/z 355.18 [M + H⁺] |
| 288 | Compound 244 from C183[6] | H₂N—CH₂CH₂—SO₂NH₂ | ¹H NMR (400 MHz, DMSO-d₆) δ 9.58 (s, 1H), 7.26 (t, J = 8.8 Hz, 1H), 7.11 (d, J = 6.58 Hz, 1H), 7.02 (t, J = 8.02 Hz, 1H), 6.98 (bs, 2H), 6.86 (bs, 1H), 6.64 (d, J = 8.8 Hz, 1H), 6.58 (d, J = 9.0 Hz, 1H), 6.07 (bs, 1H), 3.97 – 3.95 (m, 2H), 3.38 (t, J = 6.2 Hz, 1H), 2.95 – 2.92 (m, 1H), 2.29 (s, 3H), 1.16 (d, J = 6.52, Hz, 6H). LCMS m/z 418.13 [M + H⁺] |

1. The order of steps was changed; hydrolysis of the ester was performed before hydrogenation/benzyl ether deprotection.

2. The t-butyl ester was deprotected with HCl in dioxane.

3. The benzyl ester was removed during hydrogenation/benzyl ether deprotection.

4. 283 and 284 were obtained after SFC chiral separation, stereochemistry is unknown.

5. 285 and 286 were obtained after C18 chromatography, stereochemistry is unknown.

6. No saponification was necessary.

Compound 289

3-isopropyl-2-methyl-4-phenylquinolin-7-ol (289)

To a mixture of S25 (60 mg, 0.2495 mmol), phenylboronic acid (76 mg, 0.6233 mmol) and Pd(dppf)Cl$_2$ (12 mg, 0.01469 mmol) in DMF (3 mL), an aqueous solution of Na$_2$CO$_3$ (400 μL of 2 M, 0.8000 mmol) was added under nitrogen and the reaction was heated in a microwave reactor at 130° C. for 4 hours. An aqueous solution of HCl (1 N; 0.5 mL) and water were added, the mixture was extracted with EtOAc and the combined organic phases were concentrated. Purification by silica gel chromatography (0 to 10% MeOH in dichloromethane) afforded crude product which was re-purified by reverse-phase HPLC (Method: C18 Waters Sunfire column, 30×150 mm, 5 micron. Gradient: MeCN in water) to afford 289 (Hydrochloride salt) (3.5 mg, 4%) 1H NMR (300 MHz, Chloroform-d and Methanol-d$_4$) δ 7.70-7.49 (m, 4H), 7.21 (td, J=11.7, 9.9, 6.3 Hz, 4H), 3.28 (q, J=7.3 Hz, 1H), 3.13 (d, J=2.5 Hz, 3H), 1.27 (d, J=7.2 Hz, 6H). LCMS m/z 278.32 [M+H]$^+$ Compound 290

3-isopropyl-2-methyl-4-(2-methyl-4-pyridyl)quinolin-7-ol (290)

Step 1: 4-chloro-3-isopropyl-7-(methoxymethoxy)-2-methyl-quinoline (C184)

To a mixture of S25 (600 mg, 2.546 mmol) and DIEA (1.4 mL, 8.038 mmol) in dichloromethane (20 mL), chloro (methoxy)methane (400 μL, 5.266 mmol) was added. The reaction mixture was stirred for 18 hours at room temperature under N$_2$. N',N'-dimethylethane-1,2-diamine (1 mL, 9 mmol) and a saturate aqueous solution of NH$_4$Cl were added. The mixture was extracted with dichloromethane (200 mL) and the organic phase was washed successively with water (100 mL) and brine, dried with Na$_2$SO$_4$ and concentrated to afford C184 (500 mg, 70%) 1H NMR (300 MHz, Chloroform-d) δ 8.15 (d, J=9.2 Hz, 1H), 7.55 (d, J=2.5 Hz, 1H), 7.28 (dd, J=9.2, 2.5 Hz, 2H), 5.33 (s, 2H), 3.76 (s, 1H), 3.52 (s, 3H), 2.81 (s, 3H), 1.49 (d, J=7.2 Hz, 6H). LCMS m/z 279.99 [M+H]$^+$ Step 2: 3-isopropyl-7-(methoxymethoxy)-2-methyl-4-(2-methyl-4-pyridyl)quinoline (C185)

To a mixture of C184 (50 mg, 0.1787 mmol), (2-methyl-4-pyridyl)boronic acid (49 mg, 0.3578 mmol) and PD(dppf) Cl$_2$ (88 mg, 0.1078 mmol) in DMF (2 mL), an aqueous solution of Na$_2$CO$_3$ (360 μL of 2 M, 0.7200 mmol) was added under nitrogen and the reaction was heated in a microwave reactor at 125° C. for 4 hours. An aqueous solution of HCl (1 N; 0.5 mL) and water were added, the mixture was extracted with EtOAc and the combined organic phases were concentrated. Purification by silica gel chromatography (0 to 10% MeOH in dichloromethane) afforded crude product which was repurified by reverse-phase HPLC (Method: C18 Waters Sunfire column, 30×150 mm, 5 micron. Gradient: MeCN in water) to afford C185 (16 mg, 27%). LCMS m/z 337.24 [M+H]$^+$

Step 3: 3-isopropyl-2-methyl-4-(2-methyl-4-pyridyl) quinolin-7-ol (290)

To a solution of C185 (16 mg, 0.04756 mmol) in MeOH (0.5 mL), a solution of hydrogen chloride (500 µL of 6M, 3.000 mmol) in MeOH was added and the reaction was stirred at room temperature for 4 hours. The mixture was concentrated to afford 290 (14 mg, 78%). $^1$H NMR (300 MHz, Methanol-d$_4$) δ 9.02 (d, J=4.9 Hz, 1H), 7.81 (d, J=26.9

Hz, 3H), 7.30 (d, J=7.8 Hz, 1H), 7.15 (d, J=8.6 Hz, 1H), 3.36 (s, 1H), 3.20 (s, 3H), 3.05 (s, 3H), 1.34 (d, J=6.2 Hz, 6H). LCMS m/z 293.31 [M+H]$^+$

Compounds 291-293

Compounds 291-293 (Table 37) were prepared in five steps from intermediate C57 and the appropriate boronic acid according to the method described for compound 253. Any modifications to methods are noted in Table 37 and accompanying footnotes.

TABLE 37

| Method of preparation, structure, physicochemical data for compounds 291-293 | | | |
|---|---|---|---|
| Compound | Method/Product | Boronic acid | $^1$H NMR; LCMS m/z [M + H]$^+$ |
| 291 | Compound 253 from C57 | B(OH)$_2$ | $^1$H NMR (400 MHz, DMSO-d$_6$) δ 9.73 (bs, 1H), 7.55 (q, J = 7.16 Hz, 1H), 7.40 – 7.36 (m, 2H), 7.27 (t, J = 7.64 Hz, 1H), 6.85 (s, 1H), 6.62 (s, 2H), 6.07 (bs, 1H), 3.77 (bs, 2H), 2.91 (t, J = 7.36 Hz, 1H), 1.21 – 1.15 (m, 6H), 1.12 – 1.04 (m, 4H). LCMS m/z 395.15 [M + H$^+$] |
| 292 | Compound 253 from C57 | B(OH)$_2$ | $^1$H NMR (400 MHz, DMSO-d$_6$) δ 8.56 (d, J = 5 Hz, 1H), 7.15 (s, 1H), 7.07 (d, J = 4..68 Hz, 1H), 6.81 (s, 1H), 6.57 (bs, 1H), 3.69 (s, 2H), 2.56 (s, 3H), 1.23 – 1.19 (m, 6H), 1.02 (bs, 2H), 0.88 (bs, 2H). LCMS m/z 392.49 [M + H$^+$] |
| 293 | Compound 253 from C57[1] | B(OH)$_2$ | $^1$H NMR (400 MHz, DMSO-d$_6$) δ 13.94 (bs, 1H), 9.73 (s, 1H), 7.57 (q, J = 7.4 Hz, 1H), 7.31 (td, J = 8.7, 2.7 Hz, 1H), 7.14 (d, J = 9.36 Hz, 1H), 7.07 (d, J = 7.5 Hz, 1H), 6.85 (bs, 1H), 6.65 – 6.59 (m, 2H), 6.07 (bs, 1H), 3.77 (d, J = 5.5 Hz, 2H), 2.92 (p, J = 7.4 Hz, 1H), 1.19 (t, J =6.9 Hz, 6H), 1.11 (q, J = 3.8, 3.0 Hz, 2H), 1.05 (t, J = 3.0 Hz, 2H). LCMS m/z 395.1 [M + H$^+$] |

[1.] The order of steps changed for the first three steps. The formation of the N-oxide was performed first, PyBrop amination at 45° C. was performed second and Suzuki coupling was performed third. The other steps proceeded as in the scheme.

503

Compound 294

(2S)-3-(7-(hydroxy)-4-(4-fluoro-3-methylphenyl)-3-
(1-methoxypropan-2-yl)quinolin-2-yl)-2-methylpro-
panoic acid (294)

S26

1) ZnCu
2) Pd(PPh₃)₄

C186

H₂, Pd/C

C187

LiOH

504

-continued

294

Compounds 294 was prepared in three steps from inter-
mediate S26 and methyl (2R)-3-iodo-2-methyl-propanoate
according to the method described for compound 263. ¹H
NMR (400 MHz, DMSO-d₆, 100° C.) δ 10.02 (s, 1H),
7.34-7.28 (m, 4H), 7.18 (s, 1H), 6.96-6.87 (m, 2H), 3.43-
3.24 (m, 6H), 3.13 (s, 1H), 3.07-3.02 (m, 1H), 1.26 (d, J=6.1
Hz, 3H), 1.18-1.15 (m, 3H). LCMS m/z 398 [M+H⁺].

Compound 295

(4-(4-fluorophenyl)-7-hydroxy-3-(1-methoxypropan-
2-yl)quinolin-2-yl)-L-alanine (295)

C61

PyBrop, DIEA

C188

H₂, Pd/C

505

-continued

295

Compound 295 was prepared in two steps (via C188) from intermediate C61 and benzyl (2S)-2-aminopropanoate hydrochloride according to the method described for compound 251. $^1$H NMR (400 MHz, DMSO-d$_6$) δ 9.63 (s, 1H), 7.35 (t, J=8.8 Hz, 2H), 7.26-7.25 (m, 2H), 6.84-6.80 (m, 1H), 6.63-6.57 (m, 2H), 4.64-4.62 (m, 1H), 3.50-3.48 (m, 2H), 3.24-3.22 (m, 3H), 3.02 (s, 1H), 1.45 (d, J=7.1 Hz, 3H), 1.20 (dd, J=7.4, 3.8 Hz, 3H). LCMS m/z 399 [M+H$^+$]

Compound 296

4-(4-fluoro-3-methylphenyl)-2-methylquinolin-7-ol (296)

S27

506

-continued

296

A mixture of S27 (144 mg, 0.5119 mmol) and pyridine (hydrochloride salt) (2.5 g, 21.63 mmol) was microwaved at 220° C. for 30 min. The mixture was cooled down to RT, 60 mL of water and 20 mL of a saturated aqueous solution of NH$_4$Cl were added. The mixture was filtered and extracted with EtOAc, the organic phases were combined and concentrated. Purification by trituration with dichloromethane to give 296 (25 mg, 17%). $^1$H NMR (300 MHz, Chloroform-d and Methanol-d$_4$) δ 7.71 (d, J=9.1 Hz, 1H), 7.35-7.22 (m, 3H), 7.20-7.02 (m, 3H), 2.70 (s, 3H), 2.37 (d, J=2.0 Hz, 3H). LCMS m/z 268.2 [M+H]$^+$ Compounds 297-310

Compound 297-310 (Table 38) were prepared in three steps from intermediate S28 and the appropriate amine according to the method described for compound 244. Any modifications to methods are noted in Table 38 and accompanying footnotes.

TABLE 38

| | Method of preparation, structure, physicochemical data for compounds 297-310 | | |
|---|---|---|---|
| Compound | Method/Product | Amine | $^1$H NMR; LCMS m/z [M + H]$^+$ |
| 297 | Compound 244 from S28 | | $^1$H NMR (400 MHz, DMSO-d$_6$) δ 9.71 (bs, 1H), 7.34 (bs, 1H), 7.26 (t, J = 8.8 Hz, 1H), 7.12 (d, J = 7.0Hz, 1H), 7.04 – 7.03 (m, 1H), 6.84 (d, J = 2Hz, 1H), 6.63 (d, J = 8.8 Hz, 1H), 6.57 (dd, J = 8.8 Hz,1.9Hz, 1H), 5.38 (bs, 1H), 3.81 (d, J = 12.6 Hz, 1H), 3.59 (m, 3H), 2.89 (m, 1H), 2.28 (s,3H), 1.22 – 0.97 (m, 7H). LCMS m/z 425 [M + H$^+$] |

TABLE 38-continued

| | Method of preparation, structure, physicochemical data for compounds 297-310 | | |
|---|---|---|---|
| Compound | Method/Product | Amine | $^1$H NMR; LCMS m/z [M + H]$^+$ |
| 298 | Compound 244 from S28[1]<br>HO-quinoline structure with F-methylphenyl and NH-ethanol substituent | H$_2$N—ethanol (H$_2$N-CH$_2$CH$_2$OH) | $^1$H NMR (400 MHz, DMSO-d$_6$) δ 9.57 (s, 1H), 7.25 (t, J = 8.8 Hz, 1H), 7.13 – 7.09 (m, 1H), 7.01 – 7.04 (m, 2H), 6.79 (d, J = 2 Hz, 1H), 6.60 (d, J = 8.8 Hz, 1H), ), 6.53 (dd, J = 8.8 Hz, 2 Hz, 1H), 5.30 (bs, 1H), 5.10 (bs, 1H), 3.62 – 3.51 (m, 6H), 2.9 (m, 1H), 2.28 (s, 3H), 1.13 (d, J = 4.5 Hz, 3H). LCMS m/z 371 [M + H$^+$] |
| 299 | Compound 244 from S28<br>HO-quinoline structure with bicyclo carboxylic acid NH substituent | Bicyclo[1.1.1]pentane carboxylic acid, NH$_2$·HCl | $^1$H NMR (400 MHz, DMSO-d$_6$) δ 9.7 (bs, 1H), 7.97 (bs, 1H), 7.25 (t, J = 9.0 Hz, 1H), 7.10 – 7.09 (m, 1H), 7.01 – 7.00 (m, 1H), 6.85 (s, 1H), 6.63 – 6.57 (m, 2H), 5.7 (bs, 1H), 3.56 – 3.54 (m, 2H), 2.86 (bs, 1H), 2.37 – 2.33 (m, 6H), 2.24 (s, 3H), 1.10 (t, J = 3 Hz, 3H). LCMS m/z 437 [M + H$^+$] |
| 300 | Compound 244 from S28[2,3]<br>HO-quinoline structure with alanine NH substituent | tert-butyl ester alanine, NH$_2$·HCl | $^1$H NMR (400 MHz, DMSO-d$_6$) δ 9.64 (bs, 1H), 7.52 (bs, 1H), 7.25 (t, J = 8.5 Hz, 1H), 7.10 (d, J = 7.1 Hz, 1H), 7.02 (m, 1H), 6.78 (d, J = 2.1 Hz, 1H), 6.63 (d, J = 8.8 Hz, 1H), 6.56 (m, 1H), 5.57 (bs, 1H), 4.64 – 4.59 (m, 1H), 3.60 (m, 2H), 2.91 (m, 1H), 2.28 (s, 3H), 1.41 (d, J = 7.08 Hz, 3H), 1.19 (t, J = 3.6 Hz, 3H). LCMS m/z 399 [M + H$^+$] |

TABLE 38-continued

Method of preparation, structure, physicochemical data for compounds 297-310

| Compound | Method/Product | Amine | $^1$H NMR; LCMS m/z [M + H]$^+$ |
|---|---|---|---|
| 301 | Compound 244 from S28$^{2,3}$ | HCl | $^1$H NMR (400 MHz, DMSO-d$_6$) δ 9.64 (bs, 1H), 7.69 (bs, 1H), 7.25 (t, J = 8.12 Hz, 1H), 7.11 (m, 1H), 7.02 (m, 1H), 6.78 (d, J = 2.2 Hz, 1H), 6.64 (t, J = 5.72 Hz, 1H), 6.58 (m, 1H), 5.57 (bs, 1H), 4.54 (m, 1H), 3.62 (m, 2H), 2.91 (m, 1H), 2.28 (s, 3H), 1.43 (t, J = 3.72 Hz, 3H), 1.17 (t, J = 3.32 Hz, 3H). LCMS m/z 399 [M + H$^+$] |
| 302 | Compound 244 from S28$^1$ | HCl | $^1$H NMR (400 MHz, DMSO-d$_6$) δ 9.6 (s, 1H), 7.25 (t, J = 8.6 Hz, 1H), 7.11 – 7.02 (m, 3H), 6.86 (d, J = 2.2 Hz, 1H), 6.64 (d, J = 8.8 Hz, 1H), 6.58 (dd, J = 8.82 Hz, 1H), 5.17 (bs, 1H), 3.92 – 3.85 (m, 2H), 3.59 – 3.47 (m, 4H), 3.07 (s, 3H), 2.92 – 2.87 (m, 1H), 2.29 (s, 3H), 1.10 (d, J = 5 Hz, 3H). LCMS m/z 433 [M + H$^+$] |
| 303 | Compound 244 from S28 | HCl | $^1$H NMR (400 MHz, DMSO-d$_6$) δ 13.1 (bs, 1H), 9.63 (bs, 1H), 7.96 (bs, 1H), 7.26 (t, J = 8.6 Hz, 1.3H), 7.13 – 7.12 (m, 1H), 7.05 – 7.04 (m, 1H), 6.76 (d, J = 2.2 Hz, 1H), 6.63 (d, J = 8.8 Hz, 1H), 6.58 (d, J = 9.2 Hz, 1H), 5.78 (bs, 1H), 3.62 (s, 2H). 2.90 – 2.87 (m, 1H), 2.28 (s, 3H), 1.56 (s, 3H), 1.52 (s, 3H), 1.17 (d, J = 3.4 Hz, 3H). LCMS m/z 413 [M + H$^+$] |

TABLE 38-continued

| | Method of preparation, structure, physicochemical data for compounds 297-310 | | |
|---|---|---|---|
| Compound | Method/Product | Amine | $^1$H NMR; LCMS m/z [M + H]+ |
| 304 | Compound 244 from S28[1] | | $^1$H NMR (400 MHz, DMSO-d6) δ 9.61 (bs, 1H), 7.8 (bs, 1H), 7.25 (t, J = 8.5 Hz, 1.3H), 7.10 – 7.08 (m, 1.3H), 7.02 – 7.01 (m, 1.3H), 6.82 (m, 1H), 6.63 – 6.61 (m, 1.3H), 6.56 – 6.53 (m, 1H), 5.76 (bs, 1H), 5.08 (d, J = 5.6 Hz, 1.3H). 4.55 – 4.54 (m, 0.3H), 4.55 – 4.54 (m, 0.3H), 4.11 – 4.05 (m, 1H), 3.96 – 3.91 (m, 1H), 3.61 (m, 2.6H), 2.89 (m, 1.3H), 2.72 – 2.53 (m, 2H), 2.28 (s, 3.9H), 2.17 – 2.07 (m, 1.3H), 1.79 – 1.72 (m, 2H), 1.12 (d, J = 3.6 Hz, 3.9H). LCMS m/z 397 [M + H+] |
| 305 | Compound 244 from S28[2,4] | | $^1$H NMR (400 MHz, DMSO-d6) δ 9.63 (bs, 1H), 7.53 (bs, 1H), 7.32 – 7.23 (m, 1H), 7.22 – 7.10 (m, 1H), 7.08 7.01 (m, 1H), 6.80 (s, 1H), 6.65 – 6.55 (m, 2H), 5.58 (bs, 1H), 4.68 – 4.59 (m, 1H), 3.65 – 3.59 (m, 2H), 2.98 – 2.92 (m, 1H), 2.29 (s, 3H), 1.43 (d, J = 4.96Hz, 3H), 1.20 – 1.15 (m, 3H). LCMS m/z 399 [M + H+] |
| 306 | Compound 244 from S28[2,4] | | $^1$H NMR (400 MHz, DMSO-d6) δ 12.7 (bs, 1H), 9.62 (s, 1H), 7.68 (bs, 1H), 7.26 (t, J = 8.32 Hz, 1H), 7.11 (t, J = 7.8 Hz, 1H), 7.05 – 7.01 (m, 1H), 6.79 (s, 1H), 6.68 – 6.54 (m, 2H), 5.6 (bs, 1H), 4.65 – 4.45 (m, 1H), 3.73 – 3.58 (m, 2H), 2.95 – 2.90 (m, 1H), 2.29 (s, 3H), 1.44 (d, J = 7.2Hz, 3H), 1.19 – 1.14 (m, 3H). LCMS m/z 399 [M + H+] |

Method of preparation, structure, physicochemical data for compounds 297-310

| Compound | Method/Product | Amine | ¹H NMR; LCMS m/z [M + H]⁺ |
|---|---|---|---|
| 307 | Compound 244 from S28 | | ¹H NMR (400 MHz, DMSO-d₆) δ 9.86 (bs, 1H), δ 7.30 – 7.16 (m, 2H), 7.28 – 7.08 (m, 1H), 7.03 (s, 1H), 6.86 – 6.79 (m, 1H), 6.74 (d, J = 9.0 Hz, 1H), 3.46 – 3.18 (m, 7H), 2.76 (s,3H), 2.30 (s,3H), 1.02 – 0.95 (m, 3H). LCMS m/z 413 [M + H⁺] |
| 308 | Compound 244 from S28 | | ¹H NMR (400 MHz, DMSO-d₆) δ 9.52 (s, 1H), 7.60 (bs, 1H), 7.25 (t, J = 9.1 Hz, 1H), 7.12 – 7.01 (m, 2H), 6.80 (d, J = 2.4 Hz, 1H), 6.60 (d, J = 8.9 Hz, 1H), 6.54 (d, J = 9.3 Hz, 1H), 5.63 (bs, 1H), 4.62 – 4.48 (m, 1H), 3.60 – 3.48 (m, 2H), 2.89 – 2.58 (m, 4H), 2.29 (s, 3H), 2.05 – 1.98 (m, 2H), 1.18 – 1.12 (m, 3H). LCMS m/z 425 [M + H⁺] |

TABLE 38-continued

Method of preparation, structure, physicochemical data for compounds 297-310

| Compound | Method/Product | Amine | $^1$H NMR; LCMS m/z [M + H]+ |
|---|---|---|---|
| 309 | Compound 244 from S28[1] | | $^1$H NMR (400 MHz, DMSO-d6) δ 9.55 (s, 1H), 7.25 (t, J = 9.1 Hz, 1H), 7.10 (d, J = 7.4 Hz, 2H), 7.02 (bs, 1H), 6.83 (d, J = 2.3 Hz, 1H), 6.62 (d, J = 8.8 Hz, 1H), 6.55 (d, J = 9.9 Hz, 1H), 5.27 (bs, 1H), 4.22 (t, J = 7.9 Hz, 2H), 3.73 – 3.58 (m, 6H), 3.45 (d, J = 6.1 Hz, 2H), 2.88 (d, J = 7.7 Hz, 1H), 2.29 (s, 3H), 1.33 – 1.21 (m, 3H). LCMS m/z 440 [M + H+] |
| 310 | Compound 244 from S28 | | $^1$H NMR (400 MHz, DMSO-d6) δ 9.59 (s, 1H), 7.25 (t, J = 8.72 Hz, 1H), 7.15 – 6.93 (m, 2H), 6.95 (s, 3H), 6.86 (s, 1H), 6.65 – 6.53 (m, 2H), 5.13 (bs, 1H), 3.87 (d, J = 5.24 Hz, 2H), 3.61 – 3.50 (m, 2H), 3.37 (t, J = 6.76 Hz, 2H), 2.91 – 2.82 (m, 1H), 2.28 (s, 3H), 1.14 – 1.07 (m, 3H). LCMS m/z 434 [M + H+] |

[1.] No ester saponification was necessary.
[2.] t-Butyl ester deprotection was performed with HCl in dioxane.
[3.] 300 and 301 are diastereomers with different stereochemistry at the C3 substituent, stereochemistry at this center is unknown.
[4.] 305 and 306 are diastereomers with different stereochemistry at the C3 substituent, stereochemistry at this center is unknown.

Preparation of C189

7-(benzyloxy)-3-(3,6-dihydro-2H-pyran-4-yl)-4-(4-fluoro-3-methylphenyl)quinoline 1-oxide (C189)

-continued

To a solution of C66 (2.75 g, 6.4631 mmol) in dichloromethane (27.005 mL), m-CPBA (1.3830 g, 8.0142 mmol) was added while at 0° C. and the reaction was stirred at room temperature for 12 h. The mixture was diluted with dichloromethane (200 mL), washed with an aqueous saturated solution of NaHCO$_3$ solution (~20 mL) and concentrated. Purification by silica gel chromatography afforded (30 to 50% EtOAc in hexanes, followed by 2 to 5% MeOH in dichloromethane) afforded C189 (2.6 g, 86%). LCMS m/z 442.3 [M+H]$^+$.

Compounds 311-320

Compound 311-320 (Table 39) were prepared in three steps from intermediate C189 and the appropriate amine according to the method described for compound 244. Any modifications to methods are noted in Table 39 and accompanying footnotes.

TABLE 39

| | Method of preparation, structure and physicochemical data for compounds 311-320 | | |
|---|---|---|---|
| Compound | Method/Product | Amine | $^1$H NMR; LCMS m/z [M + H]$^+$ |
| 311 | Compound 244 from C189 | | $^1$H NMR (DMSO-d$_6$) δ 13.9 (br, 1H), 9.74 (s, 1H), 7.27 (t, J = 9.1Hz, 1H), 7.16 (t, J = 6.4Hz, 1H), 7.09-7.06 (m, 1H), 6.84 (d, J = 2.0Hz, 1H), 6.68-6.59 (m, 2H), 6.22 (br, 1H), 3.84-3.74 (m, 4H), 3.31-3.04 (m, 2H), 2.82-2.79 (m, 1H), 2.30 (s, 3H), 2.07-2.04 (m, 2H), 1.40-1.37 (m, 2H), 1.10-1.06 (m, 4H). LCMS m/z 451.3 [M + H$^+$] |
| 312 | Compound 244 from C189 | | $^1$H NMR (DMSO-d$_6$) δ 12.5 (br, 1H), 10.8 (br, 1H), 8.1 (br, 1H), 7.33 (t, J = 8.8 Hz, 1H), 7.20 (d, J = 8.2 Hz, 1H), 7.12-7.08 (m, 1H), 6.96-6.76 (m, 2H), 3.89-3.78 (m, 4H), 3.14-3.12 (m, 2H), 2.91-2.88 (m, 1H), 1.75-1.74 (m, 2H), 2.31 (s, 3H), 1.88 (br, 2H), 1.39-1.36 (m, 2H). LCMS m/z 424.9 [M + H$^+$] |
| 313 | Compound 244 from C189$^1$ | | $^1$H NMR (DMSO-d$_6$) δ 9.67 (s, 1H), 7.28 (t, J = 8.8 Hz, 1H), 7.15 (t, J = 5.8 Hz, 1H), 7.07-7.06 (m, 1H), 6.79 (d, J = 2.1 Hz, 1H), 6.69-6.67 (m, 1H), 6.61-6.59 (m, 1H), 6.1 (br, 1H), 4.66 (br, 1H), 3.90-3.84 (m, 4H), 3.06-3.04 (m, 2H), 2.86-2.84 (m, 1H), 2.30 (s, 3H), 2.28 (br, 2H), 1.44-1.41 (m, 2H). LCMS m/z 441.4 [M + H$^+$] |

TABLE 39-continued

Method of preparation, structure and physicochemical data for compounds 311-320

| Compound | Method/Product | Amine | $^1$H NMR; LCMS m/z [M + H]$^+$ |
|---|---|---|---|
| 314 | Compound 244 from C189 | HCl | $^1$H NMR (DMSO-d$_6$) δ 9.66 (s, 1H), 7.28 (t, J = 8.8Hz, 1H), 7.15 (t, J = 7.68Hz, 1H), 7.09-7.07 (m, 1H), 6.80 (d, J = 2.1Hz, 1H), 6.69-6.67 (m, 1H), 6.62-6.59 (m, 1H), 5.95 (br, 1H), 4.76 (br, 1H), 3.94-3.84 (m, 3H), 3.09-3.06 (m, 1H), 2.88-2.82 (m, 1H), 2.30 (s, 2H), 1.45-1.42 (m, 1H). LCMS m/z 441 [M + H$^+$] |
| 315 | Compound 244 from C189$^2$ | | $^1$H NMR (DMSO-d$_6$) δ 12.5 (br, 1H), 9.66 (s, 1H), 7.27 (t, J = 8.8Hz, 1H), 7.16-7.06 (m, 2H), 6.81 (d, J = 1.88 Hz, 1H), 6.66-6.58 (m, 2H), 6.06 (br, 1H), 4.80 (br, 1H), 3.82 (d, J = 7.2 Hz, 2H), 3.14-3.12 (m, 2H), 2.89-2.87 (m, 1H), 2.32-2.30 (m, 3H), 1.90 (br, 2H), 1.50-1.41 (m, 5H). LCMS m/z 424.9 [M + H$^+$] |
| 316 | Compound 244 from C189 | | $^1$H NMR (DMSO-d$_6$) δ 9.2 (br, 1H), 7.26 (t, J = 9.0 Hz, 1H), 7.13-7.05 (m, 2H), 6.84 (d, J = 1.84 Hz, 1H), 6.64-6.56 (m, 2H), 5.88 (br, 1H), 4.72-4.70 (m, 1H), 3.80-3.78 (m, 2H), 3.12-3.09 (m, 2H), 2.79-2.69 (m, 1H), 2.67-2.64 (m, 2H), 2.29 (s, 3H), 1.95-1.90 (m, 2H), 1.37-1.23 (m, 5H). LCMS m/z 439 [M + H$^+$] |

TABLE 39-continued

Method of preparation, structure and physicochemical data for compounds 311-320

| Compound | Method/Product | Amine | $^{1}$H NMR; LCMS m/z [M + H]$^{+}$ |
|---|---|---|---|
| 317 | <br>Compound 244 from C189[2] | | $^{1}$H NMR (DMSO-d$_{6}$) δ 12.5 (br, 1H), 9.7 (br, 1H), 7.26 (t, J = 8.7 Hz, 1H), 7.22-6.97 (m, 2H), 6.87 (br, 1H), 6.67-6.47 (m, 2H), 4.22 (br, 2H), 3.83-3.81 (m, 2H), 3.13-2.97 (m, 2H), 2.90-2.88 (m, 1H), 2.30 (s, 3H), 1.96-1.90 (m, 2H), 1.41-1.38 (m, 2H). LCMS m/z 411 [M + H$^{+}$] |
| 318 | <br>Compound 244 from C189[2] | <br>HCl | $^{1}$H NMR (DMSO-d$_{6}$) δ 12.5 (br, 1H), 9.6 (br, 1H), 7.26 (t, J = 8.7 Hz, 1H), 7.15-7.05 (m, 2H), 6.81 (d, J = 2.2 Hz, 1H), 6.66-6.58 (m, 2H), 6.05 (br, 1H), 4.68 (t, J = 6.7 Hz, 1H), 3.82 (d, J = 8 Hz, 1H), 3.12-2.89 (m, 3H), 2.30 (s, 3H), 1.98 (br, 2H), 1.50-1.60 (m, 6H). LCMS m/z 425.2 [M + H$^{+}$] |

TABLE 39-continued

Method of preparation, structure and physicochemical data for compounds 311-320

| Compound | Method/Product | Amine | $^1$H NMR; LCMS m/z [M + H]$^+$ |
|---|---|---|---|
| 319 | Compound 244 from C189 | | $^1$H NMR (DMSO-d$_6$) δ 12.4 (br, 1H), 7.30 (t, J = 8.4 Hz, 1H), 7.18-7.10 (m, 3H), 6.70 (brs, 2H), 4.76 (br, 1H), 3.79-3.78 (m, 2H), 3.14-3.13 (m, 2H), 2.88-2.66 (m, 3H), 2.30 (s, 3H), 1.80-1.70 (m, 2H), 1.43-1.36 (m, 2H), 1.35 (d, J = 5.5 Hz, 3H). LCMS m/z 439 [M + H$^+$] |
| 320 | Compound 244 from C189 | | $^1$H NMR (DMSO-d$_6$) δ 12.5 (br, 1H), 9.6 (s, 1H), 7.26 (t, J = 8.8 Hz, 1H), 7.14 (d, J = 8.0 Hz, 1H), 7.05-7.04 (m, 1H), 6.83 (d, J = 2.12 Hz, 1H), 6.62 (d, J = 8.8 Hz, 1H), 6.57 (dd, J = 8.4, 2.1 Hz, 1H), 6.70 (brs, 2H), 3.81-3.80 (m, 2H), 3.79-3.63 (m, 2H), 3.12-3.06 (m, 2H), 2.97-2.92 (m, 1H), 2.82-2.79 (m, 1H), 2.29 (s, 3H), 2.07-1.98 (m, 2H), 1.37-1.34 (m, 2H), 1.15 (d, J = 7.0 Hz, 3H). LCMS m/z 439 [M + H$^+$] |

[1]Benzyl ester was removed during the hydrogenation/benzyl ether deprotection step.

[2]t-Butyl ester deprotection was performed with HCl in EtOAc.

Compounds 321-324

Compounds 321-324 (Table 40) were prepared in three steps from intermediate S30 and the appropriate amine according to the method described for compound 254. Any modifications to methods are noted in Table 40 and accompanying footnotes.

TABLE 40

Method of preparation, structure, physicochemical data for compounds 321-324

| Compound | Method/Product | Amine | ¹H NMR; LCMS m/z [M + H]⁺ |
|---|---|---|---|
| 321 | Compound 254 from S30 | HCl | ¹H NMR (DMSO-d₆) δ 9.82 (s, 1H), 7.28 (dd, J = 9.8, 8.3 Hz, 1H), 7.18 (dd, J = 7.7, 2.2 Hz, 1H), 7.09 (ddd, J = 7.8, 5.0, 2.2 Hz, 1H), 6.93 (d, J = 2.4 Hz, 1H), 6.69-6.63 (m, 2H), 4.35-4.22 (m, 4H), 3.77-3.69 (m, 2H), 3.57-3.45 (m, 1H), 3.32-3.22 (m, 3H), 2.96 (s, 1H), 2.31 (s, 3H), 1.50-1.45 (m, 4H). LCMS m/z 437.2 [M + H⁺] |
| 322 | Compound 254 from S30 | | ¹H NMR (DMSO-d₆) δ 9.83 (bs, 1H), 7.3-7.25 (m, 1H), 7.2-7.19 (m 1H), 7.12-7.1 (m, 2H), 6.94 (d, J = 2.3 Hz, 1H), 6.71-6.63 (m, 2H), 4.66-4.58 (m, 2H), 4.32-4.24 (m, 2H), 3.72-3.69 (m, 2H), 3.31-3.25 (m, 2H), 2.97-2.89 (m, 1H), 2.32 (s, 3H), 1.55-1.45 (m, 4H). LCMS m/z 455.1 [M + H⁺] |
| 323 | Compound 254 from S30 | HCl | ¹H NMR (DMSO-d₆) δ 7.28 (t, J = 9.0 Hz, 1H), 7.19 (s, 1H), 7.11 (s, 1H), 6.95 (d, J = 2.4 Hz, 1H), 6.73 (dd, J = 9.1, 2.4 Hz, 1H), 6.66 (d, J = 9.0 Hz, 1H), 3.72 (s, 3H), 3.53 (dt, J = 10.5, 7.6 Hz, 2H), 3.44 (s, 1H), 3.30-3.18 (m, 3H), 3.10 (q, J = 7.2 Hz, 1H), 2.32 (s, 3H), 2.17-2.06 (m, 2H), 1.59-1.54 (m, 3H), 1.40-1.39 (m, 1H). LCMS m/z 451.2 [M + H⁺] |

TABLE 40-continued

Method of preparation, structure, physicochemical data for compounds 321-324

| Compound | Method/Product | Amine | $^1$H NMR; LCMS m/z [M + H]$^+$ |
|---|---|---|---|
| 324 | Compound 254 from S30 | | $^1$H NMR (DMSO-d$_6$) δ 9.87 (bs, 1H), 7.28 (t, J = 9.0 Hz, 1H), 7.19 (t, J = 5.5 Hz, 1H), 7.11 (s, 1H), 6.95 (d, J = 2.4 Hz, 1H), 6.73 (dd, J = 9.0, 2.4 Hz, 1H), 6.66 (d, J = 9.0 Hz, 1H), 3.74-3.71 (m, 3H), 3.56-3.48 (m, 2H), 3.44 (bs, 1H), 3.31-3.18 (m, 4H), 3.11-3.08 (m, 1H), 2.32 (s, 3H), 2.17-2.06 (m, 2H), 1.62-1.54 (m, 3H), 1.38 (d, J = 12.8 Hz, 1H). LCMS m/z 451.2 [M + H$^+$] |

Compounds 325-330

Compounds 325-330 (Table 41) were prepared in five steps from intermediate C65 and the appropriate boronic acid according to the method described for compound 253. Any modifications to methods are noted in Table 41 and accompanying footnotes.

TABLE 41

Method of preparation, structure, physicochemical data for compounds 325-330

| Compound | Method/Product | Boronic acid | $^1$H NMR; LCMS m/z [M + H]$^+$ |
|---|---|---|---|
| 325 | Compound 253 from C65 | | $^1$H NMR (400 MHz, DMSO-d$_6$) δ 13.9 (bs, 1H), 9.75 (bs, 1H), 7.59-7.54 (m, 1H), 7.33 (t, J = 8.04 Hz, 1H,), 7.16 (d, J = 9.04, 1H), 7.08 (d, J = 7.52 Hz, 1H,), 6.84 (d, J = 1.6 Hz 1H), 6.65-6.59 (m, 2H), 6.24 (bs, 1H) 3.83 (d, J = 9.76 Hz, 2H), 3.75 (d, J = 3.96, 2H), 3.03 (bs, 1H), 2.77-2.66 (m, 1H), 2.07 (bs, 2H), 1.445-1.37 (m,2H), 0.88-0.86 (m, 4H). LCMS m/z 437.4 [M + H$^+$] |
| 326 | Compound 253 from C65 | | $^1$H NMR (400 MHz, DMSO-d$_6$) δ 9.95 (bs, 1H), 7.58 (dt, J = 10.8, 8.4 Hz, 3H), 7.45 (td, J = 9.1, 8.6, 4.2 Hz, 3H), 7.11 (t, J = 6.4 Hz, 3H), 6.84 (d, J = 2.3 Hz, 3H), 6.60-6.67 (m, 2H), 6.26 (s, 1H), 3.83 (d, J = 9.08 Hz, 2H), 3.74 (s, 2H), 3.09 (d, J = 10.28 Hz, 2H), 2.77 (s, 2H), 2.03 (bs, 2H), 1.33-1.46 (m, 2H), 1.03-1.08 (m, 2H), 1.08-1.03 (m, 4H). LCMS m/z 455.6 [M + H$^+$] |

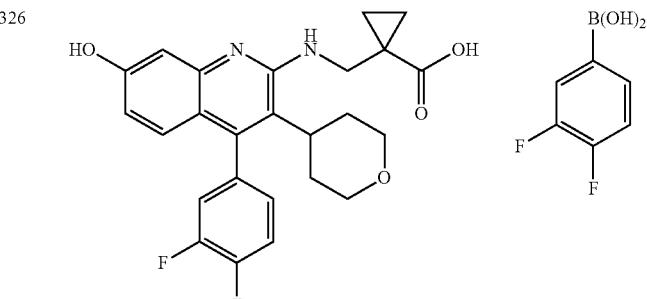

TABLE 41-continued

Method of preparation, structure, physicochemical data for compounds 325-330

| Compound | Method/Product | Boronic acid | $^1$H NMR; LCMS m/z [M + H]$^+$ |
|---|---|---|---|
| 327 | 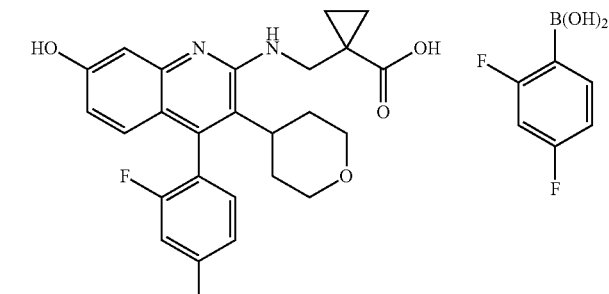 Compound 253 from C65 | | $^1$H NMR (400 MHz, DMSO-d$_6$) δ 9.90 (bs, 1H), 7.40 (td, J = 9.6, 4.9 Hz, 2H), 7.08 (d, J = 5.80 Hz, 3H), 6.83 (d, J = 1.68 Hz, 2H), 6.62-6.66 (m, 2H), 3.85-3.83 (m, 2H), 3.71 (s, 2H), 3.09 (s, 2H), 2.74 (s, 1H), 2.05 (s, 1H), 1.44 (d, J = 11.36 Hz, 2H), 1.06 (s, 3H), 0.97 (s,2H). LCMS m/z 455.6 [M + H$^+$] |
| 328 | 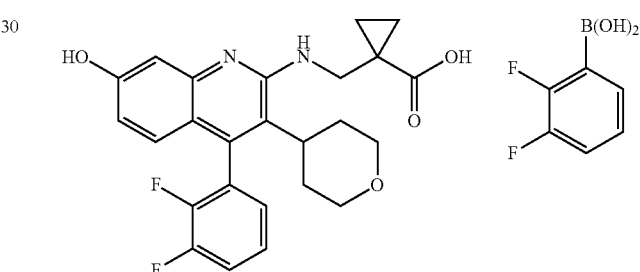 Compound 253 from C65 | | $^1$H NMR (400 MHz, DMSO-d$_6$) δ 13.61 (bs, 1H), 9.76 (bs, 1H), 7.49-7.47 (m, 1H), 7.39-7.36 (m, 1H), 7.27-7.26 (m, 1H), 6.86 (bs, 1H), 6.64 (bs, 2H), 6.25 (bs, 2H), 3.85-3.74 (m, 4H), 3.08 (bs, 2H), 2.77(bs, 2H), 1.40 (d, J = 12.9 Hz, 2H), 2.07 (bs, 2H), 1.42-1.39 (m, 2H), 1.23-1.06 (m, 4H). LCMS m/z 437.5 [M + H$^+$] |
| 329 | Compound 253 from C65 | | $^1$H NMR (400 MHz, DMSO-d$_6$) δ 13.66 (bs, 1H), 9.78 (bs, 1H), 7.49-7.44 (m, 1H), 7.41-7.35 (m, 1H), 7.29-7.23 (m, 1H), 6.85 (bs, 1H), 6.64 (bs, 2H), 6.28 (bs, 1H), 3.86-3.81 (m, 2H), 3.76 (s, 2H), 3.15-3.10 (m, 2H), 2.77 (s, 1H), 1.99 (bs, 2H), 1.41 (d, J = 8.48 Hz, 2H), 1.17-1.05 (m, 4H). LCMS m/z 455.47 [M + H$^+$] |
| 330 | Compound 253 from C65 | | $^1$H NMR (400 MHz, DMSO-d$_6$) δ 9.79 (bs, 1H), 7.64-7.58 (m, 1H), 7.41-7.36 (m, 1H), 7.15 (t, J = 6.52 Hz, 1H), 6.85 (s, 1H), 6.65 (s, 2H), 6.29 (s, 1H), 3.86-3.71 (m, 4H), 3.76 (s, 2H), 3.15-3.06 (m, 2H), 2.79 (s, 1H), 2.04 (bs, 2H), 1.42 (d, J = 11.76 Hz, 2H), 1.10-1.06 (m, 4H). LCMS m/z 455.5 [M + H$^+$] |

531

Preparation of C198

7-benzyloxy-2-chloro-4-(2-methyl-4-pyridyl)-3-
tetrahydropyran-4-yl-quinoline (C198)

532

-continued

Step 1: 4-chloro-3-(3,6-dihydro-2H-pyran-4-yl)-7-
methoxy-quinoline (C191)

To a suspension of C190 (20 g, 73.387 mmol) and 2-(3,6-dihydro-2H-pyran-4-yl)-4,4,5,5-tetramethyl-1,3,2-dioxaborolane (16.959 g, 80.726 mmol) in 1,4-dioxane (200 mL) and water (20 mL) was added Pd(dppf) Cl₂·dichloromethane (5.9931 g, 7.3387 mmol). The mixture was purged with argon and the reaction was heated for at 90° C. for 12 hours. The mixture was filtered through a Celite® plug, washed with EtOAc and concentrated. Purification by silica gel column chromatography with (40-50% EtOAc in hexane) afforded C191 (13 g, 64%). $^1$H NMR (400 MHz, DMSO-d$_6$) δ 8.68 (s, 1H), 8.14 (d, J=9.2 Hz, 1H), 7.46 (bs, 1H), 7.4 (d, J=9.2 Hz, 1H), 5.99 (bs, 1H), 4.26 (bs, 2H), 3.93 (s, 3H), 3.86 (t, J=5.32 Hz, 2H), 2.47 (bs, 2H). LCMS m/z 275.8 [M+H]$^+$ Step 2: 4-chloro-3-(3,6-dihydro-2H-pyran-4-yl)-7-
methoxy-1-oxido-quinolin-1-ium (C192)

To a solution of C191 (1 g, 3.6267 mmol) in dichloromethane (25 mL), m-CPBA (813.60 mg, 4.7147 mmol) was added at 0° C. and stirred at room temperature for 3 hours. The reaction was concentrated, the residue was washed with aqueous NaHCO₃ solution (25 mL), extracted with EtOAc (2×30 mL), and the organic phases combined, dried with MgSO₄ and concentrated. Purification by silica gel column chromatography (40-60% EtOAc in hexane) afforded C192 (850 mg, 69%). $^1$H NMR (400 MHz, DMSO-d$_6$) δ 8.54 (s, 1H), 8.18 (d, J 9.26 Hz, 1H), 7.93 (bs, 1H), 7.51 (d, J=7.68 Hz, 1H), 6.04 (bs, 1H), 4.23 (bs, 2H), 3.97 (s, 3H), 3.83 (t, J=5.2 Hz, 1H), 2.44 (bs, 2H). LCMS m/z 292.11 [M+H]$^+$

Step 3: 4-chloro-3-(3,6-dihydro-2H-pyran-4-yl)-7-methoxy-quinolin-2-ol (C193)

To a solution of C192 (6 g, 20.567 mmol) in water (50 mL) and THF (10 mL), methanesulfonyl chloride (4.7120 g, 3.1838 mL, 41.134 mmol) was added and the reaction was stirred at room temperature for 15 minutes. The mixture was diluted with EtOAc (30 mL), washed successively with water (2×20 mL) and brine, dried over $Na_2SO_4$ and concentrated. Purification by silica gel column chromatography (50-60% EtOAc and hexane) afforded C193 (5 g, 77%). $^1$H NMR (400 MHz, DMSO-$d_6$) δ 11.95 (s, 1H), 7.79 (d, J=9.0 Hz, 1H), 6.91 (dd, J=9.0, 2.5 Hz, 1H), 6.85 (d, J=2.5 Hz, 1H), 5.71 (d, J=2.9 Hz, 1H), 4.19 (q, J=2.8 Hz, 2H), 3.80 (t, J=5.4 Hz, 2H), 3.33 (s, 2H), 2.27-2.20 (m, 2H). LCMS m/z 292.0 [M+H]$^+$

Step 4: 3-(3,6-dihydro-2H-pyran-4-yl)-7-methoxy-4-(2-methyl-4-pyridyl)quinolin-2-ol (C194)

To a solution of (2-methyl-4-pyridyl)boronic acid (3.5206 g, 25.708 mmol) and C193 (5 g, 17.139 mmol) in 1,4 dioxane (10 mL) and water (2 mL) was added $K_2CO_3$ (5.9217 g, 42.847 mmol). Then, under inert atmosphere, Pd(PPh$_3$)$_4$ was added and the reaction was heated at 90° C. for 12 hours. The mixture was filtered through celite plug, washed with 10% MeOH in dichloromethane and concentrated. Purification by silica gel column chromatography (50-60% EtOAc and hexane) afforded C194 (5 g, 80%). $^1$H NMR (400 MHz, DMSO-$d_6$) δ 11.87 (s, 1H), 8.52 (d, J=5.0 Hz, 1H), 7.16 (s, 1H), 7.12-7.06 (m, 1H), 6.87 (d, J=2.5 Hz, 1H), 6.82 (d, J=9.0 Hz, 1H), 6.72 (dd, J=9.0, 2.5 Hz, 1H), 5.29 (s, 1H), 3.80 (d, J=6.0 Hz, 5H), 3.58-3.51 (m, 2H), 2.14 (s, 2H). LCMS m/z 349.2 [M+H]$^+$

Step 5: 7-methoxy-4-(2-methyl-4-pyridyl)-3-tetrahydropyran-4-yl-quinolin-2-ol (C195)

To a stirred solution of C194 (3 g, 8.6109 mmol) in AcOH (10 mL) and MeOH (20 mL), Pd (4.5819 g, 10% w/w, 4.3055 mmol) was added at room temperature. The reaction was purged with hydrogen gas, kept at 45 psi and stirred at room temperature for 12 hours. The mixture was filtered through a Celite® plug, washed with EtOH and concentrated to afford C195 (2.5 g, 52%). $^1$H NMR (400 MHz, DMSO-$d_6$) δ 11.76 (s, 1H), 8.61 (d, J=5.0 Hz, 1H), 7.18 (s, 1H), 7.11 (d, J=5.1 Hz, 1H), 6.85 (d, J=2.5 Hz, 1H), 6.71-6.64 (m, 1H), 6.62 (d, J=9.0 Hz, 1H), 3.79 (d, J=10.0 Hz, 5H), 3.00 (t, J=11.7 Hz, 2H), 2.55 (s, 3H), 2.38 (d, J=11.1 Hz, 1H), 1.70 (s, 5H), 1.25 (d, J=11.6 Hz, 2H), 1.09 (t, J=7.1 Hz, 1H). LCMS m/z 351.0 [M+H]$^+$

Step 6: 2-chloro-7-methoxy-4-(2-methyl-4-pyridyl)-3-tetrahydropyran-4-yl-quinoline (C196)

To a solution of C195 (4 g, 11.415 mmol) in POCl$_3$ (20 mL) was added DMF (1.6687 g, 1.7677 mL, 22.830 mmol), and the reaction was heated at 100° C. for 4 h. The mixture was concentrated, diluted with EtOAc (100 mL) and washed with a saturated aqueous solution of NaHCO$_3$ solution (~20 mL), and the organic phase was dried over $Na_2SO_4$ and concentrated. Purification by silica gel column chromatography (60% EtOAc in hexane) afforded C196 (3.5 g, 77%). $^1$H NMR (400 MHz, DMSO-$d_6$) δ 8.65 (d, J=5.0 Hz, 1H), 7.40 (d, J=2.6 Hz, 1H), 7.29 (s, 1H), 7.24-7.15 (m, 2H), 6.99 (d, J=9.3 Hz, 1H), 3.91 (s, 3H), 3.89-3.81 (m, 2H), 3.08 (s, 2H), 2.89 (s, 1H), 2.57 (s, 3H), 2.54 (s, 1H), 1.47 (d, J=12.5 Hz, 2H). LCMS m/z 93.02 [M+H]$^+$

Step 7: 2-chloro-4-(3-methyl-4-pyridyl)-3-tetrahydropyran-4-yl-quinolin-7-ol (C197)

To a mixture of AlCl$_3$ (2.1691 g, 16.267 mmol) in dichloromethane (10 mL), 1-dodecanethiol (1.37 g, 1.63 mL, 6.78 mmol) was added at 0° C. and the mixture was stirred for 30 min. Then, a solution of C196 (1 g, 2.7111 mmol) in dichloromethane (10 mL) was added at 0° C. and the mixture was stirred at RT for 12 h. The mixture was poured into ice water, an aqueous solution of NaHCO$_3$ 1M (~16 mL) was added and extracted with dichloromethane (150 mL). The combined organic phases were dried over $Na_2SO_4$ and concentrated. Purification by silica gel column chromatography (20% MeOH in dichloromethane) afforded C197 (750 mg, 68%). $^1$H NMR (400 MHz, DMSO-$d_6$) δ 10.47 (s, 1H), 8.65 (d, J=5.0 Hz, 1H), 7.29 (s, 1H), 7.20 (dd, J=14.9, 3.9 Hz, 2H), 7.10 (dd, J=9.2, 2.5 Hz, 1H), 6.94 (d, J=9.1 Hz, 1H), 3.85 (d, J=10.4 Hz, 2H), 3.56 (q, J=7.2 Hz, 1H), 3.08 (qd, J=7.2, 4.6 Hz, 7H), 2.57 (s, 3H), 1.45 (d, J=12.5 Hz, 2H), 1.34 (s, 1H), 1.22 (dt, J=29.3, 7.2 Hz, 13H). LCMS m/z 355.0 [M+H]$^+$

Step 8: 7-benzyloxy-2-chloro-4-(2-methyl-4-pyridyl)-3-tetrahydropyran-4-yl-quinoline (C198)

To a stirred solution of C197 (1 g, 2.81 mmol) in dry DMF (10 mL), NaH (225.44 mg, 60% w/w, 5.637 mmol) was added at 0° C., and the mixture was stirred at room temperature for 10 minutes. Then, benzyl chloride (678 mg, 0.616 mL, 5.355 mmol) was added and the reaction was stirred at room temperature for 4 hours. The mixture was concentrated, diluted with water, extracted with EtOAc (10×2 mL), the organic phases were combined, washed sequentially with water (10 mL) and brine (10 mL), dried over MgSO$_4$ and concentrated. Purification by silica gel column chromatography (50% EtOAc in dichloromethane) afforded C198 (1 g, 76%). $^1$H NMR (400 MHz, DMSO-$d_6$) δ 8.65 (d, J=4.9 Hz, 1H), 7.52-7.46 (m, 3H), 7.40 (dd, J=8.3, 6.5 Hz, 2H), 7.34 (dd, J=8.5, 5.9 Hz, 1H), 7.30-7.23 (m, 2H), 7.23-7.18 (m, 1H), 7.00 (d, J=9.3 Hz, 1H), 5.30 (s, 2H), 3.85 (d, J=10.5 Hz, 2H), 3.07 (s, 2H), 2.89 (s, 1H), 2.73 (s, 1H), 2.57 (s, 3H), 1.47 (d, J=12.4 Hz, 2H). LCMS m/z 445.0 [M+H]$^+$

Compounds 331-332

Compounds 331-332 (Table 42) were prepared in two steps from intermediate C198 and the appropriate amine according to the method described for compound 254 without performing the final saponification step. Any modifications to methods are noted in Table 42 and accompanying footnotes.

TABLE 42

Method of preparation, structure, physicochemical data for compounds 331-332

| Compound | Method/Product | Amine | ¹H NMR; LCMS m/z [M + H]⁺ |
|---|---|---|---|
| 331 | <br>Compound 254 from C198[1] | | ¹H NMR (400 MHz, DMSO-d₆) δ 9.71 (s, 1H), 8.58 (d, J = 5.1 Hz, 1H), 7.17 (s, 1H), 7.10 (d, J = 5.0 Hz, 1H), 6.89 (s, 1H), 6.66-6.55 (m, 2H), 6.38 (s, 1H), 3.96 (d, J = 6.0 Hz, 2H), 3.81 (d, J = 11.0 Hz, 2H), 3.51 (t, J = 6.7 Hz, 2H), 3.09 (s, 3H), 2.74 (s, 1H), 2.55 (s, 3H), 1.99 (s, 3H), 1.36 (d, J = 12.8 Hz, 2H). LCMS m/z 442 [M + H⁺] |
| 332 | <br>Compound 254 from C198[1] | | ¹H NMR (400 MHz, DMSO-d₆) δ 9.64 (s, 1H), 8.57 (d, J = 5.0 Hz, 1H), 7.15 (s, 1H), 7.08 (d, J = 5.0 Hz, 1H), 6.85 (d, J = 2.2 Hz, 1H), 6.62-6.52 (m, 2H), 6.27 (s, 1H), 4.21 (t, J = 7.9 Hz, 2H), 3.80 (d, J = 10.3 Hz, 3H), 3.70 (t, J = 7.7 Hz, 4H), 3.47 (t, J = 6.1 Hz, 2H), 3.12 (s, 3H), 2.75 (s, 1H), 2.54 (s, 3H), 1.92 (s, 2H), 1.35 (d, J = 12.8 Hz, 2H). LCMS m/z 449 [M + H⁺] |

[1]Saponification was not necessary for these compounds.

Compound 333

(2S)-2-[[4-(4-fluorophenyl)-7-hydroxy-3-isoprope-nyl-2-quinolyl]amino]propanoic acid (333)

Step 1: tert-butyl (2S)-2-[[7-benzyloxy-4-(4-fluoro-phenyl)-3-isopropenyl-2-quinolyl]amino]propanoate (C199)

To a solution of S32 (150 mg, 0.3892 mmol) and L-ala-nine tert-butyl ester hydrochloride (212.11 mg, 1.1676 mmol) in dichloromethane (6 mL), DIEA (251.51 mg, 0.3493 mL, 1.9460 mmol) and PyBrop (544.31 mg, 1.1676 mmol) were added and the reaction was heated at 45° C. for 18 hours. The mixture was diluted with dichloromethane (5 mL), washed successively with an aqueous solution of NaHCO$_3$ (5 mL) and water (10 mL), dried over Na$_2$SO$_4$ and concentrated. Purification by silica gel chromatography (10% EtOAc in hexanes) afforded C199 (115 mg, 51%). LCMS m/z 513.4 [M+H]$^+$

Step 2: tert-butyl (2S)-2-[[4-(4-fluorophenyl)-7-hydroxy-3-isopropenyl-2-quinolyl]amino]propanoate (C200)

To a solution of C199 (620 mg, 1.21 mmol) in MeOH (3 mL), 10% Pd/C (128.7 mg, 50% w/w, 0.726 mmol) was added under nitrogen. The reaction was purged with hydro-gen and stirred at room temperature for 1 hours. The mixture was filtered through a Celite® plug, washed with MeOH (~15 mL) and concentrated to afford C200 (470 mg, 64%). LCMS m/z 423.0 [M+H]$^+$

Step 3: (2S)-2-[[4-(4-fluorophenyl)-7-hydroxy-3-isopropenyl-2-quinolyl]amino]propanoic acid (333)

Through a solution of C200 (370 mg, 0.6130 mmol) in 1,4-Dioxane (10 mL), dry HCl(gas) (using NaCl+conc. H$_2$SO$_4$) was purged for 15 minutes at 0° C. and then stirred at room temperature for 1.5 hours. The mixture was con-centrated and purified by reverse-phase HPLC (Method: C18 YMC Triart Actus column, 20×250 mm, 5 micron. Gradient: acetonitrile in water with 20 mM Ammonium Bicarbonate) to afford 333 (132 mg, 58%). $^1$H NMR (400 MHz, DMSO-d$_6$) δ 9.98 (bs, 1H), 7.29-7.27 (m, 4H), 6.86-6.83 (m, 2H), 6.65-6.63 (m, 1H), 5.94 (bs, 1H), 5.27 (s, 1H), 4.94 (s, 1H), 4.60-4.59 (m, 1H), 1.67 (s, 3H), 1.44 (d, J=7.04, 3H). LCMS m/z 367.09 [M+H]$^+$

Compound 334

3-[[4-(4-fluorophenyl)-8-hydroxy-3-tetrahydropy-ran-4-yl-1-isoquinolyl]oxy]benzoic acid (334)

S33

-continued

C201

334

Step 1: 3-[[8-benzyloxy-4-(4-fluorophenyl)-3-tetra-hydropyran-4-yl-1-isoquinolyl]oxy]-benzoic acid (C201)

A mixture of S33 (240 mg, 0.5358 mmol), 3-hydroxy-benzoic acid (240 mg, 1.738 mmol) and Cs$_2$CO$_3$ (900 mg, 2.762 mmol) in DMSO (5.3 mL) was stirred and heated at 140° C. under nitrogen for 1 week. The mixture filtered, concentrated. Purification by reverse phase C18 chromatog-raphy (water: acetonitrile with 0.1% TFA modifier) afforded C201 (111 mg, 30%). $^1$H NMR (300 MHz, Chloroform-d) δ 8.00 (s, 1H), 7.91 (dd, J=6.5, 2.2 Hz, 1H), 7.56-7.51 (m, 3H), 7.49-7.24 (m, 6H), 7.21-7.15 (m, 5H), 6.96 (d, J=8.0 Hz, 1H), 6.80 (dd, J=8.4, 0.9 Hz, 1H), 5.26 (s, 2H), 3.83 (dd, J=11.4, 4.1 Hz, 3H), 3.18 (t, J=11.7 Hz, 3H), 2.66-2.54 (m, 1H), 1.85 (tt, J=12.5, 6.4 Hz, 2H), 1.35 (d, J=13.2 Hz, 2H). LCMS m/z 550.4 [M+H]$^+$

Step 2: 3-[[4-(4-fluorophenyl)-8-hydroxy-3-tetrahy-dropyran-4-yl-1-isoquinolyl]oxy]benzoic acid (334)

A solution of C201 (111 mg, 0.160 mmol) in MeOH (8 mL) was added under nitrogen to palladium on carbon (85 mg of 10% w/w, 0.079 mmol). The reaction was purged with hydrogen and stirred at room temperature for 2 hours. The mixture was filtered through a Celite plug and concentrated.

Purification by reverse phase HPLC (Method: C18 Waters Sunfire column, 30×150 mm, 5 micron. Gradient: MeCN in water with 0.2% formic acid) afforded 334 (63.3 mg, 77%). $^1$H NMR (300 MHz, DMSO-d$_6$) δ 13.10 (s, OH), 10.07 (s, 1H), 7.85-7.76 (m, 2H), 7.59 (t, J=7.8 Hz, 1H), 7.54-7.43 (m, 2H), 7.39-7.28 (m, 4H), 7.00 (dd, J=7.9, 1.0 Hz, 1H), 6.58 (dd, J=8.4, 1.0 Hz, 1H), 3.69 (dd, J=11.3, 4.1 Hz, 2H), 3.04 (t, J=11.4 Hz, 2H), 2.56 (s, 0H), 1.59 (dd, J=12.3, 4.2

Hz, 1H), 1.33 (d, J=12.8 Hz, 2H). LCMS m/z 460.48 [M+H]$^+$

Compounds 335-336

Compounds 335-336 (Table 43) were prepared in two steps from intermediate S33 and the appropriate phenol according to the method described for 334. Any modifications to methods are noted in Table 43 and accompanying footnotes.

TABLE 43

| Method of preparation, structure, physicochemical data for compounds 335-336 | | | |
|---|---|---|---|
| Compound | Method/Product | Phenol | $^1$H NMR; LCMS m/z [M + H]$^+$ |
| 335 | <br>Compound 334 from S33 | | $^1$H NMR (300 MHz, DMSO-d$_6$) δ 12.92 (s, 1H), 10.15 (s, 1H), 8.03 (d, J = 8.6 Hz, 2H), 7.47 (t, J = 8.1 Hz, 1H), 7.41-7.26 (m, 6H), 6.98 (d, J = 7.8 Hz, 1H), 6.59 (d, J = 8.4 Hz, 1H), 3.73 (d, J = 10.9 Hz, 2H), 3.06 (t, J = 11.7 Hz, 2H), 2.55 (m, 1H), 1.71-1.52 (m, 2H), 1.35 (d, J = 13.1 Hz, 2H). LCMS m/z 460.48 [M + H$^+$] |
| 336 | <br>Compound 334 from S33[1, 2] | | $^1$H NMR (300 MHz, Chloroform-d and Methanol-d$_4$) δ 8.06-7.90 (m, 2H), 7.50 (ddd, J = 13.5, 8.4, 7.6 Hz, 2H), 7.22 (d, J = 7.1 Hz, 4H), 7.05 (dd, J = 7.8, 1.0 Hz, 1H), 6.77 (dd, J = 8.4, 1.0 Hz, 1H), 3.93-3.73 (m, 2H), 3.31-3.10 (m, 2H), 2.63 (ddd, J = 11.5, 7.8, 3.3 Hz, 1H), 1.74 (qd, J = 12.3, 11.9, 4.2 Hz, 2H), 1.37 (d, J = 13.3 Hz, 2H). LCMS m/z 477.93 [M + H$^+$] |

[1]Nucleophilic aromatic substitution was performed in DMF. The conditions allowed for one pot hydrolysis of ester.

[2]1.0 equivalent of acetic acid was used during the benzyl ether deprotection.

Preparation of C202

1-(8-(benzyloxy)-4-(3,4-difluorophenyl)-3-(tetra-
hydro-2H-pyran-4-yl)isoquinolin-1-yl)-1,4-diazabi-
cyclo[2.2.2]octan-1-ium (C202)

S34

DABCO
TFAA

C202

To a solution of S34 (1.82 g, 4.067 mmol) and 1,4-diazabicyclo[2.2.2]octane (2.4 g, 21.40 mmol) in dichloromethane (40 mL), TFAA (2.4 mL, 17.27 mmol) was added at 0° C. The reaction was stirred at room temperature for 1 hour. The mixture was concentrated and purified by reverse phase C18 chromatography (10 to 100% acetonitrile in water, 0.1% TFA modifier) to afford C202 (2620 mg, 82%) LCMS m/z 542.37 [M+H]$^+$

Compound 337

3-[[4-(3,4-difluorophenyl)-8-hydroxy-3-tetrahydro-
pyran-4-yl-1-isoquinolyl]oxy]cyclobutanecarboxylic
acid (337)

C202

NaH

-continued

C203

H$_2$, Pd/C

337

Step 1: 3-[[8-benzyloxy-4-(3,4-difluorophenyl)-3-tetrahydropyran-4-yl-1-isoquinolyl]oxy]-cyclobutanecarboxylic acid (C203)

To a solution of 3-hydroxycyclobutanecarboxylic acid (180 mg, 1.55 mmol) in anhydrous DMSO (5 mL), heptane prewashed NaH (120 mg, 3.000 mmol) was added and the reaction was stirred at room temperature for 10 minutes. Then, C202 was added (400 mg, 0.519 mmol) and the reaction was stirred at room temperature for 2 hours. TFA (250 μL, 3.245 mmol) was added and the mixture was purified by C18 reverse phase chromatography (10-100% acetonitrile in water with 0.1% TFA) to afford C203 (140 mg, 48%). LCMS m/z 546.24 [M+H]$^+$

Step 2: 3-[[4-(3,4-difluorophenyl)-8-hydroxy-3-tetrahydropyran-4-yl-1-isoquinolyl]oxy]-cyclobutanecarboxylic acid (337)

To a solution of C203 (60 mg, 0.105 mmol) in EtOH (5 mL), 10% palladium on carbon (50 mg, 0.047 mmol) was added. The reaction was purged with hydrogen and stirred at room temperature for 2 hours. The mixture was filtered and concentrated. Purification by C18 reverse phase chromatography (10-100% acetonitrile in water with 0.1% formic acid) afforded 337 (26.1 mg, 52%). $^1$H NMR (300 MHz, Chloroform-d) δ 9.15 (s, 1H), 7.43 (t, J=8.1 Hz, 1H), 7.39-7.25 (m, 1H), 7.07 (ddd, J=10.4, 7.7, 2.0 Hz, 1H), 7.03-6.89 (m, 2H), 6.66 (dd, J=8.3, 1.0 Hz, 1H), 5.87-5.69 (m, 1H), 4.05 (d, J=11.1 Hz, 2H), 3.35 (h, J=6.8 Hz, 3H), 3.07 (ddt, J=11.6, 7.3, 4.3 Hz, 2H), 2.83-2.59 (m, 3H), 2.16 (q, J=12.2 Hz, 2H), 1.47 (d, J=13.2 Hz, 2H). LCMS m/z 456.15 [M+H]$^+$ Compounds 338-342

Compounds 338-342 (Table 44) were prepared in two steps from intermediate C202 according to the method described for compound 337. Any modifications to methods are noted in Table 44 and accompanying footnotes.

TABLE 44

| Method of preparation, structure, physicochemical data for compounds 338-342 | | | |
|---|---|---|---|
| Compound | Method/Product | Alcohol | $^1$H NMR; LCMS m/z [M + H]$^+$ |
| 338 | <br>Compound 337 from C202[1] | | $^1$H NMR (400 MHz, Chloroform-d) δ 7.43 (t, J = 8.0 Hz, 1H), 7.31 (d, J = 16.1 Hz, 1H), 7.11-7.02 (m, 1H), 6.96 (d, J = 7.8 Hz, 2H), 6.67 (d, J = 8.3 Hz, 1H), 5.92 (q, J = 6.5 Hz, 1H), 4.04 (dt, J = 9.9, 4.3 Hz, 2H), 3.38 (p, J = 13.3, 10.9 Hz, 3H), 3.28-3.01 (m, 4H), 2.69 (tt, J = 11.6, 3.7 Hz, 1H), 2.15 (dt, J = 14.0, 6.4 Hz, 2H), 1.46 (s, 1H). LCMS m/z 474.22 [M + H$^+$] |
| 339 | <br>Compound 337 from C202 | | $^1$H NMR (400 MHz, Methanol-d$_4$) δ 7.53-7.36 (m, 2H), 7.19 (ddd, J = 11.1, 7.7, 2.1 Hz, 1H), 7.05 (ddt, J = 8.1, 3.9, 1.7 Hz, 1H), 6.91 (dd, J = 7.9, 1.0 Hz, 1H), 6.63 (dd, J = 8.4, 1.0 Hz, 1H), 5.51 (p, J = 7.0 Hz, 1H), 3.97 (dd, J = 10.9, 5.0 Hz, 2H), 3.42-3.23 (m, 4H), 2.70 (dtd, J = 13.4, 9.7, 8.8, 4.8 Hz, 1H), 2.55 (s, 2H), 2.15 (qt, J = 12.9, 4.6 Hz, 2H), 1.53 (d, J = 13.2 Hz, 2H). LCMS m/z 472.2 [M + H$^+$] |

TABLE 44-continued

Method of preparation, structure, physicochemical data for compounds 338-342

| Compound | Method/Product | Alcohol | $^1$H NMR; LCMS m/z [M + H]+ |
|---|---|---|---|
| 340 | Compound 337 from C202 | | LCMS m/z 500.24 [M + H+] |
| 341 | Compound 337 from C202 | | $^1$H NMR (400 MHz, Methanol-d4) δ 7.42 (tdd, J = 8.4, 6.1, 5.1 Hz, 2H), 7.19 (ddd, J = 11.3, 7.7, 2.1 Hz, 1H), 7.10-7.01 (m, 1H), 6.88 (ddd, J = 7.9, 1.8, 1.0 Hz, 1H), 6.62 (ddd, J = 8.4, 1.8, 1.0 Hz, 1H), 4.80 (d, J = 7.2 Hz, 1H), 4.71 (d, J = 6.7 Hz, 1H), 4.03-3.90 (m, 2H), 3.27-2.91 (m, 2H), 2.79-2.65 (m, 1H), 2.58-2.39 (m, 2H), 2.32-2.08 (m, 4H), 1.63-1.47 (m, 2H). LCMS m/z 470.26 [M + H+] |

TABLE 44-continued

| Compound | Method/Product | Alcohol | $^1$H NMR; LCMS m/z [M + H]$^+$ |
|---|---|---|---|
| 342 | Compound 337 from C202[2] | | 1H NMR (400 MHz, Methanol-d4) δ 7.49-7.35 (m, 2H), 7.25-7.16 (m, 1H), 7.11-7.01 (m, 1H), 6.90 (dd, J = 7.8, 0.9 Hz, 1H), 6.62 (dd, J = 8.3, 0.9 Hz, 1H), 5.87 (t, J = 6.9 Hz, 1H), 3.97 (dt, J = 9.4, 4.1 Hz, 2H), 3.31 (dt, J = 3.3, 1.7 Hz, 2H), 3.02 (dd, J = 20.1, 7.0 Hz, 4H), 2.71 (tt, J = 11.7, 3.8 Hz, 1H), 2.15 (qt, J = 12.5, 4.5 Hz, 2H), 1.62-1.46 (m, 2H). LCMS m/z 474.27 [M + H$^+$] |

[1]Hydrolysis of ester observed during nucleophilic aromatic substitution step.
[2]342 was isolated by SFC from 338, stereochemistry unknown.

Compounds 343-344

Compounds 343-344 (Table 45) were prepared in three steps from intermediate S34 and the appropriate amine according to the method described for 244. Any modifications to methods are noted in Table 45 and accompanying footnotes.

TABLE 45

| Compound | Method/Product | Amine | $^1$H NMR; LCMS m/z [M + H]$^+$ |
|---|---|---|---|
| 343 | Compound 244 from S34[1] | | $^1$H NMR (400 MHz, Methanol-d$_4$) δ 7.35 (dt, J = 10.8, 8.4 Hz, 1H), 7.19 (t, J = 8.0 Hz, 1H), 7.10 (ddd, J = 11.3, 7.8, 2.1 Hz, 1H), 6.99 (ddd, J = 8.0, 4.0, 1.6 Hz, 1H), 6.72 (dd, J = 7.8, 1.0 Hz, 1H), 6.46 (dd, J = 8.3, 0.9 Hz, 1H), 4.79 (p, J = 7.7 Hz, 1H), 3.95 (dt, J = 12.1, 4.2 Hz, 2H), 3.36-3.25 (m, 2H), 3.15 (ddd, J = 6.6, 5.2, 3.0 Hz, 1H), 2.80 (ddt, J = 12.6, 7.9, 4.1 Hz, 2H), 2.66-2.54 (m, 1H), 2.34 (ddd, J = 12.5, 9.8, 7.1 Hz, 2H), 2.19 (qt, J = 12.4, 4.4 Hz, 2H), 1.46 (d, J = 13.5 Hz, 2H). LCMS m/z 455.05 [M + H$^+$] |

TABLE 45-continued

Method of preparation, structure and physicochemical data for compounds 343-344

| Compound | Method/Product | Amine | $^1$H NMR; LCMS m/z [M + H]$^+$ |
|---|---|---|---|
| 344 |  Compound 244 from S34[1] | | $^1$H NMR (400 MHz, Methanol-d$_4$) δ 7.56 (t, J = 8.1 Hz, 1H), 7.46 (dt, J = 10.7, 8.4 Hz, 1H), 7.26 (ddd, J = 10.3, 7.6, 2.1 Hz, 1H), 7.18-7.08 (m, 1H), 7.04 (d, J = 8.0 Hz, 1H), 6.57 (d, J = 8.1 Hz, 1H), 4.60 (p, J = 7.5 Hz, 1H), 4.08-3.93 (m, 2H), 3.23 (ddq, J = 9.5, 6.6, 3.1 Hz, 1H), 3.10 (p, J = 8.4 Hz, 1H), 2.86 (ddt, J = 11.8, 7.3, 4.0 Hz, 2H), 2.73 (ddd, J = 12.3, 7.5, 4.9 Hz, 1H), 2.48 (qd, J = 11.5, 8.5 Hz, 2H), 2.40-2.24 (m,3H), 2.19 (ddd, J = 11.0, 7.7, 2.3 Hz, 1H), 2.07-1.90 (m, 4H), 1.66 (d, J = 13.0 Hz, 2H). LCMS m/z 495.29 [M + H$^+$] |

Preparation of C211

1-(4-aza-1-azoniabicyclo[2.2.2]octan-1-yl)-8-benzy-
loxy-4-(3,4-difluorophenyl)-6-fluoro-3-tetrahydro-
pyran-4-yl-isoquinoline (C211)

-continued

C210

C211

Step 1:
1-benzyloxy-3-bromo-5-fluoro-2-iodo-benzene (C205)

To a suspension of C204 (14.5 g, 45.76 mmol), K₂CO₃ (10 g, 72.36 mmol) and NaI (1.74 g, 11.61 mmol) in acetone (130 mL), BnBr (5.8 mL, 48.76 mmol) was added and the reaction was stirred at room temperature for 18 hours. The mixture was filtered, washed with Et₂O (50 mL), and concentrated to afford C205 (19.4 g, 99%) as a light brown solid. ¹H NMR (400 MHz, Chloroform-d) δ 7.48 (d, J=7.5 Hz, 2H), 7.45-7.39 (m, 2H), 7.37-7.32 (m, 1H), 7.09 (dt, J=8.1, 2.2 Hz, 1H), 6.56 (dt, J=10.2, 2.2 Hz, 1H), 5.13 (s, 2H). LCMS m/z 405.67 [M+H]⁺

Step 2:
2-benzyloxy-6-bromo-4-fluoro-benzaldehyde (C206)

To a 1.3 M THF solution of isopropylmagnesium chloride (Lithium Chloride (I)) (2.65 mL of 1.3 M, 3.4450 mmol) in anhydrous THF (6 mL) at −60° C., a solution of C205 (1.2 g, 2.8009 mmol) in anhydrous THF (11 mL) was added dropwise over 5 minutes, and stirred for 1 hour. Then, 4-formylmorpholine (855.00 mg, 0.75 mL, 7.4264 mmol) was added. The mixture was stirred from −65° C. to −40° C. over 2 hours. MTBE (100 mL) was added followed by saturated aqueous NH₄Cl (20 mL), the organic phase was washed successively with saturated aqueous NH₄Cl (2×20 mL) and brine (2×20 mL), dried over Na₂SO₄ and concentrated. Purification by silica gel chromatography (0-15% EtOAc in heptane) afforded C206 (620 mg, 67%). ¹H NMR (300 MHz, Chloroform-d) δ 10.40 (s, 1H), 7.49-7.30 (m, 5H), 7.02 (dd, J=7.9, 2.2 Hz, 1H), 6.74 (dd, J=10.3, 2.2 Hz, 1H), 5.16 (s, 2H). LCMS m/z 331.0 [M+H]⁺

Step 3: 2-benzyloxy-4-fluoro-6-(2-tetrahydropyran-4-ylethynyl)benzaldehyde (C207)

Under nitrogen atmosphere, to a solution of C206 (165 mg, 0.4323 mmol) in anhydrous dioxane (2 mL), diisopropylamine (361.00 mg, 0.5 mL, 3.5675 mmol), C71 (118.80 mg, 0.12 mL, 0.6515 mmol), copper iodide (6.1 mg, 0.0320 mmol), Pd(PPh₃)Cl₂ (12.4 mg, 0.0176 mmol) and a 1 M THF solution of TBAF (0.63 mL of 1 M, 0.6300 mmol) were added and the reaction was heated at 50° C. for 5. MTBE (20 mL) and EtOAc (5 mL) were added, the mixture was washed with 5% aqueous NaHCO₃ (5×10 mL) and brine (2×10 mL), dried over Na₂SO₄, and concentrated. Purification by silica gel chromatography (0-45% EtOAc in heptane) afforded C207 (120 mg, 76%). ¹H NMR (300 MHz, Chloroform-d) δ 10.5 (s, 1H), 7.47-7.31 (m, 5H), 6.80 (dd, J=8.8, 2.3 Hz, 1H), 6.68 (dd, J=10.5, 2.3 Hz, 1H), 5.17 (s, 2H), 4.00-3.91 (m, 2H), 3.62-3.52 (m, 2H), 2.93 (sept, J=4.2 Hz, 1H), 2.00-1.88 (m, 2H), 1.86-1.72 (m, 2H), ¹⁹F NMR (282 MHz, Chloroform-d) δ −101.7 (t, J=9.7 Hz, 1F), LCMS m/z 339.2 [M+H]⁺

Step 4: 2-benzyloxy-4-fluoro-6-(2-tetrahydropyran-4-ylethynyl)benzaldehyde oxime (C208)

To a solution of C207 (718 mg, 2.12 mmol) in DCE (4.5 mL) and acetonitrile (7.5 mL) at 0° C., pyridine (3.42 g, 3.5 mL, 43.27 mmol) was added, followed by NH₂OH—HCl (440 mg, 6.3318 mmol) and stirred at 0° C. for 35 min. The mixture was diluted with EtOAc (100 mL) and water (50 mL), the organic phase was washed successively with an aqueous solution of HCl 1N (2×25 mL), water (25 mL), brine, dried over Na₂SO₄, and concentrated to give a mixture of E/Z C208 (710 mg, 79%). Major isomer described: ¹H NMR (300 MHz, Chloroform-d) δ 8.56 (s, 1H), 7.49-7.29 (m, 5H), 6.80 (dd, J=8.8, 2.6 Hz, 1H), 6.64 (dd, J=10.6, 2.3 Hz, 1H), 5.18 (s, 2H), 3.96 (ddd, J=11.5, 5.9, 3.7 Hz, 2H), 3.57 (ddd, J=11.5, 8.1, 2.9 Hz, 2H), 2.91 (tt, J=8.2, 4.1 Hz, 1H), 2.01-1.86 (m, 2H), 1.86-1.69 (m, 2H). ¹⁹F NMR (282 MHz, Chloroform-d) δ −108.58-109.64 (m, 1F). LCMS m/z 354.2 [M+H]⁺

Step 5: 8-benzyloxy-4-bromo-6-fluoro-2-oxido-3-tetrahydropyran-4-yl-isoquinolin-2-ium (C209)

To a solution of C208 (710 mg, 2.0091 mmol) in DMA (5.5 mL), CuBr₂ (1.15 g, 5.1488 mmol) was added and the reaction was heated at 60° C. for 1 h. The mixture was cooled to 0° C. and aqueous solution of NH₄OH and water (2:1, 6 mL) were slowly added, and the mixture was stirred at 0° C. for 20 min. The solids were filtered and washed with water. The residue was dissolved in dichloromethane, dried over Na₂SO₄, and concentrated. Purification by trituration with MTBE (7 mL) and washes with heptane afforded C209 (479 mg, 53%). ¹H NMR (300 MHz, Chloroform-d) δ 9.11 (br. s., 1H), 7.49-7.34 (m, 6H), 6.76 (dd, J=10.1, 1.9 Hz, 1H), 5.24 (s, 2H), 4.14 (dd, J=11.2, 4.1 Hz, 2H), 3.59 (t, J=11.4 Hz, 2H), 3.18 (br. s, 2H), 1.57-1.45 (m, 3H). ¹⁹F NMR (282 MHz, Chloroform-d) δ −103.29-104.31 (m, 1F). LCMS m/z 432.1 [M+H]⁺

Step 6: 8-benzyloxy-4-(3,4-difluorophenyl)-6-fluoro-2-oxido-3-tetrahydropyran-4-yl-isoquinolin-2-ium (C210)

C210 was prepared by Suzuki coupling of C209 with (3,4-difluorophenyl)boronic acid according to the method described for C41. $^1$H NMR (300 MHz, Chloroform-d) δ 9.21 (s, 1H), 7.50-7.33 (m, 6H), 7.09 (ddd, J=10.1, 7.6, 2.1 Hz, 1H), 7.00 (ddd, J=8.2, 4.3, 1.6 Hz, 1H), 6.72 (dd, J=10.3, 2.1 Hz, 1H), 6.29 (dd, J=10.0, 1.5 Hz, 1H), 5.25 (s, 2H), 4.03-3.92 (m, 2H), 3.39-3.19 (m, 2H), 2.72 (br. s., 1H), 1.57-1.54 (m, 2H), 1.47-1.36 (m, 2H). LCMS m/z 466.2 [M+H]$^+$

Step 7: 1-(4-aza-1-azoniabicyclo[2.2.2]octan-1-yl)-8-benzyloxy-4-(3,4-difluorophenyl)-6-fluoro-3-tetrahydropyran-4-yl-isoquinoline (C211)

C211 was prepared by amination of C210 using DABCO according to the method described for S2. $^1$H NMR (300

MHz, acetonitrile-d$_3$) δ 7.73-7.64 (m, 2H), 7.63-7.55 (m, 3H), 7.53-7.45 (m, 1H), 7.38 (dd, J=10.7, 2.5 Hz, 1H), 7.24 (ddd, J=10.9, 7.6, 2.1 Hz, 1H), 7.13-7.04 (m, 1H), 6.83 (dd, J=9.8, 2.5 Hz, 1H), 5.36 (s, 2H), 4.13-3.99 (m, 6H), 3.89 (dd, J=11.6, 4.3 Hz, 2H), 3.34-3.18 (m, 2H), 2.86-2.70 (m, 7H), 2.09-1.98 (m, 2H), 1.62-1.48 (m, 2H). LCMS m/z 560.5 [M+H]$^+$

Compounds 345-346

Compounds 345-346 (Table 46) were prepared in two steps from intermediate C211 according to the method described for compound 337. Any modifications to methods are noted in Table 46 and accompanying footnotes

TABLE 46

| Compound | Method/Product | Alcohol | $^1$H NMR; LCMS m/z [M + H]$^+$ |
|---|---|---|---|
| 345 |  Compound 337 from C211 | | $^1$H NMR (300 MHz, Chloroform-d) δ 9.31 (d, J = 1.5 Hz, 1H), 7.37-7.27 (m, 1H), 7.08-6.99 (m, 1H), 6.93 (ddd, J = 6.1, 4.0, 1.9 Hz, 1H), 6.69 (dd, J = 10.0, 2.3 Hz, 1H), 6.27 (dd, J = 10.3, 2.3 Hz, 1H), 5.82-5.68 (m, 1H), 4.02 (d, J = 10.9 Hz, 2H), 3.42-3.21 (m, 3H), 3.13-2.97 (m, 2H), 2.76-2.57 (m, 3H), 2.22-2.02 (m, 2H), 1.44 (d, J = 12.6 Hz, 2H). LCMS m/z 474.2 [M + H$^+$] |
| 346 |  Compound 337 from C211 | | $^1$H NMR (300 MHz, Chloroform-d) δ 9.00 (s, 1H), 8.26 (d, J = 8.8 Hz, 2H), 7.41 (d, J = 8.5 Hz, 2H), 7.36-7.27 (m, 1H), 7.12-7.00 (m, 1H), 6.98-6.91 (m, 1H), 6.81 (dd, J = 10.1, 2.2 Hz, 1H), 6.37 (dd, J = 10.4, 2.5 Hz, 1H), 3.89 (d, J = 11.4 Hz, 2H), 3.29-3.15 (m, 2H), 2.64-2.51 (m, 1H), 1.86-1.67 (m, 2H), 1.33 (d, J = 12.9 Hz, 2H). LCMS m/z 496.1 [M + H$^+$] |

Compounds 347-348

Compounds 347-348 (Table 47) were prepared in two steps from intermediate S35 and the appropriate phenol according to the method described for 336. Any modifications to methods are noted in Table 47 and accompanying footnotes.

TABLE 47

Method of preparation, structure, physicochemical data for compounds 347-348

| Compound | Method/Product | Phenol | ¹H NMR; LCMS m/z [M + H]⁺ |
|---|---|---|---|
| 347 |  Compound 336 from S35[1] | | ¹H NMR (300 MHz, DMSO-d₆) δ 12.96 (s, 1H), 10.21 (s, 1H), 8.03 (dd, J = 9.0, 2.3 Hz, 2H), 7.59 (dt, J = 11.0, 8.5 Hz, 1H), 7.53-7.40 (m, 2H), 7.30 (dd, J = 9.0, 2.3 Hz, 2H), 7.14 (d, J = 8.3 Hz, 1H), 7.00 (d, J = 7.8 Hz, 1H), 6.60 (d, J = 8.3 Hz, 1H), 3.72 (d, J = 11.3 Hz, 2H), 3.09 (q, J = 5.2 Hz, 2H), 2.59-2.52 (m, 2H), 1.61 (dd, J = 12.2, 4.2 Hz, 1H), 1.37 (t, J = 12.0 Hz, 2H). LCMS m/z 478.39 [M + H⁺] |
| 348 |  Compound 336 from S35 | | ¹H NMR (300 MHz, DMSO-d₆) δ 13.10 (s, 1H), 10.11 (s, 1H), 7.83 (dt, J = 7.6, 1.4 Hz, 1H), 7.78 (t, J = 1.9 Hz, 1H), 7.58 (dt, J = 11.6, 8.3 Hz, 2H), 7.53-7.41 (m, 3H), 7.18-7.10 (m, 1H), 7.01 (dd, J = 7.8, 1.0 Hz, 1H), 6.60 (dd, J = 8.4, 0.9 Hz, 1H), 3.69 (d, J = 11.0 Hz, 2H), 3.08 (td, J = 11.4, 10.9, 6.3 Hz, 2H), 1.57 (qd, J = 12.4, 4.3 Hz, 2H), 1.35 (t, J = 12.2 Hz, 2H). LCMS m/z 478.44 [M + H⁺] |

[1]Hydrolysis was performed with LiOH after the nucleophilic aromatic substitution andbefore benzyl ether deprotection.

Compound 349

4-[4-(3,4-difluorophenyl)-8-hydroxy-3-tetrahydropy-
ran-4-yl-1-isoquinolyl]benzoic acid (349)

-continued

349

Step 1: tert-butyl 4-[8-benzyloxy-4-(3,4-difluoro-phenyl)-3-tetrahydropyran-4-yl-1-isoquinolyl]benzo-ate (C212)

To a mixture of S35 (67 mg, 0.144 mmol), tert-butyl 4-(4,4,5,5-tetramethyl-1,3,2-dioxaborolan-2-yl)benzoate (70 mg, 0.2301 mmol) and Pd(PPh$_3$)$_4$ (10 mg, 0.0086 mmol) in DMF (3.5 mL) was added an aqueous solution of Na$_2$CO$_3$ (400 µL of 2M, 0.80 mmol) under nitrogen atmosphere and the reaction was heated in a microwave reactor at 130° C. for 1 hours. Water was added and the mixture was extracted with EtOAc. The organic phases were combined, washed successively with water and brine, dried over Na$_2$SO$_4$ and concentrated. Purification by silica gel chromatography (10 to 100% of EtOAc in hexanes) afforded C212 (75 mg, 86%). LCMS m/z 608.41 [M+H]$^+$

Step 2: tert-butyl 4-[4-(3,4-difluorophenyl)-8-hy-droxy-3-tetrahydropyran-4-yl-1-isoquinolyl]benzo-ate (C213)

A suspension of palladium on carbon (22 mg of 10% w/w, 0.02067 mmol) and C212 (75 mg, 0.1234 mmol) in MeOH (20 mL) and EtOAc (10 mL) was purged with hydrogen and stirred at RT for 4 h. The mixture was filtered and concentrated. Purification by silica gel chromatography (10 to 50% of EtOAc in hexanes) afforded C213 (40 mg, 63%). LCMS m/z 517.91 [M+H]$^+$

Step 3: 4-[4-(3,4-difluorophenyl)-8-hydroxy-3-tetra-hydropyran-4-yl-1-isoquinolyl]benzoic acid (349)

C213 (38 mg, 0.0734 mmol) was treated with a solution of HCl (4 mL of 4M, 16.00 mmol) in dioxane and the reaction was heated in a microwave reactor at 80° C. for 45 min. The mixture was concentrated and the residue was triturated successively with acetonitrile, water, dichlo-romethane and MeOH to afford 349 (35 mg, 91%). $^1$H NMR (400 MHz, DMSO-d$_6$) δ 10.41 (s, 1H), 8.11-7.88 (m, 2H), 7.77-7.38 (m, 5H), 7.27-7.17 (m, 1H), 6.91 (d, J=7.6 Hz, 1H), 6.71 (dd, J=8.4, 1.0 Hz, 1H), 3.84 (d, J=11.4 Hz, 2H), 3.20 (q, J=10.6 Hz, 2H), 2.80-2.70 (m, 1H), 2.10-1.97 (m, 2H), 1.52 (t, J=14.5 Hz, 2H) ppm. LCMS m/z 462.37 [M+H]$^+$ Compound 350

3-[4-(3,4-difluorophenyl)-8-hydroxy-3-tetrahydropy-
ran-4-yl-1-isoquinolyl]benzoic acid (350)

S35

C214

C215

-continued

350

Step 1: tert-butyl 3-[8-benzyloxy-4-(3,4-difluoro-phenyl)-3-tetrahydropyran-4-yl-1-isoquinolyl]benzo-ate (C214)

To a mixture of S35, tert-butyl 3-(4,4,5,5-tetramethyl-1,3,2-dioxaborolan-2-yl)benzoate (71 mg, 0.2334 mmol) and Pd(PPh$_3$)$_4$ (11 mg, 0.009519 mmol) in DMF (3.5 mL), an aqueous solution of Na$_2$CO$_3$ (400 µL of 2M, 0.8000 mmol) was added under nitrogen and the reaction was heated in a microwave reactor at 130° C. for 1 hours. Water was added and the mixture was extracted with EtOAc. The organic phases were combined, washed successively with water and brine, dried over Na$_2$SO$_4$ and concentrated. Purification by silica gel chromatography (10 to 50% of EtOAc in hexanes) afforded C214 (72 mg, 81%). LCMS m/z 608.45 [M+H]$^+$

Step 2: tert-butyl 3-[4-(3,4-difluorophenyl)-8-hy-droxy-3-tetrahydropyran-4-yl-1-isoquinolyl]benzo-ate (C215)

A suspension of palladium on carbon (21 mg of 10% w/w, 0.01973 mmol) and C214 (72 mg, 0.1185 mmol) in MeOH (15 mL) and EtOAc (30 mL) was purged with hydrogen and stirred at room temperature for 18 hours. The mixture was filtered and concentrated. Purification by silica gel chroma-tography (10 to 50% of EtOAc in hexanes) afforded C215 (43 mg, 70%). LCMS m/z 518.0 [M+H]$^+$

Step 3: 3-[4-(3,4-difluorophenyl)-8-hydroxy-3-tetra-hydropyran-4-yl-1-isoquinolyl]benzoic acid (350)

C215 (43 mg, 0.08308 mmol) was treated with a solution of HCl (2.5 mL of 4M, 10.00 mmol) in dioxane and the reaction was heated in a microwave reactor at 80° C. for 45 min. The mixture was concentrated and purification by silica gel chromatography (0 to 20% of MeOH in dichlorometh-ane) afforded 350 (34 mg, 77%) $^1$H NMR (300 MHz, DMSO-d$_6$) δ 10.42 (s, 1H), 8.07 (t, J=1.7 Hz, 1H), 8.00 (dt, J=7.7, 1.5 Hz, 1H), 7.77 (dt, J=7.7, 1.4 Hz, 1H), 7.70-7.44 (m, 4H), 7.31-7.17 (m, 1H), 7.00-6.87 (m, 1H), 6.72 (dd, J=8.4, 1.0 Hz, 1H), 3.85 (d, J=11.2 Hz, 2H), 3.22 (dd, J=11.8, 7.0 Hz, 2H), 2.85-2.68 (m, 1H), 2.03 (q, J=12.9, 12.1 Hz, 2H), 1.53 (t, J=12.3 Hz, 2H). LCMS m/z 462.37 [M+H]$^+$ Compound 351

3-[4-(3,4-difluorophenyl)-8-hydroxy-3-tetrahydropy-
ran-4-yl-1-isoquinolyl]propanoic acid (351)

S35

C216

C217

-continued

351

Step 1: tert-butyl 3-[8-benzyloxy-4-(3,4-difluoro-phenyl)-3-tetrahydropyran-4-yl-1-isoquinolyl]pro-panoate (C216)

To a mixture of S35 (65 mg, 0.1395 mmol) and Pd(PPh$_3$)$_4$ (13 mg, 0.01125 mmol) in THF (1.5 mL), bromo-(3-tert-butoxy-3-oxo-propyl)zinc (1.5 mL of 0.5M, 0.7500 mmol) was slowly added under nitrogen and the reaction was heated at 90° C. for 60 min. The mixture was concentrated, dissolved in dichloromethane, washed successively with an aqueous solution of NaOH (0.5 M, 6 mL), water and brine, dried over Na$_2$SO$_4$ and concentrated. Purification by silica gel chromatography (10 to 100% of EtOAc in hexanes) afforded C216 (78 mg, 100%). LCMS m/z 559.94 [M+H]$^+$

Step 2: tert-butyl 3-[4-(3,4-difluorophenyl)-8-hy-droxy-3-tetrahydropyran-4-yl-1-isoquinolyl]pro-panoate (C217)

A suspension of palladium on carbon (25 mg of 10% w/w, 0.02349 mmol) and C216 (78 mg, 0.139 mmol) in MeOH (20 mL) and EtOAc (10 mL) was purged with hydrogen and stirred at RT for 4 h. The mixture was concentrated to afford C217 (65 mg, 99%). LCMS m/z 469.98 [M+H]$^+$

Step 3: 3-[4-(3,4-difluorophenyl)-8-hydroxy-3-tetra-hydropyran-4-yl-1-isoquinolyl]propanoic acid (351)

C217 (65 mg, 0.1384 mmol) was treated with a solution of HCl (4 mL of 4M, 16.00 mmol) in dioxane and the reaction was heated in a microwave reactor at 80° C. for 45 min. The mixture was concentrated and purification by silica gel chromatography (0 to 20% of MeOH in dichloromethane) afforded 351 (50 mg, 76%). $^1$H NMR (300 MHz, Methanol-d$_4$) δ 7.72 (t, J=8.1 Hz, 1H), 7.48-7.40 (m, 1H), 7.25 (dd, J=8.0, 0.8 Hz, 1H), 7.12 (t, J=8.9 Hz, 1H), 7.03 (d, J=5.4 Hz, 1H), 6.82 (dd, J=8.3, 0.9 Hz, 1H), 4.02 (d, J=12.4 Hz, 2H), 3.36 (s, 3H), 3.30 (d, J=8.8 Hz, 1H), 3.12-2.86 (m, 3H), 2.21 (q, J=13.0, 12.4 Hz, 2H), 1.61 (d, J=12.8 Hz, 2H). LCMS m/z 414.45 [M+H]$^+$ Compounds 352-357

Compounds 352-357 (Table 48) were prepared in three steps from intermediate S36 and the appropriate amine according to the method described for 244. Any modifications to methods are noted in Table 48 and accompanying footnotes.

TABLE 48

| Method of preparation, structure, physicochemical data for compounds 352-357 | | | |
|---|---|---|---|
| Compound | Method/Product | Amine | $^1$H NMR; LCMS m/z [M + H][+] |
| 352 | Compound 244 from S36[1, 2] | | $^1$H NMR (400 MHz, DMSO-d[6]) δ 7.27 (t, J = 9.00 Hz, 1H), 7.15 (bs, 1H), 7.06 (d, J = 5.4 Hz, 1H), 6.89-6.83 (m, 2H), 6.48 (s, 1H), 6.28 (d, J = 7.6 Hz, 1H) 4.66 (t, J = 5.84 Hz, 1H), 3.07-3.02 (m, 1H), 2.30 (s, 3H), 1.47 (d, J = 6.68 Hz, 3H), 1.23 (d, J = 10.0 Hz, 6H). LCMS m/z 383 [M + H[+]] |
| 353 | Compound 244 from S36[1] | | $^1$H NMR (400 MHz, DMSO-d[6]) δ 8.35 (s, 1H) 7.26 (t, J = 9.7 Hz, 1H), 7.14 (d, J = 7.16 Hz, 1H), 7.06 (s, 1H), 6.90-6.83 (m, 2H), 6.27-6.24 (m, 1H), 6.08 (bs, 1H) 4.98-4.93 (m, 1H), 3.12-3.02 (m, 2H), 2.79-2.76 (m, 1H), 2.59-2.68 (m, 2H), 2.50-2.29 (m, 5H), 1.23-1.14 (m, 6H). LCMS m/z 409 [M + H[+]] |
| 354 | Compound 244 from S36[1, 3] | | $^1$H NMR (400 MHz, DMSO-d[6]) δ 8.25 (s, 1H), 7.28 (t, J = 9.1 Hz, 1H), 7.20-7.12 (m, 1H), 7.12-7.04 (m, 2H), 6.91-6.81 (m, 2H), 6.63 (s, 1H), 6.28 (dd, J = 7.4, 2.2 Hz, 1H), 4.55 (s, 1H), 3.09-3.01 (m, 1H), 2.30 (d, J = 9.92 Hz, 3H), 1.46 (d, J = 6.08 Hz, 3H), 1.29-1.20 (m, 6H). LCMS m/z 383 [M + H[+]] |

TABLE 48-continued

Method of preparation, structure, physicochemical data for compounds 352-357

| Compound | Method/Product | Amine | ¹H NMR; LCMS m/z [M + H]⁺ |
|---|---|---|---|
| 355 | 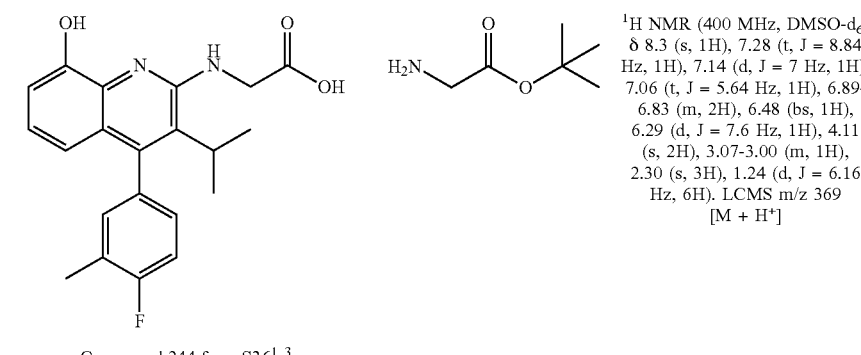<br>Compound 244 from S36[1] | | ¹H NMR (400 MHz, DMSO-d₆) δ 12.56 (s, 1H), 8.57 (s, 1H), 7.28 (t, J = 9.0 Hz, 1H), 7.16 (d, J = 7.4 Hz, 1H), 7.11-7.05 (m, 1H), 6.91-6.80 (m, 2H), 6.27 (d, J = 7.8 Hz, 1H), 6.04 (s, 1H), 3.97 (d, J = 5.4 Hz, 2H), 3.07-2.97 (m, 1H), 2.30 (s, 3H), 1.25-1.18 (m, 6H), 1.08 (d, J = 8.9 Hz, 4H). LCMS m/z 409 [M + H⁺] |
| 356 | Compound 244 from S36[1] | | ¹H NMR (400 MHz, DMSO-d₆) δ 7.33-7.29 (m, 2H), 7.23-7.17 (m, 2H), 7.10 (s, 1H), 7.04 (d, 1H), 6.35 (bs, 1H), 3.92 (d, J = 5.8 Hz, 2H), 3.06-3.01 (m, 1H), 2.74-2.67 (m, 2H), 2.30 (s, 3H), 1.16-1.23 (m, 6H). LCMS m/z 383 [M + H⁺] |
| 357 | Compound 244 from S36[1, 3] | | ¹H NMR (400 MHz, DMSO-d₆) δ 8.3 (s, 1H), 7.28 (t, J = 8.84 Hz, 1H), 7.14 (d, J = 7 Hz, 1H), 7.06 (t, J = 5.64 Hz, 1H), 6.89-6.83 (m, 2H), 6.48 (bs, 1H), 6.29 (d, J = 7.6 Hz, 1H), 4.11 (s, 2H), 3.07-3.00 (m, 1H), 2.30 (s, 3H), 1.24 (d, J = 6.16 Hz, 6H). LCMS m/z 369 [M + H⁺] |

[1]PyBrop amination was performed at 60° C.,

[2]Benzyl ester was removed during hydrogenation/benzyl ether deprotection step.

[3]t-Butyl ester was deprotected with HCl in dioxane.

Preparation of C221

8-benzyloxy-2-chloro-4-(4-fluoro-3-methyl-phenyl)-
3-isopropyl-quinoline (C221)

C84

C218

C219

C220

-continued

C221

Step 1: 4-(4-fluoro-3-methyl-phenyl)-3-isopropyl-quinolin-8-ol (C218)

To a solution of C84 (4 g, 10.431 mmol) in EtOH (25 mL), Pd/C (3.9963 g, 37.55 mmol) was degassed under nitrogen. The reaction was purged with hydrogen and stirred at room temperature for 12 hours. The mixture was filtered through a celite plug and concentrated to afford C218 (2.8 g, 89%). LCMS m/z 296.0 [M+H]$^+$

Step 2: 8-benzyloxy-4-(4-fluoro-3-methyl-phenyl)-3-isopropyl-quinoline (C219)

To a solution of C218 (1.9 g, 6.4330 mmol) in DMF (7 mL), NaH (643 mg, 16.08 mmol) and BnCl (1.63 g, 1.48 mL, 12.87 mmol) were added and the reaction was stirred at room temperature for 12 hours. The mixture was diluted with EtOAc and water was added, the organic phase was washed with brine, dried over Na$_2$SO$_4$, and concentrated. Purification by silica gel chromatography (0 to 50% EtOAc in hexanes) afforded C219 (2.4 g, 90%). LCMS m/z 386.0 [M+H]$^+$

Step 3: 8-benzyloxy-4-(4-fluoro-3-methyl-phenyl)-3-isopropyl-1-oxido-quinolin-1-ium (C220)

To a solution of C219 (2.51 g, 6.51 mmol) in dichloromethane (25 mL) at 0° C., m-CPBA (2.25 g, 13.02 mmol) was added and the reaction mixture was stirred at room temperature for 13 hours. The mixture was diluted with water and extracted with dichloromethane. The organic phases were combined, washed with brine, Na$_2$SO$_4$, and concentrated. Purification by silica gel chromatography (0 to 30% EtOAc in hexanes) afforded C220 (2.1 g, 75%). LCMS m/z 402.0 [M+H]$^+$ as off white solid.

Step 4: 8-benzyloxy-2-chloro-4-(4-fluoro-3-methyl-phenyl)-3-isopropyl-quinoline (C221)

To a solution of C220 in toluene (2 mL) was added POCl$_3$ (1.76 g, 1.07 mL, 11.46 mmol) followed by DMF (8.38 mg, 0.009 mL, 0.115 mmol) and the mixture was refluxed for 2 hours. The mixture was concentrated, diluted with dichloromethane, quenched with an aqueous solution of NaHCO$_3$ solution and extracted with dichloromethane. The organic phases were combined, washed with brine, Na$_2$SO$_4$, and concentrated. Purification by silica gel chromatography (0 to 50% EtOAc in hexanes) afforded C221 (290 mg, 60%). $^1$H NMR (400 MHz, DMSO-d$_6$) δ 7.54 (d, J=7.2 Hz, 2H), 7.44-7.35 (m, 5H), 7.31-7.16 (m, 3H), 6.65 (d, J=8.4 Hz, 1H), 5.35 (s, 2H), 3.05-3.25 (m, 1H), 2.31 (s, 1H), 1.28 (d, J=6.64 Hz, 6H).

Compounds 358-360

Compounds 358-360 (Table 49) were prepared in three steps from intermediate C221 according to the method described for 254. Any modifications to methods are noted in Table 49 and accompanying footnotes.

TABLE 49

Method of preparation, structure, physicochemical data for compounds 358-360

| Compound | Method/Product | Amine | $^1$H NMR; LCMS m/z [M + H]$^+$ |
|---|---|---|---|
| 358 | Compound 254 from C221 | | $^1$H NMR (400 MHz, DMSO-d$_6$) δ 8.55-8.72 (bs, 1H), 7.26 (t, J = 8.72 Hz, 1H), 7.19 (d, J = 6.88 Hz, 1H), 7.08-7.12 (m, 1H), 6.98-6.94 (m, 1H), 6.90 (d, J = 7.16 Hz, 1H) 6.28 (d, J = 8.04 Hz, 1H), 4.36-4.28 (m, 4H), 3.23-3.19 (m, 2H) 2.30 (s, 3H), 1.00-0.97 (m, 6H). LCMS m/z 394 [M + H$^+$] |
| 359 | Compound 254 from C221 | | $^1$H NMR (400 MHz, DMSO-d$_6$) δ 8.62-8.81 (bs, 1H), 7.27 (t, J = 8.72 Hz, 1H), 7.21 (d, J = 7.32, Hz, 1H), 7.12-7.15 (m, 1H), 7.01 (t. J = 7.84 Hz, 1H), 6.91 (d, J = 7.48 Hz, 1H), 6.31 (d, J = 8.24 Hz, 1H) 3.72 (d, J = 7.64 Hz, 2H), 3.60-3.53 (m, 2H), 3.44-3.39 (m, 1H), 3.15-3.11 (m, 1H), 2.30 (s, 3H), 2.18-2.12 (m, 2H), 1.07-1.00 (m, 6H). LCMS m/z 409 [M + H$^+$] |
| 360 | Compound 254 from C221 | | $^1$H NMR (400 MHz, DMSO-d$_6$) δ 8.75-8.97 (bs, 1H), 7.27 (t, J = 8.64 Hz, 1H), 7.21 (d, J = 7.4, Hz, 1H), 7.12-7.15 (m, 1H), 7.00 (t, J = 7.76 Hz, 1H), 6.91 (d, J = 7.24 Hz, 1H), 6.30 (d, J = 8.4 Hz, 1H), 3.74-3.69 (m, 2H), 3.57-3.53 (m, 2H), 3.45-3.41 (m, 1H), 3.10-3.07 (m, 1H), 2.30 (s, 3H), 2.12 (d, J = 7.32 Hz, 2H) 1.07-1.00 (m, 6H). LCMS m/z 409 [M + H$^+$] |

Compound 361

3-[4-(3,4-difluorophenyl)-8-hydroxy-3-isopropyl-1-oxo-2-isoquinolyl]propanoic acid (361)

C222

C223

C224

-continued

C225

361

Step 1: methyl 3-[[2-benzyloxy-6-[1-(3,4-difluoro-phenyl)-3-methyl-2-oxo-butyl]benzoyl]amino]pro-panoate (C223)

To a solution of C222 (which was prepared using the same procedure as for C133) (80 mg, 0.1715 mmol), HATU (92 mg, 0.2420 mmol), and methyl 3-aminopropanoate (hydrochloride salt) (33 mg, 0.2364 mmol) in DMF (2 mL), DIEA (70 0.4019 mmol) was added. The reaction was stirred at room temperature for 18 hours. The mixture was diluted with EtOAc, washed with a saturated aqueous solution of $NH_4Cl$, and the organic phase was dried with $Na_2SO_4$ and concentrated. Purification by silica gel chromatography (50 to 100% EtOAc in heptane) afforded C223 as a white solid, which was used directly in the next step.

Step 2: methyl 3-[8-benzyloxy-4-(3,4-difluorophe-nyl)-3-isopropyl-1-oxo-2-isoquinolyl]propanoate (C224)

To a solution of C223 in dichloromethane (2 mL), was added MsOH (10 μL, 0.1541 mmol) and the reaction was stirred at RT for 6 h. The mixture was concentrated and purified by silica gel chromatography (50 to 100% EtOAc in heptane) to afford C224 which was used directly in the next step.

Step 3: methyl 3-[4-(3,4-difluorophenyl)-8-hy-droxy-3-isopropyl-1-oxo-2-isoquinolyl]propanoate (C225)

To a vial loaded with palladium on carbon (9 mg, 0.0086 mmol), C224 was added as a solution in MeOH (8 mL)

under inert atmosphere, the vial was purged with $H_2$ and the reaction was stirred at RT for 18 h. The mixture was filtered through a Celite® plug and concentrated. Purification by silica gel chromatography (0 to 30% EtOAc in Heptane) afforded C225 (2.2 mg, 3% yield over three steps).

Step 4: 3-[4-(3,4-difluorophenyl)-8-hydroxy-3-iso-propyl-1-oxo-2-isoquinolyl]propanoic acid (361)

To a solution of C225 in a mixture of THF (1.2 mL), MeOH (0.4 mL), $H_2O$ (0.4 mL), LiOH (4 mg, 0.167 mmol) was added and the reaction was stirred at RT for 1 h. An aqueous solution of 1 M HCl was added to adjust the pH to ~3, and the aqueous phase was extracted with dichloromethane and then concentrated to afford 361(2.6 mg, 4%). $^1H$ NMR (400 MHz, Methanol-$d_4$) δ 7.57-7.51 (m, 2H), 7.37-7.23 (m, 2H), 7.12-7.05 (m, 1H), 6.95-6.89 (m, 1H), 3.88 (p, J=6.8 Hz, 1H), 3.41-3.22 (m, 12H), 2.28 (ddd, J=9.5, 6.3, 5.2 Hz, 2H), 1.10 (dd, J=6.8, 6.0 Hz, 6H). LCMS m/z 388.44 $[M+H]^+$ Assays for Detecting and Measuring AAT Modulator Properties of Compounds A. AAT Function Assay (MSD Assay NL20-SI Cell Line)

Alpha-1 antitrypsin (AAT) is a SERPIN (serine protease inhibitor) that inactivates enzymes by binding to them covalently. This assay measured the amount of functionally active AAT in a sample in the presence of the disclosed compounds 1-361 by determining the ability of AAT to form an irreversible complex with human neutrophil Elastase (hNE). In practice, the sample (cell supernatant, blood sample, or other) was incubated with excess hNE to allow AAT-Elastase complex to be formed with all functional AAT in the sample. This complex was then captured to a microplate coated with an anti-AAT antibody. The complex captured to the plate was detected with a labeled anti-Elastase antibody and quantitated using a set of AAT standards spanning the concentration range present in the sample. Meso Scale Discovery (MSD) plate reader, Sulfo-tag labeling, and microplates were used to provide high sensitivity and wide dynamic range.

Assay Protocol

Day 1 Cell Culture
1. Harvest NL20 human bronchial epithelial cells expressing human Z-AAT in OptiMEM™ containing Pen/Strep (P/S)
2. Seed at 16,000 cells/well in 30 μL (384 well plate)
3. Centrifuge plates briefly up to speed (1200 rpm) and place into 37° C. incubator overnight Day 2: Compound Addition and Coating Plates with Capture Antibody Compound Addition:
1. Dispense 40 μL of OptiMEM™ (P/S) with doxycycline (1:1000 stock=0.1 μM final) to each well of the compound plate using a multidrop Combi in hood
2. Remove cell plate from incubator, flip/blot and take immediately to Bravo to transfer compounds
3. Return plates to incubator overnight Coat MSD Plates
1. Dilute capture antibody (Polyclonal Goat anti-AAT) to 5 μg/mL (1:200) in PBS (no BSA).
2. Dispense 25 μL of diluted capture antibody into all wells of MSD 384-well High Bind plate using the Multidrop equipped with a standard cassette.
3. Incubate overnight at 4° C.

Prepare Blocker A (BSA) Solutions
1. Prepare solution of 5% MSD Blocker A (BSA) following the manufacturer's instructions.
2. Further dilute the 5% MSD Blocker A in PBS to 1% (Blocker A) as needed.

Day 3: Run MSD Assay

Block Plates
1. Wash plate 1× with 50 μL Wash buffer (PBS+0.5% Tween 20), and adds 35 μL 5% Block A buffer to block non-specific binding on washer dispenser
2. Rotate plates on shaker for 1 hour at 600 rpm Prepare M-AAT Standards
1. Dilute M-AAT stock to 1.6 μg/mL in 1% BSA Blocker A (Stock in −70° C.); then prepare 12×1:2 serial dilutions in 1% Blocker A

| MATERIALS: | |
| --- | --- |
| Reagents/Plates | Concentration |
| Goat anti-human Alpha-1-Antitrypsin Polyclonal Antibody Use at 5 μg/mL in phosphate buffered saline (PBS) | 1 mL @ 1 mg/mL |
| Human Neutrophil Elastase Stock at 3.4 pM (0.1 mg + 1 mL PBS) Working at 1ug/mL (34 nm) in MSD Assay buffer (1% bovine serum albumin (BSA)) | 100 μg lyophilized |
| Mouse anti-human Neutrophil Elastase Monoclonal Antibody Sulfo-tagged @12:1 using MSD Gold Sulfo-tag N-hydroxysuccinimide (NHS) ester; use at 0.45 μg/mL in MSD Assay buffer (1% BSA) | 900 μg/mL |
| M-AAT (Alpha-1-Antitrypsin) | 5 mg lyophilized |
| MSD Blocker A (BSA) 5% solution in PBS for blocking 1% solution in PBS for assay buffer | 250 mL |
| MSD Read Buffer T (4X) with Surfactant MSD 384 high bind plates Polypropylene for dilution 384 well plate Tissue culture treated black well 384 well plate | 1 L or 250 mL |
| INSTRUMENT(S): | |
| Meso Sector S600 Bravo Washer dispenser Multidrop Combi | |

2. The top starting final concentration on MSD plate is 320 ng/mL. These dilutions correspond to a final concentration of 320, 160, 80, 40, 20, 10, 5, 2.5, 1.25, 0.625, 0.312, 0.156 ng/mL.

Dilution Plate
1. Add 80 μL of 1% Assay buffer to all wells except columns ¼4 (standards) with Multidrop Combi
2. Add diluted standards to columns 1 and 24
3. Centrifuge dilution plates 1200 rpm briefly Cell Plate
1. Aspirate columns which will have the standards from the cell plates in the hood using 16-pin aspirator Prepare Human Neutrophil Elastase (hNE)
1. Prepare 1 μg/mL Human Neutrophil Elastase by diluting in 1% Blocker A.
   a. Small 100 μg vial—add 1 mL PBS (100 μg/mL)
      i. This can then be diluted 1:100 in 1% Assay Buffer for a final 1 μg/mL concentration MSD—Add hNE (20 μL/Well)
1. After the MSD plate has blocked for at least 1 hour, wash plate 1× with 50 μL Wash buffer (PBS+0.5% Tween 20) and then add 20 μL hNE to each well Bravo—Cell Plate—Dilution Plate—MSD Plate
Using the Bravo aspirate 10 μL from the cell plate, transfer to the dilution plate (9-fold dilution)
1. Mix 25 μL 3×, then aspirate 5 μL, transfer to MSD plate (5-fold dilution)
2. Mix 10 μL 3×. Total dilution is 45 fold.
3. Shake plates at 600 rpm for 1.5 hours Add Functional Detection hNE Antibody
1. Wash plate 1× with wash buffer
2. Add 25 μL Sulfo-tagged anti-Elastase Monoclonal Mouse anti-Elastase) diluted to 0.45 μg/mL (1:2000) in 1% Blocker A into all wells of the functional activity MSD plates using the washer/dispenser
   Note: The dilution required for sufficient signal must be determined for each new lot of labeled antibody.
3. Incubate at RT shaking at 600 rpm for 1 hour.

Final Wash and MSD Imager Read
1. Wash the plate 1×, and add 25 μL of Wash Buffer to the plate.
2. Make 2× Read buffer
3. Remove wash buffer from MSD plate
4. Transfer 35 μL 2× Read Buffer to MSD plate using Bravo and take to MSD to read immediately Data analysis in MSD Discovery Workbench 4.0 software and EC$_{50}$ values were determined using Genedata.

B. Biochemical Assay (Z-AAT Elastase Activity Assay)

This assay measured the modulation of compounds 1-361 on Z-AAT SERPIN activity using purified Z-AAT protein and purified human neutrophil elastase (hNE). Normally, when active monomeric Z-AAT encounters a protease such as trypsin or elastase, it forms a 1:1 covalent "suicide" complex in which both the AAT and protease are irreversibly inactivated. However, compounds binding to Z-AAT can lead to a decrease in SERPIN activity. In such cases, when a protease encounters compound-bound Z-AAT, the protease cleaves and inactivates Z-AAT without itself being inactivated.

Materials
Reagents
   PBS buffer (media prep)+0.01% BRIJ35 detergent (Calbiochem catalog #203728)
   Opti-MEM media (Fisher 11058-021)
   Human neutrophil elastase (hNE, Athens Research #16-14-051200)

3.4 μM stock (0.1 mg/mL) prepared in 50 mM Na Acetate, pH 5.5, 150 mM NaCl, stored at −80° C.
Elastase substrate V (ES V, fluorescent peptide substrate MeOSuc-Ala-Ala-Pro-Val-AMC, Calbiochem catalog #324740)
   20 mM stock in DMSO, stored at −20° C.
Purified Z-AAT protein from human plasma;
   12.9 μM (0.67 mg/mL) Z-AAT Vertex Cambridge Sample 4942, from patient #061-SSN, stored at −80C Plates
   Corning 4511 (384 well black low volume)
Instruments
   PerkinElmer® EnVision™
Assay Protocol
Pre-Incubation of Z-AAT with Compounds
1. 7.5 μL of Z-AAT (20 nM) was incubated with Compounds 1-361 in a GCA plate for 1 hour at room temperature Addition of hNE
1. 7.5 ul of HNE solution (3 nM in PBS+0.01% BRIJ35) added into GCA plate
2. Incubate plate for 30 minutes to allow Z-AAT/HNE suicide complex formation.

Addition of Substrate and Read Plate on PE Envision
1. 7.5 μL of substrate (300 μM solution of elastase substrate (ES V) in PBS+0.01% BRIJ35) dispensed per well into GCA plate
2. Immediately read on Envision.

C. EC50 and Z-AAT Elastase Activity Data for Compounds 1-361

The compounds of formula (I) are useful as modulators of AAT activity. Table 50 below illustrates the EC$_{50}$ of the compounds 1-361 using procedures described in Section A above. Table 50 below also provides the Z-AAT elastase activity using procedures described in Section B above. In Table 50 below, the following meanings apply for both EC$_{50}$ and IC$_{50}$: "+++" means <1.2 μM; "++" means between 1.2 μM and 3.0 μM; "+" means greater than 3.0 μM; and "N/A" means activity not assessed. For IC$_{50}$, "N.D." means activity not detected up to 30 μM.

TABLE 50

| | EC50 and IC50 data for Compounds 1-361 | |
|---|---|---|
| Compound No. | NL20 Functional EC50 (μM) | Z-AAT Elastase Activity IC50 (μM) |
| 1 | + | N.D. |
| 2 | + | N.D. |
| 3 | ++ | + |
| 4 | +++ | +++ |
| 5 | +++ | + |
| 6 | +++ | ++ |
| 7 | ++ | N.D. |
| 8 | +++ | +++ |
| 9 | +++ | +++ |
| 10 | +++ | +++ |
| 11 | ++ | + |
| 12 | +++ | + |
| 13 | + | N.D. |
| 14 | +++ | +++ |
| 15 | ++ | + |
| 16 | +++ | +++ |
| 17 | + | N.D. |
| 18 | ++ | N.D. |
| 19 | ++ | + |
| 20 | +++ | N.D. |
| 21 | +++ | +++ |

TABLE 50-continued

EC50 and IC50 data for Compounds 1-361

| Compound No. | NL20 Functional EC50 (μM) | Z-AAT Elastase Activity IC50 (μM) |
|---|---|---|
| 22 | +++ | +++ |
| 23 | ++ | ++ |
| 24 | +++ | +++ |
| 25 | + | N.D. |
| 26 | + | N.D. |
| 27 | + | +++ |
| 28 | ++ | + |
| 29 | + | N.D. |
| 30 | + | ++ |
| 31 | + | + |
| 32 | + | + |
| 33 | ++ | + |
| 34 | ++ | N.D. |
| 35 | +++ | + |
| 36 | +++ | + |
| 37 | +++ | +++ |
| 38 | ++ | N.D. |
| 39 | +++ | +++ |
| 40 | + | N.D. |
| 41 | + | +++ |
| 42 | + | N.D. |
| 43 | + | N.D. |
| 44 | + | + |
| 45 | +++ | +++ |
| 46 | +++ | + |
| 47 | +++ | +++ |
| 48 | +++ | N.D. |
| 49 | +++ | +++ |
| 50 | +++ | + |
| 51 | +++ | N.D. |
| 52 | ++ | N.D. |
| 53 | +++ | + |
| 54 | +++ | + |
| 55 | ++ | + |
| 56 | +++ | ++ |
| 57 | +++ | +++ |
| 58 | +++ | N.D. |
| 59 | ++ | +++ |
| 60 | ++ | + |
| 61 | ++ | + |
| 62 | + | N.D. |
| 63 | + | + |
| 64 | + | N.D. |
| 65 | +++ | + |
| 66 | + | N.D. |
| 67 | ++ | + |
| 68 | +++ | + |
| 69 | +++ | ++ |
| 70 | + | N.D. |
| 71 | ++ | + |
| 72 | ++ | N.D. |
| 73 | ++ | + |
| 74 | + | N.D. |
| 75 | + | N.D. |
| 76 | + | N.D. |
| 77 | + | N.D. |
| 78 | + | N.D. |
| 79 | ++ | N.D. |
| 80 | +++ | + |
| 81 | +++ | + |
| 82 | ++ | + |
| 83 | ++ | N.D. |
| 84 | +++ | + |
| 85 | +++ | + |
| 86 | ++ | + |
| 87 | ++ | + |
| 88 | ++ | + |
| 89 | +++ | + |
| 90 | ++ | + |
| 91 | + | N.D. |
| 92 | + | N.D. |
| 93 | + | N.D. |
| 94 | ++ | N.D. |
| 95 | + | N.D. |

TABLE 50-continued

EC50 and IC50 data for Compounds 1-361

| Compound No. | NL20 Functional EC50 (μM) | Z-AAT Elastase Activity IC50 (μM) |
|---|---|---|
| 96 | + | N.D. |
| 97 | +++ | ++ |
| 98 | +++ | ++ |
| 99 | +++ | + |
| 100 | +++ | + |
| 101 | +++ | ++ |
| 102 | +++ | N.D. |
| 103 | ++ | N.D. |
| 104 | ++ | N.D. |
| 105 | + | N.D. |
| 106 | ++ | + |
| 107 | ++ | + |
| 108 | ++ | + |
| 109 | ++ | + |
| 110 | +++ | +++ |
| 111 | +++ | + |
| 112 | +++ | + |
| 113 | ++ | + |
| 114 | + | N.D. |
| 115 | + | N.D. |
| 116 | + | N.D. |
| 117 | + | N.D. |
| 118 | +++ | ++ |
| 119 | +++ | + |
| 120 | +++ | + |
| 121 | + | N.D. |
| 122 | +++ | N.D. |
| 123 | ++ | N.D. |
| 124 | +++ | + |
| 125 | +++ | + |
| 126 | + | N.D. |
| 127 | +++ | +++ |
| 128 | ++ | N.D. |
| 129 | +++ | N.D. |
| 130 | ++ | N.D. |
| 131 | ++ | N.D. |
| 132 | ++ | + |
| 133 | ++ | N.D. |
| 134 | +++ | N.D. |
| 135 | +++ | + |
| 136 | + | N.D. |
| 137 | ++ | N.D. |
| 138 | ++ | N.D. |
| 139 | ++ | N.D. |
| 140 | + | N.D. |
| 141 | + | + |
| 142 | +++ | + |
| 143 | + | N.D. |
| 144 | + | N.D. |
| 145 | + | N.D. |
| 146 | + | N.D. |
| 147 | ++ | N.D. |
| 148 | + | N.D. |
| 149 | + | N.D. |
| 150 | + | N.D. |
| 151 | + | N.D. |
| 152 | + | N.D. |
| 153 | + | N.D. |
| 154 | + | N.D. |
| 155 | + | N.D. |
| 156 | + | N.D. |
| 157 | + | N.D. |
| 158 | + | N.D. |
| 159 | + | N.D. |
| 160 | + | N.D. |
| 161 | + | N.D. |
| 162 | + | N.D. |
| 163 | + | N.D. |
| 164 | + | N.D. |
| 165 | ++ | N.D. |
| 166 | +++ | +++ |
| 167 | ++ | N.D. |
| 168 | + | N.D. |
| 169 | ++ | + |

(Column markers between the two tables: 5, 10, 15, 20, 25, 30, 35, 40, 45, 50, 55, 60, 65)

TABLE 50-continued

EC50 and IC50 data for Compounds 1-361

| Compound No. | NL20 Functional EC50 (μM) | Z-AAT Elastase Activity IC50 (μM) |
|---|---|---|
| 170 | + | N.D. |
| 171 | + | N.D. |
| 172 | + | N.D. |
| 173 | +++ | + |
| 174 | ++ | N.D. |
| 175 | + | + |
| 176 | + | N.D. |
| 177 | + | N.D. |
| 178 | + | N.D. |
| 179 | + | N.D. |
| 180 | + | N.D. |
| 181 | + | N.D. |
| 182 | +++ | ++ |
| 183 | +++ | N.D. |
| 184 | +++ | N.D. |
| 185 | +++ | N.D. |
| 186 | + | N.D. |
| 187 | +++ | N.D. |
| 188 | +++ | ++ |
| 189 | +++ | + |
| 190 | ++ | N.D. |
| 191 | + | N.D. |
| 192 | ++ | N.D. |
| 193 | ++ | N.D. |
| 194 | ++ | N.D. |
| 195 | + | N.D. |
| 196 | + | N.D. |
| 197 | + | + |
| 198 | ++ | + |
| 199 | + | N.D. |
| 200 | + | N.D. |
| 201 | +++ | ++ |
| 202 | +++ | + |
| 203 | ++ | + |
| 204 | + | N.D. |
| 205 | +++ | ++ |
| 206 | + | N.D. |
| 207 | + | N.D. |
| 208 | ++ | N.D. |
| 209 | + | N.D. |
| 210 | +++ | N.D. |
| 211 | + | N.D. |
| 212 | ++ | N.D. |
| 213 | +++ | + |
| 214 | + | N.D. |
| 215 | ++ | N.D. |
| 216 | +++ | + |
| 217 | +++ | + |
| 218 | +++ | + |
| 219 | ++ | N.D. |
| 220 | +++ | + |
| 221 | ++ | N.D. |
| 222 | + | N.D. |
| 223 | + | + |
| 224 | + | + |
| 225 | + | + |
| 226 | + | N.D. |
| 227 | + | + |
| 228 | + | N.D. |
| 229 | + | N.D. |
| 230 | + | N.D. |
| 231 | + | N.D. |
| 232 | + | N.D. |
| 233 | + | N.D. |
| 234 | ++ | +++ |
| 235 | + | N.D. |
| 236 | +++ | N.D. |
| 237 | + | + |
| 238 | ++ | + |
| 239 | ++ | N.D. |
| 240 | +++ | N.D. |
| 241 | +++ | + |
| 242 | +++ | +++ |
| 243 | ++ | N.D. |

TABLE 50-continued

EC50 and IC50 data for Compounds 1-361

| Compound No. | NL20 Functional EC50 (μM) | Z-AAT Elastase Activity IC50 (μM) |
|---|---|---|
| 244 | ++ | + |
| 245 | +++ | + |
| 246 | +++ | +++ |
| 247 | +++ | + |
| 248 | + | + |
| 249 | ++ | + |
| 250 | + | N.D. |
| 251 | + | N.D. |
| 252 | ++ | N.D. |
| 253 | +++ | +++ |
| 254 | +++ | ++ |
| 255 | ++ | +++ |
| 256 | +++ | +++ |
| 257 | +++ | ++ |
| 258 | +++ | +++ |
| 259 | +++ | +++ |
| 260 | +++ | + |
| 261 | +++ | N.D. |
| 262 | +++ | + |
| 263 | ++ | + |
| 264 | +++ | ++ |
| 265 | +++ | + |
| 266 | +++ | ++ |
| 267 | +++ | +++ |
| 268 | +++ | +++ |
| 269 | +++ | ++ |
| 270 | +++ | ++ |
| 271 | + | N.D. |
| 272 | ++ | N.D. |
| 273 | +++ | + |
| 274 | +++ | N.D. |
| 275 | ++ | N.D. |
| 276 | +++ | + |
| 277 | +++ | N.D. |
| 278 | ++ | + |
| 279 | +++ | +++ |
| 280 | +++ | + |
| 281 | ++ | + |
| 282 | + | N.D. |
| 283 | +++ | N.D. |
| 284 | +++ | N.D. |
| 285 | ++ | + |
| 286 | ++ | + |
| 287 | ++ | N.D. |
| 288 | ++ | ++ |
| 289 | + | + |
| 290 | + | N.D. |
| 291 | + | + |
| 292 | + | N.D. |
| 293 | ++ | + |
| 294 | + | N.D. |
| 295 | + | N.D. |
| 296 | + | N.D. |
| 297 | + | N.D. |
| 298 | + | N.D. |
| 299 | + | N.D. |
| 300 | + | N.D. |
| 301 | + | N.D. |
| 302 | +++ | + |
| 303 | ++ | + |
| 304 | + | N.D. |
| 305 | + | N.D. |
| 306 | + | N.D. |
| 307 | + | + |
| 308 | + | + |
| 309 | ++ | + |
| 310 | ++ | N.D. |
| 311 | ++ | N.D. |
| 312 | + | + |
| 313 | + | N.D. |
| 314 | +++ | N.D. |
| 315 | ++ | N.D. |
| 316 | + | N.D. |
| 317 | + | N.D. |

TABLE 50-continued

EC50 and IC50 data for Compounds 1-361

| Compound No. | NL20 Functional EC50 (μM) | Z-AAT Elastase Activity IC50 (μM) |
|---|---|---|
| 318 | ++ | N.D. |
| 319 | ++ | N.D. |
| 320 | + | N.D. |
| 321 | + | N.D. |
| 322 | + | + |
| 323 | +++ | N.D. |
| 324 | ++ | N.D. |
| 325 | + | + |
| 326 | + | N.D. |
| 327 | + | + |
| 328 | + | + |
| 329 | + | N.D. |
| 330 | + | + |
| 331 | + | N.D. |
| 332 | + | N.D. |
| 333 | +++ | + |
| 334 | ++ | N.D. |
| 335 | +++ | + |
| 336 | +++ | + |
| 337 | +++ | N.D. |
| 338 | ++ | N.D. |
| 339 | ++ | N.D. |
| 340 | + | N.D. |
| 341 | ++ | N.D. |
| 342 | + | N.D. |
| 343 | +++ | N.D. |
| 344 | +++ | N.D. |
| 345 | +++ | N.D. |
| 346 | +++ | + |
| 347 | +++ | N.D. |
| 348 | ++ | N.D. |
| 349 | ++ | N.D. |
| 350 | + | N.D. |
| 351 | ++ | N.D. |
| 352 | ++ | N.D. |
| 353 | + | N.D. |
| 354 | + | N.D. |
| 355 | ++ | N.D. |
| 356 | + | N.D. |
| 357 | + | N.D. |
| 388 | ++ | N.D. |
| 359 | ++ | N.D. |
| 360 | + | N.D. |
| 361 | + | N.D. |

Other Embodiments

This description provides merely exemplary embodiments of the disclosed subject matter. One skilled in the art will readily recognize from the disclosure and accompanying claims, that various changes, modifications and variations can be made therein without departing from the spirit and scope of the disclosure as defined in the following claims.

What is claimed is:

1. A compound of Formula I:

I a deuterated derivative of the compound of Formula I, and/or a pharmaceutically acceptable salt of any of the foregoing, wherein:

$R^1$ is —OH;

$R^{1'}$ is hydrogen or halogen;

$W^1$ and $W^2$ are —CH;

X is selected from —C═O, —CR$^2$, N, and —NR$^3$;

Y is selected from —C═O, —CR$^2$, N, and —NR$^3$, wherein if X is —C═O, then Y is —NR$^3$, if X is —CR$^2$, then Y is N, if X is N, then Y is —CR$^2$, and if X is —NR$^3$, then Y is —C═O;

(z) is a double bond unless X or Y is C═O, and when X or Y is C═O, then (z) is a single bond;

$R^2$ is selected from —CN, —C(═O)OH, —C(═O)NH$_2$, —C(═O)NHR$^7$, —C(═O)NHCH$_2$R$^7$, —OCH$_2$R$^7$, —OR$^7$, —NHR$^7$, —NHCH$_2$R$^7$, $C_6$ or $C_{10}$ aryl, 5 to 10-membered heteroaryl, $C_1$-$C_8$ alkyl, $C_3$-$C_8$ cycloalkyl, $C_2$-$C_8$ alkenyl, $C_2$-$C_8$ heteroalkyl, and 3 to 10-membered heterocyclyl, wherein the alkyl, heteroalkyl, alkenyl, heterocyclyl, aryl, or heteroaryl of R$^2$ is optionally substituted with 1-3 groups independently selected from halogen, —C(═O)OH, $C_1$-$C_6$ alkyl, $C_3$-$C_8$ cycloalkyl, $C_6$ or $C_{10}$ aryl, 3 to 10-membered heterocyclyl, 5 to 10-membered heteroaryl (optionally further substituted with halogen, —OH, —OCH$_3$, —C(═O)OH) and $C_3$-$C_6$ cycloalkyl (optionally further substituted with halogen, —OH, —OCH$_3$, and/or —C(═O) OH), and wherein the heteroalkyl of R$^2$ contains 1-3 heteroatoms independently selected from N, O, and S;

$R^3$ is selected from hydrogen, $C_6$ or $C_{10}$ aryl, $C_1$-$C_8$ alkyl, and $C_3$-$C_8$ cycloalkyl;

wherein R$^3$ is optionally substituted with 1-3 groups independently selected from ═O, —OH, —CH$_2$OH, —C(═O)OH, NH$_2$, $C_3$-$C_6$ cycloalkyl (optionally substituted with ═O, —CH$_2$OH, and/or —C(═O) OH), and 3 to 6-membered heterocyclyl (optionally substituted with ═O, —CH$_2$OH, and/or —C(═O) OH), and wherein the heterocyclyl of R$^3$ contains 1-3 nitrogen atoms; and wherein R$^3$ is optionally fused to a $C_3$-$C_6$ cycloalkyl;

$R^4$ is selected from

-continued

, and .

$R^5$ is selected from $C_6$ or $C_{10}$ aryl, —O(phenyl), 5 or 6-membered heteroaryl, $C_3$-$C_6$ carbocyclyl, and 3 to 6-membered heterocyclyl, wherein the heterocyclyl or heteroaryl contains 1-3 nitrogens and wherein $R^5$ is optionally substituted with $(R^6)_n$, wherein n is 1, 2, or 3;

provided that $R^5$ is not imidazolyl;

$R^6$, for each occurrence, is independently selected from halogen, $C_1$-$C_3$ alkyl, $C_1$-$C_3$ haloalkyl, $C_1$-$C_3$ alkoxy, and $C_1$-$C_3$ haloalkoxy;

$R^7$ is selected from $C_1$-$C_8$ alkyl, $C_3$-$C_8$ cycloalkyl, $C_6$ or $C_{10}$ aryl, $C_2$-$C_8$ heteroalkyl, 3 to 8-membered heterocyclyl, and 5 to 8-membered heteroaryl, wherein $R^7$ is optionally substituted with 1-3 groups independently selected from halogen, =O, —OH, —OCH$_3$, —CH$_3$, —C(=O)OH, —C(=O)NR$^8$, —CN, —NH$_2$, $C_1$-$C_6$ alkyl (optionally substituted with 1-3 groups independently selected from =O, —OH, —CN, —C(=O)OH, and —NH$_2$), $C_3$-$C_6$ cycloalkyl (optionally substituted with 1-3 groups selected from =O, —OH, —CN, —C(=O)OH, and —NH$_2$), $C_6$ or $C_{10}$ aryl (optionally substituted with 1-3 groups independently selected from =O, —OH, —CN, —C(=O)OH, and —NH$_2$), $C_2$-$C_6$ heteroalkyl (optionally substituted with 1-3 groups independently selected from =O, —OH, —CN, —C(=O) OH, and —NH$_2$), and 3 to 6-membered heterocyclyl (optionally substituted with 1-3 groups independently selected from halogen, =O, OH, CN, COOH, and NH$_2$), 5 or 6-membered heteroaryl (optionally substituted with 1-3 groups independently selected from =O, —OH, —CN, —COOH, and —NH$_2$), and wherein the heteroalkyl, heterocyclyl, or heteroaryl of $R^7$ contains 1-3 atoms independently selected from N, O, and S; and $R^8$ is selected from $C_1$-$C_6$ alkyl and $C_6$ or $C_{10}$ aryl, wherein $R^8$ is optionally substituted with halogen and/ or —OH.

2. The compound, deuterated derivative, or pharmaceutically acceptable salt according to claim 1, wherein $R^3$ is selected from phenyl and $C_3$-$C_8$ cycloalkyl, wherein $R^3$ is optionally substituted with 1-2 groups independently selected from =O, —OH, —CH$_2$OH, —C(=O)OH, —NH$_2$, $C_3$-$C_6$ cycloalkyl (optionally further substituted with 1-2 groups independently selected from =O, —CH$_2$OH, and —C(=O)OH), and 3 to 6-membered heterocyclyl (optionally further substituted with 1-3 groups independently selected from =O, —CH$_2$OH, and —C(=O)OH);

wherein the 3 to 6-membered heterocyclyl contains 1-2 nitrogen atoms; and wherein $R^3$ is optionally fused to a $C_3$-$C_6$ cycloalkyl.

3. The compound, deuterated derivative, or pharmaceutically acceptable salt according to claim 1, wherein $R^3$ is $C_1$-$C_6$ alkyl optionally substituted with 1-2 groups independently selected from =O, —OH, —CH$_2$OH, —C(=O)OH, —NH$_2$, $C_3$-$C_6$ cycloalkyl (optionally further substituted with 1-2 groups independently selected from =O, —CH$_2$OH, and —C(=O)OH), and 3 to 6-membered heterocyclyl (optionally further substituted with 1-3 groups independently selected from =O, —CH$_2$OH, and —C(=O) OH), wherein the 3 to 6-membered heterocyclyl contains 1-2 nitrogen atoms; and wherein $R^3$ is optionally fused to a $C_3$-$C_6$ cycloalkyl.

4. The compound, deuterated derivative, or pharmaceutically acceptable salt according to claim 1, wherein $R^3$ is selected from $C_4$ cyclic and $C_8$ spirocyclic alkyls optionally substituted with 1-2 groups independently selected from =O, —OH, —CH$_2$OH, —C(=O)OH, and —NH$_2$.

5. The compound, deuterated derivative, or pharmaceutically acceptable salt according to claim 1, wherein $R^3$ is selected from:

585

-continued

, and

6. The compound, deuterated derivative, or pharmaceutically acceptable salt according to claim 1, wherein $R^3$ is hydrogen.

7. The compound, deuterated derivative, or pharmaceutically acceptable salt according claim 1, wherein $R^5$ is selected from phenyl, 5 or 6-membered heteroaryl, $C_3$-$C_6$ carbocyclyl, and 3 to 6-membered heterocyclyl, wherein $R^5$ is optionally substituted with 1 or 2 groups independently selected from halogen and —$CH_3$.

8. The compound, deuterated derivative, or pharmaceutically acceptable salt according to claim 1, wherein $R^5$ is selected from

586

-continued

| 587 | 588 |

587

-continued

9. The compound, deuterated derivative, or pharmaceutically acceptable salt according to claim 1, wherein $R^2$ is selected from —$OR^7$, —$NHR^7$, —$C(=O)NHR^7$, and —$NHCH_2R^7$.

10. The compound, deuterated derivative, or pharmaceutically acceptable salt according to claim 1, wherein $R^2$ is selected from —CN, —$C(=O)OH$, —$C(=O)NH_2$, —$C(=O)NHCH_2R^7$, and —$OCH_2R^7$.

11. The compound, deuterated derivative, or pharmaceutically acceptable salt according to claim 1, wherein $R^7$ is selected from $C_1$-$C_8$ alkyl and $C_3$-$C_8$ cycloalkyl, each of which is optionally substituted with 1-3 groups independently selected from Br, Cl, F, —$CH_3$, —$C(=O)OH$, =O, —$OCH_3$, and —OH.

12. The compound, deuterated derivative, or pharmaceutically acceptable salt according to claim 1, wherein $R^7$ is selected from $C_2$-$C_8$ heteroalkyl and 3 to 8-membered heterocyclyl, wherein the heteroalkyl or heterocyclyl contains 1-3 heteroatoms independently selected from N, O, and S; and wherein the heteroalkyl or heterocyclyl is optionally substituted with 1-3 groups independently selected from Br, Cl, F, —$CH_3$, —$C(=O)OH$, =O, —$OCH_3$, and —OH.

13. The compound, deuterated derivative, or pharmaceutically acceptable salt according to claim 1, wherein $R^7$ is selected from aryl and 5 to 8-membered heteroaryl, wherein the aryl or heteroaryl contain 1-3 heteroatoms independently selected from N, O, and S; and wherein the aryl or heteroaryl is optionally substituted with 1-3 groups independently selected from Br, Cl, F, —$CH_3$, —$C(=O)OH$, =O, —$OCH_3$, and —OH.

14. The compound, deuterated derivative, or pharmaceutically acceptable salt according to claim 1, wherein $R^7$ is selected from $C_1$-$C_8$ alkyl, $C_3$-$C_8$ cycloalkyl, $C_2$-$C_8$ heteroalkyl, 3 to 8-membered heterocyclyl, phenyl, and 5 to 8-membered heteroaryl, wherein $R^7$ is optionally substituted with 1-3 groups independently selected from halogen, =O, —$C(=O)$ OH, phenyl, 5 to 8-membered heteroaryl, $C_1$-$C_6$ alkyl (optionally further substituted with 1-3 groups independently selected from =O, OH, CN, COOH, and $NH_2$), $C_3$-$C_6$ cycloalkyl (optionally further substituted with 1-3 groups independently selected from =O, —OH, —CN, —COOH, and —$NH_2$), $C_2$-$C_6$ heteroalkyl (optionally further substituted with 1-3 groups independently selected from halogen, =O, —OH, —CN, —COOH, and —$NH_2$), and 3 to 6-membered heterocyclyl (optionally further substituted with 1-3 groups independently selected from =O, —OH, —CN, —COOH, and —$NH_2$); and wherein the heteroalkyl, heterocyclyl, or heteroaryl of $R^7$ contains 1-3 atoms independently selected from N, O, and S.

15. The compound, deuterated derivative, or pharmaceutically acceptable salt according to claim 1, wherein $R^2$ is selected from

589

-continued

590

-continued

591
-continued

592
-continued

16. The compound, deuterated derivative, or pharmaceutically acceptable salt according to claim 1, wherein R² is selected from

593

594

17. The compound, deuterated derivative, or pharmaceutically acceptable salt according to claim 1, wherein R$^2$ is selected from -continued -continued

18. The compound, deuterated derivative, or pharmaceutically acceptable salt according to claim 1, wherein R² is selected from

597

19. A compound selected from:

598

599

9

10

11

600

12

13

14

15

601

16

17

18

19

602

20

21

22

| 603 | 604 |
| --- | --- |
| -continued | -continued |

23

24

25

26

27

28

29

605

-continued

30

606

-continued

34

31

32

33

35

36

37

607

38

39

40

41

608

42

43

44

45

609

-continued

46

47

48

49

610

-continued

50

51

52

53

611

54

55

56

612

57

58

59

60

613

614

61

62

63

64

65

66

67

68

615

69

70

71

72

616

73

74

75

76

617

-continued

618

-continued

77

78

79 35

50 80

81

82

83

84

619

-continued

85

620

-continued

89

86

90

87

91

88

92

621

-continued

93

94

95

96

622

-continued

97

98

99

100

623
-continued

624
-continued

101

105

102

106

103

107

104

108

625

-continued

109

110

111

112

626

-continued

113

114

115

116

627

117

118

628

120

121

119

122

629

-continued

630

-continued

123

124

125

126

127

128

129

631

130

131

132

632

133

134

135

633

136

137

138

139

634

140

141

142

143

635

144

636

148

149

150

637

-continued

151

125

153

638

-continued

154

155

156

639

-continued

157

640

-continued

161

162

158

159

163

160

164

641

165

166

167

168

642

169

170

171

172

643
-continued

173

174

175

176

644
-continued

177

178

179

180

645

-continued

646

-continued

647

648

188

189

190

191

192

193

194

195

649
-continued

650
-continued

196

197

198

199

200

201

202

651

-continued

203

204

205

206

652

-continued

207

208

209

210

653
-continued

654
-continued

211

212

213

214

215

216

217

655
-continued

656
-continued

218

221

219

222

223

220

224

657

225

658

228

20

226

229

230

227

231

659

660

232

233

234

235

236

237

238

239

661

-continued

662

-continued

240

244

241

245

242

246

243

247

663

-continued

248

664

-continued

252

249

253

250

254

251

255

665

-continued

256

257

258

259

666

-continued

260

261

262

263

| 667 | 668 |
|---|---|
| -continued | -continued |

264

265

266

267

268

269

270

271

669

-continued

272

273

274

275

670

-continued

276

277

278

279

671

280

281

282

283

672

284

285

286

287

673

-continued

288

289

15

290

291

292 45

293

674

-continued

294

295

296

297

675

298

299

300

301

676

302

303

304

305

677
-continued

678
-continued

306

307

308

309

310

311

312

313

| 679 | 680 |
|---|---|
| -continued | -continued |

314

315 20

316

317 55

318

319

320

321

681
-continued

682
-continued

322

327

323

328

324

329

325

330

326

331

683

-continued

332

333

334

335

684

-continued

336

337

338

685
-continued

686
-continued

339

342

340

343

341

344

687
-continued

688
-continued

345

347

346

348

346

349

689

350

351

352

690

354

355

356

357

691
-continued

692
-continued

357

360

358

361

359

deuterated derivatives thereof, and pharmaceutically accept-
able salts of any of the foregoing.

20. A pharmaceutical composition comprising the com-
pound according to claim 1, a deuterated derivative thereof,
and/or a pharmaceutically acceptable salt of any of the
foregoing, and a pharmaceutically acceptable carrier.

21. A method of treating alpha-1 antitrypsin deficiency
comprising administering to a patient in need thereof at least
one compound chosen from the compounds, deuterated
derivatives, and pharmaceutically acceptable salts according
to claim 1.

22. A method of increasing alpha-1 antitrypsin activity
comprising contacting said alpha-1 antitrypsin with at least
one compound chosen from the compounds, deuterated
derivatives, and pharmaceutically acceptable salts according
to claim 1.

\* \* \* \* \*